US009878031B2

(12) United States Patent
Stinchcomb et al.

(10) Patent No.: US 9,878,031 B2
(45) Date of Patent: Jan. 30, 2018

(54) COMPOSITIONS, METHODS OF ADMINISTRATION AND USES FOR TRIVALENT DENGUE VIRUS FORMULATIONS

(71) Applicant: Takeda Vaccines, Inc., Deerfield, IL (US)

(72) Inventors: Dan T. Stinchcomb, Fort Collins, CO (US); Joseph N. Brewoo, Madison, WI (US); Jorge E. Osorio, Mount Horeb, WI (US); Charalambos D. Partidos, Chicago, IL (US)

(73) Assignee: Takeda Vaccines, Inc., Cambridge, MA (US)

( * ) Notice: Subject to any disclaimer, the term of this patent is extended or adjusted under 35 U.S.C. 154(b) by 0 days.

(21) Appl. No.: 14/652,066

(22) PCT Filed: Dec. 7, 2013

(86) PCT No.: PCT/US2013/073757
§ 371 (c)(1),
(2) Date: Jun. 12, 2015

(87) PCT Pub. No.: WO2014/093182
PCT Pub. Date: Jun. 19, 2014

(65) Prior Publication Data

US 2015/0335727 A1 Nov. 26, 2015

Related U.S. Application Data

(60) Provisional application No. 61/737,679, filed on Dec. 14, 2012.

(51) Int. Cl.

| | |
|---|---|
| ***A61K 39/12*** | (2006.01) |
| ***C12N 15/00*** | (2006.01) |
| ***A61K 45/06*** | (2006.01) |
| *A61K 39/00* | (2006.01) |

(52) U.S. Cl.
CPC .............. *A61K 39/12* (2013.01); *A61K 45/06* (2013.01); *A61K 2039/5254* (2013.01); *A61K 2039/5256* (2013.01); *A61K 2039/70* (2013.01); *C12N 2770/24134* (2013.01)

(58) Field of Classification Search
None
See application file for complete search history.

(56) References Cited

U.S. PATENT DOCUMENTS

| | | | | |
|---|---|---|---|---|
| 7,641,907 | B2 * | 1/2010 | Kinney | A61K 39/12 424/186.1 |
| 7,641,908 | B2 | 1/2010 | Kinney et al. | |
| 8,968,996 | B2 * | 3/2015 | Stinchcomb | A61K 39/12 424/202.1 |
| 9,211,323 | B2 * | 12/2015 | Stinchcomb | A61K 39/12 |
| 2004/0120964 | A1 | 6/2004 | Mikszta et al. | |
| 2004/0259224 | A1 | 12/2004 | Guirakhoo | |
| 2006/0062803 | A1 | 3/2006 | Kinney et al. | |
| 2007/0269458 | A1 | 11/2007 | Guirakhoo et al. | |
| 2008/0085288 | A1 | 4/2008 | Guy et al. | |
| 2008/0193477 | A1 | 8/2008 | Monath et al. | |

FOREIGN PATENT DOCUMENTS

| | | | |
|---|---|---|---|
| WO | 0160847 | A2 | 8/2001 |
| WO | 2008022196 | A2 | 2/2008 |
| WO | 2008157136 | A1 | 12/2008 |
| WO | 2010085358 | A2 | 7/2010 |
| WO | 2012065105 | A2 | 5/2012 |
| WO | 2013188315 | A1 | 12/2013 |

OTHER PUBLICATIONS

Durbin, A. P., et. al. Update on Dengue Vaccines in Pre-Clinical and Clinical Development. Oct. 24, 2013, XP055265480, Retrieved from the Internet: URL: http://www.denguevaccines.org/sites/default/files/files/Durbin_Vaccines. pdf [retrieved on Apr. 14, 2016], 42 pages.

Guy, Bruno et al., Evaluation of Interferences between Dengue Vaccine Serotypes in a Monkey Model, Am.J.Trop. Med.Hyg., vol. 80, No. 2, (2009) pp. 302-311.

Osorio, Jorge E. et al., Development of DENVax: A chimeric dengue-2 PDK-53-based tetravalent vaccine for protection against dengue fever, Vaccine, vol. 29, (2011) pp. 7251-7260.

Schmitz, J., et. al. Next Generation Dengue Vaccines: A Review of Candidates in Preclinical Development. Vaccine, 29:7276-7284, 2011.

International Search Report and Written Opinion issued in PCT/US2013/073757, dated Feb. 14, 2014, 15 pages.

Apt et al. Tetravalent Neutralizing Antibody Response Against Four Dengue Serotypes by a Single Chimeric Dengue Envelope Antigen; Vaccine vol. 24, Issue 3, Jan. 16, 2006, pp. 335-344.

Blaney, Joseph E. Jr. et al., Recombinant, Live-Attenuated Tetravalent Dengue Virus Vaccine Formulations Induce a Balanced, Broad, and Protective Neutralizing Antibody Response against Each of the Four Serotypes in Rhesus Monkeys, Journal of Virology, vol. 79, No. 9, (May 2005) pp. 5516-5528.

Brewoo, Joseph N. et al., Immunogenicity and efficacy of chimeric dengue vaccine (DENVax) formulations in Interferon-deficient AG129 mice, Vaccine, (Nov. 19, 2011).

Cannon, D.A. et al., Mass vaccination against yellow fever by scarification with 17d strain vaccine, Federal Laboratory Service, Yaba, Lagos, Nigeria, Apr. 30, 1957, pp. 256-263.

(Continued)

*Primary Examiner* — Stacy B Chen
(74) *Attorney, Agent, or Firm* — Faegre Baker Daniels LLP

(57) ABSTRACT

Embodiments of the present invention report compositions and methods for vaccinating a subject using trivalent dengue virus vaccine compositions. In some embodiments, more than one vaccine composition may be administered to a subject in different anatomical locations in order to induce a rapid response to at least three of four dengue virus serotypes. In certain embodiments, administration of a trivalent dengue virus vaccine composition can be combined with administration of a monovalent dengue virus vaccine composition.

14 Claims, 1 Drawing Sheet

(56) References Cited

OTHER PUBLICATIONS

Cannon, D.A. et al., Vaccination by scarification with 17d yellow fever vaccine prepared at YABA, Lagos, Nigeria, Laboratory Service Headquarters, Yaba, Lagos, Nigeria, Oct. 8, 1953, pp. 380-393.
Capeding, Rosario Z. et al., Live-attenuated, tetravalent dengue vaccine in children, adolescents and adults in a dengue endemic country: Randomized controlled phase I trial in the Philippines, Elsevier, Vaccine, vol. 29, (2011) pp. 3863-3872.
Dean, Cheryl H. et al., Cutaneous Delivery of a Live, Attenuated Chimeric Flavivirus Vaccine Against Japanese Encephalitis, Human Vaccines, vol. 1, No. 3, (2005) pp. 106-111.
Higgs, et al., Growth Characteristics of Chimerivax-Den Vaccine Viruses in Aedes Aegypti and Aedes Albopictus From Thailand, Am. J. Trop. Med. Hyg., 75(5), (2006), pp. 986-993.
Huang C Y-H et al: "Dengue 2 PDK-53 virus as a chimeric carrier for tetravalent dengue vaccine development" Journal of Virology. The American Society for Microbiology. US. vol. 77. No. 21. Nov. 1, 2003 (Nov. 1, 2003). pp. 11436-11447. XP003005064. ISSN: 0022-538X. DOI: 10.1128/JVI.77.21.11436-11447.2003 p. 11436-col. 2; table 1.
International Search Report and Written Opinion issued in PCT/US2013/069287, dated Jan. 7, 2014, 14 pages.
International Search Report and Written Opinion, Application No. PCT/US10/36726, dated Jul. 28, 2010.
Inviragen, Dengue, Feb. 13, 2013, found at http://www.inviragen.com/dengue.php, 2 pages.
Kelly et al. Evolution of Attenuating Mutations in Dengue-2 Strain S16803 PDK50 Vaccine and Comparison of Growth Kinetics With Parent Virus; Virus Genes (2011) 43: 18-26, DOI 10.1007/s11262-011-0602-z.
Meers, Captain P.D., Further Observations on 17D-Yellow Fever Vaccination by Scarification, With and Without Simultaneous Smallpox Vaccination, Transactions of the Royal Society of Tropical Medicine and Hygiene, vol. 54, No. 5, (1960) pp. 493-501.
Osorio, Jorge E et al., Efficacy of a Tetravalent Chimeric Dengue Vaccine (DENVax) in Cynomolgus Macaques, Am.J. Trop.Med. Hyg., vol. 84, No. 6, (2011) pp. 978-987.
Sabin, Albert B., Research on Dengue During World War II, History of Preventive Medicine, U.S. Army Medical Department, World War II, pp. 30-50.
Webster et al., Lancet Infectious Disease, 2009, 9:678-687.
Zompi and Harris, Viruses, 2012, 4:62-82.

* cited by examiner

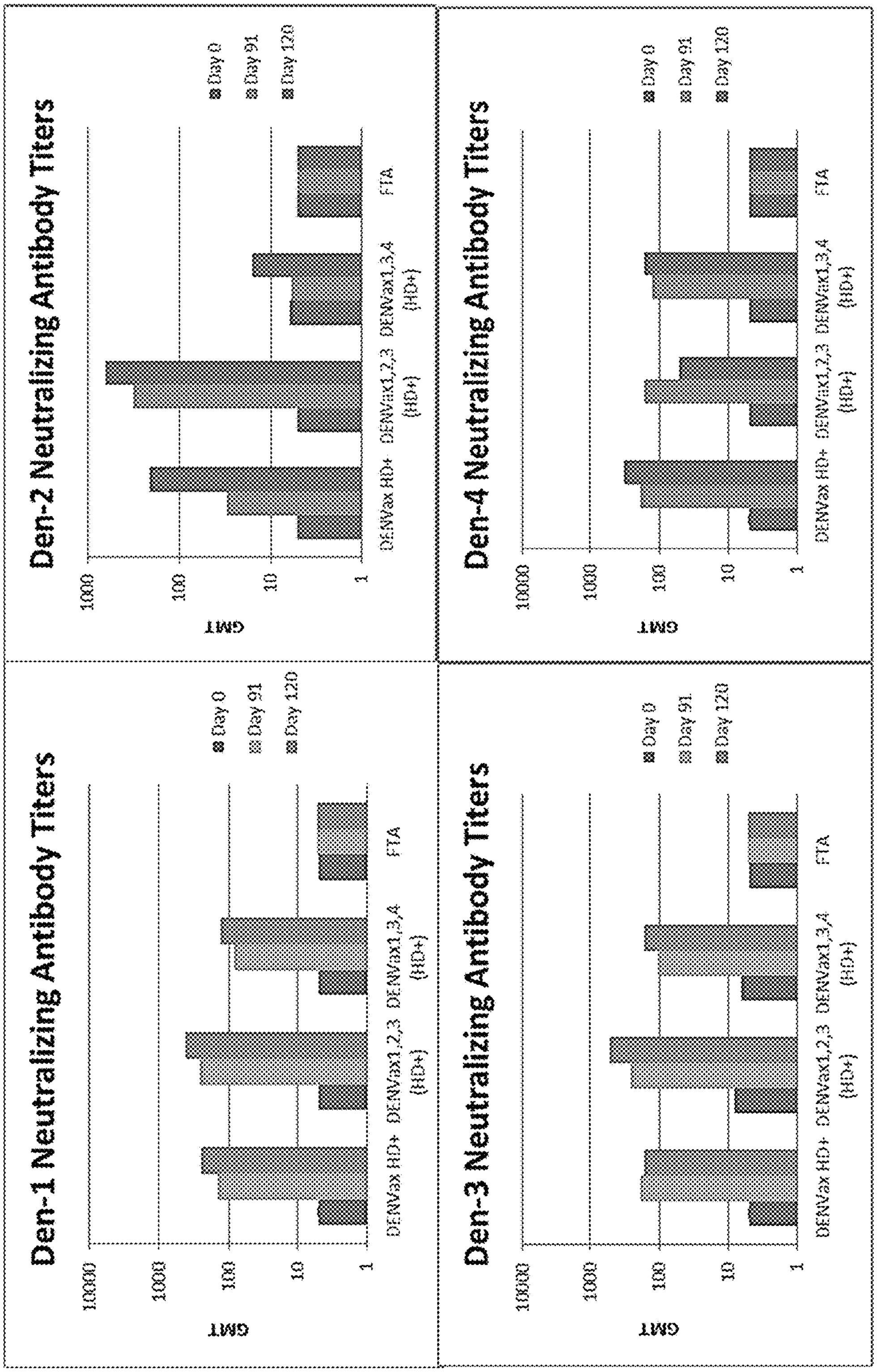
Den-1 Neutralizing Antibody Titers
GMT
10000
1000
100
10
1
DENVax HD+
DENVax1,2,3 (HD+)
DENVax1,3,4 (HD+)
FTA
Day 0
Day 91
Day 120
Den-2 Neutralizing Antibody Titers
GMT
1000
100
10
1
DENVax HD+
DENVax1,2,3 (HD+)
DENVax1,3,4 (HD+)
FTA
Day 0
Day 91
Day 120
Den-3 Neutralizing Antibody Titers
GMT
10000
1000
100
10
1
DENVax HD+
DENVax1,2,3 (HD+)
DENVax1,3,4 (HD+)
FTA
Day 0
Day 91
Day 120
Den-4 Neutralizing Antibody Titers
GMT
10000
1000
100
10
1
DENVax HD+
DENVax1,2,3 (HD+)
DENVax1,3,4 (HD+)
FTA
Day 0
Day 91
Day 120

COMPOSITIONS, METHODS OF ADMINISTRATION AND USES FOR TRIVALENT DENGUE VIRUS FORMULATIONS

PRIORITY

This U.S. Non-Provisional Application claims priority to PCT application No. PCT/US2013/073757, filed Dec. 7, 2013, and U.S. Provisional Application Serial No. 61/737,679 filed Dec. 14, 2012. These applications are incorporated herein by reference in their entirety for all purposes.

FIELD

Embodiments of the present invention report compositions and methods for administering a vaccine to a subject against dengue virus serotypes. In some embodiments, vaccine compositions disclosed herein may be administered by subcutaneous, intradermal, intramuscular or other injection or introduction methods against three dengue virus serotypes. In other embodiments, vaccine compositions disclosed herein may be administered to a subject against three dengue virus serotypes (trivalent formulation) followed by a monovalent formulation, bivalent or other trivalent dengue virus vaccine formulation. In certain embodiments, administration of a vaccine to a subject can include administration to two or more anatomical sites of one or more trivalent and optionally, monovalent vaccine compositions. Other embodiments include follow-on injections from within days of a first vaccination to up to 12 months after initial injection(s). In certain embodiments, compositions against dengue virus include trivalent formulations where the formulations comprise chimera constructs having a DEN-2 backbone and for example having combination compositions of chimeras of DEN 1, 3 or 4 on a DEN-2 backbone.

BACKGROUND

Vaccines for protection against viral infections have been effectively used to reduce the incidence of human disease. One of the most successful technologies for viral vaccines is to immunize animals or humans with a weakened or attenuated strain of the virus (a "live, attenuated virus"). Due to limited replication after immunization, the attenuated strain does not cause disease. However, the limited viral replication is sufficient to express the full repertoire of viral antigens and can generate potent and long-lasting immune responses to the virus. Thus, upon subsequent exposure to a pathogenic strain of the virus, the immunized individual is protected from disease. These live, attenuated viral vaccines are among the most successful vaccines used in public health.

Dengue viruses are mosquito-borne pathogens of the genus *Flavivirus* (family Flaviviridae). Four serotypes of dengue virus (often abbreviated "DEN" or "DENV") had been identified, including dengue-1, dengue-2, dengue-3 and dengue-4 (DEN-1 to DEN-4). The flavivirus genome is a single-stranded, positive-sense RNA approximately 11 kb in length, containing a 5'-noncoding region (5'NC); a coding region encoding the viral structural proteins; five nonstructural proteins, designated NS1, NS2A, NS2B, NS3, NS4A, NS4B, NS5; and a 3'-noncoding region (3'NC). The viral structural proteins include the capsid, premembrane/membrane and envelope. The structural and nonstructural proteins are translated as a single polyprotein. The polyprotein is then processed by cellular and viral proteases.

Transmitted by *Aedes aegypti* mosquitoes to humans in tropical and subtropical regions of the world, dengue viruses cause millions of cases of disease every year, ranging from dengue fever to the often fatal dengue hemorrhagic fever/dengue shock syndrome (DHF/DSS). Secondary infection of humans with a heterologous serotype of DEN virus may induce an immunopathological response and is considered a possible risk factor for DHF/DSS. Therefore, the need exists for development of a vaccine that confers simultaneous protection against all dengue virus strains.

SUMMARY

Embodiments of the present invention generally relate to methods and compositions for inducing protection in a subject against multiple a dengue viruses by, for example, by administering a trivalent dengue virus vaccine composition to a subject. In accordance with these embodiments, a trivalent dengue virus vaccine composition includes immunogenic agents to at least three of four dengue virus serotypes or even five of the dengue virus serotypes.

Some embodiments can include introducing a trivalent dengue virus vaccine composition disclosed herein to a subject in one or more anatomical locations in the subject. In accordance with these embodiments, dengue virus vaccine composition can be introduced to a subject by any method known in the art to, for example, induce neutralizing antibodies against at least three dengue virus serotypes. Other embodiments include administering a trivalent dengue virus vaccine formulation to a subject and then following administration of the trivalent formulation with a monovalent formulation on the same or within 12 months after first administration. Other embodiments include treating a subject with a monovalent dengue virus vaccine composition first and then administering on the same or sometime later, but at least within 12 months of the monovalent dengue virus vaccine formulation at least one trivalent dengue virus vaccine composition.

Some embodiments concern administering a single trivalent dengue virus vaccine composition to a subject in need thereof to induce a response to three or four dengue virus serotypes.

In certain embodiments, a vaccine composition can include, but is not limited to, a single dose formulation of a trivalent dengue virus serotype vaccine. In accordance with these embodiments, a trivalent formulation can be a trivalent formulation of dengue-1 (DEN-1); dengue-2 (DEN-2), dengue-3 (DEN-3) and/or dengue-4 (DEN-4). Further, these formulations can be a predetermined ratio of dengue virus serotypes.

In other embodiments, a vaccine composition may include, but is not limited to; an initial dose of a trivalent dengue virus vaccine composition followed by one or more boosts of the same, or a different trivalent or one or more monovalent dengue-virus vaccine composition administered to a subject in need thereof.

Other aspects herein can concern inducing a humoral or cellular immune response in a subject by, for example, introducing a vaccine composition to a subject via an intradermal route wherein the vaccine composition includes, but is not limited to, a dengue virus vaccine. In accordance with these embodiments, compositions disclosed can be administered intradermally to a subject for modulating neutralizing antibody production in the subject against three or more dengue virus serotypes. Some aspects concern predetermined composition ratios of three of DEN-1:DEN-2:DEN:3 :DEN:4 (e.g. 1:1:1, 1:2:1, 1:1:100,000 etc. or any ratio of three serotypes) of the various serotypes of dengue virus or fragments thereof or attenuated compositions thereof in a single vaccine composition in order to increase cross protection and levels of neutralizing antibodies in a subject against at least three dengue virus serotypes when the subject is administered the single vaccine composition. Other embodiments concern administering a trivalent dengue virus vaccine composition to a subject in need thereof via subcutaneously or by other mode known in the art. In addition, certain embodiments concern treating a subject with at least one additional injection(s) of a trivalent or monovalent dengue virus vaccine composition administered at a separate site from the first injection, for example, in close proximity to the initial injection or in a distant anatomical site on the subject. In addition, at least one additional intradermal injection(s) may be performed less than 30 days after the first administration to the subject while others are performed 30 days and up to 12 months after the first administration of the vaccine.

In some embodiments, a single dose trivalent vaccine against dengue virus can include constructs of three different dengue virus serotype antigens (e.g. structural proteins) in a single trivalent composition. In accordance with these embodiments, constructs contemplated herein include attenuated dengue-2 virus as a backbone for one or more structural dengue virus proteins capsid (C), premembrane/membrane (prM/M), or envelope (E). In addition, nonstructural proteins may also be included in a construct, including, nonstructural proteins NS1-NS2A-NS2B-NS3-NS4A-NS4B-NS5, and 3' NCR. In certain embodiments, a trivalent dengue virus vaccine composition can include constructs having an attenuated dengue-2 virus (e.g. PDK-53) where structural proteins of dengue-2 are replace with one or more structural proteins of DEN-1, DEN-3 or DEN-4. Trivalent dengue virus vaccine compositions can be DENVax 1, 2, 3; DENVax 2, 3, 4; DENVax1, 2, 4 or DENVax1, 3, 4 on an attenuated DEN-2 backbone.

In certain embodiments, a trivalent dengue virus vaccine composition disclosed herein can include dengue virus constructs in any combination of three where pfus of the various compositions can range from 1 to about 100,000 fold difference depending on desired ratio and endemic conditions in a given location. Some embodiments include up to 100,000 fold pfu difference between DEN-2 and DEN-4 where DEN-4 can be represented up to 100,000 fold higher than DEN-2. Certain embodiments include compositions where dengue virus serotypes are 10 fold higher to 10 fold lower than for example when DENVax1 is $1.25\times10^4$; DENVax2 is $6.04\times10^{4\prime}$ DENVax3 is $1.30\times10^5$ and DENVax4 is $1.34\times10.^6$ Other embodiments disclosed herein relate to methods and compositions for inducing protection in a subject against all dengue virus serotypes by, for example, administering a trivalent vaccine to a subject against three dengue virus serotypes in two or more doses in one or more than one anatomical location consecutively within a short interval of time. Some embodiments can include introducing a vaccine composition to a subject via intradermal (ID), subcutaneous (SC), or intramuscular (IM) injection in one location and consecutively in another anatomical location by ID, SC, IM or by other introduction method at a second different anatomical location. Other embodiments include using any combination of modes of administration for introducing a dengue virus vaccine of all dengue virus serotypes to a subject where administration of the vaccine occurs at two or more anatomical sites or by two or more different routes consecutively on the same day to the subject.

In other embodiments, a subject may be administered dengue virus trivalent vaccinations consecutively at two or more anatomical locations, then the subject can be administered at least a third vaccine within 30 days such as about 7, about 14, about 21 or about 28 days later with a composition comprising dengue virus serotypes which can include a monovalent formulation. Subsequent vaccinations may depend on personalized titers of antibodies post dual injection or other criteria such as results of test populations. In certain embodiments, a subsequent vaccination may only include a single dengue serotype (e.g. DEN-4).

In certain embodiments, the composition introduced to the subject comprises vaccines against three of four dengue virus serotypes, for example a trivalent formulation based on DENVax or another similar formulation. DENVax comprises a tetravalent dengue vaccine of predetermined ratio where the vaccine is made up of constructs on an attenuated DEN-2 backbone (see for example, PCT Application Number PCT/US01/05142 filed on Feb. 16, 2001 incorporated herein by reference in its entirety for all purposes). In other compositions, all dengue vaccine virus serotypes are in equal proportions in the composition. In yet other compositions, each dengue vaccine virus serotype may be in a particular ratio to one another such that introduction of the composition induces sufficient levels of neutralizing antibodies which would provide the subject with sufficient protection against infection (e.g. DEN-1, DEN-2, DEN-3 and/or DEN-4). In accordance with these embodiments, samples from a subject may be analyzed for resistance to dengue infection using standard means known in the art in order to assess immunity to dengue virus serotypes.

In other embodiments, a vaccine composition can include attenuated dengue virus serotypes in combination with other anti-pathogenic compositions (e.g. Japanese encephalitis, yellow fever, West Nile, influenza, Chikungunya or other).

BRIEF DESCRIPTION OF THE DRAWINGS

The following drawings form part of the present specification and are included to further demonstrate certain embodiments. Some embodiments may be better understood by reference to one or more of these drawings alone or in combination with the detailed description of specific embodiments presented.

FIG. 1 represents neutralizing antibody titers produced against two different trivalent formulations over time compared to control compositions (e.g. FTA).

DEFINITIONS

As used herein, "a" or "an" may mean one or more than one of an item.

As used herein, vessel can include, but is not limited to, test tube, mini- or micro-fuge tube, channel, vial, microtiter plate or container.

As used herein the specification, "subject" or "subjects" may include but are not limited mammals such as humans or mammals, domesticated or wild, for example dogs, cats, other household pets (e.g., hamster, guinea pig, mouse, rat), ferrets, rabbits, pigs, horses, cattle, prairie dogs, or zoo animals.

As used herein, "about" or "approximately" can mean plus or minus ten percent.

As used herein, "Dengue viruses" or "DENs" or "DENVs" are positive, single-stranded RNA viruses belonging to the *Flavivirus* genus of the flaviviridae family. The genomic RNA contains a type I cap at the 5' end but lacks a poly-A tail at the 3' end. The genomic organization consists of the following elements: 5' noncoding region (NCR), structural proteins (capsid (C), premembrane/membrane (prM/M), envelope (E)) and nonstructural proteins (NS1-NS2A-NS2B-NS3-NS4A-NS4B-NS5), and 3' NCR. The genomic viral RNA is associated with the capsid proteins so as to form a nucleocapsid. As for the other flaviviruses, the DEN viral genome encodes an uninterrupted coding region which is translated into a single polyprotein.

As used herein, "attenuated virus" can mean a virus that demonstrates reduced or no clinical signs of disease when administered to a subject such as a mammal (e.g., human or an animal).

As used herein, "consecutively" can mean in close temporal proximity, usually within a single patient visit and within 24 hours.

As used herein, "administration" can mean delivery of a vaccine or therapy to an individual animal or human by any one of many methods such as intradermal, subcutaneous, intramuscular, intranasal, inhalation, vaginal, intravenous, oral, buccal, by inhalation, intranasally, or any others known in the art.

DESCRIPTION

In the following sections, various exemplary compositions and methods are described in order to detail various embodiments. It will be obvious to one skilled in the art that practicing the various embodiments does not require the employment of all or even some of the details outlined herein, but rather that concentrations, times and other details may be modified through routine experimentation. In some cases, well-known methods or components have not been included in the description.

Certain aspects of the present invention include, but are not limited to, administration of vaccine compositions against dengue virus.

Embodiments of the present invention generally relate to methods and compositions for inducing protective neutralizing antibodies in a subject against three or more dengue virus serotypes. Other embodiments can include introducing a vaccine composition to a subject via any method known in the art including, but not limited to, intradermal, subcutaneous, intramuscular, intranasal, inhalation, orally, intranasally, vaginal, intravenous, ingested, and any other method wherein the vaccine composition so introduced induces neutralizing antibodies against three or more dengue virus serotypes. In certain embodiments, the vaccine composition comprises a dose of a vaccine against three (trivalent) dengue virus serotypes administered to a subject. In other embodiments, the vaccine composition comprises an initial dose against three dengue serotypes then, one or more of the same other vaccine compositions administered to a subject.

Vaccines against dengue virus may include a composition comprising predetermined ratios of three of the four live, attenuated dengue vaccine viruses, recombinant dengue vaccine viruses, chimeric viruses or mutants thereof. The ratios of various dengue serotypes may be equivalent or nearly equal in representation or certain serotypes may be represented at higher concentrations than others depending on need or ability to induce a balanced neutralizing antibody response in the subject. In accordance with these embodiments, ratios of different dengue vaccines may differ by 2 to 100,000 fold (e.g. plaque forming units (pfus)) between any two serotypes. This can depend on, for example, number of serotypes represented in the formulation, predetermined response and desired effect. It is contemplated that any dengue vaccine virus serotype formulation may be used to generate a vaccine (e.g. attenuated virus etc.) of use in consecutive administration to a subject in need thereof where the composition includes, but is not limited to, three or more dengue virus serotypes.

In other embodiments, compositions of dengue virus vaccine formulations may be introduced to a subject prior to, during or after exposure to dengue virus by the subject. In accordance with these embodiments, a subject may receive more than one administration consecutively or more than one administration comprising a dengue virus formulation, optionally, followed by one or more additional administrations at a later time. Intradermal, subcutaneous, intramuscular, intranasal, inhalation, vaginal, intravenous, oral, and any other method of applications of formulations described herein may be combined with any other anti-viral treatment. In some embodiments, it is contemplated that intradermal, subcutaneous, intramuscular introduction of a formulation contemplated herein may be administered to any appropriate region of a subject's body (e.g. arm, shoulder, hip, intranasally etc). In addition, parenteral administration of vaccine formulations may be combined with other modes of administration such as intranasal, pulmonary, oral, buccal, or vaginal in consecutive administrations. In some embodiments, it is contemplated that, after consecutive administrations as described herein primary or booster administrations may occur consecutively on the same day, consecutive days, weekly, monthly, bi-monthly or other appropriate treatment regimen.

Dengue is endemic in Asia, Central and South America including Colombia, the Caribbean, the Pacific Islands, and parts of Africa and Australia. It is estimated that 3.6 billion people (55% of the world's population) live in areas at risk of dengue virus transmission (DVI). Infection with a dengue virus can result in a range of symptoms, from subclinical disease to debilitating but transient dengue fever to life-threatening dengue hemorrhagic fever (DHF) or dengue shock syndrome (DSS). Currently, there is no therapeutic treatment or prophylactic vaccine for dengue fever. Given the impact of dengue on populations in endemic countries and on travelers to those regions, a vaccine to prevent dengue is needed.

Dengue is a mosquito borne viral disease, transmitted from human to human primarily by the mosquito, *Aedes aegypti*. Dengue viruses (DEN) contain a single-stranded, positive-sense RNA genome of approximately 11 kb. The genome consists of three structural proteins, capsid (C), premembrane (prM), and envelope (E), and seven nonstructural proteins, NS1, NS2A, NS2B, NS3, NS4A, NS4B, and NS5. There are four different serotypes of dengue viruses, DEN-1, DEN-2, DEN-3 and DEN-4. Primary infection with a given serotype induces lifelong serotype specific immunity. However, there is no long-term cross-protective immunity against the other three dengue virus serotypes, and subsequent infection with an alternate serotype leads to increased probability of more severe disease, such as DHF or DSS.

Due to the disease enhancement associated with secondary DENV infections, a multivalent (e.g. trivalent) vaccine that stimulates immunity against at least three dengue virus serotypes is contemplated. Several DENV vaccine candidates attenuated by classical serial passage in cell culture have proven unsafe or poorly immunogenic. Chimeric live-attenuated, recombinant DENV vaccines candidates, including viruses based on the attenuated genetic background of yellow fever 17D (YF-17D) vaccine virus, DENV-2 PDK- 53 vaccine virus, or DENV-4 containing a 30-nucleotide 3' non-coding region (NCR) deletion are known in the art.

Live, attenuated dengue viruses of all four serotypes have been developed at Mahidol University in Thailand by passaging the wild-type viruses in cell culture. These are currently the most promising live, attenuated vaccine candidates for immunization against dengue virus infection and/or disease. These vaccine candidates have been designated by a combination of their dengue serotype, the cell line through which they were passaged and the number of times they were passaged.

Preliminary human clinical trials with these attenuated viruses have indicated that DEN-2 PDK-53 has the lowest infectious dose (50% minimal infectious dose of 5 plaque forming units or PFU) in humans, is strongly immunogenic, and produces no unacceptable clinical symptoms. The DEN-1 PDK-13, DEN-3 PGMK-30/FRhL-3 and DEN-4 PDK-48 vaccine virus candidates have higher 50% minimal infectious doses of 10,000, 3500, and 150 PFU, respectively, in humans.

The DEN-2 PDK-53 virus vaccine candidate, henceforth abbreviated PDK-53, has several measurable biological markers associated with attenuation, including temperature sensitivity, small plaque size, decreased replication in mosquito C6136 cell culture, decreased replication in intact mosquitoes, loss of neurovirulence for suckling mice and decreased incidence of viremia in monkeys. Clinical trials of the candidate PDK-53 vaccine have demonstrated its safety and immunogenicity in humans. Furthermore, the PDK-53 vaccine induces dengue virus-specific T-cell memory responses in human vaccine recipients. In certain embodiments herein, a chimeric dengue virus construct can include a dengue-2 backbone where PDK-53 has been selected to differ from the known PDK-53 backbone and contain additional mutations that further attenuate the virus.

Accordingly, there is a need for avirulent, yet immunogenic, dengue viruses to be used in the development of dengue virus vaccines to confer protection against all dengue virus serotypes.

A challenging issue in the development of an effective live-attenuated dengue virus (DENV) vaccine is the interference between the four dengue vaccine viruses when administered as a tetravalent formulation. Interference is manifest when one or more components of a multivalent mixture will induce lower immune responses than those elicited by each individual monovalent vaccine. Interference has been observed with vaccines for diseases with multiple pathogenic serotypes, such as polio, dengue or others. Due in part to this interference, it was previously discovered that three dose regimen of oral polio vaccine is required to induce adequate immune responses to the three key serotypes. Historically studies with live attenuated tetravalent dengue vaccines have shown that the DENV serotype that elicits the strongest neutralizing antibody response when administered alone tends to dominate immune responses when administered in the context of a multivalent formulation containing other serotypes. As an example, tetravalent mixtures of four different live, attenuated dengue vaccines showed dominant responses to the DEN-3 component and reduced immune responses to DEN-1, -2 and -4 (see for example, Sabchareon, et al., 2002, Kitchener, et al. 2006). As a result of this dominance, clinical development of the tetravalent mixtures was suspended. Interference has been seen with recombinant, live attenuated viruses as well. Interference was documented in tetravalent mixtures of dengue/yellow fever chimeras (Guy, et al. 2009. Evaluation of Interferences between Dengue Vaccine Serotypes in a Monkey Model. Am. J. Trop Med. Hyg. 80: 3012-311). In these studies, two serotypes were found to dominate the responses in tetravalent formulations of ChimeriVax vaccine strains. Interference could be overcome by administering two bivalent vaccine formulations, either in separate anatomical locations or sequentially in time, or by a third administration of the tetravalent formulation after one year. Similarly, it was demonstrated that improved multivalent responses with tetravalent recombinant vaccine strains (in this case, formulations containing DENV or chimeric DENV with deletions in the 3' non-coding region) could be obtained only with a prolonged four month internal between the first and second administration. (Blaney, et al., 2005. Recombinant, Live-Attenuated Tetravalent Dengue Virus Vaccine Formulations Induce a Balanced, Broad, and Protective Neutralizing Antibody Response against Each of the Four Serotypes in Rhesus Monkeys. J. Virology 79: 5516-5528).

Certain embodiments disclosed herein concern derivatives of DENVax (a tetravalent vaccine composition). DENVax is a dengue vaccine that consists of a mixture of four recombinant dengue virus strains designed to generate immune responses to the four dengue serotypes (DEN-1, DEN-2, DEN-3 and DEN-4). Not to be bound by any limitations to a particular tetravalent formulation, DENVax™, the dengue serotype 2 vaccine component (DENVax-2) corresponds to an attenuated DEN-2 PDK-53 strain. This construct has already been investigated in many clinical studies. The other dengue vaccine strains (DENVax-1, DENVax-3 and DENVax-4) are chimeras consisting of the DEN-1, DEN-3 or DEN-4 structural pre-membrane (prM) and envelope (E) protein genes cloned into a DEN-2 PDK-53 non-structural gene backbone. These recombinant viruses express the surface antigens of DEN-1, DEN-3 or DEN-4 and retain the genetic alterations responsible for the attenuation of the DEN-2 PDK-53 strain. In certain embodiments, DENVax can be used as an example of a trivalent live, attenuated dengue vaccine having three of four dengue virus serotypes represented in one vaccine composition at various ratios. Other embodiments relate to optimizing tetravalent vaccine administrations. Yet other embodiments relate to DENVax™ immunization methods.

In some embodiments, a mixture of three or more attenuated dengue viruses comprises one or more attenuated dengue-2 viruses and one or more dengue-dengue chimeric viruses further comprising capsid and non-structural proteins of the attenuated dengue-2 virus and pre-membrane and envelope proteins of at least a second dengue virus.

In certain embodiments, a chimeric construct of the instant application can include the pre-membrane (PM) and envelope (E) proteins of at least a second dengue virus are dengue-2, dengue-3 or dengue-4 when the attenuated dengue virus is dengue-1; or dengue-1, dengue-3 or dengue-4 when the attenuated dengue virus is dengue-2; or dengue-1, dengue-2 or dengue-4 when the attenuated dengue virus is dengue-3; or dengue-1, dengue-2 or dengue-3 when the attenuated dengue virus is dengue-4.

In other embodiments, the composition introduced to the subject comprises vaccines against three of dengue virus serotypes (DEN-1, DEN-2, DEN-3, and DEN-4). In other embodiments, a composition contemplated herein can include a modified formula of DENVax where three of four dengue virus serotypes are represented or other similar formulation. In some compositions, vaccine viruses against all dengue serotypes are in equal proportions in the composition. In yet other compositions, each dengue vaccine virus serotype may be in a particular ratio to one another such that introduction of the composition provides the subject with sufficient levels of neutralizing antibodies against all dengue viruses (e.g. DEN-1, DEN-2, DEN-3, DEN-4).

Certain embodiments disclosed herein relate to methods and compositions for a rapid induction of protection in a subject against all dengue virus serotypes by, for example, administering a vaccine to a subject against three of four dengue virus serotypes in more than one anatomical location consecutively on the same day. Some embodiments can include introducing a vaccine composition to a subject via intradermal (ID) or subcutaneous (SC) injection or other administration mode in one anatomical location then introducing at least a second vaccine composition at another anatomical location by ID, SC or other administration mode. Some embodiments include using any combination of modes of administration for introducing a dengue virus vaccine of all dengue virus serotypes using a trivalent formulation to a subject where administration of the vaccine occurs at two or more anatomical sites or by two or more different routes on day 0 to the subject. Some embodiments include using the same mode of administration but at different anatomical locations.

Some dengue virus vaccine compositions described herein range in dosage from $10^2$ to $5\times10^6$ PFU for each serotype in a single trivalent composition. Other compositions (e.g. follow-on vaccinations) contemplated herein include compositions that have dosages less than or more than this range based on immune response in the subject after primary immunization. In certain embodiments, ratios can vary for the various Dengue vaccine virus serotypes depending on need and immune response in a subject.

In certain embodiments, compositions introduced on the first vaccination or in any follow-on vaccination contemplated herein may include one trivalent dengue virus composition. In accordance with these embodiments, the composition can include three of four dengue virus serotypes of a DENVax composition or other similar trivalent formulation of equal or equivalent ratios or at predetermined serotype ratios. Other embodiments, can include using different formulations (e.g. serotype ratios) for each of the vaccine compositions administered at the primary vaccination or any follow-on vaccinations (e.g. less than 30 days later).

Some embodiments herein include treating a subject in need of such a vaccine, on day 0 at two or more anatomical locations then administering at least a second vaccine within 30 days such as about 7, about 14, about 21 or about 28 days later with a composition comprising dengue virus serotypes which may or may not have all serotypes. In certain embodiments, each vaccination has all dengue virus serotypes represented in the vaccine formulation. Vaccine compositions of follow-on administration disclosed herein may include two or more dengue virus serotypes at a predetermined ratio for the subsequent administration(s).

In certain vaccine compositions, the ratio of three of four of DEN-1:DEN-2:DEN-3:DEN-4 or even DEN-5 can be 3:3:3, 4:3:4, 5:4:5,:4:5:5, 5:5:5, 1:10:100 or other ratio where the ratio between 2 serotypes can be about 2 to about 100,000 fold difference in a single composition. In certain embodiments a dengue serotype ratio can be DEN-1 at $2\times10^4$: DEN-2 at $5\times10^4$: DEN-3 at $1\times10^5$: DEN-4 at $3\times10^5$ PFUs; DEN-1 at $8\times10^3$: DEN-2 at $5\times10^3$: DEN-3 at $1\times10^4$: DEN-4 at $2\times10^5$ PFUs and in any combination of three of the four dengue virus serotypes. In certain embodiments, a trivalent formulation can contain a ratio that includes a higher ratio for dengue-4 than for other serotypes. In some compositions, all dengue vaccine virus serotypes are in equal proportions in the composition. In yet other compositions, each dengue vaccine virus serotype may be in a particular ratio to another serotype such that introduction of the composition provides the subject with adequate or more than adequate levels of neutralizing antibodies which confer protection against all dengue viruses (e.g. any combination of three of the four of Dengue 1, 2, 3 and 4). For example, if after receiving two or more consecutive vaccinations on day 0 at two or more anatomical locations, the subject has lower protection to one or more particular dengue virus serotypes, then a booster for that subject can contain an increased concentration of the one or more dengue vaccine virus serotype (that demonstrated lower neutralizing antibodies) to provide better protection against all dengue virus types. In accordance with these embodiments, samples from a subject may be analyzed for an immune response to dengue serotype infection (e.g. DEN-1, -2, -3, -4) using standard means known in the art.

In certain embodiments, the vaccine composition can be simultaneously or consecutively introduced to a subject intradermally in multiple anatomical locations to, for example, protect against all dengue serotypes (e.g. cross protection). In certain embodiments, a vaccine composition can include, but is not limited to, a single formulation of three of four dengue vaccine virus serotypes administered to a subject capable of providing full protection against infection by all dengue virus serotypes. In other embodiments, a vaccine composition can include attenuated dengue virus serotypes in combination with other anti-pathogenic compositions (e.g. Japanese encephalitis, West Nile, influenza etc.). Compositions contemplated herein can be administered by any method known in the art including, but not limited to, intradermal, subcutaneous, intramuscular, intranasal, inhalation, vaginal, intravenous, ingested, and any other method. Introduction in two or more anatomical sites can include any combination administration including by the same mode in two or more anatomical sites or by two different modes that include two separate anatomical sites. In accordance with these embodiments, two or more anatomical sites can include different limbs.

For example, if a subject, after receiving two or more consecutive vaccinations on day 0 at two or more anatomical locations and the subject does not induce poor levels of neutralizing antibodies to one or more particular dengue virus serotypes, then a booster vaccination for that subject can contain an increased concentration of the one or more dengue vaccine virus serotype (that demonstrated lower levels of neutralizing antibodies) to provide complete protection against infection by all dengue virus types. In accordance with these embodiments, samples from a subject may be analyzed for resistance to dengue infection using standard means known in the art.

In certain embodiments, vaccine compositions disclosed herein can be chimeric constructs that can include a mixture of constructs that make up three dengue serotypes in a vaccine composition for administration to a subject. In other embodiments, dengue virus vaccines can include constructs having an attenuated flavivirus backbone with various dengue serotype substitutions representing each of the four serotypes where the constructs can be mixed in a composition for administration as a vaccine.

Trivalent formulations, e.g. using a variation of DENVax, can be prepared by mixing predetermined amounts of each monovalent vaccine component. Based on input titer of each vaccine component, a defined volume of monovalent vaccines can be added to a final volume of either 0.1 mL (e.g. for intradermal) or 0.5 mL (e.g. for subcutaneous) vaccine formulation. The remaining volume of the tetravalent DEN- Vax™ vaccine can be composed of diluent containing Trehalose (15%) F127 (1%) and human serum albumin (0.1%) in a saline buffer to stabilize the live, attenuated vaccine formulation. FTA (F127: Trehalose: Albumin)

Methods

Construction of Flavivirus Chimeras

The flavivirus chimeras described herein can be produced by splicing one or more of the structural protein genes of the flavivirus against which immunity is desired into a PDK-53 dengue virus genome backbone, or the equivalent thereof as described above, using recombinant engineering techniques well known to those skilled in the art to remove the corresponding PDK-53 gene and replace it with the desired gene.

Alternatively, using the sequences, nucleic acid molecules encoding the flavivirus proteins may be synthesized using known nucleic acid synthesis techniques and inserted into an appropriate vector. Avirulent, immunogenic virus is therefore produced using recombinant engineering techniques known to those skilled in the art.

As recited above, a target gene to be inserted into the backbone encodes a flavivirus structural protein. In accordance with these embodiments, a flavivirus gene to be inserted is a gene encoding a C protein, a PrM protein and/or an E protein. The sequence inserted into the dengue-2 backbone can encode both the PrM and E structural proteins. The sequence inserted into the dengue-2 backbone can encode the C, prM and E structural proteins. The dengue virus backbone is the PDK-53 dengue-2 virus genome and includes either the spliced genes that encode the C, PrM and/or E structural proteins of dengue-1 (DEN-2/1), the spliced genes that encode the PrM and/or E structural proteins of dengue-3 (DEN-2/3), or the spliced genes encode the PrM and/or E structural proteins of dengue-4 (DEN-2/4). In a particular embodiment of this invention, the spliced gene that encodes the structural protein of dengue-3 virus directs the synthesis of an E protein that contains a leucine at amino acid position 345.

In a particular embodiment, the chimera of this invention encodes the C structural protein of dengue-2 virus and directs the synthesis of a C protein that contains a serine at amino acid position 100 and comprises a spliced gene encoding the structural proteins of dengue-4 which directs the synthesis of an E protein that contains a leucine at amino acid position 447.

In a further embodiment, the chimera of this invention encodes the C structural protein of dengue-2 virus and directs the synthesis of a C protein that contains a serine at amino acid position 100 and comprises a spliced gene encoding the structural proteins of dengue-4 which directs the synthesis of an E protein that contains a leucine at amino acid position 447 and a valine at amino acid position 364. The structural proteins described herein can be present as the only flavivirus structural protein or in any combination of flavivirus structural proteins in a viral chimera of this invention.

Certain chimeras contemplated herein are engineered by recombination of full genome-length cDNA clones derived from both DEN-2 16681 wild type virus and either of the PDK-53 dengue-2 virus variants (-E or -V(SEQ ID NO: 15)). The uncloned PDK-53 vaccine contains a mixture of two genotypic variants, designated herein as PDK-53-E and PDK-53-V. The PDK-53-V variant contains all nine PDK-53 vaccine-specific nucleotide mutations, including the Glu-to-Val mutation at amino acid position NS3-250. The PDK-53-E variant contains eight of the nine mutations of the PDK-53 vaccine and the NS3-250-Glu of the parental 16681 virus. Infectious cDNA clones are constructed for both variants, and viruses derived from both clones are attenuated in mice. The phenotypic markers of attenuation of DEN-2 PDK-53 virus include small plaque size, temperature sensitivity (particularly in LLC-MK.sub.2 cells), limited replication (particularly in C6/36 cells), attenuation for newborn mice (specifically loss of neurovirulence for suckling mice) and decreased incidence of viremia in monkeys. The chimeras that are useful as vaccine candidates are constructed in the genetic backgrounds of the two DEN-2 PDK-53 variants which all contain mutations in nonstructural regions of the genome, including 5'NC-57 C-to-T (16681-to-PDK-53) in the 5' noncoding region, as well as mutations in the amino acid sequence of the nonstructural proteins, such as, for example, NS1-53 Gly-to-Asp and NS3-250 Glu-to-Val.

In certain embodiments, an immunogenic composition that includes chimeric dengue constructs of the present invention can be a combination of three or more of DEN-1, DEN-2, DEN-3 or DEN-4 to confer simultaneous protection against all four dengue virus serotypes in a single vaccine administration. In other embodiments, an immunogenic composition including combinations of three DEN-1, DEN-2, DEN-3 and DENV-4 constructs of embodiments disclosed herein can be administered to a subject to induce improved immunogenic responses against each dengue virus serotype and where immune response interference to the dengue virus constructs is reduced.

In certain embodiments, dengue virus constructs can include a dengue-dengue chimeric construct having adaptive mutations in the structural or non-structural regions of the various dengue virus serotypes. In other embodiments, a chimeric construct can include a DEN-2 backbone where structural or non-structural regions of DENV-1, -3, -4 are substituted for DEN-2 structural or non-structural regions. In accordance with these embodiments, a DEN-2 backbone can include any live attenuated DEN-2 virus. In other embodiments, a DEN-2 backbone can include live attenuated DEN-2 PDK-53 virus as a backbone where the live attenuated DEN-2 PDK virus further includes structural proteins of one or more of prM (premembrane) and E (envelope) structural proteins of DEN-1, DEN-3 or DEN-4. In addition, a DEN-2 PDK-53 backbone can include additional mutations or reversions of mutations of DEN-2 PDK-53 generating a novel construct in order to enhance in vitro growth, or in vivo the immune response to DEN-1, DEN-3 or DEN-4 in a subject upon administration.

In some embodiments, a current dengue chimeric construct denoted as DENVax-4 strain was modified to contain a capsid/PrM junction of the DEN-2 backbone to be more genetically similar to that of DENV-4 instead of DEN-2 in order to improve replication efficiency of the virus both in vitro for production and in vivo as a construct of use for inducing an immune response to DENV-4. The current strain of DEN-4, DENVax-4, has a capsid/PrM sequence that is identical to DEN-2 instead of DEN-4, possibly creating an inefficient transcription and translation from the genomic RNA, which is different than that of wild type DENV-4. It is contemplated that these DENV-4 constructs can be used in any trivalent composition contemplated herein, in combination with DEN-1, DEN-2 and DEN-3 as live, attenuated and/or chimeric dengue-dengue constructs.

In some embodiments, structural protein genes can include prM and E genes of DENV-4 on another dengue virus backbone (e.g. dengue-2, DEN-2 PDK-53), making a dengue-dengue chimera. For example, a DEN-4 construct, in certain embodiments can include those construct termed DENVax-4e (Capsid 107 Cysteine to Tyrosine; DenVax-4b backbone, modifications at Capsid/prM junction), DENVax-4f (where the PDK-53 backbone NS2A and NS4A mutations are reverted to that of 16681) or DENVax-4h (Envelope 417 Glu to Lys) where for certain constructs the DEN-2 PDK-53 backbone has one or more reversions to wild-type DEN-2 (e.g. in the non-coding region (NCR) or a non-structural region (NS2 etc.)) and one or more mutations in the DENV-4 structural region (e.g. prM or E), while encoding one or more structural proteins of DENV-4 (e.g. strain 1036). A modified DENV-4 construct disclosed herein can include a modified attenuated DEN-2 PDK-53 backbone, having one or more modified structural proteins of DENV-4 strain 1036. In some embodiments, one or more mutations present in live, attenuated DEN-2 PDK-53 virus can be reverted back to a wildtype nucleic acid (which may be a silent mutation) or another nucleic acid to produce constructs herein that generate a modified DEN-2/DENV-4 construct having increased replication ability and immunogenicity without affecting its attenuation or safety but may affect growth and/or replication of the DEN-4 virus. In certain embodiment, the reversions may lead to increased growth and/or replication.

In other embodiments, trivalent compositions disclosed herein can include a modified DENV-4 (or DENV-1 or DENV-3) construct can incorporate mutations introduced to one or more structural regions and/or non-structural regions of the dengue serotype in order to generate constructs inducing an improved immunological response while maintaining safety and viral attenuation. For example, a modified or mutated dengue-dengue chimera of DEN-2/DENV-4 may contain mutations at one or more non-structural regions of a DEN-2 PDK-53 backbone, such as NS2A, and NS4A, and/or mutations at 5' non-coding region (5'NCR). In another embodiment, a modified DENV-4 chimera construct can include NS2A and NS4A of DEN-2 16681 by reverting mutations at NS2A and NS4A of PDK-53 (e.g. an M-L substitution at NS4A). Some embodiments include a modified DENV-4 chimera construct having 5'NCR, NS2A and NS4A of DEN-2 16681 by reverting corresponding mutations in the DEN-2 PDK-53 backbone of a target construct. Other embodiments can include a modified DENV-4 chimera construct having 5'NCR of DEN-2 16681 by reverting corresponding mutations in the DEN-2 PDK-53 backbone. A modified DEN-4 chimera construct can also include DEN-2 PDK-53 backbone, and encode one or more structural proteins of DEN-4 strain H241. It is contemplated that, to induce an immune response, any DEN-4 structural protein can be substituted for structural regions of a chimeric virus containing a dengue -2 serotype backbone (e.g. PDK-53 or modified PDK-53). In some embodiments, a modified DEN-4 construct contains live attenuated DEN-2 PDK-53 as a backbone, and DEN-4, DEN-2 or DEN-3 structural proteins where mutations can be introduced to modify structural regions of a DEN-4 (e.g. strain 1036) or DEN-1 or DEN-3 strain.

In other embodiments, trivalent compositions can include constructs with mutations introduced to capsid/prM junction amino acid sequences of a DENV virus in order to increase immunogenicity of a construct containing such a mutation. For example, a mutation in DEN-4 can be a Cys-Tyr mutation at capsid position 107 of the DEN-4. In other embodiments, it is contemplated that the cysteine in position 107 can be mutated to any other aromatic amino acid with a hydrophobic side chain (see for example DEN-4e). Other DEN-2 PDK-53 reversion of a chimeric construct can be found in NS2A or NS4A. Yet other embodiments include a DEN-4 construct where a DEN-2 backbone comprises PDK-53 (MVS, SEQ ID NO:21) where amino acid positions 102-107 of the capsid region of PDK-53 are converted to a homologous DEN-4 counterpart amino acid to generate DENV-4b. These backbone constructs can then further comprise a cysteine in the capsid region to aromatic amino acid in position (e.g. tyrosine, tryptophan etc). In certain embodiments, this construct is represented by SEQ ID NO:22 or SEQ ID NO:23.

Other DENV-4 constructs of use in trivalent compositions disclosed herein can include a virus construct with an amino acid substitution at Envelope position 417. For example, DEN-4 strain 1036 strain sequence or equivalent strain position thereof where a PDK-53 (MVS DEN2/4, SEQ ID NO:21) backbone of Dengue-2 with DEN-4 structural proteins is provided. Embodiments include further mutating Envelope position 417 from a negative to a positively charged side-chain amino acid (e.g. lysine). It is contemplated that any charged side chain will provide increased immunogenicity of the DEN-4 construct without affecting its safety or attenuation. In certain embodiments, this construct is represented by SEQ ID NO:24 or SEQ ID NO:25.

In certain embodiments, DEN-2 PDK-53 reversions of a chimeric DENV construct have the 5' NC, NS1 and NS3 mutations found in DEN-2 PDK-53 MVS while having other reversions or mutations that differ from DEN-2 PDK-53. It has been demonstrated that these three mutations can be important for attenuation (e.g. small plaque size, reduced growth rate, lower titer, increased temperature sensitivity and decreased neurovirulence compared to a control).

In other embodiments, DEN-2 PDK-53 genome backbones can be used to generate chimeric constructs of DEN-1 and DEN-3, where one or more structural protein genes of DEN-2 PDK-53 genome can be replaced by one or more structural protein genes of DEN-1 and DEN-3. These constructs can include a combination of both DEN-1 and DEN-3 in a single chimera having a DEN-2 PDK-53 backbone. In some embodiments, a structural protein can be the C, prM or E protein of DEN-1 and/or DEN-3. In certain embodiments, structural protein genes include the prM and E genes of DEN-1 or DEN-3. These hybrid/chimeric viruses express the surface antigens of DEN-1, DEN-3 or DENV-4 while retaining the attenuation phenotypes of the parent DEN-2. In certain embodiments, these constructs can be represented by SEQ ID NO:15, DEN-2/DEN-1 and SEQ ID NO: 19, DEN-2/DEN-3 where these constructs can be used in di-, tri or tetravalent compositions disclosed herein.

In some embodiment, constructs disclosed herein can include chimeric constructs of DENV-4, DEN-2, DEN-1, and DEN-3 expressing surface antigens of DEN-1, DEN-3 and DENV-4 using attenuated DEN-2 PDK-53 virus as a backbone.

Suitable chimeric viruses or nucleic acid chimeras containing nucleotide sequences encoding structural proteins of other flaviviruses or dengue virus serotypes can be evaluated for usefulness as vaccines by screening them for the phenotypic markers of attenuation that indicate avirulence and by screening them for immunogenicity. Antigenicity and immunogenicity can be evaluated using in vitro or in vivo reactivity with flavivirus antibodies or immunoreactive serum using routine screening procedures known to those skilled in the art.

Flavivirus Vaccines

Chimeric viruses and nucleic acid chimeras provide live, attenuated viruses useful as immunogens or vaccines. In a preferred embodiment, chimeras exhibit high immunogenicity while at the same time producing no dangerous pathogenic or lethal effects. Chimeric viruses or nucleic acid chimeras of this invention can comprise the structural genes of either wild-type or attenuated virus in a virulent or an attenuated DEN-2 virus backbone. For example, the chimera may express the structural protein genes of wild-type DEN-1 16007 virus or its candidate PDK-13 vaccine derivative in either of the DEN-2 PDK-53 backgrounds.

All of the chimeric DEN-2/1 viruses containing the C, prM and B proteins of either DEN-1 16007 virus (DEN-2/1-EP and -VP chimeras) or PDK-13 virus (DEN-2/1-EV and -VV (SEQ ID NO:7) chimeras) in the backbones of DEN-2 PDK-53 retain all of the phenotypic attenuation markers of the DEN-2 PDK-53 virus. The chimeric DEN-2/1-EP and -VP(SEQ ID NO:5) viruses, which contain the C, prM and E proteins of DEN-1 16007 virus are more genetically stable after passing in cell culture than the DEN-2/1-EV and -VV viruses. The immunogenicity of the chimeric viruses expressing the structural proteins of DEN-1 16007 virus was higher as compared with the neutralizing antibody titers elicited by the PDK-13 vaccine virus and the chimeras expressing the structural proteins of the PDK-13 virus. Thus, the chimeric DEN-2/1-EP and -VP viruses, which express the structural genes of wild-type DEN-1 16007 virus within the genetic background of the two DEN-2 PDK-53 variants, are potential DEN-1 vaccine candidates that are superior to the candidate PDK-13 vaccine. These two chimeras replicate well in LLC-MK.sub.2 cells and retain the attenuation markers associated with DEN-2 PDK-53 virus, including small plaque size, temperature sensitivity, restricted replication in mosquito cells and attenuation for mice. They are at least as immunogenic as wild-type DEN-1 16007 virus in mice.

Other examples, such as DEN-2/3 and DEN-2/4 chimeras, are chimeric viruses containing structural protein genes from wild-type DEN-3 or DEN-4 virus within the DEN-2 PDK-53 backbones, are suitable vaccine candidates which retain all of the attenuated phenotypic markers of the DEN-2 PDK-53 viruses, while providing immunogenicity against DEN-3 or DEN-4 virus. The strategy described herein of using a genetic background that contains the determinants of attenuation in nonstructural regions of the genome to express the structural protein genes of heterologous viruses has lead to development of live, attenuated flavivirus vaccine candidates that express wild-type structural protein genes of optimal immunogenicity. Thus, vaccine candidates for immunogenic variants of multiple flaviviral pathogens can be designed.

Viruses used in the chimeras described herein are typically grown using techniques known in the art. Virus plaque titrations are then performed and plaques counted in order to assess the viability and phenotypic characteristics of the growing cultures. Wild type viruses are passaged through cultured cell lines to derive attenuated candidate starting materials.

Chimeric infectious clones are constructed from the various dengue serotype clones available. The cloning of virus-specific cDNA fragments can also be accomplished, if desired. The cDNA fragments containing the structural protein or nonstructural protein genes are amplified by reverse transcriptase-polymerase chain reaction (RT-PCR) from dengue virus RNA with various primers. Amplified fragments are cloned into the cleavage sites of other intermediate clones. Intermediate, chimeric dengue virus clones are then sequenced to verify the accuracy of the inserted dengue virus-specific cDNA.

Full genome-length chimeric plasmids constructed by inserting the structural protein or nonstructural protein gene region of dengue serotype viruses into vectors are obtainable sing recombinant techniques well known to those skilled in the art.

Nucleotide and Amino Acid Analysis

A comparison of the critical nucleotide and amino acid substitutions that have been discovered between the parent strain and the attenuated virus are incorporated herein by reference. The sequence of the DEN-2 cDNA amplicons was amplified from DEN-2 viral genomic RNA by reverse transcriptase-polymerase chain reaction (RT-PCR).

Unlike PDK-53, which contains no amino acid mutations in the E protein relative to wild type dengue-2 virus, DEN-1, DEN-3 and DEN-4 attenuated viruses all have amino acid mutations in the E protein. The wild-type DEN-3 16562 was shown to include traces of a variant comprising a T at nucleotide position 1521 which directs incorporation of a leucine at polyprotein position 476, amino acid residue position 476 of the E protein.

Each of the latter three viruses possesses a Glu-to-Lys (parent-to-vaccine) mutation in the E protein, although the mutation is located at a different amino acid residue in the E protein. This substitution causes a shift from a negatively charged amino acid to a positively charged one. The Glu-to-Lys substitution in the E protein of DEN-4 vaccine virus was the only mutation present in the E protein, while the E proteins of DEN-1 and DEN-3 vaccine viruses had five and three amino acid mutations, respectively.

The NS1-53 mutation in the DEN-2 PDK-53 vaccine virus is significant for the attenuated phenotype of this virus, because the NS1-53-Gly of the DEN-2 16681 virus is conserved in nearly all flaviviruses, including the tick-borne viruses, sequenced to date. The mutations that occurred in the NS2A, NS2B, NS4A, and NS4B proteins of the DEN-1, -2, -3 and -4 attenuated strains were all conservative in nature. The NS4A-75 and NS4A-95 mutations of DEN-2 and DEN-4 vaccine viruses, respectively, occurred at sites of amino acid conservation among dengue viruses, but not among flaviviruses in general.

The flaviviral NS3 protein possesses at least two recognized functions: the viral proteinase and RNA helicase/NTPase. The 698-aa long (DEN-2 virus) NS3 protein contains an amino-terminal serine protease domain (NS3-51-His, -75-Asp, -135-Ser catalytic triad) that is followed by sequence motifs for RNA helicase/NTPase functions NS3-196-GAGKT, -284-DEAH, -459-GRIGR. None of the mutations in the NS3 proteins of DEN-1, DEN-2, or DEN-3 virus occurred within a recognized motif The NS3-510 Tyr-to-Phe mutation in DEN-1 PDK-13 virus was conservative. Since the wild-type DEN-2, -3 and -4 viruses contain Phe at this position, it is unlikely that the Tyr-to-Phe mutation plays a role in the attenuation of DEN-1 virus. The NS3-182 Glu-to-Lys mutation in DEN-1 PDK-13 virus occurred at a position that is conserved as Asp or Glu in most mosquito-borne flaviviruses and it may play some role in attenuation. This mutation was located 15 amino acid residues upstream of the GAGKT (helicase motif As noted in previous reports, the NS3-250-Glu in DEN-2 16681 virus is conserved in all mosquito-borne flaviviruses except for yellow fever virus.

Nucleic Acid Amplification

Nucleic acids may be used in any formulation or used to generate any formulation contemplated herein. Nucleic acid sequences used as a template for amplification can be isolated viruses (e.g. dengue viruses), according to standard methodologies. A nucleic acid sequence may be genomic DNA or fractionated or whole cell RNA. Where RNA is used, it may be desired to convert the RNA to a complementary cDNA. In some embodiments, the RNA is whole cell RNA and is used directly as the template for amplification. Any method known in the art for amplifying nucleic acid molecules is contemplated (e.g., PCR, LCR, Qbeta Replicase, etc).

Expressed Proteins or Peptides

Genes can be expressed in any number of different recombinant DNA expression systems to generate large amounts of the polypeptide product, which can then be purified and used in methods and compositions reported herein. Any method known in the art for generating and using constructs is contemplated. In certain embodiments, genes or gene fragments encoding one or more polypeptide may be inserted into an expression vector by standard cloning or subcloning techniques known in the art.

Proteins, peptides and/or antibodies or fragments thereof may be detected or analyzed by any means known in the art. In certain embodiments, methods for separating and analyzing molecules may be used such as gel electrophoresis or column chromatography methods.

Electrophoresis

Electrophoresis may be used to separate molecules (e.g., large molecules such as proteins or nucleic acids) based on their size and electrical charge. There are many variations of electrophoresis known in the art. A solution through which the molecules move may be free, usually in capillary tubes or it may be embedded in a matrix or other material known in the art. Common matrices can include, but are not limited to, polyacrylamide gels, agarose gels, mass spec, blotting and filter paper.

Some embodiments, using a gene or gene fragment encoding a polypeptide may be inserted into an expression vector by standard subcloning techniques. An expression vector may be used which produces the recombinant polypeptide as a fusion protein, allowing rapid affinity purification of a peptide or protein. Examples of such fusion protein expression systems are the glutathione S-transferase system (Pharmacia, Piscataway, N.J.), the maltose binding protein system (NEB, Beverley, Mass.), the FLAG system (IBI, New Haven, Conn.), and the 6×His system (Qiagen, Chatsworth, Calif.). Pharmaceutical Formulations Any pharmaceutical formulation known in the art for a vaccine is contemplated herein. In certain embodiments, a formulation disclosed herein contains chimeric or live, attenuated virus that represent three dengue virus serotypes in various ratios in a single vaccine or one to all serotypes for follow-on compositions. It is contemplated that formulations can contain other agents of use in vaccination of a subject including, but not limited to other active or inactive ingredients or compositions known to one skilled in the art.

All contemplated vaccinal viruses herein can be administered in the form of vaccinal compositions which can be prepared by any method known to one skilled in the art. In certain embodiments, the virus compositions are lyophilized and are mixed with a pharmaceutically acceptable excipient (e.g. water, phosphate buffered saline (PBS), wetting agents etc.) In other embodiments, vaccine compositions can include stabilizers that are known to reduce degradation of the formulation and prolong shelf-life of the compositions.

In other embodiments, an adjuvant may be added to the composition to induce, increase, stimulate or strengthen a cellular or humoral immune response to administration of a vaccination described herein. Any adjuvant known in the art that is compatible with compositions disclosed herein is contemplated.

Some embodiments herein concern amounts or doses or volumes of administration of a trivalent dengue virus composition and the amount or dose can depend on route of administration and other specifications such as the subject getting the vaccine (e.g. age, health condition, weight etc.).

It is contemplated herein that compositions described can be administered to a subject living in an area having dengue virus, a subject traveling to an area having dengue virus or other subject such as any human or animal capable of getting dengue fever or other dengue virus condition. In certain embodiments, it may be recommended that a subject traveling to an area having dengue virus is administered one or more vaccine compositions (e.g. or two or more on Day 0) about 1 to about 3 months prior to dengue virus exposure. Vaccines herein can be administered as a prophylactic treatment to prevent infection in adults and children. A subject can be naïve or non-naïve subject with respect to exposure to dengue virus and vaccine regimens disclosed herein.

Kits

Other embodiments concern kits of use with the methods (e.g. methods of application or administration of a vaccine) and compositions described herein. Some embodiments concern kits having vaccine trivalent compositions of use to prevent or reduce the incidence of a subject having been exposed or suspected of being exposed to one or more dengue viruses to get an infection from the virus. In certain embodiments, a kit may contain one or more than one formulation of dengue virus serotype(s) (e.g. live, attenuated viruses or chimeric constructs to make a trivalent formulation, DENVax) at predetermined ratios of the dengue virus serotypes. Kits can be portable, for example, able to be transported and used in remote areas such as military installations or remote villages in dengue endemic areas. Other kits may be of use in a health facility to treat a subject having been exposed to one or more dengue viruses or suspected of being at risk of exposure to dengue virus.

Kits can also include a suitable container, for example, a vessel, vials, tubes, mini- or microfuge tubes, test tube, flask, bottle, syringe or other container. Where an additional component or agent is provided, the kit can contain one or more additional containers into which this agent or component may be placed. Kits herein will also typically include a means for containing the agent (e.g. a vessel), composition and any other reagent containers in close confinement for commercial sale. Such containers may include injection or blow-molded plastic containers into which the desired vials are retained. Optionally, one or more additional agents such as immunogenic agents or other anti-viral agents, anti-fungal or anti-bacterial agents may be needed for compositions described, for example, for compositions of use as a vaccine against one or more additional microorganisms.

In other embodiments, kits can include devices for administering one or more vaccination to a subject such as an ID, SQ, IM, an inhaler, intranasal applicator or other device for administering a vaccine composition disclosed herein.

The following examples are included to demonstrate certain embodiments presented herein. It should be appreciated by those of skill in the art that the techniques disclosed in the examples that follow represent techniques discovered to function well in the practices disclosed herein. However, those of skill in the art should, in light of the present disclosure, appreciate that many changes can be made in the certain embodiments which are disclosed and still obtain a like or similar result without departing from the spirit and scope herein.

EXAMPLES

Example 1

In one exemplary method, dengue virus trivalent vaccine compositions studies were performed using various trivalent dengue virus formulations alone, in multiple doses or in combination with follow-on monovalent dengue virus formulations. In certain exemplary methods, the following concentrations of dengue virus serotypes were used: DENVax-1: $1\times10^5$PFU, DENVax-2; $1\times10^5$PFU, DENVax3: $1\times10^5$PFU, and DENVax4: $1\times10^5$PFU. See for example Table 1 and 2. In certain embodiments various dengue-4 serotypes can be combined with live, attenuated dengue-2 and a chimeric construct of dengue-1 in order to induce immunity in the subject against all four serotypes.

Animals: *Cynomolgus macaques*

Route of Immunization & Challenge: Subcutaneous (0.5 mL)

Vaccination Schedule & Dose: Days 0, 91 (DENVax-HD+)

Challenge: Day 120

Dose: DENV-2 (105 pfu), DENV-4 (106 pfu)

Sampling

Viremia: qRT-PCR using primer for E-gene

Pre & Post primary vaccination: 0, 5, 8, 11, 14, 17, 20, 23, 25

Pre & Post Boost: 91, 94, 98

Pre & Post Challenge:120, 122, 124, 126, 128, 130, 132, 134

Serology: 0, 30, 60, 91, 105, 120, 134, 148

Post-vaccination viremia (vRNA) is dominated by DENVax-2. DENVax-4 vRNA detected in one animal from DENVax-HD+ on day 8 post-vaccination. The trivalent DENVax-1,-2,-3 is more immunogenic and elicits a more balanced response than the DENVax-1,-3,-4 formulation. It is contemplated that the modified DEN-4 strains disclosed herein will improve this outcome. (See for example, FIG. 1).

TABLE 1

Preclinical evaluation of trivalent DENVax in non-human primates
Route of Immunization & Challenge: Subcutaneous (0.5 mL)
DENVax Formulation

| | | | | | |
|---|---|---|---|---|---|
| DENVax HD+: | DENVax1 - $1.25\times10^4$ | Trivalent (DENVax1,2,3) | DENVax1 - $1.25\times10^4$ | Trivalent (DENVax1,3,4) | DENVax1 - $1.25\times10^4$ |
| | DENVax2 - $6.04\times10^4$ | | DENVax2 - $6.04\times10^4$ | | |
| | DENVax3 - $1.30\times10^5$ | | DENVax3 - $1.30\times10^5$ | | DENVax3 - $1.30\times10^5$ |
| | DENVax4 - $1.34\times10^6$ | | | | DENVax4 - $1.34\times10^6$ |

TABLE 2

Design:

| Group | Treatment on Day 0 and 90 | Challenge on day 120 | Aim |
|---|---|---|---|
| 1 | DENVax HD+ | Challenge with DENV-2 and DENV-4 | Clinical dosing |
| 2 | Trivalent (DENVax1,2,3-same titers as HD+) | Challenge with DENV-4 | Assess trivalent vaccine protection against dengue virus serotypes (e.g. DEN-4) |
| 3 | Trivalent (DENVax1,3,4-same titers as HD+) | Challenge wit DENV-2 | Assess trivalent followed by monovalent administration and assess protection against dengue virus serotypes (e.g. What is the neutralizing antibody level against DEN-2 using only a DEN-2 backbone for immunization) |
| 4 | FTA | Challenge with DENV-2 and DENV-4 | Challenge control group |
| 5 | Trivalent formulation on Day 0 and a monovalent formulation on the same day or within 90 days of the Trivalent formulation (or reverse: monovalent first) DENVax 1, 2, 3; DENVax 2, 3, 4; DENVax1, 2, 4 or DENVax1, 3, 4 on a DEN-2 backbone | Challenge with DENV-2 and DENV-4 | Challenge control group |
| 6 | Trivalent formulation on Day 0 and a monovalent formulation on the same day in a different anatomical site; or within 90 days of the Trivalent formulation (or reverse: monovalent first) DENVax 1, 2, 3; DENVax 2, 3, 4; DENVax1, 2, 4 or DENVax1, 3, 4 on a DEN-2 backbone | Challenge with DENV-2 and DENV-4 | Challenge control group |

All of the COMPOSITIONS and METHODS disclosed and claimed herein can be made and executed without undue experimentation in light of the present disclosure. While the compositions and methods have been described in terms of preferred embodiments, it is apparent to those of skill in the art that variations maybe applied to the COMPOSITIONS and METHODS and in the steps or in the sequence of steps of the methods described herein without departing from the concept, spirit and scope herein. More specifically, certain agents that are both chemically and physiologically related may be substituted for the agents described herein while the same or similar results would be achieved. All such similar substitutes and modifications apparent to those skilled in the art are deemed to be within the spirit, scope and concept as defined by the appended claims.

What is claimed is:

1. A method for inducing neutralizing antibodies in a subject against three or more dengue virus serotypes, the method comprising;

administering a first dose of a single trivalent dengue virus immunogenic composition comprising a mixture of three or more different live, attenuated dengue viruses, wherein the mixture comprises at least three dengue virus serotypes comprising dengue-dengue chimeras, wherein the dengue-dengue chimeras comprise dengue virus structural proteins on an attenuated dengue-2 virus backbone, and one or more structural elements of dengue-1, dengue-2, dengue-3 or dengue-4, and one or more structural or non-structural elements of a live, attenuated dengue virus, and wherein the attenuated dengue-2 virus comprises dengue-2 strain PDK-53, and wherein three of four dengue virus serotype structural elements are present in the single trivalent dengue virus immunogenic composition; and administering at least a second dose of a live, attenuated dengue virus immunogenic composition comprising a single live, attenuated dengue virus chimera or a monovalent live, attenuated dengue virus on the same day or up to 180 days after administration of the first dose of the single trivalent dengue virus immunogenic composition.

2. A method for inducing neutralizing antibodies in a subject against three or more dengue virus serotypes, the method comprising;

administering a first dose of a single trivalent dengue virus immunogenic composition comprising a mixture of three or more different live, attenuated dengue viruses, wherein the mixture comprises at least three dengue virus serotypes comprising dengue-dengue chimeras, wherein the dengue-dengue chimeras comprise one or more structural elements of dengue-1, dengue-2, dengue-3 or dengue-4, and one or more structural or non-structural elements of a live, attenuated dengue virus, and wherein three of four dengue virus serotype structural elements are present in the single trivalent dengue virus immunogenic composition, wherein the single trivalent dengue virus immunogenic composition comprises constructs comprising a predetermined ratio of dengue virus serotype constructs comprising dengue-1, dengue-2, and dengue-3; dengue-1, dengue-3, and dengue-4; dengue-1, dengue-2, and dengue-4; or dengue-2, dengue-3 and dengue-4, wherein concentration measured by plaque forming units (pfus) of at least one dengue virus serotype is higher in concentration than at least one other dengue virus serotype in the single trivalent dengue virus immunogenic composition; and administering at least a second dose of a live, attenuated dengue virus immunogenic composition comprising a single live, attenuated dengue virus chimera or a monovalent live, attenuated dengue virus on the same day or up to 180 days after administration of the first dose of the single trivalent dengue virus immunogenic composition.

3. The method of claim 2, wherein the higher concentration is 2 to 100,000 fold higher concentration.

4. A method for inducing neutralizing antibodies in a subject against three or more dengue virus serotypes, the method comprising;

administering a first dose of a single trivalent dengue virus immunogenic composition comprising a mixture of three or more different live, attenuated dengue viruses, wherein the mixture comprises at least three dengue virus serotypes comprising dengue-dengue chimeras, wherein the dengue-dengue chimeras comprise one or more structural elements of dengue-1, dengue-2, dengue-3 or dengue-4, and one or more structural or non-structural elements of a live, attenuated dengue virus, and wherein three of four dengue virus serotype structural elements are present in the single trivalent dengue virus immunogenic composition; and administering at least a second dose of a live, attenuated dengue virus immunogenic composition comprising a single live, attenuated dengue virus chimera or a monovalent live, attenuated dengue virus on the same day, wherein administration of the at least second immunogenic composition on the same day comprises administering at a second anatomical site using different modes of administration.

5. The method of claim 1, wherein at least one additional booster is administered to the subject less than 180 days after the same day immunogenic compositions.

6. The method of claim 1, wherein at least one additional booster is administered to the subject 90 days or less after the same day administrations.

7. The method of claim 1, further comprising administering at least one additional immunogenic agent to the subject.

8. A method for inhibiting dengue virus infection in a subject, the method comprising:

administering to the subject a first immunogenic composition of a trivalent composition of live, attenuated dengue virus comprising three dengue virus serotypes dengue-1, dengue-2, and dengue-3; dengue-1, dengue-3, and dengue-4; dengue-1, dengue-2, and dengue-4; or dengue-2, dengue-3 and dengue-4; and administering consecutively to the subject at least a second administration of an immunogenic composition of live, attenuated dengue virus comprising a single dengue virus serotype (monovalent), the first and second immunogenic compositions are administered to the subject in different anatomical sites on the subject, wherein the single dengue virus serotype comprises a dengue virus serotype not having a structural protein in the trivalent dengue virus immunogenic composition.

9. The method of claim 8, wherein the trivalent dengue virus immunogenic compositions comprise unequivalent distribution of the three dengue virus serotypes in the immunogenic composition where concentration of one serotype can vary from 2 to 100,000 fold compared to another.

10. The method according to claim 3, wherein the three dengue virus serotypes are each in a predetermined ratio, and wherein the trivalent immunogenic composition comprises dengue-4 (DEN-4) at 2 to 100,000 times higher concentration than the other two dengue virus serotypes.

11. The method of claim 4, wherein the trivalent immunogenic composition comprises dengue-dengue chimeras having attenuated dengue-2 virus backbones.

12. The method of claim 11, wherein the attenuated dengue-2 virus is strain PDK-53.

13. A method for inducing neutralizing antibodies in a subject against three or more dengue virus serotypes, the method comprising;

administering a first dose of a single trivalent dengue virus immunogenic composition comprising a mixture of three or more different live, attenuated dengue viruses, wherein the mixture comprises at least three dengue virus serotypes comprising dengue-dengue chimeras, wherein the dengue-dengue chimeras comprise one or more structural elements of dengue-1, dengue-2, dengue-3 or dengue-4, and one or more structural or non-structural elements of a live, attenuated dengue virus, and wherein three of four dengue virus serotype structural elements are present in the single trivalent dengue virus immunogenic composition, wherein the dengue virus serotypes are present in a range of $10^3$ pfus to $10^7$ pfus; and administering at least a second dose of a live, attenuated dengue virus immunogenic composition comprising a single live, attenuated dengue virus chimera or a monovalent live, attenuated dengue virus on the same day or up to 180 days after administration of the first dose of the single trivalent dengue virus immunogenic composition.

14. A method for inducing neutralizing antibodies in a subject against three or more dengue virus serotypes, the method comprising;

administering a first dose of a single trivalent dengue virus immunogenic composition comprising a mixture of three or more different live, attenuated dengue viruses, wherein the mixture comprises at least three dengue virus serotypes comprising dengue-dengue chimeras, wherein the dengue-dengue chimeras comprise one or more structural elements of dengue-1, dengue-2, dengue-3 or dengue-4, and one or more structural or non-structural elements of a live, attenuated dengue virus, and wherein three of four dengue virus serotype structural elements are present in the single trivalent dengue virus immunogenic composition; and administering at least a second dose of a live, attenuated dengue virus immunogenic composition comprising a single live, attenuated dengue virus chimera or a monovalent live, attenuated dengue virus on the same day or up to 180 days after administration of the first dose of the single trivalent dengue virus immunogenic composition, wherein the monovalent live, attenuated dengue virus comprises dengue-4 serotype virus.

* * * * *

SEQUENCE LISTING

<160> NUMBER OF SEQ ID NOS: 33

<210> SEQ ID NO 1
<211> LENGTH: 29
<212> TYPE: PRT
<213> ORGANISM: Artificial
<220> FEATURE:
<223> OTHER INFORMATION: Derived from Dengue virus serotype 2 (DENV-2)

<400> SEQUENCE: 1

Asn Ile Leu Asn Arg Arg Arg Arg Ser Ala Gly Met Ile Ile Met Leu
1               5                   10                  15

Ile Pro Thr Val Met Ala Phe His Leu Thr Thr Arg Asn
            20                  25

<210> SEQ ID NO 2
<211> LENGTH: 29
<212> TYPE: PRT
<213> ORGANISM: Artificial
<220> FEATURE:
<223> OTHER INFORMATION: Derived from Dengue virus serotype 4 (DENV-4 WT)

<400> SEQUENCE: 2

Asn Ile Leu Asn Gly Arg Lys Arg Ser Thr Ile Thr Leu Leu Cys Leu
1               5                   10                  15

Ile Pro Thr Val Met Ala Phe His Leu Ser Thr Arg Asp
            20                  25

<210> SEQ ID NO 3
<211> LENGTH: 29
<212> TYPE: PRT
<213> ORGANISM: Artificial
<220> FEATURE:
<223> OTHER INFORMATION: Derived from Dengue virus seroptype 4 (DENVax-4ori)

<400> SEQUENCE: 3

Asn Ile Leu Asn Arg Arg Arg Ser Ser Ala Gly Met Ile Ile Met Leu
1               5                   10                  15

Ile Pro Thr Val Met Ala Phe His Leu Thr Thr Arg Asp
            20                  25

<210> SEQ ID NO 4
<211> LENGTH: 29
<212> TYPE: PRT
<213> ORGANISM: Artificial
<220> FEATURE:
<223> OTHER INFORMATION: Derived from Dengue virus serotype 4 (DENVax-4b)

<400> SEQUENCE: 4

Asn Ile Leu Asn Arg Arg Arg Ser Ser Thr Ile Thr Leu Leu Cys Leu
1               5                   10                  15

Ile Pro Thr Val Met Ala Phe His Leu Ser Thr Arg Asp
            20                  25

<210> SEQ ID NO 5
<211> LENGTH: 29
<212> TYPE: PRT
<213> ORGANISM: Artificial
<220> FEATURE:
<223> OTHER INFORMATION: Derived from Dengue virus serotype 4 (DENVax-4c)

-continued

<400> SEQUENCE: 5

Asn Ile Leu Asn Gly Arg Lys Arg Ser Thr Ile Thr Leu Leu Cys Leu
1 5 10 15

Ile Pro Thr Val Met Ala Phe His Leu Ser Thr Arg Asp
20 25

<210> SEQ ID NO 6
<211> LENGTH: 28
<212> TYPE: PRT
<213> ORGANISM: Artificial
<220> FEATURE:
<223> OTHER INFORMATION: Derived from Dengue virus serotype 4 (DENVax-4d)

<400> SEQUENCE: 6

Ile Leu Asn Gly Arg Lys Arg Ser Thr Ile Thr Leu Leu Cys Leu Ile
1 5 10 15

Pro Thr Val Met Ala Phe His Leu Ser Thr Arg Asp
20 25

<210> SEQ ID NO 7
<211> LENGTH: 10722
<212> TYPE: DNA
<213> ORGANISM: Artificial
<220> FEATURE:
<223> OTHER INFORMATION: Dengue virus chimeric construct DENVax-4e

<400> SEQUENCE: 7
agttgttagt ctacgtggac cgacaaagac agattctttg agggagctaa gctcaatgta 60
gttctaacag tttttaatt agagagcaga tctctgatga ataaccaacg gaaaaaggcg 120
aaaaacacgc ctttcaatat gctgaaacgc gagagaaacc gcgtgtcgac tgtgcaacag 180
ctgacaaaga gattctcact tggaatgctg cagggacgag gaccattaaa actgttcatg 240
gccctggtgg cgttccttcg tttcctaaca atcccaccaa cagcagggat attgaagaga 300
tggggaacaa ttaaaaaatc aaaagctatt aatgttttga gagggttcag gaaagagatt 360
ggaaggatgc tgaacatctt gaataggaga cgcagctcaa cgataacatt gctgtacttg 420
attcccaccg taatggcgtt tcacttgtca acgcgtgatg gcgaacccct catgatagtg 480
gcaaaacatg aaagggggag acctctcttg tttaagacaa cagaggggat caacaaatgc 540
actctcattg ccatggactt gggtgaaatg tgtgaggaca ctgtcacgta taaatgcccc 600
ttactggtca ataccgaacc tgaagacatt gattgctggt gcaatctcac gtctacctgg 660
gtcatgtatg ggacatgcac ccagagcgga gaacggagac gagagaagcg ctcagtagct 720
ttaacaccac attcaggaat gggattggaa acaagagctg agacatggat gtcatcggaa 780
ggggcttgga agcatgctca gagagtagag agctggatac tcagaaaccc aggattcgcg 840
ctcttggcag gatttatggc ttatatgatt gggcaaacag gaatccagcg aactgtcttc 900
tttgtcctaa tgatgctggt cgccccatcc tacggaatgc gatgcgtagg agtaggaaac 960
agagactttg tggaaggagt ctcaggtgga gcatgggtcg atctggtgct agaacatgga 1020
ggatgcgtca caaccatggc ccagggaaaa ccaaccttgg attttgaact gactaagaca 1080
acagccaagg aagtggctct gttaagaacc tattgcattg aagcctcaat atcaaacata 1140
accacggcaa caagatgtcc aacgcaagga gagccttatc taaaagagga acaagaccaa 1200
cagtacattt gccggagaga tgtggtagac agagggtggg gcaatggctg tggcttgttt 1260
ggaaaaggag gagttgtgac atgtgcgaag ttttcatgtt cggggaagat aacaggcaat 1320

-continued

```
ttggtccaaa ttgagaacct tgaatacaca gtggttgtaa cagtccacaa tggagacacc   1380
catgcagtag gaaatgacac gtccaatcat ggagttacag ccacgataac tcccaggtca   1440
ccatcggtgg aagtcaaatt gccggactat ggagaactaa cactcgattg tgaacccagg   1500
tctggaattg actttaatga gatgattctg atgaaaatga aaaagaaaac atggcttgtg   1560
cataagcaat ggtttttgga tctacctcta ccatggacag caggagcaga cacatcagag   1620
gttcactgga attacaaaga gagaatggtg acatttaagg ttcctcatgc caagagacag   1680
gatgtgacag tgctgggatc tcaggaagga gccatgcatt ctgccctcgc tggagccaca   1740
gaagtggact ccggtgatgg aaatcacatg tttgcaggac atctcaagtg caaagtccgt   1800
atggagaaat tgagaatcaa gggaatgtca tacacgatgt gttcaggaaa gttctcaatt   1860
gacaaagaga tggcagaaac acagcatggg acaacagtgg tgaaagtcaa gtatgaaggt   1920
gctggagctc cgtgtaaagt ccccatagag ataagagatg tgaacaagga aaaagtggtt   1980
gggcgtatca tctcatccac ccctttggct gagaatacca acagtgtaac caacatagag   2040
ttagaacccc cctttgggga cagctacata gtgataggtg ttggaaacag tgcattaaca   2100
ctccattggt tcaggaaagg gagttccatt ggcaagatgt ttgagtccac atacagaggt   2160
gcaaaacgaa tggccattct aggtgaaaca gcttgggatt ttggttccgt tggtggactg   2220
ttcacatcat tgggaaaggc tgtgcaccag gtttttggaa gtgtgtatac aaccctgttt   2280
ggaggagtct catggatgat tagaatccta attgggttcc tagtgttgtg gattggcacg   2340
aactcaagga acacttcaat ggctatgacg tgcatagctg ccggcattgt gacactgtat   2400
ttgggagtca tggtgcaggc cgatagtggt tgcgttgtga gctggaaaaa caaagaactg   2460
aaatgtggca gtgggatttt catcacagac aacgtgcaca catggacaga acaatacaag   2520
ttccaaccag aatccccttc aaaactagct tcagctatcc agaaagccca tgaagaggac   2580
atttgtggaa tccgctcagt aacaagactg gagaatctga tgtggaaaca aataacacca   2640
gaattgaatc acattctatc agaaaatgag gtgaagttaa ctattatgac aggagacatc   2700
aaaggaatca tgcaggcagg aaaacgatct ctgcggcctc agcccactga gctgaagtat   2760
tcatggaaaa catggggcaa agcaaaaatg ctctctacag agtctcataa ccagaccttt   2820
ctcattgatg gccccgaaac agcagaatgc cccaacacaa atagagcttg gaattcgttg   2880
gaagttgaag actatggctt tggagtattc accaccaata tatggctaaa attgaaagaa   2940
aaacaggatg tattctgcga ctcaaaactc atgtcagcgg ccataaaaga caacagagcc   3000
gtccatgccg atatgggtta ttggatagaa agtgcactca atgacacatg gaagatagag   3060
aaagcctctt tcattgaagt taaaaactgc cactggccaa aatcacacac cctctggagc   3120
aatggagtgc tagaaagtga gatgataatt ccaaagaatc tcgctggacc agtgtctcaa   3180
cacaactata gaccaggcta ccatacacaa ataacaggac catggcatct aggtaagctt   3240
gagatggact ttgatttctg tgatggaaca acagtggtag tgactgagga ctgcggaaat   3300
agaggaccct ctttgagaac aaccactgcc tctggaaaac tcataacaga atggtgctgc   3360
cgatcttgca cattaccacc gctaagatac agaggtgagg atgggtgctg gtacgggatg   3420
gaaatcagac cattgaagga gaaagaagag aatttggtca actccttggt cacagctgga   3480
catgggcagg tcgacaactt ttcactagga gtcttgggaa tggcattgtt cctggaggaa   3540
atgcttagga cccgagtagg aacgaaacat gcaatactac tagttgcagt ttcttttgtg   3600
acattgatca cagggaacat gtcctttaga gacctgggaa gagtgatggt tatggtaggc   3660
gccactatga cggatgacat aggtatgggc gtgacttatc ttgccctact agcagccttc   3720
```

-continued

```
aaagtcagac caacttttgc agctggacta ctcttgagaa agctgacctc caaggaattg   3780

atgatgacta ctataggaat tgtactcctc tcccagagca ccataccaga gaccattctt   3840

gagttgactg atgcgttagc cttaggcatg atggtcctca aaatggtgag aaatatggaa   3900

aagtatcaat tggcagtgac tatcatggct atcttgtgcg tcccaaacgc agtgatatta   3960

caaaacgcat ggaaagtgag ttgcacaata ttggcagtgg tgtccgtttc cccactgttc   4020

ttaacatcct cacagcaaaa aacagattgg ataccattag cattgacgat caaaggtctc   4080

aatccaacag ctatttttct aacaaccctc tcaagaacca gcaagaaaag gagctggcca   4140

ttaaatgagg ctatcatggc agtcgggatg gtgagcattt tagccagttc tctcctaaaa   4200

aatgatattc ccatgacagg accattagtg gctggagggc tcctcactgt gtgctacgtg   4260

ctcactggac gatcggccga tttggaactg gagagagcag ccgatgtcaa atgggaagac   4320

caggcagaga tatcaggaag cagtccaatc ctgtcaataa caatatcaga agatggtagc   4380

atgtcgataa aaaatgaaga ggaagaacaa acactgacca tactcattag aacaggattg   4440

ctggtgatct caggactttt tcctgtatca ataccaatca cggcagcagc atggtacctg   4500

tgggaagtga agaaacaacg ggccggagta ttgtgggatg ttccttcacc cccacccatg   4560

ggaaaggctg aactggaaga tggagcctat agaattaagc aaaaagggat tcttggatat   4620

tcccagatcg gagccggagt ttacaaagaa ggaacattcc atacaatgtg gcatgtcaca   4680

cgtggcgctg ttctaatgca taaaggaaag aggattgaac catcatgggc ggacgtcaag   4740

aaagacctaa tatcatatgg aggaggctgg aagttagaag gagaatggaa ggaaggagaa   4800

gaagtccagg tattggcact ggagcctgga aaaaatccaa gagccgtcca aacgaaacct   4860

ggtcttttca aaaccaacgc cggaacaata ggtgctgtat ctctggactt ttctcctgga   4920

acgtcaggat ctccaattat cgacaaaaaa ggaaaagttg tgggtcttta tggtaatggt   4980

gttgttacaa ggagtggagc atatgtgagt gctatagccc agactgaaaa aagcattgaa   5040

gacaacccag agatcgaaga tgacattttc cgaaagagaa gactgaccat catggacctc   5100

cacccaggag cgggaaagac gaagagatac cttccggcca tagtcagaga agctataaaa   5160

cggggtttga gaacattaat cttggccccc actagagttg tggcagctga aatggaggaa   5220

gcccttagag gacttccaat aagataccag accccagcca tcagagctgt gcacaccggg   5280

cgggagattg tggacctaat gtgtcatgcc acatttacca tgaggctgct atcaccagtt   5340

agagtgccaa actacaacct gattatcatg gacgaagccc atttcacaga cccagcaagt   5400

atagcagcta gaggatacat ctcaactcga gtggagatgg gtgaggcagc tgggattttt   5460

atgacagcca ctcccccggg aagcagagac ccatttcctc agagcaatgc accaatcata   5520

gatgaagaaa gagaaatccc tgaacgctcg tggaattccg gacatgaatg ggtcacggat   5580

tttaaaggga agactgtttg gttcgttcca agtataaaag caggaaatga tatagcagct   5640

tgcctgagga aaaatggaaa gaaagtgata caactcagta ggaagacctt tgattctgag   5700

tatgtcaaga ctagaaccaa tgattgggac ttcgtggtta caactgacat ttcagaaatg   5760

ggtgccaatt tcaaggctga gagggttata gaccccagac gctgcatgaa accagtcata   5820

ctaacagatg gtgaagagcg ggtgattctg gcaggaccta tgccagtgac ccactctagt   5880

gcagcacaaa gaagagggag aataggaaga aatccaaaaa atgagaatga ccagtacata   5940

tacatggggg aacctctgga aaatgatgaa gactgtgcac actggaaaga agctaaaatg   6000

ctcctagata acatcaacac gccagaagga atcattccta gcatgttcga accagagcgt   6060
```

gaaaaggtgg atgccattga tggcgaatac cgcttgagag gagaagcaag gaaaaccttt 6120
gtagacttaa tgagaagagg agacctacca gtctggttgg cctacagagt ggcagctgaa 6180
ggcatcaact acgcagacag aaggtggtgt tttgatggag tcaagaacaa ccaaatccta 6240
gaagaaaacg tggaagttga aatctggaca aaagaagggg aaaggaagaa attgaaaccc 6300
agatggttgg atgctaggat ctattctgac ccactggcgc taaaagaatt taaggaattt 6360
gcagccggaa gaaagtctct gaccctgaac ctaatcacag aaatgggtag gctcccaacc 6420
ttcatgactc agaaggcaag agacgcactg gacaacttag cagtgctgca cacggctgag 6480
gcaggtggaa gggcgtacaa ccatgctctc agtgaactgc cggagaccct ggagacattg 6540
cttttactga cacttctggc tacagtcacg ggagggatct tttattcttt gatgagcgca 6600
aggggcatag ggaagatgac cctgggaatg tgctgcataa tcacggctag catcctccta 6660
tggtacgcac aaatacagcc acactggata gcagcttcaa taatactgga gtttttctc 6720
atagttttgc ttattccaga acctgaaaaa cagagaacac cccaagacaa ccaactgacc 6780
tacgttgtca tagccatcct cacagtggtg gccgcaacca tggcaaacga gatgggtttc 6840
ctagaaaaaa cgaagaaaga tctcggattg ggaagcattg caacccagca acccgagagc 6900
aacatcctgg acatagatct acgtcctgca tcagcatgga cgctgtatgc cgtggccaca 6960
acatttgtta caccaatgtt gagacatagc attgaaaatt cctcagtgaa tgtgtcccta 7020
acagctatag ccaaccaagc cacagtgtta atgggtctcg ggaaaggatg gccattgtca 7080
aagatggaca tcggagttcc ccttctcgcc attggatgct actcacaagt caaccccata 7140
actctcacag cagctctttt cttattggta gcacattatg ccatcatagg gccaggactc 7200
caagcaaaag caaccagaga agctcagaaa agagcagcgg cgggcatcat gaaaaaccca 7260
actgtcgatg gaataacagt gattgaccta gatccaatac cttatgatcc aaagtttgaa 7320
aagcagttgg gacaagtaat gctcctagtc ctctgcgtga ctcaagtatt gatgatgagg 7380
actacatggg ctctgtgtga ggctttaacc ttagctaccg ggcccatctc cacattgtgg 7440
gaaggaaatc cagggaggtt ttggaacact accattgcgg tgtcaatggc taacattttt 7500
agagggagtt acttggccgg agctggactt ctcttttcta ttatgaagaa cacaaccaac 7560
acaagaaggg gaactggcaa cataggagag acgcttggag agaaatggaa aagccgattg 7620
aacgcattgg gaaaaagtga attccagatc tacaagaaaa gtggaatcca ggaagtggat 7680
agaaccttag caaaagaagg cattaaaaga ggagaaacgg accatcacgc tgtgtcgcga 7740
ggctcagcaa aactgagatg gttcgttgag agaaacatgg tcacaccaga agggaaagta 7800
gtggacctcg gttgtggcag aggaggctgg tcatactatt gtggaggact aaagaatgta 7860
agagaagtca aaggcctaac aaaaggagga ccaggacacg aagaacccat ccccatgtca 7920
acatatgggt ggaatctagt gcgtcttcaa agtggagttg acgttttctt catcccgcca 7980
gaaaagtgtg acacattatt gtgtgacata ggggagtcat caccaaatcc cacagtggaa 8040
gcaggacgaa cactcagagt ccttaactta gtagaaaatt ggttgaacaa caacactcaa 8100
ttttgcataa aggttctcaa cccatatatg ccctcagtca tagaaaaaat ggaagcacta 8160
caaaggaaat atggaggagc cttagtgagg aatccactct cacgaaactc cacacatgag 8220
atgtactggg tatccaatgc ttccgggaac atagtgtcat cagtgaacat gatttcaagg 8280
atgttgatca acagatttac aatgagatac aagaaagcca cttacgagcc ggatgttgac 8340
ctcggaagcg gaacccgtaa catcgggatt gaaagtgaga taccaaacct agatataatt 8400
gggaaaagaa tagaaaaaat aaagcaagag catgaaacat catggcacta tgaccaagac 8460

-continued

```
cacccataca aaacgtgggc ataccatggt agctatgaaa caaaacagac tggatcagca   8520
tcatccatgg tcaacggagt ggtcaggctg ctgacaaaac cttgggacgt cgtccccatg   8580
gtgacacaga tggcaatgac agacacgact ccatttggac aacagcgcgt tttaaagag    8640
aaagtggaca cgagaaccca agaaccgaaa gaaggcacga agaaactaat gaaaataaca   8700
gcagagtggc tttggaaaga attagggaag aaaaagacac ccaggatgtg caccagagaa   8760
gaattcacaa gaaaggtgag aagcaatgca gccttggggg ccatattcac tgatgagaac   8820
aagtggaagt cggcacgtga ggctgttgaa gatagtaggt tttgggagct ggttgacaag   8880
gaaaggaatc tccatcttga aggaaagtgt gaaacatgtg tgtacaacat gatgggaaaa   8940
agagagaaga agctagggga attcggcaag gcaaaaggca gcagagccat atggtacatg   9000
tggcttggag cacgcttctt agagtttgaa gccctaggat tcttaaatga agatcactgg   9060
ttctccagag agaactccct gagtggagtg gaaggagaag ggctgcacaa gctaggttac   9120
attctaagag acgtgagcaa gaaagaggga ggagcaatgt atgccgatga caccgcagga   9180
tgggatacaa gaatcacact agaagaccta aaaaatgaag aaatggtaac aaaccacatg   9240
gaaggagaac acaagaaact agccgaggcc attttcaaac taacgtacca aaacaaggtg   9300
gtgcgtgtgc aaagaccaac accaagaggc acagtaatgg acatcatatc gagaagagac   9360
caaagaggta gtggacaagt tggcacctat ggactcaata ctttcaccaa tatggaagcc   9420
caactaatca gacagatgga gggagaagga gtctttaaaa gcattcagca cctaacaatc   9480
acagaagaaa tcgctgtgca aaactggtta gcaagagtgg ggcgcgaaag gttatcaaga   9540
atggccatca gtggagatga ttgtgttgtg aaacctttag atgacaggtt cgcaagcgct   9600
ttaacagctc taaatgacat gggaaagatt aggaaagaca tacaacaatg ggaaccttca   9660
agaggatgga atgattggac acaagtgccc ttctgttcac accatttcca tgagttaatc   9720
atgaaagacg gtcgcgtact cgttgttcca tgtagaaacc aagatgaact gattggcaga   9780
gcccgaatct cccaaggagc agggtggtct ttgcgggaga cggcctgttt ggggaagtct   9840
tacgcccaaa tgtggagctt gatgtacttc cacagacgcg acctcaggct ggcggcaaat   9900
gctatttgct cggcagtacc atcacattgg gttccaacaa gtcgaacaac ctggtccata   9960
catgctaaac atgaatggat gacaacggaa gacatgctga cagtctggaa cagggtgtgg  10020
attcaagaaa acccatggat ggaagacaaa actccagtgg aatcatggga ggaaatccca  10080
tacttgggga aaagagaaga ccaatggtgc ggctcattga ttgggttaac aagcagggcc  10140
acctgggcaa agaacatcca agcagcaata aatcaagtta gatcccttat aggcaatgaa  10200
gaatacacag attacatgcc atccatgaaa agattcagaa gagaagagga agaagcagga  10260
gttctgtggt agaaagcaaa actaacatga aacaaggcta gaagtcaggt cggattaagc  10320
catagtacgg aaaaaactat gctacctgtg agccccgtcc aaggacgtta aaagaagtca  10380
ggccatcata aatgccatag cttgagtaaa ctatgcagcc tgtagctcca cctgagaagg  10440
tgtaaaaaat ccgggaggcc acaaaccatg gaagctgtac gcatggcgta gtggactagc  10500
ggttagagga gacccctccc ttacaaatcg cagcaacaat gggggcccaa ggcgagatga  10560
agctgtagtc tcgctggaag gactagaggt tagaggagac ccccccgaaa caaaaaacag  10620
catattgacg ctgggaaaga ccagagatcc tgctgtctcc tcagcatcat tccaggcaca  10680
gaacgccaga aaatggaatg gtgctgttga atcaacaggt tc                     10722
```

<210> SEQ ID NO 8

<211> LENGTH: 10722
<212> TYPE: DNA
<213> ORGANISM: Artificial
<220> FEATURE:
<223> OTHER INFORMATION: Dengue virus chimeric construct DENVax-4h

<400> SEQUENCE: 8
agttgttagt ctacgtggac cgacaaagac agattctttg agggagctaa gctcaatgta 60
gttctaacag tttttaatt agagagcaga tctctgatga ataaccaacg gaaaaaggcg 120
aaaaacacgc ctttcaatat gctgaaacgc gagagaaacc gcgtgtcgac tgtgcaacag 180
ctgacaaaga gattctcact tggaatgctg cagggacgag gaccattaaa actgttcatg 240
gccctggtgg cgttccttcg tttcctaaca atcccaccaa cagcagggat attgaagaga 300
tggggaacaa ttaaaaaatc aaaagctatt aatgttttga gagggttcag gaaagagatt 360
ggaaggatgc tgaacatctt gaataggaga cgcagctctg caggcatgat cattatgctg 420
attccaacag tgatggcgtt ccatttaacc acgcgtgatg gcgaacccct catgatagtg 480
gcaaaacatg aaagggggag acctctcttg tttaagacaa cagaggggat caacaaatgc 540
actctcattg ccatggactt gggtgaaatg tgtgaggaca ctgtcacgta taaatgcccc 600
ttactggtca ataccgaacc tgaagacatt gattgctggt gcaatctcac gtctacctgg 660
gtcatgtatg ggacatgcac ccagagcgga gaacggagac gagagaagcg ctcagtagct 720
ttaacaccac attcaggaat gggattggaa acaagagctg agacatggat gtcatcggaa 780
ggggcttgga agcatgctca gagagtagag agctggatac tcagaaaccc aggattcgcg 840
ctcttggcag gatttatggc ttatatgatt gggcaaacag gaatccagcg aactgtcttc 900
tttgtcctaa tgatgctggt cgccccatcc tacggaatgc gatgcgtagg agtaggaaac 960
agagactttg tggaaggagt ctcaggtgga gcatgggtcg atctggtgct agaacatgga 1020
ggatgcgtca caaccatggc ccagggaaaa ccaaccttgg attttgaact gactaagaca 1080
acagccaagg aagtggctct gttaagaacc tattgcattg aagcctcaat atcaaacata 1140
accacggcaa caagatgtcc aacgcaagga gagccttatc taaaagagga acaagaccaa 1200
cagtacattt gccggagaga tgtggtagac agagggtggg gcaatggctg tggcttgttt 1260
ggaaaaggag gagttgtgac atgtgcgaag ttttcatgtt cggggaagat aacaggcaat 1320
ttggtccaaa ttgagaacct tgaatacaca gtggttgtaa cagtccacaa tggagacacc 1380
catgcagtag gaaatgacac gtccaatcat ggagttacag ccacgataac tcccaggtca 1440
ccatcggtgg aagtcaaatt gccggactat ggagaactaa cactcgattg tgaacccagg 1500
tctggaattg actttaatga gatgattctg atgaaaatga aaaagaaaac atggcttgtg 1560
cataagcaat ggtttttgga tctacctcta ccatggacag caggagcaga cacatcagag 1620
gttcactgga attacaaaga gagaatggtg acatttaagg ttcctcatgc caagagacag 1680
gatgtgacag tgctgggatc tcaggaagga gccatgcatt ctgccctcgc tggagccaca 1740
gaagtggact ccggtgatgg aaatcacatg tttgcaggac atctcaagtg caaagtccgt 1800
atggagaaat tgagaatcaa gggaatgtca tacacgatgt gttcaggaaa gttctcaatt 1860
gacaaagaga tggcagaaac acagcatggg acaacagtgg tgaaagtcaa gtatgaaggt 1920
gctggagctc cgtgtaaagt ccccatagag ataagagatg tgaacaagga aaaagtggtt 1980
gggcgtatca tctcatccac ccctttggct gagaatacca acagtgtaac caacatagag 2040
ttagaacccc cctttgggga cagctacata gtgataggtg ttggaaacag tgcattaaca 2100
ctccattggt tcaggaaagg gagttccatt ggcaagatgt ttgagtccac atacagaggt 2160

-continued

```
gcaaaacgaa tggccattct aggtaaaaca gcttgggatt ttggttccgt tggtggactg   2220
ttcacatcat tgggaaaggc tgtgcaccag gtttttggaa gtgtgtatac aaccctgttt   2280
ggaggagtct catggatgat tagaatccta attgggttcc tagtgttgtg gattggcacg   2340
aactcaagga acacttcaat ggctatgacg tgcatagctg ccggcattgt gacactgtat   2400
ttgggagtca tggtgcaggc cgatagtggt tgcgttgtga gctggaaaaa caaagaactg   2460
aaatgtggca gtgggatttt catcacagac aacgtgcaca catggacaga acaatacaag   2520
ttccaaccag aatccccttc aaaactagct tcagctatcc agaaagccca tgaagaggac   2580
atttgtggaa tccgctcagt aacaagactg gagaatctga tgtggaaaca aataacacca   2640
gaattgaatc acattctatc agaaaatgag gtgaagttaa ctattatgac aggagacatc   2700
aaaggaatca tgcaggcagg aaaacgatct ctgcggcctc agcccactga gctgaagtat   2760
tcatggaaaa catggggcaa agcaaaaatg ctctctacag agtctcataa ccagaccttt   2820
ctcattgatg gccccgaaac agcagaatgc cccaacacaa atagagcttg gaattcgttg   2880
gaagttgaag actatggctt tggagtattc accaccaata tatggctaaa attgaaagaa   2940
aaacaggatg tattctgcga ctcaaaactc atgtcagcgg ccataaaaga caacagagcc   3000
gtccatgccg atatgggtta ttggatagaa agtgcactca atgacacatg gaagatagag   3060
aaagcctctt tcattgaagt taaaaactgc cactggccaa aatcacacac cctctggagc   3120
aatggagtgc tagaaagtga gatgataatt ccaaagaatc tcgctggacc agtgtctcaa   3180
cacaactata gaccaggcta ccatacacaa ataacaggac catggcatct aggtaagctt   3240
gagatggact ttgatttctg tgatggaaca acagtggtag tgactgagga ctgcggaaat   3300
agaggaccct ctttgagaac aaccactgcc tctggaaaac tcataacaga atggtgctgc   3360
cgatcttgca cattaccacc gctaagatac agaggtgagg atgggtgctg gtacgggatg   3420
gaaatcagac cattgaagga gaaagaagag aatttggtca actccttggt cacagctgga   3480
catgggcagg tcgacaactt ttcactagga gtcttgggaa tggcattgtt cctggaggaa   3540
atgcttagga cccgagtagg aacgaaacat gcaatactac tagttgcagt ttcttttgtg   3600
acattgatca cagggaacat gtcctttaga gacctgggaa gagtgatggt tatggtaggc   3660
gccactatga cggatgacat aggtatgggc gtgacttatc ttgccctact agcagccttc   3720
aaagtcagac caacttttgc agctggacta ctcttgagaa agctgacctc caaggaattg   3780
atgatgacta ctataggaat tgtactcctc tcccagagca ccataccaga gaccattctt   3840
gagttgactg atgcgttagc cttaggcatg atggtcctca aaatggtgag aaatatggaa   3900
aagtatcaat tggcagtgac tatcatggct atcttgtgcg tcccaaacgc agtgatatta   3960
caaaacgcat ggaaagtgag ttgcacaata ttggcagtgg tgtccgtttc cccactgttc   4020
ttaacatcct cacagcaaaa aacagattgg ataccattag cattgacgat caaaggtctc   4080
aatccaacag ctatttttct aacaaccctc tcaagaacca gcaagaaaag gagctggcca   4140
ttaaatgagg ctatcatggc agtcgggatg gtgagcattt tagccagttc tctcctaaaa   4200
aatgatattc ccatgacagg accattagtg gctggagggc tcctcactgt gtgctacgtg   4260
ctcactggac gatcggccga tttggaactg gagagagcag ccgatgtcaa atgggaagac   4320
caggcagaga tatcaggaag cagtccaatc ctgtcaataa caatatcaga agatggtagc   4380
atgtcgataa aaaatgaaga ggaagaacaa acactgacca tactcattag aacaggattg   4440
ctggtgatct caggactttt tcctgtatca ataccaatca cggcagcagc atggtacctg   4500
```

-continued tgggaagtga agaaacaacg ggccggagta ttgtgggatg ttccttcacc cccacccatg 4560
ggaaaggctg aactggaaga tggagcctat agaattaagc aaaaagggat tcttggatat 4620
tcccagatcg gagccggagt ttacaaagaa ggaacattcc atacaatgtg gcatgtcaca 4680
cgtggcgctg ttctaatgca taaaggaaag aggattgaac catcatgggc ggacgtcaag 4740
aaagacctaa tatcatatgg aggaggctgg aagttagaag gagaatggaa ggaaggagaa 4800
gaagtccagg tattggcact ggagcctgga aaaaatccaa gagccgtcca aacgaaacct 4860
ggtcttttca aaaccaacgc cggaacaata ggtgctgtat ctctggactt ttctcctgga 4920
acgtcaggat ctccaattat cgacaaaaaa ggaaaagttg tgggtcttta tggtaatggt 4980
gttgttacaa ggagtggagc atatgtgagt gctatagccc agactgaaaa aagcattgaa 5040
gacaacccag agatcgaaga tgacattttc cgaaagagaa gactgaccat catggacctc 5100
cacccaggag cgggaaagac gaagagatac cttccggcca tagtcagaga agctataaaa 5160
cggggtttga gaacattaat cttggccccc actagagttg tggcagctga aatggaggaa 5220
gcccttagag gacttccaat aagataccag accccagcca tcagagctgt gcacaccggg 5280
cgggagattg tggacctaat gtgtcatgcc acatttacca tgaggctgct atcaccagtt 5340
agagtgccaa actacaacct gattatcatg gacgaagccc atttcacaga cccagcaagt 5400
atagcagcta gaggatacat ctcaactcga gtggagatgg gtgaggcagc tgggattttt 5460
atgacagcca ctcccccggg aagcagagac ccatttcctc agagcaatgc accaatcata 5520
gatgaagaaa gagaaatccc tgaacgctcg tggaattccg gacatgaatg ggtcacggat 5580
tttaaaggga agactgtttg gttcgttcca agtataaaag caggaaatga tatagcagct 5640
tgcctgagga aaaatggaaa gaaagtgata caactcagta ggaagacctt tgattctgag 5700
tatgtcaaga ctagaaccaa tgattgggac ttcgtggtta caactgacat ttcagaaatg 5760
ggtgccaatt tcaaggctga gagggttata gaccccagac gctgcatgaa accagtcata 5820
ctaacagatg gtgaagagcg ggtgattctg gcaggaccta tgccagtgac ccactctagt 5880
gcagcacaaa gaagagggag aataggaaga aatccaaaaa atgagaatga ccagtacata 5940
tacatggggg aacctctgga aaatgatgaa gactgtgcac actggaaaga agctaaaatg 6000
ctcctagata acatcaacac gccagaagga atcattccta gcatgttcga accagagcgt 6060
gaaaaggtgg atgccattga tggcgaatac cgcttgagag gagaagcaag gaaaaccttt 6120
gtagacttaa tgagaagagg agacctacca gtctggttgg cctacagagt ggcagctgaa 6180
ggcatcaact acgcagacag aaggtggtgt tttgatggag tcaagaacaa ccaaatccta 6240
gaagaaaacg tggaagttga aatctggaca aaagaagggg aaaggaagaa attgaaaccc 6300
agatggttgg atgctaggat ctattctgac ccactggcgc taaaagaatt taaggaattt 6360
gcagccggaa gaaagtctct gaccctgaac ctaatcacag aaatgggtag gctcccaacc 6420
ttcatgactc agaaggcaag agacgcactg gacaacttag cagtgctgca cacggctgag 6480
gcaggtggaa gggcgtacaa ccatgctctc agtgaactgc cggagaccct ggagacattg 6540
cttttactga cacttctggc tacagtcacg ggagggatct tttattcttt gatgagcgca 6600
aggggcatag ggaagatgac cctgggaatg tgctgcataa tcacggctag catcctccta 6660
tggtacgcac aaatacagcc acactggata gcagcttcaa taatactgga gtttttttctc 6720 atagttttgc ttattccaga acctgaaaaa cagagaacac cccaagacaa ccaactgacc 6780
tacgttgtca tagccatcct cacagtggtg gccgcaacca tggcaaacga gatgggtttc 6840
ctagaaaaaa cgaagaaaga tctcggattg ggaagcattg caacccagca acccgagagc 6900

-continued

```
aacatcctgg acatagatct acgtcctgca tcagcatgga cgctgtatgc cgtggccaca   6960
acatttgtta caccaatgtt gagacatagc attgaaaatt cctcagtgaa tgtgtcccta   7020
acagctatag ccaaccaagc cacagtgtta atgggtctcg ggaaaggatg gccattgtca   7080
aagatggaca tcggagttcc ccttctcgcc attggatgct actcacaagt caaccccata   7140
actctcacag cagctctttt cttattggta gcacattatg ccatcatagg gccaggactc   7200
caagcaaaag caaccagaga agctcagaaa agagcagcgg cgggcatcat gaaaaaccca   7260
actgtcgatg gaataacagt gattgaccta gatccaatac cttatgatcc aaagtttgaa   7320
aagcagttgg gacaagtaat gctcctagtc ctctgcgtga ctcaagtatt gatgatgagg   7380
actacatggg ctctgtgtga ggctttaacc ttagctaccg ggcccatctc cacattgtgg   7440
gaaggaaatc cagggaggtt ttggaacact accattgcgg tgtcaatggc taacattttt   7500
agagggagtt acttggccgg agctggactt ctcttttcta ttatgaagaa cacaaccaac   7560
acaagaaggg gaactggcaa cataggagag acgcttggag agaaatggaa aagccgattg   7620
aacgcattgg gaaaaagtga attccagatc tacaagaaaa gtggaatcca ggaagtggat   7680
agaaccttag caaaagaagg cattaaaaga ggagaaacgg accatcacgc tgtgtcgcga   7740
ggctcagcaa aactgagatg gttcgttgag agaaacatgg tcacaccaga agggaaagta   7800
gtggacctcg gttgtggcag aggaggctgg tcatactatt gtggaggact aaagaatgta   7860
agagaagtca aaggcctaac aaaaggagga ccaggacacg aagaacccat ccccatgtca   7920
acatatgggt ggaatctagt gcgtcttcaa agtggagttg acgttttctt catcccgcca   7980
gaaaagtgtg acacattatt gtgtgacata ggggagtcat caccaaatcc cacagtggaa   8040
gcaggacgaa cactcagagt ccttaactta gtagaaaatt ggttgaacaa caacactcaa   8100
ttttgcataa aggttctcaa cccatatatg ccctcagtca tagaaaaaat ggaagcacta   8160
caaaggaaat atggaggagc cttagtgagg aatccactct cacgaaactc cacacatgag   8220
atgtactggg tatccaatgc ttccgggaac atagtgtcat cagtgaacat gatttcaagg   8280
atgttgatca acagatttac aatgagatac aagaaagcca cttacgagcc ggatgttgac   8340
ctcggaagcg gaacccgtaa catcgggatt gaaagtgaga taccaaacct agatataatt   8400
gggaaaagaa tagaaaaaat aaagcaagag catgaaacat catggcacta tgaccaagac   8460
cacccataca aaacgtgggc ataccatggt agctatgaaa caaaacagac tggatcagca   8520
tcatccatgg tcaacggagt ggtcaggctg ctgacaaaac cttgggacgt cgtccccatg   8580
gtgacacaga tggcaatgac agacacgact ccatttggac aacagcgcgt tttaaagag    8640
aaagtggaca cgagaaccca agaaccgaaa gaaggcacga agaaactaat gaaaataaca   8700
gcagagtggc tttggaaaga attagggaag aaaaagacac ccaggatgtg caccagagaa   8760
gaattcacaa gaaaggtgag aagcaatgca gccttggggg ccatattcac tgatgagaac   8820
aagtggaagt cggcacgtga ggctgttgaa gatagtaggt tttgggagct ggttgacaag   8880
gaaaggaatc tccatcttga aggaaagtgt gaaacatgtg tgtacaacat gatgggaaaa   8940
agagagaaga agctagggga attcggcaag gcaaaaggca gcagagccat atggtacatg   9000
tggcttggag cacgcttctt agagtttgaa gccctaggat tcttaaatga agatcactgg   9060
ttctccagag agaactccct gagtggagtg gaaggagaag ggctgcacaa gctaggttac   9120
attctaagag acgtgagcaa gaaagaggga ggagcaatgt atgccgatga caccgcagga   9180
tgggatacaa gaatcacact agaagaccta aaaaatgaag aaatggtaac aaaccacatg   9240
```

-continued

```
gaaggagaac acaagaaact agccgaggcc attttcaaac taacgtacca aaacaaggtg   9300
gtgcgtgtgc aaagaccaac accaagaggc acagtaatgg acatcatatc gagaagagac   9360
caaagaggta gtggacaagt tggcacctat ggactcaata ctttcaccaa tatggaagcc   9420
caactaatca gacagatgga gggagaagga gtctttaaaa gcattcagca cctaacaatc   9480
acagaagaaa tcgctgtgca aaactggtta gcaagagtgg ggcgcgaaag gttatcaaga   9540
atggccatca gtggagatga ttgtgttgtg aaacctttag atgacaggtt cgcaagcgct   9600
ttaacagctc taaatgacat gggaaagatt aggaaagaca tacaacaatg ggaaccttca   9660
agaggatgga atgattggac acaagtgccc ttctgttcac accatttcca tgagttaatc   9720
atgaaagacg gtcgcgtact cgttgttcca tgtagaaacc aagatgaact gattggcaga   9780
gcccgaatct cccaaggagc agggtggtct ttgcgggaga cggcctgttt ggggaagtct   9840
tacgcccaaa tgtggagctt gatgtacttc cacagacgcg acctcaggct ggcggcaaat   9900
gctatttgct cggcagtacc atcacattgg gttccaacaa gtcgaacaac ctggtccata   9960
catgctaaac atgaatggat gacaacggaa gacatgctga cagtctggaa cagggtgtgg  10020
attcaagaaa acccatggat ggaagacaaa actccagtgg aatcatggga ggaaatccca  10080
tacttgggga aaagagaaga ccaatggtgc ggctcattga ttgggttaac aagcagggcc  10140
acctgggcaa agaacatcca agcagcaata aatcaagtta gatcccttat aggcaatgaa  10200
gaatacacag attacatgcc atccatgaaa agattcagaa gagaagagga agaagcagga  10260
gttctgtggt agaaagcaaa actaacatga aacaaggcta gaagtcaggt cggattaagc  10320
catagtacgg aaaaaactat gctacctgtg agccccgtcc aaggacgtta aaagaagtca  10380
ggccatcata aatgccatag cttgagtaaa ctatgcagcc tgtagctcca cctgagaagg  10440
tgtaaaaaat ccgggaggcc acaaaccatg gaagctgtac gcatggcgta gtggactagc  10500
ggttagagga gacccctccc ttacaaatcg cagcaacaat gggggcccaa ggcgagatga  10560
agctgtagtc tcgctggaag gactagaggt tagaggagac ccccccgaaa caaaaaacag  10620
catattgacg ctgggaaaga ccagagatcc tgctgtctcc tcagcatcat tccaggcaca  10680
gaacgccaga aaatggaatg gtgctgttga atcaacaggt tc                     10722
```

<210> SEQ ID NO 9
<211> LENGTH: 10722
<212> TYPE: DNA
<213> ORGANISM: Artificial
<220> FEATURE:
<223> OTHER INFORMATION: Dengue virus chimeric construct DENVax-4i

<400> SEQUENCE: 9

```
agttgttagt ctacgtggac cgacaaagac agattctttg agggagctaa gctcaatgta     60
gttctaacag tttttaatt agagagcaga tctctgatga ataaccaacg gaaaaaggcg    120
aaaaacacgc ctttcaatat gctgaaacgc gagagaaacc gcgtgtcgac tgtgcaacag    180
ctgacaaaga gattctcact tggaatgctg cagggacgag gaccattaaa actgttcatg    240
gccctggtgg cgttccttcg tttcctaaca atcccaccaa cagcagggat attgaagaga    300
tggggaacaa ttaaaaaatc aaaagctatt aatgttttga gagggttcag gaaagagatt    360
ggaaggatgc tgaacatctt gaataggaga cgcagctctg caggcatgat cattatgctg    420
attccaacag tgatggcgtt ccatttaacc acgcgtgatg gcgaacccct catgatagtg    480
gcaaaacatg aaagggggag acctctcttg tttaagacaa cagaggggat caacaaatgc    540
actctcattg ccatggactt gggtgaaatg tgtgaggaca ctgtcacgta taaatgcccc    600
```

-continued

```
ttactggtca ataccgaacc tgaagacatt gattgctggt gcaatctcac gtctacctgg     660
gtcatgtatg ggacatgcac ccagagcgga gaacggagac gagagaagcg ctcagtagct     720
ttaacaccac attcaggaat gggattggaa acaagagctg agacatggat gtcatcggaa     780
ggggcttgga agcatgctca gagagtagag agctggatac tcagaaaccc aggattcgcg     840
ctcttggcag gatttatggc ttatatgatt gggcaaacag gaatccagcg aactgtcttc     900
tttgtcctaa tgatgctggt cgccccatcc tacggaatgc gatgcgtagg agtaggaaac     960
agagactttg tggaaggagt ctcaggtgga gcatgggtcg atctggtgct agaacatgga    1020
ggatgcgtca caaccatggc ccagggaaaa ccaaccttgg attttgaact gactaagaca    1080
acagccaagg aagtggctct gttaagaacc tattgcattg aagcctcaat atcaaacata    1140
accacggcaa caagatgtcc aacgcaagga gagccttatc taaaagagga acaagaccaa    1200
cagtacattt gccggagaga tgtggtagac agagggtggg gcaatggctg tggcttgttt    1260
ggaaaaggag gagttgtgac atgtgcgaag ttttcatgtt cggggaagat aacaggcaat    1320
ttggtccaaa ttgagaacct tgaatacaca gtggttgtaa cagtccacaa tggagacacc    1380
catgcagtag gaaatgacac gtccaatcat ggagttacag ccacgataac tcccaggtca    1440
ccatcggtgg aagtcaaatt gccggactat ggagaactaa cactcgattg tgaacccagg    1500
tctggaattg actttaatga gatgattctg atgaaaatga aaaagaaaac atggcttgtg    1560
cataagcaat ggtttttgga tctacctcta ccatggacag caggagcaga cacatcagag    1620
gttcactgga attacaaaga gagaatggtg acatttaagg ttcctcatgc caagagacag    1680
gatgtgacag tgctgggatc tcaggaagga gccatgcatt ctgccctcgc tggagccaca    1740
gaagtggact ccggtgatgg aaatcacatg tttgcaggac atctcaagtg caaagtccgt    1800
atggagaaat tgagaatcaa gggaatgtca tacacgatgt gttcaggaaa gttctcaatt    1860
gacaaagaga tggcagaaac acagcatggg acaacagtgg tgaaagtcaa gtatgaaggt    1920
gctggagctc cgtgtaaagt ccccatagag ataagagatg tgaacaagga aaaagtggtt    1980
gggcgtatca tctcatccac ccctttggct gagaatacca acagtgtaac caacatagag    2040
ttagaacccc cctttgggga cagctacata gtgataggtg ttggaaacag tgcattaaca    2100
ctccattggt tcaggaaagg gagttccatt ggcaagatgt ttgagtccac atacagaggt    2160
gcaaaacgaa tggccattct aggtgaaaca gcttgggatt ttggttccgt tggtggactg    2220
ttcacatcat tgggaaaggc tgtgcaccag gtttttggaa gtgtgtatac aaccctgttt    2280
ggaggagtct catggatgat tagaatccta attgggttcc tagtgttgtg gattggcacg    2340
aactcaagga acacttcaat ggctatgacg tgcatagctg ccggcattgt gacactgtat    2400
ttgggagtca tggtgcaggc cgatagtggt tgcgttgtga gctggaaaaa caaagaactg    2460
aaatgtggca gtgggatttt catcacagac aacgtgcaca catggacaga acaatacaag    2520
ttccaaccag aatccccttc aaaactagct tcagctatcc agaaagccca tgaagaggac    2580
atttgtggaa tccgctcagt aacaagactg gagaatctga tgtggaaaca aataacacca    2640
gaattgaatc acattctatc agaaaatgag gtgaagttaa ctattatgac aggagacatc    2700
aaaggaatca tgcaggcagg aaaacgatct ctgcggcctc agcccactga gctgaagtat    2760
tcatggaaaa catggggcaa agcaaaaatg ctctctacag agtctcataa ccagaccttt    2820
ctcattgatg gccccgaaac agcagaatgc cccaacacaa atagagcttg gaattcgttg    2880
gaagttgaag actatggctt tggagtattc accaccaata tatggctaaa attgaaagaa    2940
```

aaacaggatg tattctgcga ctcaaaactc atgtcagcgg ccataaaaga caacagagcc 3000
gtccatgccg atatgggtta ttggatagaa agtgcactca atgacacatg gaagatagag 3060
aaagcctctt tcattgaagt taaaaactgc cactggccaa aatcacacac cctctggagc 3120
aatggagtgc tagaaagtga gatgataatt ccaaagaatc tcgctggacc agtgtctcaa 3180
cacaactata gaccaggcta ccatacacaa ataacaggac catggcatct aggtaagctt 3240
gagatggact ttgatttctg tgatggaaca acagtggtag tgactgagga ctgcggaaat 3300
agaggaccct ctttgagaac aaccactgcc tctggaaaac tcataacaga atggtgctgc 3360
cgatcttgca cattaccacc gctaagatac agaggtgagg atgggtgctg gtacgggatg 3420
gaaatcagac cattgaagga gaaagaagag aatttggtca actccttggt cacagctgga 3480
catgggcagg tcgacaactt ttcactagga gtcttgggaa tggcattgtt cctggaggaa 3540
atgcttagga cccgagtagg aacgaaacat gcaatactac tagttgcagt ttcttttgtg 3600
acattgatca cagggaacat gtcctttaga gacctgggaa gagtgatggt tatggtaggc 3660
gccactatga cggatgacat aggtatgggc gtgacttatc ttgccctact agcagccttc 3720
aaagtcagac caacttttgc agctggacta ctcttgagaa agctgacctc caaggaattg 3780
atgatgacta ctataggaat tgtactcctc tcccagagca ccataccaga gaccattctt 3840
gagttgactg atgcgttagc cttaggcatg atggtcctca aaatggtgag aaatatggaa 3900
aagtatcaat tggcagtgac tatcatggct atcttgtgcg tcccaaacgc agtgatatta 3960
caaaacgcat ggaaagtgag ttgcacaata ttggcagtgg tgtccgtttc cccactgttc 4020
ttaacatcct cacagcaaaa aacagattgg ataccattag cattgacgat caaaggtctc 4080
aatccaacag ctatttttct aacaaccctc tcaagaacca gcaagaaaag gagctggcca 4140
ttaaatgagg ctatcatggc agtcgggatg gtgagcattt tagccagttc tctcctaaaa 4200
aatgatattc ccatgacagg accattagtg gctggagggc tcctcactgt gtgctacgtg 4260
ctcactggac gatcggccga tttggaactg gagagagcag ccgatgtcaa atgggaagac 4320
caggcagaga tatcaggaag cagtccaatc ctgtcaataa caatatcaga agatggtagc 4380
atgtcgataa aaaatgaaga ggaagaacaa acactgacca tactcattag aacaggattg 4440
ctggtgatct caggactttt tcctgtatca ataccaatca cggcagcagc atggtacctg 4500
tgggaagtga agaaacaacg ggccggagta ttgtgggatg ttccttcacc cccacccatg 4560
ggaaaggctg aactggaaga tggagcctat agaattaagc aaaaagggat tcttggatat 4620
tcccagatcg gagccggagt ttacaaagaa ggaacattcc atacaatgtg gcatgtcaca 4680
cgtggcgctg ttctaatgca taaaggaaag aggattgaac catcatgggc ggacgtcaag 4740
aaagacctaa tatcatatgg aggaggctgg aagttagaag gagaatggaa ggaaggagaa 4800
gaagtccagg tattggcact ggagcctgga aaaaatccaa gagccgtcca aacgaaacct 4860
ggtcttttca aaaccaacgc cggaacaata ggtgctgtat ctctggactt ttctcctgga 4920
acgtcaggat ctccaattat cgacaaaaaa ggaaaagttg tgggtcttta tggtaatggt 4980
gttgttacaa ggagtggagc atatgtgagt gctatagccc agactgaaaa aagcattgaa 5040
gacaacccag agatcgaaga tgacattttc cgaaagagaa gactgaccat catggacctc 5100
cacccaggag cgggaaagac gaagagatac cttccggcca tagtcagaga agctataaaa 5160
cggggtttga gaacattaat cttggccccc actagagttg tggcagctga aatggaggaa 5220
gcccttagag gacttccaat aagataccag accccagcca tcagagctgt gcacaccggg 5280
cgggagattg tggacctaat gtgtcatgcc acatttacca tgaggctgct atcaccagtt 5340

-continued

```
agagtgccaa actacaacct gattatcatg gacgaagccc atttcacaga cccagcaagt   5400
atagcagcta gaggatacat ctcaactcga gtggagatgg gtgaggcagc tgggattttt   5460
atgacagcca ctcccccggg aagcagagac ccatttcctc agagcaatgc accaatcata   5520
gatgaagaaa gagaaatccc tgaacgctcg tggaattccg gacatgaatg ggtcacggat   5580
tttaaaggga agactgtttg gttcgttcca agtataaaag caggaaatga tatagcagct   5640
tgcctgagga aaaatggaaa gaaagtgata caactcagta ggaagacctt tgattctgag   5700
tatgtcaaga ctagaaccaa tgattgggac ttcgtggtta caactgacat ttcagaaatg   5760
ggtgccaatt tcaaggctga gagggttata gaccccagac gctgcatgaa accagtcata   5820
ctaacagatg gtgaagagcg ggtgattctg gcaggaccta tgccagtgac ccactctagt   5880
gcagcacaaa gaagagggag aataggaaga aatccaaaaa atgagaatga ccagtacata   5940
tacatggggg aacctctgga aaatgatgaa gactgtgcac actggaaaga agctaaaatg   6000
ctcctagata acatcaacac gccagaagga atcattccta gcatgttcga accagagcgt   6060
gaaaaggtgg atgccattga tggcgaatac cgcttgagag gagaagcaag gaaaaccttt   6120
gtagacttaa tgagaagagg agacctacca gtctggttgg cctacagagt ggcagctgaa   6180
ggcatcaact acgcagacag aaggtggtgt tttgatggag tcaagaacaa ccaaatccta   6240
gaagaaaacg tggaagttga aatctggaca aaagaagggg aaaggaagaa attgaaaccc   6300
agatggttgg atgctaggat ctattctgac ccactggcgc taaaagaatt taaggaattt   6360
gcagccggaa gaaagtctct gaccctgaac ctaatcacag aaatgggtag gctcccaacc   6420
ttcttgactc agaaggcaag agacgcactg gacaacttag cagtgctgca cacggctgag   6480
gcaggtggaa gggcgtacaa ccatgctctc agtgaactgc cggagaccct ggagacattg   6540
cttttactga cacttctggc tacagtcacg ggagggatct tttattcttg gatgagcgca   6600
aggggcatag ggaagatgac cctgggaatg tgctgcataa tcacggctag catcctccta   6660
tggtacgcac aaatacagcc acactggata gcagcttcaa taatactgga gtttttctc    6720
atagttttgc ttattccaga acctgaaaaa cagagaacac cccaagacaa ccaactgacc   6780
tacgttgtca tagccatcct cacagtggtg gccgcaacca tggcaaacga gatgggtttc   6840
ctagaaaaaa cgaagaaaga tctcggattg ggaagcattg caacccagca acccgagagc   6900
aacatcctgg acatagatct acgtcctgca tcagcatgga cgctgtatgc cgtggccaca   6960
acatttgtta caccaatgtt gagacatagc attgaaaatt cctcagtgaa tgtgtcccta   7020
acagctatag ccaaccaagc cacagtgtta atgggtctcg ggaaaggatg gccattgtca   7080
aagatggaca tcggagttcc ccttctcgcc attggatgct actcacaagt caaccccata   7140
actctcacag cagctctttt cttattggta gcacattatg ccatcatagg gccaggactc   7200
caagcaaaag caaccagaga agctcagaaa agagcagcgg cgggcatcat gaaaaaccca   7260
actgtcgatg gaataacagt gattgaccta gatccaatac cttatgatcc aaagtttgaa   7320
aagcagttgg gacaagtaat gctcctagtc ctctgcgtga ctcaagtatt gatgatgagg   7380
actacatggg ctctgtgtga ggctttaacc ttagctaccg ggcccatctc cacattgtgg   7440
gaaggaaatc cagggaggtt ttggaacact accattgcgg tgtcaatggc taacattttt   7500
agagggagtt acttggccgg agctggactt ctcttttcta ttatgaagaa cacaaccaac   7560
acaagaaggg gaactggcaa cataggagag acgcttggag agaaatggaa aagccgattg   7620
aacgcattgg gaaaaagtga attccagatc tacaagaaaa gtggaatcca ggaagtggat   7680
```

-continued

```
agaaccttag caaaagaagg cattaaaaga ggagaaacgg accatcacgc tgtgtcgcga   7740
ggctcagcaa aactgagatg gttcgttgag agaaacatgg tcacaccaga agggaaagta   7800
gtggacctcg gttgtggcag aggaggctgg tcatactatt gtggaggact aaagaatgta   7860
agagaagtca aaggcctaac aaaaggagga ccaggacacg aagaacccat ccccatgtca   7920
acatatgggt ggaatctagt gcgtcttcaa agtggagttg acgttttctt catcccgcca   7980
gaaaagtgtg acacattatt gtgtgacata ggggagtcat caccaaatcc cacagtggaa   8040
gcaggacgaa cactcagagt ccttaactta gtagaaaatt ggttgaacaa caacactcaa   8100
ttttgcataa aggttctcaa cccatatatg ccctcagtca tagaaaaaat ggaagcacta   8160
caaaggaaat atggaggagc cttagtgagg aatccactct cacgaaactc cacacatgag   8220
atgtactggg tatccaatgc ttccgggaac atagtgtcat cagtgaacat gatttcaagg   8280
atgttgatca acagatttac aatgagatac aagaaagcca cttacgagcc ggatgttgac   8340
ctcggaagcg gaacccgtaa catcgggatt gaaagtgaga taccaaacct agatataatt   8400
gggaaaagaa tagaaaaaat aaagcaagag catgaaacat catggcacta tgaccaagac   8460
cacccataca aaacgtgggc ataccatggt agctatgaaa caaaacagac tggatcagca   8520
tcatccatgg tcaacggagt ggtcaggctg ctgacaaaac cttgggacgt cgtccccatg   8580
gtgacacaga tggcaatgac agacacgact ccatttggac aacagcgcgt tttaaaagag   8640
aaagtggaca cgagaaccca agaaccgaaa gaaggcacga agaaactaat gaaaataaca   8700
gcagagtggc tttggaaaga attagggaag aaaaagacac ccaggatgtg caccagagaa   8760
gaattcacaa gaaaggtgag aagcaatgca gccttggggg ccatattcac tgatgagaac   8820
aagtggaagt cggcacgtga ggctgttgaa gatagtaggt tttgggagct ggttgacaag   8880
gaaaggaatc tccatcttga aggaaagtgt gaaacatgtg tgtacaacat gatgggaaaa   8940
agagagaaga agctagggga attcggcaag gcaaaaggca gcagagccat atggtacatg   9000
tggcttggag cacgcttctt agagtttgaa gccctaggat tcttaaatga agatcactgg   9060
ttctccagag agaactccct gagtggagtg gaaggagaag ggctgcacaa gctaggttac   9120
attctaagag acgtgagcaa gaaagaggga ggagcaatgt atgccgatga caccgcagga   9180
tgggatacaa gaatcacact agaagaccta aaaaatgaag aaatggtaac aaaccacatg   9240
gaaggagaac acaagaaact agccgaggcc attttcaaac taacgtacca aaacaaggtg   9300
gtgcgtgtgc aaagaccaac accaagaggc acagtaatgg acatcatatc gagaagagac   9360
caaagaggta gtggacaagt tggcacctat ggactcaata ctttcaccaa tatggaagcc   9420
caactaatca gacagatgga gggagaagga gtctttaaaa gcattcagca cctaacaatc   9480
acagaagaaa tcgctgtgca aaactggtta gcaagagtgg ggcgcgaaag gttatcaaga   9540
atggccatca gtggagatga ttgtgttgtg aaacctttag atgacaggtt cgcaagcgct   9600
ttaacagctc taaatgacat gggaaagatt aggaaagaca tacaacaatg ggaaccttca   9660
agaggatgga atgattggac acaagtgccc ttctgttcac accatttcca tgagttaatc   9720
atgaaagacg gtcgcgtact cgttgttcca tgtagaaacc aagatgaact gattggcaga   9780
gcccgaatct cccaaggagc agggtggtct ttgcgggaga cggcctgttt ggggaagtct   9840
tacgcccaaa tgtggagctt gatgtacttc cacagacgcg acctcaggct ggcggcaaat   9900
gctatttgct cggcagtacc atcacattgg gttccaacaa gtcgaacaac ctggtccata   9960
catgctaaac atgaatggat gacaacggaa gacatgctga cagtctggaa cagggtgtgg  10020
attcaagaaa acccatggat ggaagacaaa actccagtgg aatcatggga ggaaatccca  10080
```

```
tacttgggga aaagagaaga ccaatggtgc ggctcattga ttgggttaac aagcagggcc  10140

acctgggcaa agaacatcca agcagcaata aatcaagtta gatcccttat aggcaatgaa  10200

gaatacacag attacatgcc atccatgaaa agattcagaa gagaagagga agaagcagga  10260

gttctgtggt agaaagcaaa actaacatga aacaaggcta gaagtcaggt cggattaagc  10320

catagtacgg aaaaaactat gctacctgtg agccccgtcc aaggacgtta aaagaagtca  10380

ggccatcata aatgccatag cttgagtaaa ctatgcagcc tgtagctcca cctgagaagg  10440

tgtaaaaaat ccgggaggcc acaaaccatg gaagctgtac gcatggcgta gtggactagc  10500

ggttagagga gacccctccc ttacaaatcg cagcaacaat gggggcccaa ggcgagatga  10560

agctgtagtc tcgctggaag gactagaggt tagaggagac ccccccgaaa caaaaaacag  10620

catattgacg ctgggaaaga ccagagatcc tgctgtctcc tcagcatcat tccaggcaca  10680

gaacgccaga aaatggaatg gtgctgttga atcaacaggt tc                     10722
```

<210> SEQ ID NO 10
<211> LENGTH: 10699
<212> TYPE: DNA
<213> ORGANISM: Artificial
<220> FEATURE:
<223> OTHER INFORMATION: Synthetic construct

<400> SEQUENCE: 10

```
agttgttagt ctacgtggac cgacaagaac agtttcgact cggaagcttg cttaacgtag     60

tgctgacagt tttttattag agagcagatc tctgatgaac aaccaacgga aaaagacggg    120

aaaaccgtct atcaatatgc tgaaacgcgt gagaaaccgt gtgtcaactg gatcacagtt    180

ggcgaagaga ttctcaagag gattgctgaa cggccaagga ccaatgaaat tggttatggc    240

atttatagct ttcctcagat ttctagccat tccaccgaca gcaggagtct tggctagatg    300

gggtaccttt aagaagtcgg gggctattaa ggtcttaaaa ggcttcaaga aggagatctc    360

aaacatgctg agcattatca acaaacggaa aaagacatcg ctctgtctca tgatgatgtt    420

accagcaaca cttgctttcc acttaacttc acgagatgga gagccgcgca tgattgtggg    480

gaagaatgaa agaggaaaat ccctactttt caagacagcc tctggaatca acatgtgcac    540

actcatagcc atggatctgg gagagatgtg tgatgacacg gtcacttaca aatgccccca    600

cattaccgaa gtggagcctg aagacattga ctgctggtgc aaccttacat cgacatgggt    660

gacttatgga acatgcaatc aagctggaga gcatagacgc gataagagat cagtggcgtt    720

agctccccat gttggcatgg gactggacac acgcactcaa acctggatgt cggctgaagg    780

agcttggaga caagtcgaga aggtagagac atgggccctt aggcacccag ggtttaccat    840

actagcccta tttcttgccc attacatagg cacttccttg acccagaaag tggttatttt    900

tatactatta atgctggtta ccccatccat gacaatgaga tgtgtaggag taggaaacag    960

agattttgtg gaaggcctat cgggagctac gtgggttgac gtggtgctcg agcacggtgg   1020

gtgtgtgact accatggcta agaacaagcc cacgctggac atagagcttc agaagaccga   1080

ggccacccaa ctggcgaccc taaggaagct atgcattgag ggaaaaatta ccaacataac   1140

aaccgactca agatgtccca cccaagggga agcgatttta cctgaggagc aggaccagaa   1200

ctacgtgtgt aagcatacat acgtggacag aggctgggga aacggttgtg gtttgtttgg   1260

caagggaagc ttggtgacat gcgcgaaatt tcaatgttta gaatcaatag agggaaaagt   1320

ggtgcaacat gagaacctca aatacaccgt catcatcaca gtgcacacag gagaccaaca   1380
```

-continued

```
ccaggtggga aatgaaacgc agggagtcac ggctgagata acaccccagg catcaaccgc   1440
tgaagccatt ttacctgaat atggaaccct cgggctagaa tgctcaccac ggacaggttt   1500
ggatttcaat gaaatgatct cattgacaat gaagaacaaa gcatggatgg tacatagaca   1560
atggttcttt gacttacccc taccatggac atcaggagct acagcagaaa caccaacttg   1620
gaacaggaaa gagcttcttg tgacatttaa aaatgcacat gcaaaaaagc aagaagtagt   1680
tgttcttgga tcacaagagg gagcaatgca tacagcactg acaggagcta cagagatcca   1740
aacctcagga ggcacaagta tctttgcggg gcacttaaaa tgtagactca agatggacaa   1800
attggaactc aaggggatga gctatgcaat gtgcttgagt agctttgtgt tgaagaaaga   1860
agtctccgaa acgcagcatg ggacaatact cattaaggtt gagtacaaag gggaagatgc   1920
accctgcaag attcctttct ccacggagga tggacaagga aaagctcaca atggcagact   1980
gatcacagcc aatccagtgg tgaccaagaa ggaggagcct gtcaacattg aggctgaacc   2040
tccttttgga gaaagtaaca tagtaattgg aattggagac aaagccctga aaatcaactg   2100
gtacaagaag ggaagctcga ttgggaagat gttcgaggcc actgccagag gtgcaaggcg   2160
catggccatc ttgggagaca cagcctggga ctttggatca gtgggtggtg ttttgaattc   2220
attagggaaa atggtccacc aaatatttgg gagtgcttac acagccctat ttggtggagt   2280
ctcctggatg atgaaaattg gaataggtgt cctcttaacc tggatagggt tgaactcaaa   2340
aaatacttct atgtcatttt catgcatcgc gataggaatc attacactct atctgggagc   2400
cgtggtgcaa gctgacatgg ggtgtgtcat aaactggaaa ggcaaagaac tcaaatgtgg   2460
aagtggaatt ttcgtcacta atgaggtcca cacctggaca gagcaataca aatttcaagc   2520
agactccccc aagagactgg caacagccat tgcaggcgct tgggaaaatg gagtgtgcgg   2580
aattaggtca acaaccagaa tggagaacct cttgtggaag caaatagcca atgaactgaa   2640
ttacatatta tgggaaaaca acattaaatt aacggtagtt gtaggcgaca taactggggt   2700
cttagagcaa gggaaaagaa cactaacacc acaacccatg gagctaaaat attcttggaa   2760
aacatgggga aaggcaaaaa tagtgacagc tgaaacacaa aattcctctt tcataataga   2820
tgggccaagc acaccggagt gtccaagtgc ctcaagagca tggaatgtgt gggaggtgga   2880
ggattacggg ttcggagttt tcacaaccaa catatggctg aaactccgag aggtgtacac   2940
ccaactatgt gaccataggc taatgtcggc agccgtcaag gatgagaggg ctgtacatgc   3000
cgacatgggc tattggatag aaagccaaaa gaatgggagt tggaagctag aaaaagcatc   3060
cttcatagag gtgaaaacct gcacatggcc aaaatcacac actctctgga gcaatggtgt   3120
gctagagagt gacatgatta tcccaaagag tctagctggt cccatttcgc aacacaacca   3180
caggcccggg taccacaccc aaacggcagg accctggcac ttaggaaaat tggagctgga   3240
cttcaactat tgtgaaggaa caacagttgt catctcagaa aactgtggga caagaggccc   3300
atcattgaga acaacaacgg tgtcagggaa gttgatacac gaatggtgct gccgctcgtg   3360
cacacttcct cccctacgat acatgggaga agacggctgc tggtatggca tggaaatcag   3420
acccattaat gagaaagaag agaatatggt aaagtctcta gcctcagcag ggagtggaaa   3480
ggtggacaac ttcacaatgg gtgtcttgtg tttggcaatc ctctttgaag aggtgatgag   3540
aggaaaattt gggaaaaaac acatgattgc aggggttctc ttcacgtttg tgctcctcct   3600
ctcagggcaa ataacatgga gagacatggc gcacacactc ataatgattg ggtccaacgc   3660
ctctgacaga atggggatgg gcgtcactta cctagctcta attgcaacat ttaaaattca   3720
gccattcctg gctttgggat tcttcctgag gaaactgaca tctagagaaa atttattgct   3780
```

-continued

```
gggagttggg ttggccatgg cagcaacgtt acgactgcca gaggacattg aacagatggc   3840
gaatggaatt gctttggggc tcatggctct taaactgata acacaatttg aaacatacca   3900
actatggacg gcattagttt ccctaacgtg ttcaaataca attttcacgt tgactgttgc   3960
ctggagaaca gccactctga ttttagccgg aatttcgctt ttgccagtgt gccagtcttc   4020
gagcatgagg aaaacagatt ggctcccaat gactgtggca gctatgggag ctcaacccct   4080
accacttttt attttcagtc tgaaagatac actcaaaagg agaagctggc cactgaatga   4140
gggggtgatg gcagttggac ttgtgagcat tctagctagt tctctcctta ggaatgatgt   4200
gcctatggct ggaccattag tggctggggg cttgctgata gcgtgctacg tcataactgg   4260
cacgtcagca gacctcactg tagaaaaagc agcagatgta acatgggagg aagaggccga   4320
gcaaacagga gtgtcccaca atttaatggt cacagttgat gatgatggaa caatgagaat   4380
aaaagatgac gagactgaga acatcttaac agtgctttta aaaacagcac tactaatagt   4440
atcaggcatc tttccatact ccatacccgc aacactgttg gtctggcata cttggcaaaa   4500
gcaaacccaa agatccggcg tcctatggga cgtacccagc cccccagaga cacagaaagc   4560
ggaactggaa gaaggggtct ataggatcaa acagcaagga atttttggga aaacccaagt   4620
gggggttgga gtacagaaag aaggagtttt ccacaccatg tggcatgtca caagaggggc   4680
agtgttgaca cacaatggga aaagactgga accaaactgg gctagcgtga aaaaagatct   4740
gatttcatac ggaggaggat ggagattgag tgcacaatgg caaaaggggg aggaggtgca   4800
ggttattgcc gtagagcctg ggaagaaccc aaagaacttt caaaccatgc caggcatttt   4860
tcagacaaca acaggggaaa taggagcaat tgcactggat ttcaagcctg gaacttcagg   4920
atctcccatc ataaacagag agggaaaggt agtgggactg tatggcaatg gagtggttac   4980
aaagaatgga ggctatgtca gtggaatagc gcaaacaaat gcagaaccag atggaccgac   5040
accagagttg gaagaagaga tgttcaaaaa gcgaaatcta accataatgg atctccatcc   5100
tgggtcagga aagacgcgga aatatcttcc agctattgtt agagaggcaa tcaagagacg   5160
cttaaggact ctaattttgg caccaacaag ggtagttgca gctgagatgg aagaagcatt   5220
gaaagggctc ccaataaggt atcaaacaac tgcaacaaaa tctgaacaca caggaagaga   5280
gattgttgat ctaatgtgtc acgcaacgtt cacaatgcgc ttgctgtcac cagtcagggt   5340
tccaaactac aacttgataa taatggatga ggcccatttc acagacccag ccagtatagc   5400
ggctagaggg tacatatcaa ctcgtgtagg aatgggagag gcagccgcaa ttttcatgac   5460
agcaacaccc cctggaacag ctgatgcctt tcctcagagc aacgctccaa ttcaagatga   5520
agagagagac ataccggaac gctcatggaa ttcaggcaat gaatggatta ctgactttgt   5580
tgggaagaca gtgtggtttg tccctagcat caaagccgga aatgacatag caaactgctt   5640
gcggaaaaat ggaaaaaagg ttattcaact cagcaggaag acctttgaca cagaatatca   5700
aaagaccaaa ctgaatgatt gggactttgt ggtgacaaca gacatttcag aaatgggagc   5760
caatttcaaa gcagatagag tgatcgaccc aagaagatgt ctcaagccgg tgattttgac   5820
agatggaccc gagcgggtga tcctggctgg accaatgcca gtcaccgtag cgagcgctgc   5880
gcaaaggaga gggagagttg gcaggaaccc acaaaaagaa aatgaccagt acatattcat   5940
gggccagcct ctcaacaatg atgaagacca tgctcactgg acagaagcaa aaatgctgct   6000
ggacaacatc aacacaccag aagggattat accagctctc tttgaaccag aaagggagaa   6060
gtcagccgcc atagacggcg aataccgcct gaagggtgag tccaggaaga ctttcgtgga   6120
```

-continued

```
actcatgagg aggggtgacc tcccagtttg gctagcccat aaagtagcat cagaagggat   6180
caaatataca gatagaaaat ggtgctttga tggagaacgt aataatcaaa ttttagagga   6240
gaatatggat gtggaaatct ggacaaagga aggagaaaag aaaaaactga gacctaggtg   6300
gcttgatgcc cgcacttatt cagatccttt agcactcaaa gaattcaagg attttgcagc   6360
tggcagaaag tcaatcgccc ttgatcttgt gacagaaata ggaagagtgc cttcacactt   6420
agcccacaga acgagaaacg ccctggataa tttggtgatg ctgcacacgt cagaacatgg   6480
cggtagggcc tacaggcatg cagtggagga actaccagaa acgatggaaa cactcttact   6540
cctgggactg atgatcttgt taacaggtgg agcaatgctc ttcttgatat caggtaaagg   6600
gattggaaag acttcaatag gactcatttg tgtaattgct tccagcggca tgttatggat   6660
ggctgatgtc ccactccaat ggatcgcatc ggctatagtc ctggagtttt ttatgatggt   6720
gttgctcata ccagaaccag aaaagcagag aactccccaa gacaaccaac tcgcatatgt   6780
cgtgataggc atacttacat tggctgcaat agtagcggcc aatgaaatgg gactgttgga   6840
aactacaaag agagatttag gaatgtctaa agaaccaggt gttgtttctc caaccagcta   6900
tttggatgtg gacttgcacc cagcatcagc ctggacattg tacgccgtgg ccacaacagt   6960
aataacacca atgttgagac acaccataga gaattccaca gcaaatgtgt ctctggcagc   7020
catagctaac caggcagtgg tcctgatggg tttagacaaa ggatggccga tatcgaaaat   7080
ggacttgggc gtaccactat tggcactggg ttgctattca caagtgaacc cactaactct   7140
tgcagcggca gtacttttgc tagtcacaca ttatgcaatt ataggtccag gattgcaggc   7200
aaaagccacc cgtgaagctc agaaaaggac agctgctgga ataatgaaga atccaacggt   7260
ggatggaata atgacaatag acctagatcc tgtaatatat gattcaaaat ttgaaaagca   7320
actaggacag gtcatgctcc tggttctgtg tgcagtccaa cttttattga tgagaacatc   7380
atgggccttg tgtgaagttc taaccctagc cacaggacca ataacaacac tctgggaagg   7440
atcacctggg aagttctgga acaccacgat agctgtttcc atggcgaaca tctttagagg   7500
gagctattta gcaggagctg ggcttgcttt ttctatcatg aaatcagttg gaacaggaaa   7560
gagaggaaca gggtcacaag gtgaaacctt aggagaaaag tggaaaaaga aattaaatca   7620
gttatcccgg aaagagtttg acctttacaa gaaatccgga atcaccgaag tggatagaac   7680
agaagccaaa gaagggttaa aaagaggaga aataacacac catgccgtgt ccagaggcag   7740
cgcaaaactt caatggttcg tggagagaaa catggtcatt cctgaaggaa gagtcataga   7800
cctaggctgt ggaagaggag gctggtcata ttactgtgca ggactgaaaa aagttacaga   7860
agtgcgagga tacacaaaag gcggcccagg acacgaagaa ccagtaccta tgtctacata   7920
cggatggaac atagtcaagt taatgagtgg aaaggatgtt ttttatctgc cacctgaaaa   7980
gtgtgatacc ctattgtgtg acattggaga atcttcacca agcccaacag tggaagaaag   8040
cagaaccata agagttttga agatggttga accatggcta aagaacaacc agttttgcat   8100
taaagtattg aacccataca tgccaactgt gattgagcac ttagaaagac tacaaaggaa   8160
acatggagga atgcttgtga gaaatccact ctcacgaaac tccacgcacg aaatgtattg   8220
gatatccaat ggtacaggca atatcgtctc ttcagtcaac atggtatcca gattgctact   8280
gaacagattc acaatgacac acaggagacc caccatagag aaagatgtgg atctaggagc   8340
aggaacccga catgtcaatg cggaaccaga aacacccaac atggatgtca ttggggaaag   8400
aataaaaagg atcaaagagg agcatagttc aacatggcac tatgatgatg aaaatcctta   8460
caaaacgtgg gcttaccatg gatcctatga agtaaaagcc acaggctcag cctcctccat   8520
```

```
gataaatgga gtcgtgaaac tcctcacaaa accatgggat gtggtgccca tggtgacaca   8580
gatggcaatg acagatacaa ctccattcgg ccagcaaaga gtttttaaag agaaagtgga   8640
caccaggaca cctaggccca tgccaggaac aagaaaggtt atggagatca cagcggagtg   8700
gctttggagg accctgggaa ggaacaaaag acccagatta tgcacaaggg aggaattcac   8760
aaagaaggtc agaaccaacg cagctatggg cgctgtcttc acagaagaga accaatggga   8820
cagtgcgaga gctgctgttg aggacgaaga attttggaaa cttgtggaca gagaacgtga   8880
actccacaaa ctgggcaagt gtggaagctg cgtttacaac atgatgggca agagagagaa   8940
aaaacttgga gagtttggta aagcaaaagg cagtagggct atatggtaca tgtggttggg   9000
agccaggtac cttgagttcg aggcgctcgg attcctcaat gaagaccact ggttctcgcg   9060
tgaaaactct tacagtggag tagaaggaga aggactgcac aagctgggat acatcttgag   9120
agatatttcc aagatacccg gaggagccat gtatgctgat gacacagccg gttgggacac   9180
aagaataaca gaagatgacc tgcacaatga ggaaaaaatc acacagcaga tggaccctga   9240
acacaggcag ctagcgaacg ctatattcaa gctcacatac caaaacaaag tggtcaaagt   9300
ccaacgacca actccaaagg gcacggtaat ggacatcata tctaggaaag accaaagagg   9360
cagtggacag gtgggaactt atggtctgaa cacattcacc aacatggaag cccagctaat   9420
cagacaaatg gaaggagaag gcgtgttgtc aaaggcagac ctcgagaacc cccatccgct   9480
agagaagaaa attacacaat ggttggaaac taaaggagtg gaaaggttaa aaagaatggc   9540
catcagcggg gatgattgcg ttgtgaaacc aatcgacgac agattcgcca atgccctgct   9600
tgccctgaac gatatgggaa aggttagaaa ggacatacct caatggcagc catcaaaggg   9660
atggcatgat tggcaacagg tccccttctg ctcccaccac tttcatgaat tgatcatgaa   9720
agatggaaga aagttggtag ttccctgcag accccaggac gaactaatag gaagagcgag   9780
aatctcccaa ggagcaggat ggagccttag agaaactgca tgtctaggga aagcctacgc   9840
tcaaatgtgg gctctcatgt attttcacag aagagatctt agactagcat ccaacgccat   9900
atgttcagca gtaccagtcc actgggtccc cacgagcaga acgacatggt ctattcatgc   9960
tcaccatcag tggatgacta cagaagacat gcttactgtc tggaacaggg tgtggataga  10020
ggacaatcca tggatggaag acaaaactcc agtcacaacg tgggaagatg ttccatatct  10080
agggaagaga gaagaccaat ggtgcggatc actcataggt ctcacttcca gagcaacctg  10140
ggcccagaac atactcacag caatccaaca ggtgagaagc ctcataggca atgaagagtt  10200
tctggactac atgccttcga tgaagagatt caggaaggag gaggagtcag agggagccat  10260
ttggtaaaag caggaggtaa actgtcaggc cacattaagc cacagtacgg aagaagctgt  10320
gcagcctgtg agccccgtcc aaggacgtta aaagaagaag tcaggcccaa aagccacggt  10380
ttgagcaaac cgtgctgcct gtagctccgt cgtggggacg taaagcctgg gaggctgcaa  10440
accgtggaag ctgtacgcac ggtgtagcag actagtggtt agaggagacc cctcccatga  10500
cacaacgcag cagcggggcc cgagcactga gggaagctgt acctccttgc aaaggactag  10560
aggttagagg agaccccccg caaacaaaaa cagcatattg acgctgggag agaccagaga  10620
tcctgctgtc tcctcagcat cattccaggc acagaacgcc agaaaatgga atggtgctgt  10680
tgaatcaaca ggttctagt                                              10699
```

<210> SEQ ID NO 11
<211> LENGTH: 3390
<212> TYPE: PRT

<213> ORGANISM: Artificial
<220> FEATURE:
<223> OTHER INFORMATION: Synthetic construct

<400> SEQUENCE: 11

```
Met Asn Asn Gln Arg Lys Lys Thr Gly Lys Pro Ser Ile Asn Met Leu
1               5                   10                  15

Lys Arg Val Arg Asn Arg Val Ser Thr Gly Ser Gln Leu Ala Lys Arg
            20                  25                  30

Phe Ser Arg Gly Leu Leu Asn Gly Gln Gly Pro Met Lys Leu Val Met
        35                  40                  45

Ala Phe Ile Ala Phe Leu Arg Phe Leu Ala Ile Pro Pro Thr Ala Gly
    50                  55                  60

Val Leu Ala Arg Trp Gly Thr Phe Lys Lys Ser Gly Ala Ile Lys Val
65                  70                  75                  80

Leu Lys Gly Phe Lys Lys Glu Ile Ser Asn Met Leu Ser Ile Ile Asn
                85                  90                  95

Lys Arg Lys Lys Thr Ser Leu Cys Leu Met Met Met Leu Pro Ala Thr
            100                 105                 110

Leu Ala Phe His Leu Thr Ser Arg Asp Gly Glu Pro Arg Met Ile Val
        115                 120                 125

Gly Lys Asn Glu Arg Gly Lys Ser Leu Leu Phe Lys Thr Ala Ser Gly
    130                 135                 140

Ile Asn Met Cys Thr Leu Ile Ala Met Asp Leu Gly Glu Met Cys Asp
145                 150                 155                 160

Asp Thr Val Thr Tyr Lys Cys Pro His Ile Thr Glu Val Glu Pro Glu
                165                 170                 175

Asp Ile Asp Cys Trp Cys Asn Leu Thr Ser Thr Trp Val Thr Tyr Gly
            180                 185                 190

Thr Cys Asn Gln Ala Gly Glu His Arg Arg Asp Lys Arg Ser Val Ala
        195                 200                 205

Leu Ala Pro His Val Gly Met Gly Leu Asp Thr Arg Thr Gln Thr Trp
    210                 215                 220

Met Ser Ala Glu Gly Ala Trp Arg Gln Val Glu Lys Val Glu Thr Trp
225                 230                 235                 240

Ala Leu Arg His Pro Gly Phe Thr Ile Leu Ala Leu Phe Leu Ala His
                245                 250                 255

Tyr Ile Gly Thr Ser Leu Thr Gln Lys Val Val Ile Phe Ile Leu Leu
            260                 265                 270

Met Leu Val Thr Pro Ser Met Thr Met Arg Cys Val Gly Val Gly Asn
        275                 280                 285

Arg Asp Phe Val Glu Gly Leu Ser Gly Ala Thr Trp Val Asp Val Val
    290                 295                 300

Leu Glu His Gly Gly Cys Val Thr Thr Met Ala Lys Asn Lys Pro Thr
305                 310                 315                 320

Leu Asp Ile Glu Leu Gln Lys Thr Glu Ala Thr Gln Leu Ala Thr Leu
                325                 330                 335

Arg Lys Leu Cys Ile Glu Gly Lys Ile Thr Asn Ile Thr Thr Asp Ser
            340                 345                 350

Arg Cys Pro Thr Gln Gly Glu Ala Ile Leu Pro Glu Glu Gln Asp Gln
        355                 360                 365

Asn Tyr Val Cys Lys His Thr Tyr Val Asp Arg Gly Trp Gly Asn Gly
    370                 375                 380

Cys Gly Leu Phe Gly Lys Gly Ser Leu Val Thr Cys Ala Lys Phe Gln
```

-continued

```
385                 390                 395                 400

Cys Leu Glu Ser Ile Glu Gly Lys Val Val Gln His Glu Asn Leu Lys
                405                 410                 415

Tyr Thr Val Ile Ile Thr Val His Thr Gly Asp Gln His Gln Val Gly
            420                 425                 430

Asn Glu Thr Gln Gly Val Thr Ala Glu Ile Thr Pro Gln Ala Ser Thr
        435                 440                 445

Ala Glu Ala Ile Leu Pro Glu Tyr Gly Thr Leu Gly Leu Glu Cys Ser
    450                 455                 460

Pro Arg Thr Gly Leu Asp Phe Asn Glu Met Ile Ser Leu Thr Met Lys
465                 470                 475                 480

Asn Lys Ala Trp Met Val His Arg Gln Trp Phe Phe Asp Leu Pro Leu
                485                 490                 495

Pro Trp Thr Ser Gly Ala Thr Ala Glu Thr Pro Thr Trp Asn Arg Lys
            500                 505                 510

Glu Leu Leu Val Thr Phe Lys Asn Ala His Ala Lys Lys Gln Glu Val
        515                 520                 525

Val Val Leu Gly Ser Gln Glu Gly Ala Met His Thr Ala Leu Thr Gly
    530                 535                 540

Ala Thr Glu Ile Gln Thr Ser Gly Gly Thr Ser Ile Phe Ala Gly His
545                 550                 555                 560

Leu Lys Cys Arg Leu Lys Met Asp Lys Leu Glu Leu Lys Gly Met Ser
                565                 570                 575

Tyr Ala Met Cys Leu Ser Ser Phe Val Leu Lys Lys Glu Val Ser Glu
            580                 585                 590

Thr Gln His Gly Thr Ile Leu Ile Lys Val Glu Tyr Lys Gly Glu Asp
        595                 600                 605

Ala Pro Cys Lys Ile Pro Phe Ser Thr Glu Asp Gly Gln Gly Lys Ala
    610                 615                 620

His Asn Gly Arg Leu Ile Thr Ala Asn Pro Val Val Thr Lys Lys Glu
625                 630                 635                 640

Glu Pro Val Asn Ile Glu Ala Glu Pro Pro Phe Gly Glu Ser Asn Ile
                645                 650                 655

Val Ile Gly Ile Gly Asp Lys Ala Leu Lys Ile Asn Trp Tyr Lys Lys
            660                 665                 670

Gly Ser Ser Ile Gly Lys Met Phe Glu Ala Thr Ala Arg Gly Ala Arg
        675                 680                 685

Arg Met Ala Ile Leu Gly Asp Thr Ala Trp Asp Phe Gly Ser Val Gly
    690                 695                 700

Gly Val Leu Asn Ser Leu Gly Lys Met Val His Gln Ile Phe Gly Ser
705                 710                 715                 720

Ala Tyr Thr Ala Leu Phe Gly Gly Val Ser Trp Met Met Lys Ile Gly
                725                 730                 735

Ile Gly Val Leu Leu Thr Trp Ile Gly Leu Asn Ser Lys Asn Thr Ser
            740                 745                 750

Met Ser Phe Ser Cys Ile Ala Ile Gly Ile Ile Thr Leu Tyr Leu Gly
        755                 760                 765

Ala Val Val Gln Ala Asp Met Gly Cys Val Ile Asn Trp Lys Gly Lys
    770                 775                 780

Glu Leu Lys Cys Gly Ser Gly Ile Phe Val Thr Asn Glu Val His Thr
785                 790                 795                 800

Trp Thr Glu Gln Tyr Lys Phe Gln Ala Asp Ser Pro Lys Arg Leu Ala
                805                 810                 815
```

-continued

```
Thr Ala Ile Ala Gly Ala Trp Glu Asn Gly Val Cys Gly Ile Arg Ser
            820                 825                 830

Thr Thr Arg Met Glu Asn Leu Leu Trp Lys Gln Ile Ala Asn Glu Leu
        835                 840                 845

Asn Tyr Ile Leu Trp Glu Asn Asn Ile Lys Leu Thr Val Val Val Gly
    850                 855                 860

Asp Ile Thr Gly Val Leu Glu Gln Gly Lys Arg Thr Leu Thr Pro Gln
865                 870                 875                 880

Pro Met Glu Leu Lys Tyr Ser Trp Lys Thr Trp Gly Lys Ala Lys Ile
                885                 890                 895

Val Thr Ala Glu Thr Gln Asn Ser Ser Phe Ile Ile Asp Gly Pro Ser
            900                 905                 910

Thr Pro Glu Cys Pro Ser Ala Ser Arg Ala Trp Asn Val Trp Glu Val
        915                 920                 925

Glu Asp Tyr Gly Phe Gly Val Phe Thr Thr Asn Ile Trp Leu Lys Leu
    930                 935                 940

Arg Glu Val Tyr Thr Gln Leu Cys Asp His Arg Leu Met Ser Ala Ala
945                 950                 955                 960

Val Lys Asp Glu Arg Ala Val His Ala Asp Met Gly Tyr Trp Ile Glu
                965                 970                 975

Ser Gln Lys Asn Gly Ser Trp Lys Leu Glu Lys Ala Ser Phe Ile Glu
            980                 985                 990

Val Lys Thr Cys Thr Trp Pro Lys  Ser His Thr Leu Trp  Ser Asn Gly
        995                 1000                1005

Val Leu  Glu Ser Asp Met Ile  Ile Pro Lys Ser Leu  Ala Gly Pro
    1010                1015                1020

Ile Ser  Gln His Asn His Arg  Pro Gly Tyr His Thr  Gln Thr Ala
    1025                1030                1035

Gly Pro  Trp His Leu Gly Lys  Leu Glu Leu Asp Phe  Asn Tyr Cys
    1040                1045                1050

Glu Gly  Thr Thr Val Val Ile  Ser Glu Asn Cys Gly  Thr Arg Gly
    1055                1060                1065

Pro Ser  Leu Arg Thr Thr Thr  Val Ser Gly Lys Leu  Ile His Glu
    1070                1075                1080

Trp Cys  Cys Arg Ser Cys Thr  Leu Pro Pro Leu Arg  Tyr Met Gly
    1085                1090                1095

Glu Asp  Gly Cys Trp Tyr Gly  Met Glu Ile Arg Pro  Ile Asn Glu
    1100                1105                1110

Lys Glu  Glu Asn Met Val Lys  Ser Leu Ala Ser Ala  Gly Ser Gly
    1115                1120                1125

Lys Val  Asp Asn Phe Thr Met  Gly Val Leu Cys Leu  Ala Ile Leu
    1130                1135                1140

Phe Glu  Glu Val Met Arg Gly  Lys Phe Gly Lys Lys  His Met Ile
    1145                1150                1155

Ala Gly  Val Leu Phe Thr Phe  Val Leu Leu Leu Ser  Gly Gln Ile
    1160                1165                1170

Thr Trp  Arg Asp Met Ala His  Thr Leu Ile Met Ile  Gly Ser Asn
    1175                1180                1185

Ala Ser  Asp Arg Met Gly Met  Gly Val Thr Tyr Leu  Ala Leu Ile
    1190                1195                1200

Ala Thr  Phe Lys Ile Gln Pro  Phe Leu Ala Leu Gly  Phe Phe Leu
    1205                1210                1215
```

-continued

```
Arg Lys  Leu Thr Ser Arg Glu  Asn Leu Leu Leu Gly  Val Gly Leu
    1220                 1225                 1230

Ala Met  Ala Ala Thr Leu Arg  Leu Pro Glu Asp Ile  Glu Gln Met
    1235                 1240                 1245

Ala Asn  Gly Ile Ala Leu Gly  Leu Met Ala Leu Lys  Leu Ile Thr
    1250                 1255                 1260

Gln Phe  Glu Thr Tyr Gln Leu  Trp Thr Ala Leu Val  Ser Leu Thr
    1265                 1270                 1275

Cys Ser  Asn Thr Ile Phe Thr  Leu Thr Val Ala Trp  Arg Thr Ala
    1280                 1285                 1290

Thr Leu  Ile Leu Ala Gly Ile  Ser Leu Leu Pro Val  Cys Gln Ser
    1295                 1300                 1305

Ser Ser  Met Arg Lys Thr Asp  Trp Leu Pro Met Thr  Val Ala Ala
    1310                 1315                 1320

Met Gly  Ala Gln Pro Leu Pro  Leu Phe Ile Phe Ser  Leu Lys Asp
    1325                 1330                 1335

Thr Leu  Lys Arg Arg Ser Trp  Pro Leu Asn Glu Gly  Val Met Ala
    1340                 1345                 1350

Val Gly  Leu Val Ser Ile Leu  Ala Ser Ser Leu Leu  Arg Asn Asp
    1355                 1360                 1365

Val Pro  Met Ala Gly Pro Leu  Val Ala Gly Gly Leu  Leu Ile Ala
    1370                 1375                 1380

Cys Tyr  Val Ile Thr Gly Thr  Ser Ala Asp Leu Thr  Val Glu Lys
    1385                 1390                 1395

Ala Ala  Asp Val Thr Trp Glu  Glu Glu Ala Glu Gln  Thr Gly Val
    1400                 1405                 1410

Ser His  Asn Leu Met Val Thr  Val Asp Asp Asp Gly  Thr Met Arg
    1415                 1420                 1425

Ile Lys  Asp Asp Glu Thr Glu  Asn Ile Leu Thr Val  Leu Leu Lys
    1430                 1435                 1440

Thr Ala  Leu Leu Ile Val Ser  Gly Ile Phe Pro Tyr  Ser Ile Pro
    1445                 1450                 1455

Ala Thr  Leu Leu Val Trp His  Thr Trp Gln Lys Gln  Thr Gln Arg
    1460                 1465                 1470

Ser Gly  Val Leu Trp Asp Val  Pro Ser Pro Pro Glu  Thr Gln Lys
    1475                 1480                 1485

Ala Glu  Leu Glu Glu Gly Val  Tyr Arg Ile Lys Gln  Gln Gly Ile
    1490                 1495                 1500

Phe Gly  Lys Thr Gln Val Gly  Val Gly Val Gln Lys  Glu Gly Val
    1505                 1510                 1515

Phe His  Thr Met Trp His Val  Thr Arg Gly Ala Val  Leu Thr His
    1520                 1525                 1530

Asn Gly  Lys Arg Leu Glu Pro  Asn Trp Ala Ser Val  Lys Lys Asp
    1535                 1540                 1545

Leu Ile  Ser Tyr Gly Gly Gly  Trp Arg Leu Ser Ala  Gln Trp Gln
    1550                 1555                 1560

Lys Gly  Glu Glu Val Gln Val  Ile Ala Val Glu Pro  Gly Lys Asn
    1565                 1570                 1575

Pro Lys  Asn Phe Gln Thr Met  Pro Gly Ile Phe Gln  Thr Thr Thr
    1580                 1585                 1590

Gly Glu  Ile Gly Ala Ile Ala  Leu Asp Phe Lys Pro  Gly Thr Ser
    1595                 1600                 1605

Gly Ser  Pro Ile Ile Asn Arg  Glu Gly Lys Val Val  Gly Leu Tyr
```

-continued

```
    1610                1615                1620

Gly Asn  Gly Val Val Thr Lys  Asn Gly Gly Tyr Val  Ser Gly Ile
    1625                1630                1635

Ala Gln  Thr Asn Ala Glu Pro  Asp Gly Pro Thr Pro  Glu Leu Glu
    1640                1645                1650

Glu Glu  Met Phe Lys Lys Arg  Asn Leu Thr Ile Met  Asp Leu His
    1655                1660                1665

Pro Gly  Ser Gly Lys Thr Arg  Lys Tyr Leu Pro Ala  Ile Val Arg
    1670                1675                1680

Glu Ala  Ile Lys Arg Arg Leu  Arg Thr Leu Ile Leu  Ala Pro Thr
    1685                1690                1695

Arg Val  Val Ala Ala Glu Met  Glu Glu Ala Leu Lys  Gly Leu Pro
    1700                1705                1710

Ile Arg  Tyr Gln Thr Thr Ala  Thr Lys Ser Glu His  Thr Gly Arg
    1715                1720                1725

Glu Ile  Val Asp Leu Met Cys  His Ala Thr Phe Thr  Met Arg Leu
    1730                1735                1740

Leu Ser  Pro Val Arg Val Pro  Asn Tyr Asn Leu Ile  Ile Met Asp
    1745                1750                1755

Glu Ala  His Phe Thr Asp Pro  Ala Ser Ile Ala Ala  Arg Gly Tyr
    1760                1765                1770

Ile Ser  Thr Arg Val Gly Met  Gly Glu Ala Ala Ala  Ile Phe Met
    1775                1780                1785

Thr Ala  Thr Pro Pro Gly Thr  Ala Asp Ala Phe Pro  Gln Ser Asn
    1790                1795                1800

Ala Pro  Ile Gln Asp Glu Glu  Arg Asp Ile Pro Glu  Arg Ser Trp
    1805                1810                1815

Asn Ser  Gly Asn Glu Trp Ile  Thr Asp Phe Val Gly  Lys Thr Val
    1820                1825                1830

Trp Phe  Val Pro Ser Ile Lys  Ala Gly Asn Asp Ile  Ala Asn Cys
    1835                1840                1845

Leu Arg  Lys Asn Gly Lys Lys  Val Ile Gln Leu Ser  Arg Lys Thr
    1850                1855                1860

Phe Asp  Thr Glu Tyr Gln Lys  Thr Lys Leu Asn Asp  Trp Asp Phe
    1865                1870                1875

Val Val  Thr Thr Asp Ile Ser  Glu Met Gly Ala Asn  Phe Lys Ala
    1880                1885                1890

Asp Arg  Val Ile Asp Pro Arg  Arg Cys Leu Lys Pro  Val Ile Leu
    1895                1900                1905

Thr Asp  Gly Pro Glu Arg Val  Ile Leu Ala Gly Pro  Met Pro Val
    1910                1915                1920

Thr Val  Ala Ser Ala Ala Gln  Arg Arg Gly Arg Val  Gly Arg Asn
    1925                1930                1935

Pro Gln  Lys Glu Asn Asp Gln  Tyr Ile Phe Met Gly  Gln Pro Leu
    1940                1945                1950

Asn Asn  Asp Glu Asp His Ala  His Trp Thr Glu Ala  Lys Met Leu
    1955                1960                1965

Leu Asp  Asn Ile Asn Thr Pro  Glu Gly Ile Ile Pro  Ala Leu Phe
    1970                1975                1980

Glu Pro  Glu Arg Glu Lys Ser  Ala Ala Ile Asp Gly  Glu Tyr Arg
    1985                1990                1995

Leu Lys  Gly Glu Ser Arg Lys  Thr Phe Val Glu Leu  Met Arg Arg
    2000                2005                2010
```

```
Gly Asp  Leu Pro Val Trp Leu  Ala His Lys Val Ala  Ser Glu Gly
    2015                 2020                 2025

Ile Lys  Tyr Thr Asp Arg Lys  Trp Cys Phe Asp Gly  Glu Arg Asn
    2030                 2035                 2040

Asn Gln  Ile Leu Glu Glu Asn  Met Asp Val Glu Ile  Trp Thr Lys
    2045                 2050                 2055

Glu Gly  Glu Lys Lys Lys Leu  Arg Pro Arg Trp Leu  Asp Ala Arg
    2060                 2065                 2070

Thr Tyr  Ser Asp Pro Leu Ala  Leu Lys Glu Phe Lys  Asp Phe Ala
    2075                 2080                 2085

Ala Gly  Arg Lys Ser Ile Ala  Leu Asp Leu Val Thr  Glu Ile Gly
    2090                 2095                 2100

Arg Val  Pro Ser His Leu Ala  His Arg Thr Arg Asn  Ala Leu Asp
    2105                 2110                 2115

Asn Leu  Val Met Leu His Thr  Ser Glu His Gly Gly  Arg Ala Tyr
    2120                 2125                 2130

Arg His  Ala Val Glu Glu Leu  Pro Glu Thr Met Glu  Thr Leu Leu
    2135                 2140                 2145

Leu Leu  Gly Leu Met Ile Leu  Leu Thr Gly Gly Ala  Met Leu Phe
    2150                 2155                 2160

Leu Ile  Ser Gly Lys Gly Ile  Gly Lys Thr Ser Ile  Gly Leu Ile
    2165                 2170                 2175

Cys Val  Ile Ala Ser Ser Gly  Met Leu Trp Met Ala  Asp Val Pro
    2180                 2185                 2190

Leu Gln  Trp Ile Ala Ser Ala  Ile Val Leu Glu Phe  Phe Met Met
    2195                 2200                 2205

Val Leu  Leu Ile Pro Glu Pro  Glu Lys Gln Arg Thr  Pro Gln Asp
    2210                 2215                 2220

Asn Gln  Leu Ala Tyr Val Val  Ile Gly Ile Leu Thr  Leu Ala Ala
    2225                 2230                 2235

Ile Val  Ala Ala Asn Glu Met  Gly Leu Leu Glu Thr  Thr Lys Arg
    2240                 2245                 2250

Asp Leu  Gly Met Ser Lys Glu  Pro Gly Val Val Ser  Pro Thr Ser
    2255                 2260                 2265

Tyr Leu  Asp Val Asp Leu His  Pro Ala Ser Ala Trp  Thr Leu Tyr
    2270                 2275                 2280

Ala Val  Ala Thr Thr Val Ile  Thr Pro Met Leu Arg  His Thr Ile
    2285                 2290                 2295

Glu Asn  Ser Thr Ala Asn Val  Ser Leu Ala Ala Ile  Ala Asn Gln
    2300                 2305                 2310

Ala Val  Val Leu Met Gly Leu  Asp Lys Gly Trp Pro  Ile Ser Lys
    2315                 2320                 2325

Met Asp  Leu Gly Val Pro Leu  Leu Ala Leu Gly Cys  Tyr Ser Gln
    2330                 2335                 2340

Val Asn  Pro Leu Thr Leu Ala  Ala Ala Val Leu Leu  Leu Val Thr
    2345                 2350                 2355

His Tyr  Ala Ile Ile Gly Pro  Gly Leu Gln Ala Lys  Ala Thr Arg
    2360                 2365                 2370

Glu Ala  Gln Lys Arg Thr Ala  Ala Gly Ile Met Lys  Asn Pro Thr
    2375                 2380                 2385

Val Asp  Gly Ile Met Thr Ile  Asp Leu Asp Pro Val  Ile Tyr Asp
    2390                 2395                 2400
```

-continued

```
Ser Lys  Phe Glu Lys Gln Leu  Gly Gln Val Met Leu  Leu Val Leu
    2405                 2410                 2415

Cys Ala  Val Gln Leu Leu Leu  Met Arg Thr Ser Trp  Ala Leu Cys
    2420                 2425                 2430

Glu Val  Leu Thr Leu Ala Thr  Gly Pro Ile Thr Thr  Leu Trp Glu
    2435                 2440                 2445

Gly Ser  Pro Gly Lys Phe Trp  Asn Thr Thr Ile Ala  Val Ser Met
    2450                 2455                 2460

Ala Asn  Ile Phe Arg Gly Ser  Tyr Leu Ala Gly Ala  Gly Leu Ala
    2465                 2470                 2475

Phe Ser  Ile Met Lys Ser Val  Gly Thr Gly Lys Arg  Gly Thr Gly
    2480                 2485                 2490

Ser Gln  Gly Glu Thr Leu Gly  Glu Lys Trp Lys Lys  Lys Leu Asn
    2495                 2500                 2505

Gln Leu  Ser Arg Lys Glu Phe  Asp Leu Tyr Lys Lys  Ser Gly Ile
    2510                 2515                 2520

Thr Glu  Val Asp Arg Thr Glu  Ala Lys Glu Gly Leu  Lys Arg Gly
    2525                 2530                 2535

Glu Ile  Thr His His Ala Val  Ser Arg Gly Ser Ala  Lys Leu Gln
    2540                 2545                 2550

Trp Phe  Val Glu Arg Asn Met  Val Ile Pro Glu Gly  Arg Val Ile
    2555                 2560                 2565

Asp Leu  Gly Cys Gly Arg Gly  Gly Trp Ser Tyr Tyr  Cys Ala Gly
    2570                 2575                 2580

Leu Lys  Lys Val Thr Glu Val  Arg Gly Tyr Thr Lys  Gly Gly Pro
    2585                 2590                 2595

Gly His  Glu Glu Pro Val Pro  Met Ser Thr Tyr Gly  Trp Asn Ile
    2600                 2605                 2610

Val Lys  Leu Met Ser Gly Lys  Asp Val Phe Tyr Leu  Pro Pro Glu
    2615                 2620                 2625

Lys Cys  Asp Thr Leu Leu Cys  Asp Ile Gly Glu Ser  Ser Pro Ser
    2630                 2635                 2640

Pro Thr  Val Glu Glu Ser Arg  Thr Ile Arg Val Leu  Lys Met Val
    2645                 2650                 2655

Glu Pro  Trp Leu Lys Asn Asn  Gln Phe Cys Ile Lys  Val Leu Asn
    2660                 2665                 2670

Pro Tyr  Met Pro Thr Val Ile  Glu His Leu Glu Arg  Leu Gln Arg
    2675                 2680                 2685

Lys His  Gly Gly Met Leu Val  Arg Asn Pro Leu Ser  Arg Asn Ser
    2690                 2695                 2700

Thr His  Glu Met Tyr Trp Ile  Ser Asn Gly Thr Gly  Asn Ile Val
    2705                 2710                 2715

Ser Ser  Val Asn Met Val Ser  Arg Leu Leu Leu Asn  Arg Phe Thr
    2720                 2725                 2730

Met Thr  His Arg Arg Pro Thr  Ile Glu Lys Asp Val  Asp Leu Gly
    2735                 2740                 2745

Ala Gly  Thr Arg His Val Asn  Ala Glu Pro Glu Thr  Pro Asn Met
    2750                 2755                 2760

Asp Val  Ile Gly Glu Arg Ile  Lys Arg Ile Lys Glu  Glu His Ser
    2765                 2770                 2775

Ser Thr  Trp His Tyr Asp Asp  Glu Asn Pro Tyr Lys  Thr Trp Ala
    2780                 2785                 2790

Tyr His  Gly Ser Tyr Glu Val  Lys Ala Thr Gly Ser  Ala Ser Ser
```

2795 2800 2805

Met Ile Asn Gly Val Val Lys Leu Leu Thr Lys Pro Trp Asp Val
2810 2815 2820

Val Pro Met Val Thr Gln Met Ala Met Thr Asp Thr Thr Pro Phe
2825 2830 2835

Gly Gln Gln Arg Val Phe Lys Glu Lys Val Asp Thr Arg Thr Pro
2840 2845 2850

Arg Pro Met Pro Gly Thr Arg Lys Val Met Glu Ile Thr Ala Glu
2855 2860 2865

Trp Leu Trp Arg Thr Leu Gly Arg Asn Lys Arg Pro Arg Leu Cys
2870 2875 2880

Thr Arg Glu Glu Phe Thr Lys Lys Val Arg Thr Asn Ala Ala Met
2885 2890 2895

Gly Ala Val Phe Thr Glu Glu Asn Gln Trp Asp Ser Ala Arg Ala
2900 2905 2910

Ala Val Glu Asp Glu Glu Phe Trp Lys Leu Val Asp Arg Glu Arg
2915 2920 2925

Glu Leu His Lys Leu Gly Lys Cys Gly Ser Cys Val Tyr Asn Met
2930 2935 2940

Met Gly Lys Arg Glu Lys Lys Leu Gly Glu Phe Gly Lys Ala Lys
2945 2950 2955

Gly Ser Arg Ala Ile Trp Tyr Met Trp Leu Gly Ala Arg Tyr Leu
2960 2965 2970

Glu Phe Glu Ala Leu Gly Phe Leu Asn Glu Asp His Trp Phe Ser
2975 2980 2985

Arg Glu Asn Ser Tyr Ser Gly Val Glu Gly Glu Gly Leu His Lys
2990 2995 3000

Leu Gly Tyr Ile Leu Arg Asp Ile Ser Lys Ile Pro Gly Gly Ala
3005 3010 3015

Met Tyr Ala Asp Asp Thr Ala Gly Trp Asp Thr Arg Ile Thr Glu
3020 3025 3030

Asp Asp Leu His Asn Glu Glu Lys Ile Thr Gln Gln Met Asp Pro
3035 3040 3045

Glu His Arg Gln Leu Ala Asn Ala Ile Phe Lys Leu Thr Tyr Gln
3050 3055 3060

Asn Lys Val Val Lys Val Gln Arg Pro Thr Pro Lys Gly Thr Val
3065 3070 3075

Met Asp Ile Ile Ser Arg Lys Asp Gln Arg Gly Ser Gly Gln Val
3080 3085 3090

Gly Thr Tyr Gly Leu Asn Thr Phe Thr Asn Met Glu Ala Gln Leu
3095 3100 3105

Ile Arg Gln Met Glu Gly Glu Gly Val Leu Ser Lys Ala Asp Leu
3110 3115 3120

Glu Asn Pro His Pro Leu Glu Lys Lys Ile Thr Gln Trp Leu Glu
3125 3130 3135

Thr Lys Gly Val Glu Arg Leu Lys Arg Met Ala Ile Ser Gly Asp
3140 3145 3150

Asp Cys Val Val Lys Pro Ile Asp Asp Arg Phe Ala Asn Ala Leu
3155 3160 3165

Leu Ala Leu Asn Asp Met Gly Lys Val Arg Lys Asp Ile Pro Gln
3170 3175 3180

Trp Gln Pro Ser Lys Gly Trp His Asp Trp Gln Gln Val Pro Phe
3185 3190 3195

```
Cys Ser His His Phe His Glu Leu Ile Met Lys Asp Gly Arg Lys
    3200                3205                3210

Leu Val Val Pro Cys Arg Pro Gln Asp Glu Leu Ile Gly Arg Ala
    3215                3220                3225

Arg Ile Ser Gln Gly Ala Gly Trp Ser Leu Arg Glu Thr Ala Cys
    3230                3235                3240

Leu Gly Lys Ala Tyr Ala Gln Met Trp Ala Leu Met Tyr Phe His
    3245                3250                3255

Arg Arg Asp Leu Arg Leu Ala Ser Asn Ala Ile Cys Ser Ala Val
    3260                3265                3270

Pro Val His Trp Val Pro Thr Ser Arg Thr Thr Trp Ser Ile His
    3275                3280                3285

Ala His His Gln Trp Met Thr Thr Glu Asp Met Leu Thr Val Trp
    3290                3295                3300

Asn Arg Val Trp Ile Glu Asp Asn Pro Trp Met Glu Asp Lys Thr
    3305                3310                3315

Pro Val Thr Thr Trp Glu Asp Val Pro Tyr Leu Gly Lys Arg Glu
    3320                3325                3330

Asp Gln Trp Cys Gly Ser Leu Ile Gly Leu Thr Ser Arg Ala Thr
    3335                3340                3345

Trp Ala Gln Asn Ile Leu Thr Ala Ile Gln Gln Val Arg Ser Leu
    3350                3355                3360

Ile Gly Asn Glu Glu Phe Leu Asp Tyr Met Pro Ser Met Lys Arg
    3365                3370                3375

Phe Arg Lys Glu Glu Glu Ser Glu Gly Ala Ile Trp
    3380                3385                3390
```

<210> SEQ ID NO 12
<211> LENGTH: 5
<212> TYPE: PRT
<213> ORGANISM: Artificial
<220> FEATURE:
<223> OTHER INFORMATION: Synthetic construct

<400> SEQUENCE: 12

```
Gly Ala Gly Lys Thr
1               5
```

<210> SEQ ID NO 13
<211> LENGTH: 5
<212> TYPE: PRT
<213> ORGANISM: Artificial
<220> FEATURE:
<223> OTHER INFORMATION: Synthetic construct

<400> SEQUENCE: 13

```
Gly Arg Ile Gly Arg
1               5
```

<210> SEQ ID NO 14
<211> LENGTH: 10723
<212> TYPE: DNA
<213> ORGANISM: Artificial Sequence
<220> FEATURE:
<223> OTHER INFORMATION: Derived from Dengue virus serotype 2/Dengue
virus serotype 1, MVS

<400> SEQUENCE: 14

```
agttgttagt ctacgtggac cgacaaagac agattctttg agggagctaa gctcaatgta     60
```

-continued

```
gttctaacag ttttttaatt agagagcaga tctctgatga ataaccaacg gaaaaaggcg    120
aaaaacacgc ctttcaatat gctgaaacgc gagagaaacc gcgtgtcgac tgtgcaacag    180
ctgacaaaga gattctcact tggaatgctg cagggacgag gaccattaaa actgttcatg    240
gccctggtgg cgttccttcg tttcctaaca atcccaccaa cagcagggat attgaagaga    300
tggggaacaa ttaaaaaatc aaaagctatt aatgttttga gagggttcag gaaagagatt    360
ggaaggatgc tgaacatctt gaataggaga cgcagatctg caggcatgat cattatgctg    420
attccaacag tgatggcgtt ccatttaacc acgcgtgggg gagagccgca tatgatagtt    480
agcaagcagg aaagaggaaa gtcacttttg ttcaagacct ctgcaggtgt caacatgtgc    540
accctcattg cgatggattt gggagagttg tgtgaggaca cgatgaccta caaatgcccc    600
cggatcactg aggcggaacc agatgacgtt gactgttggt gcaatgccac ggacacatgg    660
gtgacctatg gaacgtgctc tcaaactggc gaacaccgac gagacaaacg ttccgtcgca    720
ttggccccac acgtggggct tggcctagaa acaagagccg aaacgtggat gtcctctgaa    780
ggtgcttgga aacagataca aaaagtagag acttgggctc tgagacatcc aggattcacg    840
gtgatagccc tttttctagc acatgccata ggaacatcca tcacccagaa agggatcatt    900
ttcattttgc tgatgctggt aacaccatct atggccatgc gatgcgtggg aataggcaac    960
agagacttcg tggaaggact gtcaggagca acatgggtgg atgtggtact ggagcatgga   1020
agttgcgtca ccaccatggc aaaaaacaaa ccaacactgg acattgaact cttgaagacg   1080
gaggtcacaa accctgcagt tctgcgtaaa ttgtgcattg aagctaaaat atcaaacacc   1140
accaccgatt cgagatgtcc aacacaagga gaagccacac tggtggaaga acaagacgcg   1200
aactttgtgt gccgacgaac gttcgtggac agaggctggg gcaatggctg tgggctattc   1260
ggaaaaggta gtctaataac gtgtgccaag tttaagtgtg tgacaaaact agaaggaaag   1320
atagttcaat atgaaaacct aaaatattca gtgatagtca ccgtccacac tggagatcag   1380
caccaggtgg gaaatgagac tacagaacat ggaacaactg caaccataac acctcaagct   1440
cctacgtcgg aaatacagct gaccgactac ggaaccctta cattagattg ttcacctagg   1500
acagggctag attttaacga gatggtgttg ctgacaatga aagaaagatc atggcttgtc   1560
cacaaacaat ggttcctaga cttaccactg ccttggacct ctggggcttc aacatcccaa   1620
gagacttgga acagacaaga tttactggtc acatttaaga cagctcatgc aaagaagcag   1680
gaagtagtcg tactaggatc acaagaagga gcaatgcaca ctgcgctgac tggagcgaca   1740
gaaatccaaa cgtcaggaac gacaacaatt ttcgcaggac acctaaaatg cagactaaaa   1800
atggacaaac taactttaaa agggatgtca tatgtgatgt gcacaggctc attcaagtta   1860
gagaaagaag tggctgagac ccagcatgga actgttctgg tgcaggttaa atatgaagga   1920
acagacgcac catgcaagat tcccttttcg acccaagatg agaaaggagc aacccagaat   1980
gggagattaa taacagccaa ccccatagtc actgacaaag aaaaaccagt caatattgag   2040
gcagaaccac cctttggtga gagctacatc gtggtaggag caggtgaaaa agctttgaaa   2100
ctaagctggt tcaagaaagg aagcagcata gggaaaatgt ttgaagcaac tgcccgagga   2160
gcacgaagga tggccattct gggagacacc gcatgggact tcggttctat aggaggagtg   2220
ttcacgtcta tgggaaaact ggtacaccag gtttttggaa ctgcatatgg agttttgttt   2280
agcggagttt cttggaccat gaaaatagga atagggattc tgctgacatg gctaggatta   2340
aattcaagga acacgtccct ttcgatgatg tgcatcgcag ccggcattgt gacactgtat   2400
ttgggagtca tggtgcaggc cgatagtggt tgcgttgtga gctggaaaaa caaagaactg   2460
```

-continued

```
aaatgtggca gtgggatttt catcacagac aacgtgcaca catggacaga acaatacaag   2520
ttccaaccag aatccccttc aaaactagct tcagctatcc agaaagccca tgaagaggac   2580
atttgtggaa tccgctcagt aacaagactg gagaatctga tgtggaaaca aataacacca   2640
gaattgaatc acattctatc agaaaatgag gtgaagttaa ctattatgac aggagacatc   2700
aaaggaatca tgcaggcagg aaaacgatct ctgcggcctc agcccactga gctgaagtat   2760
tcatggaaaa catggggcaa agcaaaaatg ctctctacag agtctcataa ccagaccttt   2820
ctcattgatg gccccgaaac agcagaatgc cccaacacaa atagagcttg gaattcgttg   2880
gaagttgaag actatggctt tggagtattc accaccaata tatggctaaa attgaaagaa   2940
aaacaggatg tattctgcga ctcaaaactc atgtcagcgg ccataaaaga caacagagcc   3000
gtccatgccg atatgggtta ttggatagaa agtgcactca atgacacatg gaagatagag   3060
aaagcctctt tcattgaagt taaaaactgc cactggccaa aatcacacac cctctggagc   3120
aatggagtgc tagaaagtga gatgataatt ccaaagaatc tcgctggacc agtgtctcaa   3180
cacaactata gaccaggcta ccatacacaa ataacaggac catggcatct aggtaagctt   3240
gagatggact ttgatttctg tgatggaaca acagtggtag tgactgagga ctgcggaaat   3300
agaggaccct ctttgagaac aaccactgcc tctggaaaac tcataacaga atggtgctgc   3360
cgatcttgca cattaccacc gctaagatac agaggtgagg atgggtgctg gtacgggatg   3420
gaaatcagac cattgaagga gaaagaagag aatttggtca actccttggt cacagctgga   3480
catgggcagg tcgacaactt ttcactagga gtcttgggaa tggcattgtt cctggaggaa   3540
atgcttagga cccgagtagg aacgaaacat gcaatactac tagttgcagt ttcttttgtg   3600
acattgatca cagggaacat gtcctttaga gacctgggaa gagtgatggt tatggtaggc   3660
gccactatga cggatgacat aggtatgggc gtgacttatc ttgccctact agcagccttc   3720
aaagtcagac caacttttgc agctggacta ctcttgagaa agctgacctc caaggaattg   3780
atgatgacta ctataggaat tgtactcctc tcccagagca ccctaccaga gaccattctt   3840
gagttgactg atgcgttagc cttaggcatg atggtcctca aaatggtgag aaatatggaa   3900
aagtatcaat tggcagtgac tatcatggct atcttgtgcg tcccaaacgc agtgatatta   3960
caaaacgcat ggaaagtgag ttgcacaata ttggcagtgg tgtccgtttc cccactgttc   4020
ttaacatcct cacagcaaaa aacagattgg ataccattag cattgacgat caaaggtctc   4080
aatccaacag ctatttttct aacaaccctc tcaagaacca gcaagaaaag gagctggcca   4140
ttaaatgagg ctatcatggc agtcgggatg gtgagcattt tagccagttc tctcctaaaa   4200
aatgatattc ccatgacagg accattagtg gctggagggc tcctcactgt gtgctacgtg   4260
ctcactggac gatcggccga tttggaactg gagagagcag ccgatgtcaa atgggaagac   4320
caggcagaga tatcaggaag cagtccaatc ctgtcaataa caatatcaga agatggtagc   4380
atgtcgataa aaaatgaaga ggaagatcaa acactgacca tactcattag aacaggattg   4440
ctggtgatct caggactttt tcctgtatca ataccaatca cggcagcagc atggtacctg   4500
tgggaagtga agaaacaacg ggccggagta ttgtgggatg ttccttcacc cccacccatg   4560
ggaaaggctg aactggaaga tggagcctat agaattaagc aaaaagggat tcttggatat   4620
tcccagatcg gagccggagt ttacaaagaa ggaacattcc atacaatgtg gcatgtcaca   4680
cgtggcgctg ttctaatgca taaaggaaag aggattgaac catcatgggc ggacgtcaag   4740
aaagacctaa tatcatatgg aggaggctgg aagttagaag gagaatggaa ggaaggagaa   4800
```

-continued

```
gaagtccagg tattggcact ggagcctgga aaaaatccaa gagccgtcca aacgaaacct   4860
ggtcttttca aaaccaacgc cggaacaata ggtgctgtat ctctggactt ttctcctgga   4920
acgtcaggat ctccaattat cgacaaaaaa ggaaaagttg tgggtcttta tggtaatggt   4980
gttgttacaa ggagtggagc atatgtgagt gctatagccc agactgaaaa aagcattgaa   5040
gacaacccag agatcgaaga tgacattttc cgaaagagaa gactgaccat catggacctc   5100
cacccaggag cgggaaagac gaagagatac cttccggcca tagtcagaga agctataaaa   5160
cggggtttga gaacattaat cttggccccc actagagttg tggcagctga aatggaggaa   5220
gcccttagag gacttccaat aagataccag accccagcca tcagagctgt gcacaccggg   5280
cgggagattg tggacctaat gtgtcatgcc acatttacca tgaggctgct atcaccagtt   5340
agagtgccaa actacaacct gattatcatg gacgaagccc atttcacaga cccagcaagt   5400
atagcagcta gaggatacat ctcaactcga gtggagatgg gtgaggcagc tgggattttt   5460
atgacagcca ctcccccggg aagcagagac ccatttcctc agagcaatgc accaatcata   5520
gatgaagaaa gagaaatccc tgaacgctcg tggaattccg gacatgaatg ggtcacggat   5580
tttaaaggga agactgtttg gttcgttcca agtataaaag caggaaatga tatagcagct   5640
tgcctgagga aaaatggaaa gaaagtgata caactcagta ggaagacctt tgattctgag   5700
tatgtcaaga ctagaaccaa tgattgggac ttcgtggtta caactgacat ttcagaaatg   5760
ggtgccaatt tcaaggctga gagggttata gaccccagac gctgcatgaa accagtcata   5820
ctaacagatg gtgaagagcg ggtgattctg gcaggaccta tgccagtgac ccactctagt   5880
gcagcacaaa gaagagggag aataggaaga aatccaaaaa atgagaatga ccagtacata   5940
tacatggggg aacctctgga aaatgatgaa gactgtgcac actggaaaga agctaaaatg   6000
ctcctagata acatcaacac gccagaagga atcattccta gcatgttcga accagagcgt   6060
gaaaaggtgg atgccattga tggcgaatac cgcttgagag gagaagcaag gaaaaccttt   6120
gtagacttaa tgagaagagg agacctacca gtctggttgg cctacagagt ggcagctgaa   6180
ggcatcaact acgcagacag aaggtggtgt tttgatggag tcaagaacaa ccaaatccta   6240
gaagaaaacg tggaagttga aatctggaca aaagaagggg aaaggaagaa attgaaaccc   6300
agatggttgg atgctaggat ctattctgac ccactggcgc taaaagaatt taaggaattt   6360
gcagccggaa gaaagtctct gaccctgaac ctaatcacag aaatgggtag gctcccaacc   6420
ttcatgactc agaaggcaag agacgcactg gacaacttag cagtgctgca cacggctgag   6480
gcaggtggaa gggcgtacaa ccatgctctc agtgaactgc cggagaccct ggagacattg   6540
cttttactga cacttctggc tacagtcacg ggagggatct tttattctt gatgagcgca   6600
aggggcatag ggaagatgac cctgggaatg tgctgcataa tcacggctag catcctccta   6660
tggtacgcac aaatacagcc acactggata gcagcttcaa taatactgga gttttttctc   6720
atagttttgc ttattccaga acctgaaaaa cagagaacac cccaagacaa ccaactgacc   6780
tacgttgtca tagccatcct cacagtggtg gccgcaacca tggcaaacga gatgggtttc   6840
ctagaaaaaa cgaagaaaga tctcggattg ggaagcattg caacccagca acccgagagc   6900
aacatcctgg acatagatct acgtcctgca tcagcatgga cgctgtatgc cgtggccaca   6960
acatttgtta caccaatgtt gagacatagc attgaaaatt cctcagtgaa tgtgtcccta   7020
acagctatag ccaaccaagc cacagtgtta atgggtctcg ggaaaggatg gccattgtca   7080
aagatggaca tcggagttcc ccttctcgcc attggatgct actcacaagt caaccccata   7140
actctcacag cagctctttt cttattggta gcacattatg ccatcatagg gccaggactc   7200
```

-continued

```
caagcaaaag caaccagaga agctcagaaa agagcagcgg cgggcatcat gaaaaaccca   7260
actgtcgatg gaataacagt gattgaccta gatccaatac cttatgatcc gaagtttgaa   7320
aagcagttgg gacaagtaat gctcctagtc ctctgcgtga ctcaagtatt gatgatgagg   7380
actacatggg ctctgtgtga ggctttaacc ttagctaccg ggcccatctc cacattgtgg   7440
gaaggaaatc cagggaggtt ttggaacact accattgcgg tgtcaatggc taacattttt   7500
agagggagtt acttggccgg agctggactt ctcttttcta ttatgaagaa cacaaccaac   7560
acaagaaggg gaactggcaa cataggagag acgcttggag agaaatggaa aagccgattg   7620
aacgcattgg gaaaaagtga attccagatc tacaagaaaa gtggaatcca ggaagtggat   7680
agaaccttag caaaagaagg cattaaaaga ggagaaacgg accatcacgc tgtgtcgcga   7740
ggctcagcaa aactgagatg gttcgttgag agaaacatgg tcacaccaga agggaaagta   7800
gtggacctcg gttgtggcag aggaggctgg tcatactatt gtggaggact aaagaatgta   7860
agagaagtca aaggcctaac aaaaggagga ccaggacacg aagaacccat ccccatgtca   7920
acatatgggt ggaatctagt gcgtcttcaa agtggagttg acgttttctt catcccgcca   7980
gaaaagtgtg acacattatt gtgtgacata ggggagtcat caccaaatcc cacagtggaa   8040
gcaggacgaa cactcagagt ccttaactta gtagaaaatt ggttgaacaa caacactcaa   8100
ttttgcataa aggttctcaa cccatatatg ccctcagtca tagaaaaaat ggaagcacta   8160
caaaggaaat atggaggagc cttagtgagg aatccactct cacgaaactc cacacatgag   8220
atgtactggg tatccaatgc ttccgggaac atagtgtcat cagtgaacat gatttcaagg   8280
atgttgatca acagatttac aatgagatac aagaaagcca cttacgagcc ggatgttgac   8340
ctcggaagcg gaacccgtaa catcgggatt gaaagtgaga taccaaacct agatataatt   8400
gggaaaagaa tagaaaaaat aaagcaagag catgaaacat catggcacta tgaccaagac   8460
cacccataca aaacgtgggc ataccatggt agctatgaaa caaaacagac tggatcagca   8520
tcatccatgg tcaacggagt ggtcaggctg ctgacaaaac cttgggacgt cgtccccatg   8580
gtgacacaga tggcaatgac agacacgact ccatttggac aacagcgcgt tttaaaagag   8640
aaagtggaca cgagaaccca agaaccgaaa gaaggcacga agaaactaat gaaaataaca   8700
gcagagtggc tttggaaaga attagggaag aaaaagacac ccaggatgtg caccagagaa   8760
gaattcacaa gaaaggtgag aagcaatgca gccttggggg ccatattcac tgatgagaac   8820
aagtggaagt cggcacgtga ggctgttgaa gatagtaggt tttgggagct ggttgacaag   8880
gaaaggaatc tccatcttga aggaaagtgt gaaacatgtg tgtacaacat gatgggaaaa   8940
agagagaaga agctagggga attcggcaag gcaaaaggca gcagagccat atggtacatg   9000
tggcttggag cacgcttctt agagtttgaa gccctaggat tcttaaatga agatcactgg   9060
ttctccagag agaactccct gagtggagtg gaaggagaag ggctgcacaa gctaggttac   9120
attctaagag acgtgagcaa gaaagaggga ggagcaatgt atgccgatga caccgcagga   9180
tgggatacaa gaatcacact agaagaccta aaaaatgaag aaatggtaac aaaccacatg   9240
gaaggagaac acaagaaact agccgaggcc attttcaaac taacgtacca aaacaaggtg   9300
gtgcgtgtgc aaagaccaac accaagaggc acagtaatgg acatcatatc gagaagagac   9360
caaagaggta gtggacaagt tggcacctat ggactcaata ctttcaccaa tatggaagcc   9420
caactaatca gacagatgga gggagaagga gtctttaaaa gcattcagca cctaacaatc   9480
acagaagaaa tcgctgtgca aaactggtta gcaagagtgg ggcgcgaaag gttatcaaga   9540
```

```
atggccatca gtggagatga ttgtgttgtg aaacctttag atgacaggtt cgcaagcgct   9600

ttaacagctc taaatgacat gggaaagatt aggaaagaca tacaacaatg ggaaccttca   9660

agaggatgga atgattggac acaagtgccc ttctgttcac accatttcca tgagttaatc   9720

atgaaagacg gtcgcgtact cgttgttcca tgtagaaacc aagatgaact gattggcaga   9780

gcccgaatct cccaaggagc agggtggtct ttgcgggaga cggcctgttt ggggaagtct   9840

tacgcccaaa tgtggagctt gatgtacttc cacagacgcg acctcaggct ggcggcaaat   9900

gctatttgct cggcagtacc atcacattgg gttccaacaa gtcgaacaac ctggtccata   9960

catgctaaac atgaatggat gacaacggaa gacatgctga cagtctggaa cagggtgtgg  10020

attcaagaaa acccatggat ggaagacaaa actccagtgg aatcatggga ggaaatccca  10080

tacttgggga aaagagaaga ccaatggtgc ggctcattga ttgggttaac aagcagggcc  10140

acctgggcaa agaacatcca agcagcaata aatcaagtta gatcccttat aggcaatgaa  10200

gaatacacag attacatgcc atccatgaaa agattcagaa gagaagagga agaagcagga  10260

gttctgtggt agaaagcaaa actaacatga aacaaggcta gaagtcaggt cggattaagc  10320

catagtacgg aaaaaactat gctacctgtg agccccgtcc aaggacgtta aaagaagtca  10380

ggccatcata aatgccatag cttgagtaaa ctatgcagcc tgtagctcca cctgagaagg  10440

tgtaaaaaat ccgggaggcc acaaaccatg gaagctgtac gcatggcgta gtggactagc  10500

ggttagagga gacccctccc ttacaaatcg cagcaacaat gggggcccaa ggcgagatga  10560

agctgtagtc tcgctggaag gactagaggt tagaggagac ccccccgaaa caaaaaacag  10620

catattgacg ctgggaaaga ccagagatcc tgctgtctcc tcagcatcat tccaggcaca  10680

gaacgccaga aaatggaatg gtgctgttga atcaacaggt tct                    10723
```

```
<210> SEQ ID NO 15
<211> LENGTH: 3391
<212> TYPE: PRT
<213> ORGANISM: Artificial Sequence
<220> FEATURE:
<223> OTHER INFORMATION: Polypeptide, Derived from Dengue virus serotype
      2/Dengue virus serotype 1, MVS

<400> SEQUENCE: 15

Met Asn Asn Gln Arg Lys Lys Ala Lys Asn Thr Pro Phe Asn Met Leu
1               5                   10                  15

Lys Arg Glu Arg Asn Arg Val Ser Thr Val Gln Gln Leu Thr Lys Arg
            20                  25                  30

Phe Ser Leu Gly Met Leu Gln Gly Arg Gly Pro Leu Lys Leu Phe Met
        35                  40                  45

Ala Leu Val Ala Phe Leu Arg Phe Leu Thr Ile Pro Pro Thr Ala Gly
    50                  55                  60

Ile Leu Lys Arg Trp Gly Thr Ile Lys Lys Ser Lys Ala Ile Asn Val
65                  70                  75                  80

Leu Arg Gly Phe Arg Lys Glu Ile Gly Arg Met Leu Asn Ile Leu Asn
                85                  90                  95

Arg Arg Arg Arg Ser Ala Gly Met Ile Ile Met Leu Ile Pro Thr Val
            100                 105                 110

Met Ala Phe His Leu Thr Thr Arg Gly Gly Glu Pro His Met Ile Val
        115                 120                 125

Ser Lys Gln Glu Arg Gly Lys Ser Leu Leu Phe Lys Thr Ser Ala Gly
    130                 135                 140

Val Asn Met Cys Thr Leu Ile Ala Met Asp Leu Gly Glu Leu Cys Glu
```

-continued

```
145                 150                 155                 160

Asp Thr Met Thr Tyr Lys Cys Pro Arg Ile Thr Glu Ala Glu Pro Asp
                165                 170                 175

Asp Val Asp Cys Trp Cys Asn Ala Thr Asp Thr Trp Val Thr Tyr Gly
            180                 185                 190

Thr Cys Ser Gln Thr Gly Glu His Arg Arg Asp Lys Arg Ser Val Ala
        195                 200                 205

Leu Ala Pro His Val Gly Leu Gly Leu Glu Thr Arg Ala Glu Thr Trp
    210                 215                 220

Met Ser Ser Glu Gly Ala Trp Lys Gln Ile Gln Lys Val Glu Thr Trp
225                 230                 235                 240

Ala Leu Arg His Pro Gly Phe Thr Val Ile Ala Leu Phe Leu Ala His
                245                 250                 255

Ala Ile Gly Thr Ser Ile Thr Gln Lys Gly Ile Ile Phe Ile Leu Leu
            260                 265                 270

Met Leu Val Thr Pro Ser Met Ala Met Arg Cys Val Gly Ile Gly Asn
        275                 280                 285

Arg Asp Phe Val Glu Gly Leu Ser Gly Ala Thr Trp Val Asp Val Val
    290                 295                 300

Leu Glu His Gly Ser Cys Val Thr Thr Met Ala Lys Asn Lys Pro Thr
305                 310                 315                 320

Leu Asp Ile Glu Leu Leu Lys Thr Glu Val Thr Asn Pro Ala Val Leu
                325                 330                 335

Arg Lys Leu Cys Ile Glu Ala Lys Ile Ser Asn Thr Thr Thr Asp Ser
            340                 345                 350

Arg Cys Pro Thr Gln Gly Glu Ala Thr Leu Val Glu Glu Gln Asp Ala
        355                 360                 365

Asn Phe Val Cys Arg Arg Thr Phe Val Asp Arg Gly Trp Gly Asn Gly
    370                 375                 380

Cys Gly Leu Phe Gly Lys Gly Ser Leu Ile Thr Cys Ala Lys Phe Lys
385                 390                 395                 400

Cys Val Thr Lys Leu Glu Gly Lys Ile Val Gln Tyr Glu Asn Leu Lys
                405                 410                 415

Tyr Ser Val Ile Val Thr Val His Thr Gly Asp Gln His Gln Val Gly
            420                 425                 430

Asn Glu Thr Thr Glu His Gly Thr Thr Ala Thr Ile Thr Pro Gln Ala
        435                 440                 445

Pro Thr Ser Glu Ile Gln Leu Thr Asp Tyr Gly Thr Leu Thr Leu Asp
    450                 455                 460

Cys Ser Pro Arg Thr Gly Leu Asp Phe Asn Glu Met Val Leu Leu Thr
465                 470                 475                 480

Met Lys Glu Arg Ser Trp Leu Val His Lys Gln Trp Phe Leu Asp Leu
                485                 490                 495

Pro Leu Pro Trp Thr Ser Gly Ala Ser Thr Ser Gln Glu Thr Trp Asn
            500                 505                 510

Arg Gln Asp Leu Leu Val Thr Phe Lys Thr Ala His Ala Lys Lys Gln
        515                 520                 525

Glu Val Val Val Leu Gly Ser Gln Glu Gly Ala Met His Thr Ala Leu
    530                 535                 540

Thr Gly Ala Thr Glu Ile Gln Thr Ser Gly Thr Thr Thr Ile Phe Ala
545                 550                 555                 560

Gly His Leu Lys Cys Arg Leu Lys Met Asp Lys Leu Thr Leu Lys Gly
                565                 570                 575
```

-continued

```
Met Ser Tyr Val Met Cys Thr Gly Ser Phe Lys Leu Glu Lys Glu Val
            580                 585                 590

Ala Glu Thr Gln His Gly Thr Val Leu Val Gln Val Lys Tyr Glu Gly
        595                 600                 605

Thr Asp Ala Pro Cys Lys Ile Pro Phe Ser Thr Gln Asp Glu Lys Gly
    610                 615                 620

Ala Thr Gln Asn Gly Arg Leu Ile Thr Ala Asn Pro Ile Val Thr Asp
625                 630                 635                 640

Lys Glu Lys Pro Val Asn Ile Glu Ala Glu Pro Pro Phe Gly Glu Ser
                645                 650                 655

Tyr Ile Val Val Gly Ala Gly Glu Lys Ala Leu Lys Leu Ser Trp Phe
            660                 665                 670

Lys Lys Gly Ser Ser Ile Gly Lys Met Phe Glu Ala Thr Ala Arg Gly
        675                 680                 685

Ala Arg Arg Met Ala Ile Leu Gly Asp Thr Ala Trp Asp Phe Gly Ser
    690                 695                 700

Ile Gly Gly Val Phe Thr Ser Met Gly Lys Leu Val His Gln Val Phe
705                 710                 715                 720

Gly Thr Ala Tyr Gly Val Leu Phe Ser Gly Val Ser Trp Thr Met Lys
                725                 730                 735

Ile Gly Ile Gly Ile Leu Leu Thr Trp Leu Gly Leu Asn Ser Arg Asn
            740                 745                 750

Thr Ser Leu Ser Met Met Cys Ile Ala Ala Gly Ile Val Thr Leu Tyr
        755                 760                 765

Leu Gly Val Met Val Gln Ala Asp Ser Gly Cys Val Val Ser Trp Lys
    770                 775                 780

Asn Lys Glu Leu Lys Cys Gly Ser Gly Ile Phe Ile Thr Asp Asn Val
785                 790                 795                 800

His Thr Trp Thr Glu Gln Tyr Lys Phe Gln Pro Glu Ser Pro Ser Lys
                805                 810                 815

Leu Ala Ser Ala Ile Gln Lys Ala His Glu Glu Asp Ile Cys Gly Ile
            820                 825                 830

Arg Ser Val Thr Arg Leu Glu Asn Leu Met Trp Lys Gln Ile Thr Pro
        835                 840                 845

Glu Leu Asn His Ile Leu Ser Glu Asn Glu Val Lys Leu Thr Ile Met
    850                 855                 860

Thr Gly Asp Ile Lys Gly Ile Met Gln Ala Gly Lys Arg Ser Leu Arg
865                 870                 875                 880

Pro Gln Pro Thr Glu Leu Lys Tyr Ser Trp Lys Thr Trp Gly Lys Ala
                885                 890                 895

Lys Met Leu Ser Thr Glu Ser His Asn Gln Thr Phe Leu Ile Asp Gly
            900                 905                 910

Pro Glu Thr Ala Glu Cys Pro Asn Thr Asn Arg Ala Trp Asn Ser Leu
        915                 920                 925

Glu Val Glu Asp Tyr Gly Phe Gly Val Phe Thr Thr Asn Ile Trp Leu
    930                 935                 940

Lys Leu Lys Glu Lys Gln Asp Val Phe Cys Asp Ser Lys Leu Met Ser
945                 950                 955                 960

Ala Ala Ile Lys Asp Asn Arg Ala Val His Ala Asp Met Gly Tyr Trp
                965                 970                 975

Ile Glu Ser Ala Leu Asn Asp Thr Trp Lys Ile Glu Lys Ala Ser Phe
            980                 985                 990
```

```
Ile Glu Val Lys Asn Cys His Trp  Pro Lys Ser His Thr  Leu Trp Ser
        995                 1000                 1005

Asn Gly  Val Leu Glu Ser Glu  Met Ile Ile Pro Lys  Asn Leu Ala
    1010                 1015                 1020

Gly Pro  Val Ser Gln His Asn  Tyr Arg Pro Gly Tyr  His Thr Gln
    1025                 1030                 1035

Ile Thr  Gly Pro Trp His Leu  Gly Lys Leu Glu Met  Asp Phe Asp
    1040                 1045                 1050

Phe Cys  Asp Gly Thr Thr Val  Val Val Thr Glu Asp  Cys Gly Asn
    1055                 1060                 1065

Arg Gly  Pro Ser Leu Arg Thr  Thr Thr Ala Ser Gly  Lys Leu Ile
    1070                 1075                 1080

Thr Glu  Trp Cys Cys Arg Ser  Cys Thr Leu Pro Pro  Leu Arg Tyr
    1085                 1090                 1095

Arg Gly  Glu Asp Gly Cys Trp  Tyr Gly Met Glu Ile  Arg Pro Leu
    1100                 1105                 1110

Lys Glu  Lys Glu Glu Asn Leu  Val Asn Ser Leu Val  Thr Ala Gly
    1115                 1120                 1125

His Gly  Gln Val Asp Asn Phe  Ser Leu Gly Val Leu  Gly Met Ala
    1130                 1135                 1140

Leu Phe  Leu Glu Glu Met Leu  Arg Thr Arg Val Gly  Thr Lys His
    1145                 1150                 1155

Ala Ile  Leu Leu Val Ala Val  Ser Phe Val Thr Leu  Ile Thr Gly
    1160                 1165                 1170

Asn Met  Ser Phe Arg Asp Leu  Gly Arg Val Met Val  Met Val Gly
    1175                 1180                 1185

Ala Thr  Met Thr Asp Asp Ile  Gly Met Gly Val Thr  Tyr Leu Ala
    1190                 1195                 1200

Leu Leu  Ala Ala Phe Lys Val  Arg Pro Thr Phe Ala  Ala Gly Leu
    1205                 1210                 1215

Leu Leu  Arg Lys Leu Thr Ser  Lys Glu Leu Met Met  Thr Thr Ile
    1220                 1225                 1230

Gly Ile  Val Leu Leu Ser Gln  Ser Thr Leu Pro Glu  Thr Ile Leu
    1235                 1240                 1245

Glu Leu  Thr Asp Ala Leu Ala  Leu Gly Met Met Val  Leu Lys Met
    1250                 1255                 1260

Val Arg  Asn Met Glu Lys Tyr  Gln Leu Ala Val Thr  Ile Met Ala
    1265                 1270                 1275

Ile Leu  Cys Val Pro Asn Ala  Val Ile Leu Gln Asn  Ala Trp Lys
    1280                 1285                 1290

Val Ser  Cys Thr Ile Leu Ala  Val Val Ser Val Ser  Pro Leu Phe
    1295                 1300                 1305

Leu Thr  Ser Ser Gln Gln Lys  Thr Asp Trp Ile Pro  Leu Ala Leu
    1310                 1315                 1320

Thr Ile  Lys Gly Leu Asn Pro  Thr Ala Ile Phe Leu  Thr Thr Leu
    1325                 1330                 1335

Ser Arg  Thr Ser Lys Lys Arg  Ser Trp Pro Leu Asn  Glu Ala Ile
    1340                 1345                 1350

Met Ala  Val Gly Met Val Ser  Ile Leu Ala Ser Ser  Leu Leu Lys
    1355                 1360                 1365

Asn Asp  Ile Pro Met Thr Gly  Pro Leu Val Ala Gly  Gly Leu Leu
    1370                 1375                 1380

Thr Val  Cys Tyr Val Leu Thr  Gly Arg Ser Ala Asp  Leu Glu Leu
```

```
    1385                1390                1395

Glu Arg  Ala Ala Asp Val Lys  Trp Glu Asp Gln Ala  Glu Ile Ser
    1400                1405                1410

Gly Ser  Ser Pro Ile Leu Ser  Ile Thr Ile Ser Glu  Asp Gly Ser
    1415                1420                1425

Met Ser  Ile Lys Asn Glu Glu  Glu Asp Gln Thr Leu  Thr Ile Leu
    1430                1435                1440

Ile Arg  Thr Gly Leu Leu Val  Ile Ser Gly Leu Phe  Pro Val Ser
    1445                1450                1455

Ile Pro  Ile Thr Ala Ala Ala  Trp Tyr Leu Trp Glu  Val Lys Lys
    1460                1465                1470

Gln Arg  Ala Gly Val Leu Trp  Asp Val Pro Ser Pro  Pro Pro Met
    1475                1480                1485

Gly Lys  Ala Glu Leu Glu Asp  Gly Ala Tyr Arg Ile  Lys Gln Lys
    1490                1495                1500

Gly Ile  Leu Gly Tyr Ser Gln  Ile Gly Ala Gly Val  Tyr Lys Glu
    1505                1510                1515

Gly Thr  Phe His Thr Met Trp  His Val Thr Arg Gly  Ala Val Leu
    1520                1525                1530

Met His  Lys Gly Lys Arg Ile  Glu Pro Ser Trp Ala  Asp Val Lys
    1535                1540                1545

Lys Asp  Leu Ile Ser Tyr Gly  Gly Gly Trp Lys Leu  Glu Gly Glu
    1550                1555                1560

Trp Lys  Glu Gly Glu Glu Val  Gln Val Leu Ala Leu  Glu Pro Gly
    1565                1570                1575

Lys Asn  Pro Arg Ala Val Gln  Thr Lys Pro Gly Leu  Phe Lys Thr
    1580                1585                1590

Asn Ala  Gly Thr Ile Gly Ala  Val Ser Leu Asp Phe  Ser Pro Gly
    1595                1600                1605

Thr Ser  Gly Ser Pro Ile Ile  Asp Lys Lys Gly Lys  Val Val Gly
    1610                1615                1620

Leu Tyr  Gly Asn Gly Val Val  Thr Arg Ser Gly Ala  Tyr Val Ser
    1625                1630                1635

Ala Ile  Ala Gln Thr Glu Lys  Ser Ile Glu Asp Asn  Pro Glu Ile
    1640                1645                1650

Glu Asp  Asp Ile Phe Arg Lys  Arg Arg Leu Thr Ile  Met Asp Leu
    1655                1660                1665

His Pro  Gly Ala Gly Lys Thr  Lys Arg Tyr Leu Pro  Ala Ile Val
    1670                1675                1680

Arg Glu  Ala Ile Lys Arg Gly  Leu Arg Thr Leu Ile  Leu Ala Pro
    1685                1690                1695

Thr Arg  Val Val Ala Ala Glu  Met Glu Glu Ala Leu  Arg Gly Leu
    1700                1705                1710

Pro Ile  Arg Tyr Gln Thr Pro  Ala Ile Arg Ala Val  His Thr Gly
    1715                1720                1725

Arg Glu  Ile Val Asp Leu Met  Cys His Ala Thr Phe  Thr Met Arg
    1730                1735                1740

Leu Leu  Ser Pro Val Arg Val  Pro Asn Tyr Asn Leu  Ile Ile Met
    1745                1750                1755

Asp Glu  Ala His Phe Thr Asp  Pro Ala Ser Ile Ala  Ala Arg Gly
    1760                1765                1770

Tyr Ile  Ser Thr Arg Val Glu  Met Gly Glu Ala Ala  Gly Ile Phe
    1775                1780                1785
```

```
Met Thr  Ala Thr Pro Pro Gly  Ser Arg Asp Pro Phe  Pro Gln Ser
    1790                 1795                 1800

Asn Ala  Pro Ile Ile Asp Glu  Glu Arg Glu Ile Pro  Glu Arg Ser
    1805                 1810                 1815

Trp Asn  Ser Gly His Glu Trp  Val Thr Asp Phe Lys  Gly Lys Thr
    1820                 1825                 1830

Val Trp  Phe Val Pro Ser Ile  Lys Ala Gly Asn Asp  Ile Ala Ala
    1835                 1840                 1845

Cys Leu  Arg Lys Asn Gly Lys  Lys Val Ile Gln Leu  Ser Arg Lys
    1850                 1855                 1860

Thr Phe  Asp Ser Glu Tyr Val  Lys Thr Arg Thr Asn  Asp Trp Asp
    1865                 1870                 1875

Phe Val  Val Thr Thr Asp Ile  Ser Glu Met Gly Ala  Asn Phe Lys
    1880                 1885                 1890

Ala Glu  Arg Val Ile Asp Pro  Arg Arg Cys Met Lys  Pro Val Ile
    1895                 1900                 1905

Leu Thr  Asp Gly Glu Glu Arg  Val Ile Leu Ala Gly  Pro Met Pro
    1910                 1915                 1920

Val Thr  His Ser Ser Ala Ala  Gln Arg Arg Gly Arg  Ile Gly Arg
    1925                 1930                 1935

Asn Pro  Lys Asn Glu Asn Asp  Gln Tyr Ile Tyr Met  Gly Glu Pro
    1940                 1945                 1950

Leu Glu  Asn Asp Glu Asp Cys  Ala His Trp Lys Glu  Ala Lys Met
    1955                 1960                 1965

Leu Leu  Asp Asn Ile Asn Thr  Pro Glu Gly Ile Ile  Pro Ser Met
    1970                 1975                 1980

Phe Glu  Pro Glu Arg Glu Lys  Val Asp Ala Ile Asp  Gly Glu Tyr
    1985                 1990                 1995

Arg Leu  Arg Gly Glu Ala Arg  Lys Thr Phe Val Asp  Leu Met Arg
    2000                 2005                 2010

Arg Gly  Asp Leu Pro Val Trp  Leu Ala Tyr Arg Val  Ala Ala Glu
    2015                 2020                 2025

Gly Ile  Asn Tyr Ala Asp Arg  Arg Trp Cys Phe Asp  Gly Val Lys
    2030                 2035                 2040

Asn Asn  Gln Ile Leu Glu Glu  Asn Val Glu Val Glu  Ile Trp Thr
    2045                 2050                 2055

Lys Glu  Gly Glu Arg Lys Lys  Leu Lys Pro Arg Trp  Leu Asp Ala
    2060                 2065                 2070

Arg Ile  Tyr Ser Asp Pro Leu  Ala Leu Lys Glu Phe  Lys Glu Phe
    2075                 2080                 2085

Ala Ala  Gly Arg Lys Ser Leu  Thr Leu Asn Leu Ile  Thr Glu Met
    2090                 2095                 2100

Gly Arg  Leu Pro Thr Phe Met  Thr Gln Lys Ala Arg  Asp Ala Leu
    2105                 2110                 2115

Asp Asn  Leu Ala Val Leu His  Thr Ala Glu Ala Gly  Gly Arg Ala
    2120                 2125                 2130

Tyr Asn  His Ala Leu Ser Glu  Leu Pro Glu Thr Leu  Glu Thr Leu
    2135                 2140                 2145

Leu Leu  Leu Thr Leu Leu Ala  Thr Val Thr Gly Gly  Ile Phe Leu
    2150                 2155                 2160

Phe Leu  Met Ser Ala Arg Gly  Ile Gly Lys Met Thr  Leu Gly Met
    2165                 2170                 2175
```

-continued

```
Cys Cys  Ile Ile Thr Ala Ser  Ile Leu Leu Trp Tyr  Ala Gln Ile
    2180                 2185                 2190

Gln Pro  His Trp Ile Ala Ala  Ser Ile Ile Leu Glu  Phe Phe Leu
    2195                 2200                 2205

Ile Val  Leu Leu Ile Pro Glu  Pro Glu Lys Gln Arg  Thr Pro Gln
    2210                 2215                 2220

Asp Asn  Gln Leu Thr Tyr Val  Val Ile Ala Ile Leu  Thr Val Val
    2225                 2230                 2235

Ala Ala  Thr Met Ala Asn Glu  Met Gly Phe Leu Glu  Lys Thr Lys
    2240                 2245                 2250

Lys Asp  Leu Gly Leu Gly Ser  Ile Ala Thr Gln Gln  Pro Glu Ser
    2255                 2260                 2265

Asn Ile  Leu Asp Ile Asp Leu  Arg Pro Ala Ser Ala  Trp Thr Leu
    2270                 2275                 2280

Tyr Ala  Val Ala Thr Thr Phe  Val Thr Pro Met Leu  Arg His Ser
    2285                 2290                 2295

Ile Glu  Asn Ser Ser Val Asn  Val Ser Leu Thr Ala  Ile Ala Asn
    2300                 2305                 2310

Gln Ala  Thr Val Leu Met Gly  Leu Gly Lys Gly Trp  Pro Leu Ser
    2315                 2320                 2325

Lys Met  Asp Ile Gly Val Pro  Leu Leu Ala Ile Gly  Cys Tyr Ser
    2330                 2335                 2340

Gln Val  Asn Pro Ile Thr Leu  Thr Ala Ala Leu Phe  Leu Leu Val
    2345                 2350                 2355

Ala His  Tyr Ala Ile Ile Gly  Pro Gly Leu Gln Ala  Lys Ala Thr
    2360                 2365                 2370

Arg Glu  Ala Gln Lys Arg Ala  Ala Ala Gly Ile Met  Lys Asn Pro
    2375                 2380                 2385

Thr Val  Asp Gly Ile Thr Val  Ile Asp Leu Asp Pro  Ile Pro Tyr
    2390                 2395                 2400

Asp Pro  Lys Phe Glu Lys Gln  Leu Gly Gln Val Met  Leu Leu Val
    2405                 2410                 2415

Leu Cys  Val Thr Gln Val Leu  Met Met Arg Thr Thr  Trp Ala Leu
    2420                 2425                 2430

Cys Glu  Ala Leu Thr Leu Ala  Thr Gly Pro Ile Ser  Thr Leu Trp
    2435                 2440                 2445

Glu Gly  Asn Pro Gly Arg Phe  Trp Asn Thr Thr Ile  Ala Val Ser
    2450                 2455                 2460

Met Ala  Asn Ile Phe Arg Gly  Ser Tyr Leu Ala Gly  Ala Gly Leu
    2465                 2470                 2475

Leu Phe  Ser Ile Met Lys Asn  Thr Thr Asn Thr Arg  Arg Gly Thr
    2480                 2485                 2490

Gly Asn  Ile Gly Glu Thr Leu  Gly Glu Lys Trp Lys  Ser Arg Leu
    2495                 2500                 2505

Asn Ala  Leu Gly Lys Ser Glu  Phe Gln Ile Tyr Lys  Lys Ser Gly
    2510                 2515                 2520

Ile Gln  Glu Val Asp Arg Thr  Leu Ala Lys Glu Gly  Ile Lys Arg
    2525                 2530                 2535

Gly Glu  Thr Asp His His Ala  Val Ser Arg Gly Ser  Ala Lys Leu
    2540                 2545                 2550

Arg Trp  Phe Val Glu Arg Asn  Met Val Thr Pro Glu  Gly Lys Val
    2555                 2560                 2565

Val Asp  Leu Gly Cys Gly Arg  Gly Gly Trp Ser Tyr  Tyr Cys Gly
```

```
    2570                2575                2580

Gly Leu Lys Asn Val Arg Glu Val Lys Gly Leu Thr Lys Gly Gly
    2585                2590                2595

Pro Gly His Glu Glu Pro Ile Pro Met Ser Thr Tyr Gly Trp Asn
    2600                2605                2610

Leu Val Arg Leu Gln Ser Gly Val Asp Val Phe Phe Ile Pro Pro
    2615                2620                2625

Glu Lys Cys Asp Thr Leu Leu Cys Asp Ile Gly Glu Ser Ser Pro
    2630                2635                2640

Asn Pro Thr Val Glu Ala Gly Arg Thr Leu Arg Val Leu Asn Leu
    2645                2650                2655

Val Glu Asn Trp Leu Asn Asn Asn Thr Gln Phe Cys Ile Lys Val
    2660                2665                2670

Leu Asn Pro Tyr Met Pro Ser Val Ile Glu Lys Met Glu Ala Leu
    2675                2680                2685

Gln Arg Lys Tyr Gly Gly Ala Leu Val Arg Asn Pro Leu Ser Arg
    2690                2695                2700

Asn Ser Thr His Glu Met Tyr Trp Val Ser Asn Ala Ser Gly Asn
    2705                2710                2715

Ile Val Ser Ser Val Asn Met Ile Ser Arg Met Leu Ile Asn Arg
    2720                2725                2730

Phe Thr Met Arg Tyr Lys Lys Ala Thr Tyr Glu Pro Asp Val Asp
    2735                2740                2745

Leu Gly Ser Gly Thr Arg Asn Ile Gly Ile Glu Ser Glu Ile Pro
    2750                2755                2760

Asn Leu Asp Ile Ile Gly Lys Arg Ile Glu Lys Ile Lys Gln Glu
    2765                2770                2775

His Glu Thr Ser Trp His Tyr Asp Gln Asp His Pro Tyr Lys Thr
    2780                2785                2790

Trp Ala Tyr His Gly Ser Tyr Glu Thr Lys Gln Thr Gly Ser Ala
    2795                2800                2805

Ser Ser Met Val Asn Gly Val Val Arg Leu Leu Thr Lys Pro Trp
    2810                2815                2820

Asp Val Val Pro Met Val Thr Gln Met Ala Met Thr Asp Thr Thr
    2825                2830                2835

Pro Phe Gly Gln Gln Arg Val Phe Lys Glu Lys Val Asp Thr Arg
    2840                2845                2850

Thr Gln Glu Pro Lys Glu Gly Thr Lys Lys Leu Met Lys Ile Thr
    2855                2860                2865

Ala Glu Trp Leu Trp Lys Glu Leu Gly Lys Lys Lys Thr Pro Arg
    2870                2875                2880

Met Cys Thr Arg Glu Glu Phe Thr Arg Lys Val Arg Ser Asn Ala
    2885                2890                2895

Ala Leu Gly Ala Ile Phe Thr Asp Glu Asn Lys Trp Lys Ser Ala
    2900                2905                2910

Arg Glu Ala Val Glu Asp Ser Arg Phe Trp Glu Leu Val Asp Lys
    2915                2920                2925

Glu Arg Asn Leu His Leu Glu Gly Lys Cys Glu Thr Cys Val Tyr
    2930                2935                2940

Asn Met Met Gly Lys Arg Glu Lys Lys Leu Gly Glu Phe Gly Lys
    2945                2950                2955

Ala Lys Gly Ser Arg Ala Ile Trp Tyr Met Trp Leu Gly Ala Arg
    2960                2965                2970
```

```
Phe Leu  Glu Phe Glu Ala Leu  Gly Phe Leu Asn Glu  Asp His Trp
    2975                 2980                 2985

Phe Ser  Arg Glu Asn Ser Leu  Ser Gly Val Glu Gly  Glu Gly Leu
    2990                 2995                 3000

His Lys  Leu Gly Tyr Ile Leu  Arg Asp Val Ser Lys  Lys Glu Gly
    3005                 3010                 3015

Gly Ala  Met Tyr Ala Asp Asp  Thr Ala Gly Trp Asp  Thr Arg Ile
    3020                 3025                 3030

Thr Leu  Glu Asp Leu Lys Asn  Glu Glu Met Val Thr  Asn His Met
    3035                 3040                 3045

Glu Gly  Glu His Lys Lys Leu  Ala Glu Ala Ile Phe  Lys Leu Thr
    3050                 3055                 3060

Tyr Gln  Asn Lys Val Val Arg  Val Gln Arg Pro Thr  Pro Arg Gly
    3065                 3070                 3075

Thr Val  Met Asp Ile Ile Ser  Arg Arg Asp Gln Arg  Gly Ser Gly
    3080                 3085                 3090

Gln Val  Gly Thr Tyr Gly Leu  Asn Thr Phe Thr Asn  Met Glu Ala
    3095                 3100                 3105

Gln Leu  Ile Arg Gln Met Glu  Gly Glu Gly Val Phe  Lys Ser Ile
    3110                 3115                 3120

Gln His  Leu Thr Ile Thr Glu  Glu Ile Ala Val Gln  Asn Trp Leu
    3125                 3130                 3135

Ala Arg  Val Gly Arg Glu Arg  Leu Ser Arg Met Ala  Ile Ser Gly
    3140                 3145                 3150

Asp Asp  Cys Val Val Lys Pro  Leu Asp Asp Arg Phe  Ala Ser Ala
    3155                 3160                 3165

Leu Thr  Ala Leu Asn Asp Met  Gly Lys Ile Arg Lys  Asp Ile Gln
    3170                 3175                 3180

Gln Trp  Glu Pro Ser Arg Gly  Trp Asn Asp Trp Thr  Gln Val Pro
    3185                 3190                 3195

Phe Cys  Ser His His Phe His  Glu Leu Ile Met Lys  Asp Gly Arg
    3200                 3205                 3210

Val Leu  Val Val Pro Cys Arg  Asn Gln Asp Glu Leu  Ile Gly Arg
    3215                 3220                 3225

Ala Arg  Ile Ser Gln Gly Ala  Gly Trp Ser Leu Arg  Glu Thr Ala
    3230                 3235                 3240

Cys Leu  Gly Lys Ser Tyr Ala  Gln Met Trp Ser Leu  Met Tyr Phe
    3245                 3250                 3255

His Arg  Arg Asp Leu Arg Leu  Ala Ala Asn Ala Ile  Cys Ser Ala
    3260                 3265                 3270

Val Pro  Ser His Trp Val Pro  Thr Ser Arg Thr Thr  Trp Ser Ile
    3275                 3280                 3285

His Ala  Lys His Glu Trp Met  Thr Thr Glu Asp Met  Leu Thr Val
    3290                 3295                 3300

Trp Asn  Arg Val Trp Ile Gln  Glu Asn Pro Trp Met  Glu Asp Lys
    3305                 3310                 3315

Thr Pro  Val Glu Ser Trp Glu  Glu Ile Pro Tyr Leu  Gly Lys Arg
    3320                 3325                 3330

Glu Asp  Gln Trp Cys Gly Ser  Leu Ile Gly Leu Thr  Ser Arg Ala
    3335                 3340                 3345

Thr Trp  Ala Lys Asn Ile Gln  Ala Ala Ile Asn Gln  Val Arg Ser
    3350                 3355                 3360
```

```
Leu Ile  Gly Asn Glu Glu Tyr  Thr Asp Tyr Met Pro  Ser Met Lys
    3365                 3370                 3375

Arg Phe  Arg Arg Glu Glu Glu  Glu Ala Gly Val Leu  Trp
    3380                 3385                 3390
```

<210> SEQ ID NO 16
<211> LENGTH: 10723
<212> TYPE: DNA
<213> ORGANISM: Artificial Sequence
<220> FEATURE:
<223> OTHER INFORMATION: Derived from Dengue virus serotype 2, PDK-53 derivative, MVS

<400> SEQUENCE: 16

```
agttgttagt ctacgtggac cgacaaagac agattctttg agggagctaa gctcaatgta     60

gttctaacag tttttttaatt agagagcaga tctctgatga ataaccaacg gaaaaaggcg    120

aaaaacacgc ctttcaatat gctgaaacgc gagagaaacc gcgtgtcgac tgtgcaacag    180

ctgacaaaga gattctcact tggaatgctg cagggacgag gaccattaaa actgttcatg    240

gccctggtgg cgttccttcg tttcctaaca atcccaccaa cagcagggat attgaagaga    300

tggggaacaa ttaaaaaatc aaaagctatt aatgttttga gagggttcag gaaagagatt    360

ggaaggatgc tgaacatctt gaataggaga cgcagatctg caggcatgat cattatgctg    420

attccaacag tgatggcgtt ccatttaacc acacgtaacg gagaaccaca catgatcgtc    480

agcagacaag agaaagggaa aagtcttctg tttaaaacag aggttggcgt gaacatgtgt    540

accctcatgg ccatggacct tggtgaattg tgtgaagaca caatcacgta cgagtgtccc    600

cttctcaggc agaatgagcc agaagacata gactgttggt gcaactctac gtccacgtgg    660

gtaacttatg ggacgtgtac caccatggga gaacatagaa gagaaaaaag atcagtggca    720

ctcgttccac atgtgggaat gggactggag acacgaactg aaacatggat gtcatcagaa    780

ggggcctgga aacatgtcca gagaattgaa acttggatct tgagacatcc aggcttcacc    840

atgatggcag caatcctggc atacaccata ggaacgacac atttccaaag agccctgatc    900

ttcatcttac tgacagctgt cactccttca atgacaatgc gttgcatagg aatgtcaaat    960

agagactttg tggaaggggt ttcaggagga agctgggttg acatagtctt agaacatgga   1020

agctgtgtga cgacgatggc aaaaaacaaa ccaacattgg attttgaact gataaaaaca   1080

gaagccaaac agcctgccac cctaaggaag tactgtatag aggcaaagct aaccaacaca   1140

acaacagaat ctcgctgccc aacacaaggg gaacccagcc taaatgaaga gcaggacaaa   1200

aggttcgtct gcaaacactc catggtagac agaggatggg gaaatggatg tggactattt   1260

ggaaagggag gcattgtgac ctgtgctatg ttcagatgca aaaagaacat ggaaggaaaa   1320

gttgtgcaac cagaaaactt ggaatacacc attgtgataa cacctcactc aggggaagag   1380

catgcagtcg gaaatgacac aggaaaacat ggcaaggaaa tcaaaataac accacagagt   1440

tccatcacag aagcagaatt gacaggttat ggcactgtca caatggagtg ctctccaaga   1500

acgggcctcg acttcaatga gatggtgttg ctgcagatgg aaaataaagc ttggctggtg   1560

cacaggcaat ggttcctaga cctgccgtta ccatggttgc ccggagcgga cacacaaggg   1620

tcaaattgga tacagaaaga gacattggtc actttcaaaa atccccatgc gaagaaacag   1680

gatgttgttg ttttaggatc ccaagaaggg gccatgcaca cagcacttac aggggccaca   1740

gaaatccaaa tgtcatcagg aaacttactc ttcacaggac atctcaagtg caggctgaga   1800

atggacaagc tacagctcaa aggaatgtca tactctatgt gcacaggaaa gtttaaagtt   1860
```

-continued gtgaaggaaa tagcagaaac acaacatgga acaatagtta tcagagtgca atatgaaggg 1920
gacggctctc catgcaagat ccccttttgag ataatggatt tggaaaaaag acatgtctta 1980
ggtcgcctga ttacagtcaa cccaattgtg acagaaaaag atagcccagt caacatagaa 2040
gcagaacctc catttggaga cagctacatc atcataggag tagagccggg acaactgaag 2100
ctcaactggt ttaagaaagg aagttctatc ggccaaatgt ttgagacaac aatgaggggg 2160
gcgaagagaa tggccatttt aggtgacaca gcctgggatt ttggatcctt gggaggagtg 2220
tttacatcta taggaaaggc tctccaccaa gtctttggag caatctatgg agctgccttc 2280
agtggggttt catggactat gaaaatcctc ataggagtca ttatcacatg gataggaatg 2340
aattcacgca gcacctcact gtctgtgaca ctagtattgg tgggaattgt gacactgtat 2400
ttgggagtca tggtgcaggc cgatagtggt tgcgttgtga gctggaaaaa caaagaactg 2460
aaatgtggca gtgggatttt catcacagac aacgtgcaca catggacaga acaatacaag 2520
ttccaaccag aatccccttc aaaactagct tcagctatcc agaaagccca tgaagaggac 2580
atttgtggaa tccgctcagt aacaagactg gagaatctga tgtggaaaca aataacacca 2640
gaattgaatc acattctatc agaaaatgag gtgaagttaa ctattatgac aggagacatc 2700
aaaggaatca tgcaggcagg aaaacgatct ctgcggcctc agcccactga gctgaagtat 2760
tcatggaaaa catggggcaa agcaaaaatg ctctctacag agtctcataa ccagaccttt 2820
ctcattgatg gccccgaaac agcagaatgc cccaacacaa atagagcttg gaattcgttg 2880
gaagttgaag actatggctt tggagtattc accaccaata tatggctaaa attgaaagaa 2940
aaacaggatg tattctgcga ctcaaaactc atgtcagcgg ccataaaaga caacagagcc 3000
gtccatgccg atatgggtta ttggatagaa agtgcactca atgacacatg gaagatagag 3060
aaagcctctt tcattgaagt taaaaactgc cactggccaa aatcacacac cctctggagc 3120
aatggagtgc tagaaagtga gatgataatt ccaaagaatc tcgctggacc agtgtctcaa 3180
cacaactata gaccaggcta ccatacacaa ataacaggac catggcatct aggtaagctt 3240
gagatggact ttgatttctg tgatggaaca acagtggtag tgactgagga ctgcggaaat 3300
agaggaccct ctttgagaac aaccactgcc tctggaaaac tcataacaga atggtgctgc 3360
cgatcttgca cattaccacc gctaagatac agaggtgagg atgggtgctg gtacgggatg 3420
gaaatcagac cattgaagga gaaagaagag aatttggtca actccttggt cacagctgga 3480
catgggcagg tcgacaactt ttcactagga gtcttgggaa tggcattgtt cctggaggaa 3540
atgcttagga cccgagtagg aacgaaacat gcaatactac tagttgcagt ttcttttgtg 3600
acattgatca cagggaacat gtcctttaga gacctgggaa gagtgatggt tatggtaggc 3660
gccactatga cggatgacat aggtatgggc gtgacttatc ttgccctact agcagccttc 3720
aaagtcagac caacttttgc agctggacta ctcttgagaa agctgacctc caaggaattg 3780
atgatgacta ctataggaat tgtactcctc tcccagagca ccataccaga gaccattctt 3840
gagttgactg atgcgttagc cttaggcatg atggtcctca aaatggtgag aaatatggaa 3900
aagtatcaat tggcagtgac tatcatggct atcttgtgcg tcccaaacgc agtgatatta 3960
caaaacgcat ggaaagtgag ttgcacaata ttggcagtgg tgtccgtttc cccactgttc 4020
ttaacatcct cacagcaaaa aacagattgg ataccattag cattgacgat caaaggtctc 4080
aatccaacag ctatttttct aacaaccctc tcaagaacca gcaagaaaag gagctggcca 4140
ttaaatgagg ctatcatggc agtcgggatg gtgagcattt tagccagttc tctcctaaaa 4200
aatgatattc ccatgacagg accattagtg gctggagggc tcctcactgt gtgctacgtg 4260

```
ctcactggac gatcggccga tttggaactg gagagagcag ccgatgtcaa atgggaagac   4320
caggcagaga tatcaggaag cagtccaatc ctgtcaataa caatatcaga agatggtagc   4380
atgtcgataa aaaatgaaga ggaagaacaa acactgacca tactcattag aacaggattg   4440
ctggtgatct caggactttt tcctgtatca ataccaatca cggcagcagc atggtacctg   4500
tgggaagtga agaaacaacg ggccggagta ttgtgggatg ttccttcacc cccacccatg   4560
ggaaaggctg aactggaaga tggagcctat agaattaagc aaaaagggat tcttggatat   4620
tcccagatcg gagccggagt ttacaaagaa ggaacattcc atacaatgtg gcatgtcaca   4680
cgtggcgctg ttctaatgca taaaggaaag aggattgaac catcatgggc ggacgtcaag   4740
aaagacctaa tatcatatgg aggaggctgg aagttagaag gagaatggaa ggaaggagaa   4800
gaagtccagg tattggcact ggagcctgga aaaaatccaa gagccgtcca aacgaaacct   4860
ggtcttttca aaaccaacgc cggaacaata ggtgctgtat ctctggactt ttctcctgga   4920
acgtcaggat ctccaattat cgacaaaaaa ggaaaagttg tgggtcttta tggtaatggt   4980
gttgttacaa ggagtggagc atatgtgagt gctatagccc agactgaaaa aagcattgaa   5040
gacaacccag agatcgaaga tgacattttc cgaaagagaa gactgaccat catggacctc   5100
cacccaggag cgggaaagac gaagagatac cttccggcca tagtcagaga agctataaaa   5160
cggggtttga gaacattaat cttggccccc actagagttg tggcagctga aatggaggaa   5220
gcccttagag gacttccaat aagataccag accccagcca tcagagctgt gcacaccggg   5280
cgggagattg tggacctaat gtgtcatgcc acatttacca tgaggctgct atcaccagtt   5340
agagtgccaa actacaacct gattatcatg gacgaagccc atttcacaga cccagcaagt   5400
atagcagcta gaggatacat ctcaactcga gtggagatgg gtgaggcagc tgggattttt   5460
atgacagcca ctcccccggg aagcagagac ccatttcctc agagcaatgc accaatcata   5520
gatgaagaaa gagaaatccc tgaacgctcg tggaattccg gacatgaatg ggtcacggat   5580
tttaaaggga agactgtttg gttcgttcca agtataaaag caggaaatga tatagcagct   5640
tgcctgagga aaaatggaaa gaaagtgata caactcagta ggaagacctt tgattctgag   5700
tatgtcaaga ctagaaccaa tgattgggac ttcgtggtta caactgacat ttcagaaatg   5760
ggtgccaatt tcaaggctga gagggttata gaccccagac gctgcatgaa accagtcata   5820
ctaacagatg gtgaagagcg ggtgattctg gcaggaccta tgccagtgac ccactctagt   5880
gcagcacaaa gaagagggag aataggaaga aatccaaaaa atgagaatga ccagtacata   5940
tacatggggg aacctctgga aaatgatgaa gactgtgcac actggaaaga agctaaaatg   6000
ctcctagata acatcaacac gccagaagga atcattccta gcatgttcga accagagcgt   6060
gaaaaggtgg atgccattga tggcgaatac cgcttgagag gagaagcaag gaaaaccttt   6120
gtagacttaa tgagaagagg agacctacca gtctggttgg cctacagagt ggcagctgaa   6180
ggcatcaact acgcagacag aaggtggtgt tttgatggag tcaagaacaa ccaaatccta   6240
gaagaaaacg tggaagttga aatctggaca aaagaagggg aaaggaagaa attgaaaccc   6300
agatggttgg atgctaggat ctattctgac ccactggcgc taaaagaatt taaggaattt   6360
gcagccggaa gaaagtctct gaccctgaac ctaatcacag aaatgggtag gctcccaacc   6420
ttcatgactc agaaggcaag agacgcactg gacaacttag cagtgctgca cacggctgag   6480
gcaggtggaa gggcgtacaa ccatgctctc agtgaactgc cggagaccct ggagacattg   6540
cttttactga cacttctggc tacagtcacg ggagggatct tttattctt gatgagcgca   6600
```

-continued

```
aggggcatag ggaagatgac cctgggaatg tgctgcataa tcacggctag catcctccta   6660
tggtacgcac aaatacagcc acactggata gcagcttcaa taatactgga gttttttctc   6720
atagttttgc ttattccaga acctgaaaaa cagagaacac cccaagacaa ccaactgacc   6780
tacgttgtca tagccatcct cacagtggtg gccgcaacca tggcaaacga gatgggtttc   6840
ctagaaaaaa cgaagaaaga tctcggattg ggaagcattg caacccagca acccgagagc   6900
aacatcctgg acatagatct acgtcctgca tcagcatgga cgctgtatgc cgtggccaca   6960
acatttgtta caccaatgtt gagacatagc attgaaaatt cctcagtgaa tgtgtcccta   7020
acagctatag ccaaccaagc cacagtgtta atgggtctcg ggaaaggatg gccattgtca   7080
aagatggaca tcggagttcc ccttctcgcc attggatgct actcacaagt caaccccata   7140
actctcacag cagctctttt cttattggta gcacattatg ccatcatagg gccaggactc   7200
caagcaaaag caaccagaga agctcagaaa agagcagcgg cgggcatcat gaaaaaccca   7260
actgtcgatg gaataacagt gattgaccta gatccaatac cttatgatcc aaagtttgaa   7320
aagcagttgg gacaagtaat gctcctagtc ctctgcgtga ctcaagtatt gatgatgagg   7380
actacatggg ctctgtgtga ggctttaacc ttagctaccg ggcccatctc cacattgtgg   7440
gaaggaaatc cagggaggtt ttggaacact accattgcgg tgtcaatggc taacattttt   7500
agagggagtt acttggccgg agctggactt ctcttttcta ttatgaagaa cacaaccaac   7560
acaagaaggg gaactggcaa cataggagag acgcttggag agaaatggaa aagccgattg   7620
aacgcattgg gaaaaagtga attccagatc tacaagaaaa gtggaatcca ggaagtggat   7680
agaaccttag caaaagaagg cattaaaaga ggagaaacgg accatcacgc tgtgtcgcga   7740
ggctcagcaa aactgagatg gttcgttgag agaaacatgg tcacaccaga agggaaagta   7800
gtggacctcg gttgtggcag aggaggctgg tcatactatt gtggaggact aaagaatgta   7860
agagaagtca aaggcctaac aaaaggagga ccaggacacg aagaacccat ccccatgtca   7920
acatatgggt ggaatctagt gcgtcttcaa agtggagttg acgttttctt catcccgcca   7980
gaaaagtgtg acacattatt gtgtgacata ggggagtcat caccaaatcc cacagtggaa   8040
gcaggacgaa cactcagagt ccttaactta gtagaaaatt ggttgaacaa caacactcaa   8100
ttttgcataa aggttctcaa cccatatatg ccctcagtca tagaaaaaat ggaagcacta   8160
caaaggaaat atggaggagc cttagtgagg aatccactct cacgaaactc cacacatgag   8220
atgtactggg tatccaatgc ttccgggaac atagtgtcat cagtgaacat gatttcaagg   8280
atgttgatca acagatttac aatgagatac aagaaagcca cttacgagcc ggatgttgac   8340
ctcggaagcg gaacccgtaa catcgggatt gaaagtgaga taccaaacct agatataatt   8400
gggaaaagaa tagaaaaaat aaagcaagag catgaaacat catggcacta tgaccaagac   8460
cacccataca aaacgtgggc ataccatggt agctatgaaa caaaacagac tggatcagca   8520
tcatccatgg tcaacggagt ggtcaggctg ctgacaaaac cttgggacgt cgtccccatg   8580
gtgacacaga tggcaatgac agacacgact ccatttggac aacagcgcgt tttaaagag   8640
aaagtggaca cgagaaccca agaaccgaaa gaaggcacga agaaactaat gaaaataaca   8700
gcagagtggc tttggaaaga attagggaag aaaaagacac ccaggatgtg caccagagaa   8760
gaattcacaa gaaaggtgag aagcaatgca gccttggggg ccgtattcac tgatgagaac   8820
aagtggaagt cggcacgtga ggctgttgaa gatagtaggt tttgggagct ggttgacaag   8880
gaaaggaatc tccatcttga aggaaagtgt gaaacatgtg tgtacaacat gatgggaaaa   8940
agagagaaga agctagggga attcggcaag gcaaaaggca gcagagccat atggtacatg   9000
```

```
tggcttggag cacgcttctt agagtttgaa gccctaggat tcttaaatga agatcactgg   9060

ttctccagag agaactccct gagtggagtg gaaggagaag ggctgcacaa gctaggttac   9120

attctaagag acgtgagcaa gaaagaggga ggagcaatgt atgccgatga caccgcagga   9180

tgggatacaa gaatcacact agaagaccta aaaaatgaag aaatggtaac aaaccacatg   9240

gaaggagaac acaagaaact agccgaggcc attttcaaac taacgtacca aaacaaggtg   9300

gtgcgtgtgc aaagaccaac accaagaggc acagtaatgg acatcatatc gagaagagac   9360

caaagaggta gtggacaagt tggcacctat ggactcaata ctttcaccaa tatggaagcc   9420

caactaatca gacagatgga gggagaagga gtctttaaaa gcattcagca cctaacaatc   9480

acagaagaaa tcgctgtgca aaactggtta gcaagagtgg ggcgcgaaag gttatcaaga   9540

atggccatca gtggagatga ttgtgttgtg aaacctttag atgacaggtt cgcaagcgct   9600

ttaacagctc taaatgacat gggaaagatt aggaaagaca tacaacaatg ggaaccttca   9660

agaggatgga atgattggac acaagtgccc ttctgttcac accatttcca tgagttaatc   9720

atgaaagacg gtcgcgtact cgttgttcca tgtagaaacc aagatgaact gattggcaga   9780

gcccgaatct cccaaggagc agggtggtct ttgcgggaga cggcctgttt ggggaagtct   9840

tacgcccaaa tgtggagctt gatgtacttc cacagacgcg acctcaggct ggcggcaaat   9900

gctatttgct cggcagtacc atcacattgg gttccaacaa gtcgaacaac ctggtccata   9960

catgctaaac atgaatggat gacaacggaa gacatgctga cagtctggaa cagggtgtgg  10020

attcaagaaa acccatggat ggaagacaaa actccagtgg aatcatggga ggaaatccca  10080

tacttgggga aaagagaaga ccaatggtgc ggctcattga ttgggttaac aagcagggcc  10140

acctgggcaa agaacatcca agcagcaata aatcaagtta gatcccttat aggcaatgaa  10200

gaatacacag attacatgcc atccatgaaa agattcagaa gagaagagga agaagcagga  10260

gttctgtggt agaaagcaaa actaacatga aacaaggcta gaagtcaggt cggattaagc  10320

catagtacgg aaaaaactat gctacctgtg agccccgtcc aaggacgtta aaagaagtca  10380

ggccatcata aatgccatag cttgagtaaa ctatgcagcc tgtagctcca cctgagaagg  10440

tgtaaaaaat ccgggaggcc acaaaccatg gaagctgtac gcatggcgta gtggactagc  10500

ggttagagga gacccctccc ttacaaatcg cagcaacaat gggggcccaa ggcgagatga  10560

agctgtagtc tcgctggaag gactagaggt tagaggagac ccccccgaaa caaaaaacag  10620

catattgacg ctgggaaaga ccagagatcc tgctgtctcc tcagcatcat tccaggcaca  10680

gaacgccaga aaatggaatg gtgctgttga atcaacaggt tct                    10723
```

<210> SEQ ID NO 17
<211> LENGTH: 3391
<212> TYPE: PRT
<213> ORGANISM: Artificial Sequence
<220> FEATURE:
<223> OTHER INFORMATION: Derived from Dengue virus serotype 2, PDK-53
derivative, MVS

<400> SEQUENCE: 17

```
Met Asn Asn Gln Arg Lys Lys Ala Lys Asn Thr Pro Phe Asn Met Leu
1               5                   10                  15

Lys Arg Glu Arg Asn Arg Val Ser Thr Val Gln Gln Leu Thr Lys Arg
            20                  25                  30

Phe Ser Leu Gly Met Leu Gln Gly Arg Gly Pro Leu Lys Leu Phe Met
        35                  40                  45
```

-continued

```
Ala Leu Val Ala Phe Leu Arg Phe Leu Thr Ile Pro Pro Thr Ala Gly
    50                  55                  60

Ile Leu Lys Arg Trp Gly Thr Ile Lys Lys Ser Lys Ala Ile Asn Val
65                  70                  75                  80

Leu Arg Gly Phe Arg Lys Glu Ile Gly Arg Met Leu Asn Ile Leu Asn
                85                  90                  95

Arg Arg Arg Arg Ser Ala Gly Met Ile Ile Met Leu Ile Pro Thr Val
            100                 105                 110

Met Ala Phe His Leu Thr Thr Arg Asn Gly Glu Pro His Met Ile Val
        115                 120                 125

Ser Arg Gln Glu Lys Gly Lys Ser Leu Leu Phe Lys Thr Glu Val Gly
    130                 135                 140

Val Asn Met Cys Thr Leu Met Ala Met Asp Leu Gly Glu Leu Cys Glu
145                 150                 155                 160

Asp Thr Ile Thr Tyr Glu Cys Pro Leu Leu Arg Gln Asn Glu Pro Glu
                165                 170                 175

Asp Ile Asp Cys Trp Cys Asn Ser Thr Ser Thr Trp Val Thr Tyr Gly
            180                 185                 190

Thr Cys Thr Thr Met Gly Glu His Arg Arg Glu Lys Arg Ser Val Ala
        195                 200                 205

Leu Val Pro His Val Gly Met Gly Leu Glu Thr Arg Thr Glu Thr Trp
    210                 215                 220

Met Ser Ser Glu Gly Ala Trp Lys His Val Gln Arg Ile Glu Thr Trp
225                 230                 235                 240

Ile Leu Arg His Pro Gly Phe Thr Met Met Ala Ala Ile Leu Ala Tyr
                245                 250                 255

Thr Ile Gly Thr Thr His Phe Gln Arg Ala Leu Ile Phe Ile Leu Leu
            260                 265                 270

Thr Ala Val Thr Pro Ser Met Thr Met Arg Cys Ile Gly Met Ser Asn
        275                 280                 285

Arg Asp Phe Val Glu Gly Val Ser Gly Gly Ser Trp Val Asp Ile Val
    290                 295                 300

Leu Glu His Gly Ser Cys Val Thr Thr Met Ala Lys Asn Lys Pro Thr
305                 310                 315                 320

Leu Asp Phe Glu Leu Ile Lys Thr Glu Ala Lys Gln Pro Ala Thr Leu
                325                 330                 335

Arg Lys Tyr Cys Ile Glu Ala Lys Leu Thr Asn Thr Thr Thr Glu Ser
            340                 345                 350

Arg Cys Pro Thr Gln Gly Glu Pro Ser Leu Asn Glu Glu Gln Asp Lys
        355                 360                 365

Arg Phe Val Cys Lys His Ser Met Val Asp Arg Gly Trp Gly Asn Gly
    370                 375                 380

Cys Gly Leu Phe Gly Lys Gly Gly Ile Val Thr Cys Ala Met Phe Arg
385                 390                 395                 400

Cys Lys Lys Asn Met Glu Gly Lys Val Val Gln Pro Glu Asn Leu Glu
                405                 410                 415

Tyr Thr Ile Val Ile Thr Pro His Ser Gly Glu Glu His Ala Val Gly
            420                 425                 430

Asn Asp Thr Gly Lys His Gly Lys Glu Ile Lys Ile Thr Pro Gln Ser
        435                 440                 445

Ser Ile Thr Glu Ala Glu Leu Thr Gly Tyr Gly Thr Val Thr Met Glu
    450                 455                 460

Cys Ser Pro Arg Thr Gly Leu Asp Phe Asn Glu Met Val Leu Leu Gln
```

```
465                 470                 475                 480

Met Glu Asn Lys Ala Trp Leu Val His Arg Gln Trp Phe Leu Asp Leu
                485                 490                 495

Pro Leu Pro Trp Leu Pro Gly Ala Asp Thr Gln Gly Ser Asn Trp Ile
            500                 505                 510

Gln Lys Glu Thr Leu Val Thr Phe Lys Asn Pro His Ala Lys Lys Gln
        515                 520                 525

Asp Val Val Val Leu Gly Ser Gln Glu Gly Ala Met His Thr Ala Leu
    530                 535                 540

Thr Gly Ala Thr Glu Ile Gln Met Ser Ser Gly Asn Leu Leu Phe Thr
545                 550                 555                 560

Gly His Leu Lys Cys Arg Leu Arg Met Asp Lys Leu Gln Leu Lys Gly
                565                 570                 575

Met Ser Tyr Ser Met Cys Thr Gly Lys Phe Lys Val Val Lys Glu Ile
            580                 585                 590

Ala Glu Thr Gln His Gly Thr Ile Val Ile Arg Val Gln Tyr Glu Gly
        595                 600                 605

Asp Gly Ser Pro Cys Lys Ile Pro Phe Glu Ile Met Asp Leu Glu Lys
    610                 615                 620

Arg His Val Leu Gly Arg Leu Ile Thr Val Asn Pro Ile Val Thr Glu
625                 630                 635                 640

Lys Asp Ser Pro Val Asn Ile Glu Ala Glu Pro Pro Phe Gly Asp Ser
                645                 650                 655

Tyr Ile Ile Ile Gly Val Glu Pro Gly Gln Leu Lys Leu Asn Trp Phe
            660                 665                 670

Lys Lys Gly Ser Ser Ile Gly Gln Met Phe Glu Thr Thr Met Arg Gly
        675                 680                 685

Ala Lys Arg Met Ala Ile Leu Gly Asp Thr Ala Trp Asp Phe Gly Ser
    690                 695                 700

Leu Gly Gly Val Phe Thr Ser Ile Gly Lys Ala Leu His Gln Val Phe
705                 710                 715                 720

Gly Ala Ile Tyr Gly Ala Ala Phe Ser Gly Val Ser Trp Thr Met Lys
                725                 730                 735

Ile Leu Ile Gly Val Ile Ile Thr Trp Ile Gly Met Asn Ser Arg Ser
            740                 745                 750

Thr Ser Leu Ser Val Thr Leu Val Leu Val Gly Ile Val Thr Leu Tyr
        755                 760                 765

Leu Gly Val Met Val Gln Ala Asp Ser Gly Cys Val Val Ser Trp Lys
    770                 775                 780

Asn Lys Glu Leu Lys Cys Gly Ser Gly Ile Phe Ile Thr Asp Asn Val
785                 790                 795                 800

His Thr Trp Thr Glu Gln Tyr Lys Phe Gln Pro Glu Ser Pro Ser Lys
                805                 810                 815

Leu Ala Ser Ala Ile Gln Lys Ala His Glu Glu Asp Ile Cys Gly Ile
            820                 825                 830

Arg Ser Val Thr Arg Leu Glu Asn Leu Met Trp Lys Gln Ile Thr Pro
        835                 840                 845

Glu Leu Asn His Ile Leu Ser Glu Asn Glu Val Lys Leu Thr Ile Met
    850                 855                 860

Thr Gly Asp Ile Lys Gly Ile Met Gln Ala Gly Lys Arg Ser Leu Arg
865                 870                 875                 880

Pro Gln Pro Thr Glu Leu Lys Tyr Ser Trp Lys Thr Trp Gly Lys Ala
                885                 890                 895
```

```
Lys Met Leu Ser Thr Glu Ser His Asn Gln Thr Phe Leu Ile Asp Gly
            900                 905                 910

Pro Glu Thr Ala Glu Cys Pro Asn Thr Asn Arg Ala Trp Asn Ser Leu
        915                 920                 925

Glu Val Glu Asp Tyr Gly Phe Gly Val Phe Thr Thr Asn Ile Trp Leu
    930                 935                 940

Lys Leu Lys Glu Lys Gln Asp Val Phe Cys Asp Ser Lys Leu Met Ser
945                 950                 955                 960

Ala Ala Ile Lys Asp Asn Arg Ala Val His Ala Asp Met Gly Tyr Trp
                965                 970                 975

Ile Glu Ser Ala Leu Asn Asp Thr Trp Lys Ile Glu Lys Ala Ser Phe
            980                 985                 990

Ile Glu Val Lys Asn Cys His Trp  Pro Lys Ser His Thr  Leu Trp Ser
        995                 1000                1005

Asn Gly  Val Leu Glu Ser Glu  Met Ile Ile Pro Lys  Asn Leu Ala
    1010                 1015                 1020

Gly Pro  Val Ser Gln His Asn  Tyr Arg Pro Gly Tyr  His Thr Gln
    1025                 1030                 1035

Ile Thr  Gly Pro Trp His Leu  Gly Lys Leu Glu Met  Asp Phe Asp
    1040                 1045                 1050

Phe Cys  Asp Gly Thr Thr Val  Val Val Thr Glu Asp  Cys Gly Asn
    1055                 1060                 1065

Arg Gly  Pro Ser Leu Arg Thr  Thr Thr Ala Ser Gly  Lys Leu Ile
    1070                 1075                 1080

Thr Glu  Trp Cys Cys Arg Ser  Cys Thr Leu Pro Pro  Leu Arg Tyr
    1085                 1090                 1095

Arg Gly  Glu Asp Gly Cys Trp  Tyr Gly Met Glu Ile  Arg Pro Leu
    1100                 1105                 1110

Lys Glu  Lys Glu Glu Asn Leu  Val Asn Ser Leu Val  Thr Ala Gly
    1115                 1120                 1125

His Gly  Gln Val Asp Asn Phe  Ser Leu Gly Val Leu  Gly Met Ala
    1130                 1135                 1140

Leu Phe  Leu Glu Glu Met Leu  Arg Thr Arg Val Gly  Thr Lys His
    1145                 1150                 1155

Ala Ile  Leu Leu Val Ala Val  Ser Phe Val Thr Leu  Ile Thr Gly
    1160                 1165                 1170

Asn Met  Ser Phe Arg Asp Leu  Gly Arg Val Met Val  Met Val Gly
    1175                 1180                 1185

Ala Thr  Met Thr Asp Asp Ile  Gly Met Gly Val Thr  Tyr Leu Ala
    1190                 1195                 1200

Leu Leu  Ala Ala Phe Lys Val  Arg Pro Thr Phe Ala  Ala Gly Leu
    1205                 1210                 1215

Leu Leu  Arg Lys Leu Thr Ser  Lys Glu Leu Met Met  Thr Thr Ile
    1220                 1225                 1230

Gly Ile  Val Leu Leu Ser Gln  Ser Thr Ile Pro Glu  Thr Ile Leu
    1235                 1240                 1245

Glu Leu  Thr Asp Ala Leu Ala  Leu Gly Met Met Val  Leu Lys Met
    1250                 1255                 1260

Val Arg  Asn Met Glu Lys Tyr  Gln Leu Ala Val Thr  Ile Met Ala
    1265                 1270                 1275

Ile Leu  Cys Val Pro Asn Ala  Val Ile Leu Gln Asn  Ala Trp Lys
    1280                 1285                 1290
```

```
Val Ser Cys Thr Ile Leu Ala Val Val Ser Val Ser Pro Leu Phe
    1295                1300                1305

Leu Thr Ser Ser Gln Gln Lys Thr Asp Trp Ile Pro Leu Ala Leu
    1310                1315                1320

Thr Ile Lys Gly Leu Asn Pro Thr Ala Ile Phe Leu Thr Thr Leu
    1325                1330                1335

Ser Arg Thr Ser Lys Lys Arg Ser Trp Pro Leu Asn Glu Ala Ile
    1340                1345                1350

Met Ala Val Gly Met Val Ser Ile Leu Ala Ser Ser Leu Leu Lys
    1355                1360                1365

Asn Asp Ile Pro Met Thr Gly Pro Leu Val Ala Gly Gly Leu Leu
    1370                1375                1380

Thr Val Cys Tyr Val Leu Thr Gly Arg Ser Ala Asp Leu Glu Leu
    1385                1390                1395

Glu Arg Ala Ala Asp Val Lys Trp Glu Asp Gln Ala Glu Ile Ser
    1400                1405                1410

Gly Ser Ser Pro Ile Leu Ser Ile Thr Ile Ser Glu Asp Gly Ser
    1415                1420                1425

Met Ser Ile Lys Asn Glu Glu Glu Glu Gln Thr Leu Thr Ile Leu
    1430                1435                1440

Ile Arg Thr Gly Leu Leu Val Ile Ser Gly Leu Phe Pro Val Ser
    1445                1450                1455

Ile Pro Ile Thr Ala Ala Ala Trp Tyr Leu Trp Glu Val Lys Lys
    1460                1465                1470

Gln Arg Ala Gly Val Leu Trp Asp Val Pro Ser Pro Pro Pro Met
    1475                1480                1485

Gly Lys Ala Glu Leu Glu Asp Gly Ala Tyr Arg Ile Lys Gln Lys
    1490                1495                1500

Gly Ile Leu Gly Tyr Ser Gln Ile Gly Ala Gly Val Tyr Lys Glu
    1505                1510                1515

Gly Thr Phe His Thr Met Trp His Val Thr Arg Gly Ala Val Leu
    1520                1525                1530

Met His Lys Gly Lys Arg Ile Glu Pro Ser Trp Ala Asp Val Lys
    1535                1540                1545

Lys Asp Leu Ile Ser Tyr Gly Gly Gly Trp Lys Leu Glu Gly Glu
    1550                1555                1560

Trp Lys Glu Gly Glu Glu Val Gln Val Leu Ala Leu Glu Pro Gly
    1565                1570                1575

Lys Asn Pro Arg Ala Val Gln Thr Lys Pro Gly Leu Phe Lys Thr
    1580                1585                1590

Asn Ala Gly Thr Ile Gly Ala Val Ser Leu Asp Phe Ser Pro Gly
    1595                1600                1605

Thr Ser Gly Ser Pro Ile Ile Asp Lys Lys Gly Lys Val Val Gly
    1610                1615                1620

Leu Tyr Gly Asn Gly Val Val Thr Arg Ser Gly Ala Tyr Val Ser
    1625                1630                1635

Ala Ile Ala Gln Thr Glu Lys Ser Ile Glu Asp Asn Pro Glu Ile
    1640                1645                1650

Glu Asp Asp Ile Phe Arg Lys Arg Arg Leu Thr Ile Met Asp Leu
    1655                1660                1665

His Pro Gly Ala Gly Lys Thr Lys Arg Tyr Leu Pro Ala Ile Val
    1670                1675                1680

Arg Glu Ala Ile Lys Arg Gly Leu Arg Thr Leu Ile Leu Ala Pro
```

```
    1685                1690                1695

Thr Arg  Val Val Ala Ala Glu  Met Glu Glu Ala Leu  Arg Gly Leu
    1700                1705                1710

Pro Ile  Arg Tyr Gln Thr Pro  Ala Ile Arg Ala Val  His Thr Gly
    1715                1720                1725

Arg Glu  Ile Val Asp Leu Met  Cys His Ala Thr Phe  Thr Met Arg
    1730                1735                1740

Leu Leu  Ser Pro Val Arg Val  Pro Asn Tyr Asn Leu  Ile Ile Met
    1745                1750                1755

Asp Glu  Ala His Phe Thr Asp  Pro Ala Ser Ile Ala  Ala Arg Gly
    1760                1765                1770

Tyr Ile  Ser Thr Arg Val Glu  Met Gly Glu Ala Ala  Gly Ile Phe
    1775                1780                1785

Met Thr  Ala Thr Pro Pro Gly  Ser Arg Asp Pro Phe  Pro Gln Ser
    1790                1795                1800

Asn Ala  Pro Ile Ile Asp Glu  Glu Arg Glu Ile Pro  Glu Arg Ser
    1805                1810                1815

Trp Asn  Ser Gly His Glu Trp  Val Thr Asp Phe Lys  Gly Lys Thr
    1820                1825                1830

Val Trp  Phe Val Pro Ser Ile  Lys Ala Gly Asn Asp  Ile Ala Ala
    1835                1840                1845

Cys Leu  Arg Lys Asn Gly Lys  Lys Val Ile Gln Leu  Ser Arg Lys
    1850                1855                1860

Thr Phe  Asp Ser Glu Tyr Val  Lys Thr Arg Thr Asn  Asp Trp Asp
    1865                1870                1875

Phe Val  Val Thr Thr Asp Ile  Ser Glu Met Gly Ala  Asn Phe Lys
    1880                1885                1890

Ala Glu  Arg Val Ile Asp Pro  Arg Arg Cys Met Lys  Pro Val Ile
    1895                1900                1905

Leu Thr  Asp Gly Glu Glu Arg  Val Ile Leu Ala Gly  Pro Met Pro
    1910                1915                1920

Val Thr  His Ser Ser Ala Ala  Gln Arg Arg Gly Arg  Ile Gly Arg
    1925                1930                1935

Asn Pro  Lys Asn Glu Asn Asp  Gln Tyr Ile Tyr Met  Gly Glu Pro
    1940                1945                1950

Leu Glu  Asn Asp Glu Asp Cys  Ala His Trp Lys Glu  Ala Lys Met
    1955                1960                1965

Leu Leu  Asp Asn Ile Asn Thr  Pro Glu Gly Ile Ile  Pro Ser Met
    1970                1975                1980

Phe Glu  Pro Glu Arg Glu Lys  Val Asp Ala Ile Asp  Gly Glu Tyr
    1985                1990                1995

Arg Leu  Arg Gly Glu Ala Arg  Lys Thr Phe Val Asp  Leu Met Arg
    2000                2005                2010

Arg Gly  Asp Leu Pro Val Trp  Leu Ala Tyr Arg Val  Ala Ala Glu
    2015                2020                2025

Gly Ile  Asn Tyr Ala Asp Arg  Arg Trp Cys Phe Asp  Gly Val Lys
    2030                2035                2040

Asn Asn  Gln Ile Leu Glu Glu  Asn Val Glu Val Glu  Ile Trp Thr
    2045                2050                2055

Lys Glu  Gly Glu Arg Lys Lys  Leu Lys Pro Arg Trp  Leu Asp Ala
    2060                2065                2070

Arg Ile  Tyr Ser Asp Pro Leu  Ala Leu Lys Glu Phe  Lys Glu Phe
    2075                2080                2085
```

```
Ala Ala  Gly Arg Lys Ser Leu  Thr Leu Asn Leu Ile  Thr Glu Met
    2090                 2095                 2100

Gly Arg  Leu Pro Thr Phe Met  Thr Gln Lys Ala Arg  Asp Ala Leu
    2105                 2110                 2115

Asp Asn  Leu Ala Val Leu His  Thr Ala Glu Ala Gly  Gly Arg Ala
    2120                 2125                 2130

Tyr Asn  His Ala Leu Ser Glu  Leu Pro Glu Thr Leu  Glu Thr Leu
    2135                 2140                 2145

Leu Leu  Leu Thr Leu Leu Ala  Thr Val Thr Gly Gly  Ile Phe Leu
    2150                 2155                 2160

Phe Leu  Met Ser Ala Arg Gly  Ile Gly Lys Met Thr  Leu Gly Met
    2165                 2170                 2175

Cys Cys  Ile Ile Thr Ala Ser  Ile Leu Leu Trp Tyr  Ala Gln Ile
    2180                 2185                 2190

Gln Pro  His Trp Ile Ala Ala  Ser Ile Ile Leu Glu  Phe Phe Leu
    2195                 2200                 2205

Ile Val  Leu Leu Ile Pro Glu  Pro Glu Lys Gln Arg  Thr Pro Gln
    2210                 2215                 2220

Asp Asn  Gln Leu Thr Tyr Val  Val Ile Ala Ile Leu  Thr Val Val
    2225                 2230                 2235

Ala Ala  Thr Met Ala Asn Glu  Met Gly Phe Leu Glu  Lys Thr Lys
    2240                 2245                 2250

Lys Asp  Leu Gly Leu Gly Ser  Ile Ala Thr Gln Gln  Pro Glu Ser
    2255                 2260                 2265

Asn Ile  Leu Asp Ile Asp Leu  Arg Pro Ala Ser Ala  Trp Thr Leu
    2270                 2275                 2280

Tyr Ala  Val Ala Thr Thr Phe  Val Thr Pro Met Leu  Arg His Ser
    2285                 2290                 2295

Ile Glu  Asn Ser Ser Val Asn  Val Ser Leu Thr Ala  Ile Ala Asn
    2300                 2305                 2310

Gln Ala  Thr Val Leu Met Gly  Leu Gly Lys Gly Trp  Pro Leu Ser
    2315                 2320                 2325

Lys Met  Asp Ile Gly Val Pro  Leu Leu Ala Ile Gly  Cys Tyr Ser
    2330                 2335                 2340

Gln Val  Asn Pro Ile Thr Leu  Thr Ala Ala Leu Phe  Leu Leu Val
    2345                 2350                 2355

Ala His  Tyr Ala Ile Ile Gly  Pro Gly Leu Gln Ala  Lys Ala Thr
    2360                 2365                 2370

Arg Glu  Ala Gln Lys Arg Ala  Ala Ala Gly Ile Met  Lys Asn Pro
    2375                 2380                 2385

Thr Val  Asp Gly Ile Thr Val  Ile Asp Leu Asp Pro  Ile Pro Tyr
    2390                 2395                 2400

Asp Pro  Lys Phe Glu Lys Gln  Leu Gly Gln Val Met  Leu Leu Val
    2405                 2410                 2415

Leu Cys  Val Thr Gln Val Leu  Met Met Arg Thr Thr  Trp Ala Leu
    2420                 2425                 2430

Cys Glu  Ala Leu Thr Leu Ala  Thr Gly Pro Ile Ser  Thr Leu Trp
    2435                 2440                 2445

Glu Gly  Asn Pro Gly Arg Phe  Trp Asn Thr Thr Ile  Ala Val Ser
    2450                 2455                 2460

Met Ala  Asn Ile Phe Arg Gly  Ser Tyr Leu Ala Gly  Ala Gly Leu
    2465                 2470                 2475
```

```
Leu Phe  Ser Ile Met Lys Asn  Thr Thr Asn Thr Arg  Arg Gly Thr
    2480                 2485                 2490

Gly Asn  Ile Gly Glu Thr Leu  Gly Glu Lys Trp Lys  Ser Arg Leu
    2495                 2500                 2505

Asn Ala  Leu Gly Lys Ser Glu  Phe Gln Ile Tyr Lys  Lys Ser Gly
    2510                 2515                 2520

Ile Gln  Glu Val Asp Arg Thr  Leu Ala Lys Glu Gly  Ile Lys Arg
    2525                 2530                 2535

Gly Glu  Thr Asp His His Ala  Val Ser Arg Gly Ser  Ala Lys Leu
    2540                 2545                 2550

Arg Trp  Phe Val Glu Arg Asn  Met Val Thr Pro Glu  Gly Lys Val
    2555                 2560                 2565

Val Asp  Leu Gly Cys Gly Arg  Gly Gly Trp Ser Tyr  Tyr Cys Gly
    2570                 2575                 2580

Gly Leu  Lys Asn Val Arg Glu  Val Lys Gly Leu Thr  Lys Gly Gly
    2585                 2590                 2595

Pro Gly  His Glu Glu Pro Ile  Pro Met Ser Thr Tyr  Gly Trp Asn
    2600                 2605                 2610

Leu Val  Arg Leu Gln Ser Gly  Val Asp Val Phe Phe  Ile Pro Pro
    2615                 2620                 2625

Glu Lys  Cys Asp Thr Leu Leu  Cys Asp Ile Gly Glu  Ser Ser Pro
    2630                 2635                 2640

Asn Pro  Thr Val Glu Ala Gly  Arg Thr Leu Arg Val  Leu Asn Leu
    2645                 2650                 2655

Val Glu  Asn Trp Leu Asn Asn  Asn Thr Gln Phe Cys  Ile Lys Val
    2660                 2665                 2670

Leu Asn  Pro Tyr Met Pro Ser  Val Ile Glu Lys Met  Glu Ala Leu
    2675                 2680                 2685

Gln Arg  Lys Tyr Gly Gly Ala  Leu Val Arg Asn Pro  Leu Ser Arg
    2690                 2695                 2700

Asn Ser  Thr His Glu Met Tyr  Trp Val Ser Asn Ala  Ser Gly Asn
    2705                 2710                 2715

Ile Val  Ser Ser Val Asn Met  Ile Ser Arg Met Leu  Ile Asn Arg
    2720                 2725                 2730

Phe Thr  Met Arg Tyr Lys Lys  Ala Thr Tyr Glu Pro  Asp Val Asp
    2735                 2740                 2745

Leu Gly  Ser Gly Thr Arg Asn  Ile Gly Ile Glu Ser  Glu Ile Pro
    2750                 2755                 2760

Asn Leu  Asp Ile Ile Gly Lys  Arg Ile Glu Lys Ile  Lys Gln Glu
    2765                 2770                 2775

His Glu  Thr Ser Trp His Tyr  Asp Gln Asp His Pro  Tyr Lys Thr
    2780                 2785                 2790

Trp Ala  Tyr His Gly Ser Tyr  Glu Thr Lys Gln Thr  Gly Ser Ala
    2795                 2800                 2805

Ser Ser  Met Val Asn Gly Val  Val Arg Leu Leu Thr  Lys Pro Trp
    2810                 2815                 2820

Asp Val  Val Pro Met Val Thr  Gln Met Ala Met Thr  Asp Thr Thr
    2825                 2830                 2835

Pro Phe  Gly Gln Gln Arg Val  Phe Lys Glu Lys Val  Asp Thr Arg
    2840                 2845                 2850

Thr Gln  Glu Pro Lys Glu Gly  Thr Lys Lys Leu Met  Lys Ile Thr
    2855                 2860                 2865

Ala Glu  Trp Leu Trp Lys Glu  Leu Gly Lys Lys Lys  Thr Pro Arg
```

```
    2870                2875                2880

Met Cys Thr Arg Glu Glu Phe Thr Arg Lys Val Arg Ser Asn Ala
    2885                2890                2895

Ala Leu Gly Ala Val Phe Thr Asp Glu Asn Lys Trp Lys Ser Ala
    2900                2905                2910

Arg Glu Ala Val Glu Asp Ser Arg Phe Trp Glu Leu Val Asp Lys
    2915                2920                2925

Glu Arg Asn Leu His Leu Glu Gly Lys Cys Glu Thr Cys Val Tyr
    2930                2935                2940

Asn Met Met Gly Lys Arg Glu Lys Lys Leu Gly Glu Phe Gly Lys
    2945                2950                2955

Ala Lys Gly Ser Arg Ala Ile Trp Tyr Met Trp Leu Gly Ala Arg
    2960                2965                2970

Phe Leu Glu Phe Glu Ala Leu Gly Phe Leu Asn Glu Asp His Trp
    2975                2980                2985

Phe Ser Arg Glu Asn Ser Leu Ser Gly Val Glu Gly Glu Gly Leu
    2990                2995                3000

His Lys Leu Gly Tyr Ile Leu Arg Asp Val Ser Lys Lys Glu Gly
    3005                3010                3015

Gly Ala Met Tyr Ala Asp Asp Thr Ala Gly Trp Asp Thr Arg Ile
    3020                3025                3030

Thr Leu Glu Asp Leu Lys Asn Glu Glu Met Val Thr Asn His Met
    3035                3040                3045

Glu Gly Glu His Lys Lys Leu Ala Glu Ala Ile Phe Lys Leu Thr
    3050                3055                3060

Tyr Gln Asn Lys Val Val Arg Val Gln Arg Pro Thr Pro Arg Gly
    3065                3070                3075

Thr Val Met Asp Ile Ile Ser Arg Arg Asp Gln Arg Gly Ser Gly
    3080                3085                3090

Gln Val Gly Thr Tyr Gly Leu Asn Thr Phe Thr Asn Met Glu Ala
    3095                3100                3105

Gln Leu Ile Arg Gln Met Glu Gly Glu Gly Val Phe Lys Ser Ile
    3110                3115                3120

Gln His Leu Thr Ile Thr Glu Glu Ile Ala Val Gln Asn Trp Leu
    3125                3130                3135

Ala Arg Val Gly Arg Glu Arg Leu Ser Arg Met Ala Ile Ser Gly
    3140                3145                3150

Asp Asp Cys Val Val Lys Pro Leu Asp Asp Arg Phe Ala Ser Ala
    3155                3160                3165

Leu Thr Ala Leu Asn Asp Met Gly Lys Ile Arg Lys Asp Ile Gln
    3170                3175                3180

Gln Trp Glu Pro Ser Arg Gly Trp Asn Asp Trp Thr Gln Val Pro
    3185                3190                3195

Phe Cys Ser His His Phe His Glu Leu Ile Met Lys Asp Gly Arg
    3200                3205                3210

Val Leu Val Val Pro Cys Arg Asn Gln Asp Glu Leu Ile Gly Arg
    3215                3220                3225

Ala Arg Ile Ser Gln Gly Ala Gly Trp Ser Leu Arg Glu Thr Ala
    3230                3235                3240

Cys Leu Gly Lys Ser Tyr Ala Gln Met Trp Ser Leu Met Tyr Phe
    3245                3250                3255

His Arg Arg Asp Leu Arg Leu Ala Ala Asn Ala Ile Cys Ser Ala
    3260                3265                3270
```

```
Val Pro Ser His Trp Val Pro Thr Ser Arg Thr Thr Trp Ser Ile
    3275                3280                3285

His Ala Lys His Glu Trp Met Thr Thr Glu Asp Met Leu Thr Val
    3290                3295                3300

Trp Asn Arg Val Trp Ile Gln Glu Asn Pro Trp Met Glu Asp Lys
    3305                3310                3315

Thr Pro Val Glu Ser Trp Glu Glu Ile Pro Tyr Leu Gly Lys Arg
    3320                3325                3330

Glu Asp Gln Trp Cys Gly Ser Leu Ile Gly Leu Thr Ser Arg Ala
    3335                3340                3345

Thr Trp Ala Lys Asn Ile Gln Ala Ala Ile Asn Gln Val Arg Ser
    3350                3355                3360

Leu Ile Gly Asn Glu Glu Tyr Thr Asp Tyr Met Pro Ser Met Lys
    3365                3370                3375

Arg Phe Arg Arg Glu Glu Glu Glu Ala Gly Val Leu Trp
    3380                3385                3390
```

<210> SEQ ID NO 18
<211> LENGTH: 10717
<212> TYPE: DNA
<213> ORGANISM: Artificial Sequence
<220> FEATURE:
<223> OTHER INFORMATION: Derived from Dengue virus serotype 2/Dengue virus serotype 3, MVS

<400> SEQUENCE: 18

```
agttgttagt ctacgtggac cgacaaagac agattctttg agggagctaa gctcaatgta     60

gttctaacag ttttttaatt agagagcaga tctctgatga ataaccaacg gaaaaaggcg    120

aaaaacacgc ctttcaatat gctgaaacgc gagagaaacc gcgtgtcgac tgtgcaacag    180

ctgacaaaga gattctcact tggaatgctg cagggacgag gaccattaaa actgttcatg    240

gccctggtgg cgttccttcg tttcctaaca atcccaccaa cagcagggat attgaagaga    300

tggggaacaa ttaaaaaatc aaaagctatt aatgttttga gagggttcag gaaagagatt    360

ggaaggatgc tgaacatctt gaataggaga cgcagatctg caggcatgat cattatgctg    420

attccaacag tgatggcgtt ccatttaacc acgcgtgatg gagagccgcg catgattgtg    480

gggaagaatg aaagaggaaa atccctactt ttcaagacag cctctggaat caacatgtgc    540

acactcatag ctatggatct gggagagatg tgtgatgaca cggtcactta caaatgcccc    600

cacattaccg aagtggagcc tgaagacatt gactgctggt gcaaccttac atcgacatgg    660

gtgacttatg gaacatgcaa tcaagctgga gagcatagac gcgataagag atcagtggcg    720

ttagctcccc atgttggcat gggactggac acacgcactc aaacctggat gtcggctgaa    780

ggagcttgga gacaagtcga gaaggtagag acatgggccc ttaggcaccc agggtttacc    840

atactagccc tatttcttgc ccattacata ggcacttcct tgacccagaa agtggttatt    900

tttatactat taatgctggt taccccatcc atgacaatga gatgtgtagg agtaggaaac    960

agagattttg tggaaggcct atcgggagct acgtgggttg acgtggtgct cgagcacggt   1020

gggtgtgtga ctaccatggc taagaacaag cccacgctgg acatagagct tcagaagacc   1080

gaggccaccc aactggcgac cctaaggaag ctatgcattg agggaaaaat taccaacata   1140

acaaccgact caagatgtcc cacccaaggg gaagcgattt tacctgagga gcaggaccag   1200

aactacgtgt gtaagcatac atacgtggac agaggctggg gaaacggttg tggtttgttt   1260

ggcaagggaa gcttggtgac atgcgcgaaa tttcaatgtt tagaatcaat agagggaaaa   1320
```

-continued gtggtgcaac atgagaacct caaatacacc gtcatcatca cagtgcacac aggagaccaa 1380
caccaggtgg gaaatgaaac gcagggagtc acggctgaga taacacccca ggcatcaacc 1440
gctgaagcca ttttacctga atatggaacc ctcgggctag aatgctcacc acggacaggt 1500
ttggatttca atgaaatgat ctcattgaca atgaagaaca aagcatggat ggtacataga 1560
caatggttct ttgacttacc cctaccatgg acatcaggag cttcagcaga aacaccaact 1620
tggaacagga aagagcttct tgtgacattt aaaaatgcac atgcaaaaaa gcaagaagta 1680
gttgttcttg gatcacaaga gggagcaatg catacagcac tgacaggagc tacagagatc 1740
caaacctcag gaggcacaag tatctttgcg ggcacttaa aatgtagact caagatggac 1800
aaattggaac tcaaggggat gagctatgca atgtgcttga gtagctttgt gttgaagaaa 1860
gaagtctccg aaacgcagca tgggacaata ctcattaagg ttgagtacaa aggggaagat 1920
gcaccctgca agattccttt ctccacggag gatggacaag gaaaagctct caatggcaga 1980
ctgatcacag ccaatccagt ggtgaccaag aaggaggagc ctgtcaacat tgaggctgaa 2040
cctccttttg gagaaagtaa catagtaatt ggaattggag acaaagccct gaaaatcaac 2100
tggtacaaga agggaagctc gattgggaag atgttcgagg ccactgccag aggtgcaagg 2160
cgcatggcca tcttgggaga cacagcctgg gactttggat cagtgggtgg tgttttgaat 2220
tcattaggga aaatggtcca ccaaatattt gggagtgctt acacagccct atttggtgga 2280
gtctcctgga tgatgaaaat tggaataggt gtcctcttaa cctggatagg gttgaactca 2340
aaaaatactt ctatgtcatt ttcatgcatc gcggccggca ttgtgacact gtatttggga 2400
gtcatggtgc aggccgatag tggttgcgtt gtgagctgga aaaacaaaga actgaaatgt 2460
ggcagtggga ttttcatcac agacaacgtg cacacatgga cagaacaata caagttccaa 2520
ccagaatccc cttcaaaact agcttcagct atccagaaag cccatgaaga ggacatttgt 2580
ggaatccgct cagtaacaag actggagaat ctgatgtgga aacaaataac accagaattg 2640
aatcacattc tatcagaaaa tgaggtgaag ttaactatta tgacaggaga catcaaagga 2700
atcatgcagg caggaaaacg atctctgcgg cctcagccca ctgagctgaa gtattcatgg 2760
aaaacatggg gcaaagcaaa aatgctctct acagagtctc ataaccagac ctttctcatt 2820
gatggccccg aaacagcaga atgccccaac acaaatagag cttggaattc gttggaagtt 2880
gaagactatg gctttggagt attcaccacc aatatatggc taaaattgaa agaaaaacag 2940
gatgtattct gcgactcaaa actcatgtca gcggccataa aagacaacag agccgtccat 3000
gccgatatgg gttattggat agaaagtgca ctcaatgaca catggaagat agagaaagcc 3060
tctttcattg aagttaaaaa ctgccactgg ccaaaatcac acaccctctg gagcaatgga 3120
gtgctagaaa gtgagatgat aattccaaag aatctcgctg gaccagtgtc tcaacacaac 3180
tatagaccag gctaccatac acaaataaca ggaccatggc atctaggtaa gcttgagatg 3240
gactttgatt tctgtgatgg aacaacagtg gtagtgactg aggactgcgg aaatagagga 3300
ccctctttga gaacaaccac tgcctctgga aaactcataa cagaatggtg ctgccgatct 3360
tgcacattac caccgctaag atacagaggt gaggatgggt gctggtacgg gatggaaatc 3420
agaccattga aggagaaaga agagaatttg gtcaactcct tggtcacagc tggacatggg 3480
caggtcgaca acttttcact aggagtcttg ggaatggcat tgttcctgga ggaaatgctt 3540
aggacccgag taggaacgaa acatgcaata ctactagttg cagtttcttt tgtgacattg 3600
atcacaggga acatgtcctt tagagacctg ggaagagtga tggttatggt aggcgccact 3660

-continued

```
atgacggatg acataggtat gggcgtgact tatcttgccc tactagcagc cttcaaagtc   3720
agaccaactt ttgcagctgg actactcttg agaaagctga cctccaagga attgatgatg   3780
actactatag gaattgtact cctctcccag agcaccatac cagagaccat tcttgagttg   3840
actgatgcgt tagccttagg catgatggtc ctcaaaatgg tgagaaatat ggaaaagtat   3900
caattggcag tgactatcat ggctatcttg tgcgtcccaa acgcagtgat attacaaaac   3960
gcatggaaag tgagttgcac aatattggca gtggtgtccg tttccccact gttcttaaca   4020
tcctcacagc aaaaaacaga ttggatacca ttagcattga cgatcaaagg tctcaatcca   4080
acagctattt ttctaacaac cctctcaaga accagcaaga aaaggagctg gccattaaat   4140
gaggctatca tggcagtcgg gatggtgagc attttagcca gttctctcct aaaaaatgat   4200
attcccatga caggaccatt agtggctgga gggctcctca ctgtgtgcta cgtgctcact   4260
ggacgatcgg ccgatttgga actggagaga gcagccgatg tcaaatggga agaccaggca   4320
gagatatcag gaagcagtcc aatcctgtca ataacaatat cagaagatgg tagcatgtcg   4380
ataaaaaatg aagaggaaga acaaacactg accatactca ttagaacagg attgctggtg   4440
atctcaggac tttttcctgt atcaatacca atcacggcag cagcatggta cctgtgggaa   4500
gtgaagaaac aacgggccgg agtattgtgg gatgttcctt cacccccacc catgggaaag   4560
gctgaactgg aagatggagc ctatagaatt aagcaaaaag ggattcttgg atattcccag   4620
atcggagccg gagtttacaa agaaggaaca ttccatacaa tgtggcatgt cacacgtggc   4680
gctgttctaa tgcataaagg aaagaggatt gaaccatcat gggcggacgt caagaaagac   4740
ctaatatcat atggaggagg ctggaagtta gaaggagaat ggaaggaagg agaagaagtc   4800
caggtattgg cactggagcc tggaaaaaat ccaagagccg tccaaacgaa acctggtctt   4860
ttcaaaacca acgccggaac aataggtgct gtatctctgg acttttctcc tggaacgtca   4920
ggatctccaa ttatcgacaa aaaaggaaaa gttgtgggtc tttatggtaa tggtgttgtt   4980
acaaggagtg gagcatatgt gagtgctata gcccagactg aaaaaagcat tgaagacaac   5040
ccagagatcg aagatgacat tttccgaaag agaagactga ccatcatgga cctccaccca   5100
ggagcgggaa agacgaagag ataccttccg gccatagtca gagaagctat aaaacggggt   5160
ttgagaacat taatcttggc ccccactaga gttgtggcag ctgaaatgga ggaagccctt   5220
agaggacttc caataagata ccagacccca gccatcagag ctgtgcacac cgggcgggag   5280
attgtggacc taatgtgtca tgccacattt accatgaggc tgctatcacc agttagagtg   5340
ccaaactaca acctgattat catggacgaa gcccatttca cagacccagc aagtatagca   5400
gctagaggat acatctcaac tcgagtggag atgggtgagg cagctgggat ttttatgaca   5460
gccactcccc cgggaagcag agacccattt cctcagagca atgcaccaat catagatgaa   5520
gaaagagaaa tccctgaacg ctcgtggaat tccggacatg aatgggtcac ggattttaaa   5580
gggaagactg tttggttcgt tccaagtata aaagcaggaa atgatatagc agcttgcctg   5640
aggaaaaatg gaaagaaagt gatacaactc agtaggaaga cctttgattc tgagtatgtc   5700
aagactagaa ccaatgattg ggacttcgtg gttacaactg acatttcaga aatgggtgcc   5760
aatttcaagg ctgagagggt tatagacccc agacgctgca tgaaaccagt catactaaca   5820
gatggtgaag agcgggtgat tctggcagga cctatgccag tgacccactc tagtgcagca   5880
caaagaagag ggagaatagg aagaaatcca aaaaatgaga atgaccagta catatacatg   5940
ggggaacctc tggaaaatga tgaagactgt gcacactgga aagaagctaa aatgctccta   6000
gataacatca acacgccaga aggaatcatt cctagcatgt tcgaaccaga gcgtgaaaag   6060
```

-continued

```
gtggatgcca ttgatggcga ataccgcttg agaggagaag caaggaaaac ctttgtagac   6120
ttaatgagaa gaggagacct accagtctgg ttggcctaca gagtggcagc tgaaggcatc   6180
aactacgcag acagaaggtg gtgttttgat ggagtcaaga acaaccaaat cctagaagaa   6240
aacgtggaag ttgaaatctg gacaaaagaa ggggaaagga agaaattgaa acccagatgg   6300
ttggatgcta ggatctattc tgacccactg gcgctaaaag aatttaagga atttgcagcc   6360
ggaagaaagt ctctgaccct gaacctaatc acagaaatgg gtaggctccc aaccttcatg   6420
actcagaagg caagagacgc actggacaac ttagcagtgc tgcacacggc tgaggcaggt   6480
ggaagggcgt acaaccatgc tctcagtgaa ctgccggaga ccctggagac attgctttta   6540
ctgacacttc tggctacagt cacgggaggg atctttttat tcttgatgag cgcaaggggc   6600
atagggaaga tgaccctggg aatgtgctgc ataatcacgg ctagcatcct cctatggtac   6660
gcacaaatac agccacactg gatagcagct tcaataatac tggagttttt tctcatagtt   6720
ttgcttattc cagaacctga aaaacagaga acaccccaag acaaccaact gacctacgtt   6780
gtcatagcca tcctcacagt ggtggccgca accatggcaa acgagatggg tttcctagaa   6840
aaaacgaaga aagatctcgg attgggaagc attgcaaccc agcaacccga gagcaacatc   6900
ctggacatag atctacgtcc tgcatcagca tggacgctgt atgccgtggc cacaacattt   6960
gttacaccaa tgttgagaca tagcattgaa aattcctcag tgaatgtgtc cctaacagct   7020
atagccaacc aagccacagt gttaatgggt ctcgggaaag gatggccatt gtcaaagatg   7080
gacatcggag ttccccttct cgccattgga tgctactcac aagtcaaccc cataactctc   7140
acagcagctc ttttcttatt ggtagcacat tatgccatca tagggccagg actccaagca   7200
aaagcaacca gagaagctca gaaaagagca gcggcgggca tcatgaaaaa cccaactgtc   7260
gatggaataa cagtgattga cctagatcca ataccttatg atccaaagtt tgaaaagcag   7320
ttgggacaag taatgctcct agtcctctgc gtgactcaag tattgatgat gaggactaca   7380
tgggctctgt gtgaggcttt aaccttagct accgggccca tctccacatt gtgggaagga   7440
aatccaggga ggttttggaa cactaccatt gcggtgtcaa tggctaacat ttttagaggg   7500
agttacttgg ccggagctgg acttctcttt tctattatga agaacacaac caacacaaga   7560
aggggaactg gcaacatagg agagacgctt ggagagaaat ggaaaagccg attgaacgcg   7620
ttgggaaaaa gtgaattcca gatctacaag aaaagtggaa tccaggaagt ggatagaacc   7680
ttagcaaaag aaggcattaa aagaggagaa acggaccatc acgctgtgtc gcgaggctca   7740
gcaaaactga gatggttcgt tgagagaaac atggtcacac cagaagggaa agtagtggac   7800
ctcggttgtg gcagaggagg ctggtcatac tattgtggag gactaaagaa tgtaagagaa   7860
gtcaaaggcc taacaaaagg aggaccagga cacgaagaac ccatccccat gtcaacatat   7920
gggtggaatc tagtgcgtct tcaaagtgga gttgacgttt tcttcatccc gccagaaaag   7980
tgtgacacat tattgtgtga catagggggag tcatcaccaa atcccacagt ggaagcagga   8040
cgaacactca gagtccttaa cttagtagaa aattggttga acaacaacac tcaattttgc   8100
ataaaggttc tcaacccata tatgccctca gtcatagaaa aaatggaagc actacaaagg   8160
aaatatggag gagccttagt gaggaatcca ctctcacgaa actccacaca tgagatgtac   8220
tgggtatcca atgcttccgg gaacatagtg tcatcagtga acatgatttc aaggatgttg   8280
atcaacagat ttacaatgag atacaagaaa gccacttacg agccggatgt tgacctcgga   8340
agcggaaccc gtaacatcgg gattgaaagt gagataccaa acctagatat aattgggaaa   8400
```

-continued

```
agaatagaaa aaataaagca agagcatgaa acatcatggc actatgacca agaccaccca   8460
tacaaaacgt gggcatacca tggtagctat gaaacaaaac agactggatc agcatcatcc   8520
atggtcaacg gagtggtcag gctgctgaca aaaccttggg acgtcgtccc catggtgaca   8580
cagatggcaa tgacagacac gactccattt ggacaacagc gcgtttttaa agagaaagtg   8640
gacacgagaa cccaagaacc gaaagaaggc acgaagaaac taatgaaaat aacagcagag   8700
tggctttgga aagaattagg gaagaaaaag acacccagga tgtgcaccag agaagaattc   8760
acaagaaagg tgagaagcaa tgcagccttg ggggccatat tcactgatga gaacaagtgg   8820
aagtcggcac gtgaggctgt tgaagatagt aggttttggg agctggttga caaggaaagg   8880
aatctccatc ttgaaggaaa gtgtgaaaca tgtgtgtaca acatgatggg aaaaagagag   8940
aagaagctag gggaattcgg caaggcaaaa ggcagcagag ccatatggta catgtggctt   9000
ggagcacgct tcttagagtt tgaagcccta ggattcttaa atgaagatca ctggttctcc   9060
agagagaact ccctgagtgg agtggaagga gaagggctgc acaagctagg ttacattcta   9120
agagacgtga gcaagaaaga gggaggagca atgtatgccg atgacaccgc aggatgggat   9180
acaagaatca cactagaaga cctaaaaaat gaagaaatgg taacaaacca catggaagga   9240
gaacacaaga aactagccga ggccattttc aaactaacgt accaaaacaa ggtggtgcgt   9300
gtgcaaagac caacaccaag aggcacagta atggacatca tatcgagaag agaccaaaga   9360
ggtagtggac aagttggcac ctatggactc aatactttca ccaatatgga agcccaacta   9420
atcagacaga tggagggaga aggagtcttt aaaagcattc agcacctaac aatcacagaa   9480
gaaatcgctg tgcaaaactg gttagcaaga gtggggcgcg aaaggttatc aagaatggcc   9540
atcagtggag atgattgtgt tgtgaaacct ttagatgaca ggttcgcaag cgctttaaca   9600
gctctaaatg acatgggaaa gattaggaaa gacatacaac aatgggaacc ttcaagagga   9660
tggaatgatt ggacacaagt gcccttctgt tcacaccatt tccatgagtt aatcatgaaa   9720
gacggtcgcg tactcgttgt tccatgtaga aaccaagatg aactgattgg cagagcccga   9780
atctcccaag gagcagggtg gtctttgcgg gagacggcct gtttggggaa gtcttacgcc   9840
caaatgtgga gcttgatgta cttccacaga cgcgacctca ggctggcggc aaatgctatt   9900
tgctcggcag taccatcaca ttgggttcca acaagtcgaa caacctggtc catacatgct   9960
aaacatgaat ggatgacaac ggaagacatg ctgacagtct ggaacagggt gtggattcaa  10020
gaaaacccat ggatggaaga caaaactcca gtggaatcat gggaggaaat cccatacttg  10080
gggaaaagag aagaccaatg gtgcggctca ttgattgggt taacaagcag ggccacctgg  10140
gcaaagaaca tccaagcagc aataaatcaa gttagatccc ttataggcaa tgaagaatac  10200
acagattaca tgccatccat gaaaagattc agaagagaag aggaagaagc aggagttctg  10260
tggtagaaag caaaactaac atgaaacaag gctagaagtc aggtcggatt aagccatagt  10320
acggaaaaaa ctatgctacc tgtgagcccc gtccaaggac gttaaaagaa gtcaggccat  10380
cataaatgcc atagcttgag taaactatgc agcctgtagc tccacctgag aaggtgtaaa  10440
aaatccggga ggccacaaac catggaagct gtacgcatgg cgtagtggac tagcggttag  10500
aggagacccc tcccttacaa atcgcagcaa caatgggggc ccaaggcgag atgaagctgt  10560
agtctcgctg gaaggactag aggttagagg agaccccccc gaaacaaaaa acagcatatt  10620
gacgctggga aagaccagag atcctgctgt ctcctcagca tcattccagg cacagaacgc  10680
cagaaaatgg aatggtgctg ttgaatcaac aggttct                           10717
```

```
<210> SEQ ID NO 19
<211> LENGTH: 3389
<212> TYPE: PRT
<213> ORGANISM: Artificial Sequence
<220> FEATURE:
<223> OTHER INFORMATION: Derived from Dengue virus serotype 2/Dengue
      virus serotype 3, MVS

<400> SEQUENCE: 19

Met Asn Asn Gln Arg Lys Lys Ala Lys Asn Thr Pro Phe Asn Met Leu
1               5                   10                  15

Lys Arg Glu Arg Asn Arg Val Ser Thr Val Gln Gln Leu Thr Lys Arg
            20                  25                  30

Phe Ser Leu Gly Met Leu Gln Gly Arg Gly Pro Leu Lys Leu Phe Met
        35                  40                  45

Ala Leu Val Ala Phe Leu Arg Phe Leu Thr Ile Pro Pro Thr Ala Gly
    50                  55                  60

Ile Leu Lys Arg Trp Gly Thr Ile Lys Lys Ser Lys Ala Ile Asn Val
65                  70                  75                  80

Leu Arg Gly Phe Arg Lys Glu Ile Gly Arg Met Leu Asn Ile Leu Asn
                85                  90                  95

Arg Arg Arg Arg Ser Ala Gly Met Ile Ile Met Leu Ile Pro Thr Val
            100                 105                 110

Met Ala Phe His Leu Thr Thr Arg Asp Gly Glu Pro Arg Met Ile Val
        115                 120                 125

Gly Lys Asn Glu Arg Gly Lys Ser Leu Leu Phe Lys Thr Ala Ser Gly
    130                 135                 140

Ile Asn Met Cys Thr Leu Ile Ala Met Asp Leu Gly Glu Met Cys Asp
145                 150                 155                 160

Asp Thr Val Thr Tyr Lys Cys Pro His Ile Thr Glu Val Glu Pro Glu
                165                 170                 175

Asp Ile Asp Cys Trp Cys Asn Leu Thr Ser Thr Trp Val Thr Tyr Gly
            180                 185                 190

Thr Cys Asn Gln Ala Gly Glu His Arg Arg Asp Lys Arg Ser Val Ala
        195                 200                 205

Leu Ala Pro His Val Gly Met Gly Leu Asp Thr Arg Thr Gln Thr Trp
    210                 215                 220

Met Ser Ala Glu Gly Ala Trp Arg Gln Val Glu Lys Val Glu Thr Trp
225                 230                 235                 240

Ala Leu Arg His Pro Gly Phe Thr Ile Leu Ala Leu Phe Leu Ala His
                245                 250                 255

Tyr Ile Gly Thr Ser Leu Thr Gln Lys Val Val Ile Phe Ile Leu Leu
            260                 265                 270

Met Leu Val Thr Pro Ser Met Thr Met Arg Cys Val Gly Val Gly Asn
        275                 280                 285

Arg Asp Phe Val Glu Gly Leu Ser Gly Ala Thr Trp Val Asp Val Val
    290                 295                 300

Leu Glu His Gly Gly Cys Val Thr Thr Met Ala Lys Asn Lys Pro Thr
305                 310                 315                 320

Leu Asp Ile Glu Leu Gln Lys Thr Glu Ala Thr Gln Leu Ala Thr Leu
                325                 330                 335

Arg Lys Leu Cys Ile Glu Gly Lys Ile Thr Asn Ile Thr Thr Asp Ser
            340                 345                 350

Arg Cys Pro Thr Gln Gly Glu Ala Ile Leu Pro Glu Glu Gln Asp Gln
        355                 360                 365
```

```
Asn Tyr Val Cys Lys His Thr Tyr Val Asp Arg Gly Trp Gly Asn Gly
    370                 375                 380

Cys Gly Leu Phe Gly Lys Gly Ser Leu Val Thr Cys Ala Lys Phe Gln
385                 390                 395                 400

Cys Leu Glu Ser Ile Glu Gly Lys Val Val Gln His Glu Asn Leu Lys
                405                 410                 415

Tyr Thr Val Ile Ile Thr Val His Thr Gly Asp Gln His Gln Val Gly
            420                 425                 430

Asn Glu Thr Gln Gly Val Thr Ala Glu Ile Thr Pro Gln Ala Ser Thr
        435                 440                 445

Ala Glu Ala Ile Leu Pro Glu Tyr Gly Thr Leu Gly Leu Glu Cys Ser
    450                 455                 460

Pro Arg Thr Gly Leu Asp Phe Asn Glu Met Ile Ser Leu Thr Met Lys
465                 470                 475                 480

Asn Lys Ala Trp Met Val His Arg Gln Trp Phe Phe Asp Leu Pro Leu
                485                 490                 495

Pro Trp Thr Ser Gly Ala Ser Ala Glu Thr Pro Thr Trp Asn Arg Lys
            500                 505                 510

Glu Leu Leu Val Thr Phe Lys Asn Ala His Ala Lys Lys Gln Glu Val
        515                 520                 525

Val Val Leu Gly Ser Gln Glu Gly Ala Met His Thr Ala Leu Thr Gly
    530                 535                 540

Ala Thr Glu Ile Gln Thr Ser Gly Gly Thr Ser Ile Phe Ala Gly His
545                 550                 555                 560

Leu Lys Cys Arg Leu Lys Met Asp Lys Leu Glu Leu Lys Gly Met Ser
                565                 570                 575

Tyr Ala Met Cys Leu Ser Ser Phe Val Leu Lys Lys Glu Val Ser Glu
            580                 585                 590

Thr Gln His Gly Thr Ile Leu Ile Lys Val Glu Tyr Lys Gly Glu Asp
        595                 600                 605

Ala Pro Cys Lys Ile Pro Phe Ser Thr Glu Asp Gly Gln Gly Lys Ala
    610                 615                 620

Leu Asn Gly Arg Leu Ile Thr Ala Asn Pro Val Val Thr Lys Lys Glu
625                 630                 635                 640

Glu Pro Val Asn Ile Glu Ala Glu Pro Pro Phe Gly Glu Ser Asn Ile
                645                 650                 655

Val Ile Gly Ile Gly Asp Lys Ala Leu Lys Ile Asn Trp Tyr Lys Lys
            660                 665                 670

Gly Ser Ser Ile Gly Lys Met Phe Glu Ala Thr Ala Arg Gly Ala Arg
        675                 680                 685

Arg Met Ala Ile Leu Gly Asp Thr Ala Trp Asp Phe Gly Ser Val Gly
    690                 695                 700

Gly Val Leu Asn Ser Leu Gly Lys Met Val His Gln Ile Phe Gly Ser
705                 710                 715                 720

Ala Tyr Thr Ala Leu Phe Gly Gly Val Ser Trp Met Met Lys Ile Gly
                725                 730                 735

Ile Gly Val Leu Leu Thr Trp Ile Gly Leu Asn Ser Lys Asn Thr Ser
            740                 745                 750

Met Ser Phe Ser Cys Ile Ala Ala Gly Ile Val Thr Leu Tyr Leu Gly
        755                 760                 765

Val Met Val Gln Ala Asp Ser Gly Cys Val Val Ser Trp Lys Asn Lys
    770                 775                 780

Glu Leu Lys Cys Gly Ser Gly Ile Phe Ile Thr Asp Asn Val His Thr
```

-continued

```
785                 790                 795                 800

Trp Thr Glu Gln Tyr Lys Phe Gln Pro Glu Ser Pro Ser Lys Leu Ala
                805                 810                 815

Ser Ala Ile Gln Lys Ala His Glu Glu Asp Ile Cys Gly Ile Arg Ser
            820                 825                 830

Val Thr Arg Leu Glu Asn Leu Met Trp Lys Gln Ile Thr Pro Glu Leu
        835                 840                 845

Asn His Ile Leu Ser Glu Asn Glu Val Lys Leu Thr Ile Met Thr Gly
    850                 855                 860

Asp Ile Lys Gly Ile Met Gln Ala Gly Lys Arg Ser Leu Arg Pro Gln
865                 870                 875                 880

Pro Thr Glu Leu Lys Tyr Ser Trp Lys Thr Trp Gly Lys Ala Lys Met
                885                 890                 895

Leu Ser Thr Glu Ser His Asn Gln Thr Phe Leu Ile Asp Gly Pro Glu
            900                 905                 910

Thr Ala Glu Cys Pro Asn Thr Asn Arg Ala Trp Asn Ser Leu Glu Val
        915                 920                 925

Glu Asp Tyr Gly Phe Gly Val Phe Thr Thr Asn Ile Trp Leu Lys Leu
    930                 935                 940

Lys Glu Lys Gln Asp Val Phe Cys Asp Ser Lys Leu Met Ser Ala Ala
945                 950                 955                 960

Ile Lys Asp Asn Arg Ala Val His Ala Asp Met Gly Tyr Trp Ile Glu
                965                 970                 975

Ser Ala Leu Asn Asp Thr Trp Lys Ile Glu Lys Ala Ser Phe Ile Glu
            980                 985                 990

Val Lys Asn Cys His Trp Pro Lys  Ser His Thr Leu Trp  Ser Asn Gly
        995                 1000                 1005

Val Leu  Glu Ser Glu Met Ile  Ile Pro Lys Asn Leu  Ala Gly Pro
    1010                 1015                 1020

Val Ser  Gln His Asn Tyr Arg  Pro Gly Tyr His Thr  Gln Ile Thr
    1025                 1030                 1035

Gly Pro  Trp His Leu Gly Lys  Leu Glu Met Asp Phe  Asp Phe Cys
    1040                 1045                 1050

Asp Gly  Thr Thr Val Val Val  Thr Glu Asp Cys Gly  Asn Arg Gly
    1055                 1060                 1065

Pro Ser  Leu Arg Thr Thr Thr  Ala Ser Gly Lys Leu  Ile Thr Glu
    1070                 1075                 1080

Trp Cys  Cys Arg Ser Cys Thr  Leu Pro Pro Leu Arg  Tyr Arg Gly
    1085                 1090                 1095

Glu Asp  Gly Cys Trp Tyr Gly  Met Glu Ile Arg Pro  Leu Lys Glu
    1100                 1105                 1110

Lys Glu  Glu Asn Leu Val Asn  Ser Leu Val Thr Ala  Gly His Gly
    1115                 1120                 1125

Gln Val  Asp Asn Phe Ser Leu  Gly Val Leu Gly Met  Ala Leu Phe
    1130                 1135                 1140

Leu Glu  Glu Met Leu Arg Thr  Arg Val Gly Thr Lys  His Ala Ile
    1145                 1150                 1155

Leu Leu  Val Ala Val Ser Phe  Val Thr Leu Ile Thr  Gly Asn Met
    1160                 1165                 1170

Ser Phe  Arg Asp Leu Gly Arg  Val Met Val Met Val  Gly Ala Thr
    1175                 1180                 1185

Met Thr  Asp Asp Ile Gly Met  Gly Val Thr Tyr Leu  Ala Leu Leu
    1190                 1195                 1200
```

```
Ala Ala Phe Lys Val Arg Pro Thr Phe Ala Ala Gly Leu Leu Leu
    1205                1210                1215

Arg Lys Leu Thr Ser Lys Glu Leu Met Met Thr Thr Ile Gly Ile
    1220                1225                1230

Val Leu Leu Ser Gln Ser Thr Ile Pro Glu Thr Ile Leu Glu Leu
    1235                1240                1245

Thr Asp Ala Leu Ala Leu Gly Met Met Val Leu Lys Met Val Arg
    1250                1255                1260

Asn Met Glu Lys Tyr Gln Leu Ala Val Thr Ile Met Ala Ile Leu
    1265                1270                1275

Cys Val Pro Asn Ala Val Ile Leu Gln Asn Ala Trp Lys Val Ser
    1280                1285                1290

Cys Thr Ile Leu Ala Val Val Ser Val Ser Pro Leu Phe Leu Thr
    1295                1300                1305

Ser Ser Gln Gln Lys Thr Asp Trp Ile Pro Leu Ala Leu Thr Ile
    1310                1315                1320

Lys Gly Leu Asn Pro Thr Ala Ile Phe Leu Thr Thr Leu Ser Arg
    1325                1330                1335

Thr Ser Lys Lys Arg Ser Trp Pro Leu Asn Glu Ala Ile Met Ala
    1340                1345                1350

Val Gly Met Val Ser Ile Leu Ala Ser Ser Leu Leu Lys Asn Asp
    1355                1360                1365

Ile Pro Met Thr Gly Pro Leu Val Ala Gly Gly Leu Leu Thr Val
    1370                1375                1380

Cys Tyr Val Leu Thr Gly Arg Ser Ala Asp Leu Glu Leu Glu Arg
    1385                1390                1395

Ala Ala Asp Val Lys Trp Glu Asp Gln Ala Glu Ile Ser Gly Ser
    1400                1405                1410

Ser Pro Ile Leu Ser Ile Thr Ile Ser Glu Asp Gly Ser Met Ser
    1415                1420                1425

Ile Lys Asn Glu Glu Glu Glu Gln Thr Leu Thr Ile Leu Ile Arg
    1430                1435                1440

Thr Gly Leu Leu Val Ile Ser Gly Leu Phe Pro Val Ser Ile Pro
    1445                1450                1455

Ile Thr Ala Ala Ala Trp Tyr Leu Trp Glu Val Lys Lys Gln Arg
    1460                1465                1470

Ala Gly Val Leu Trp Asp Val Pro Ser Pro Pro Pro Met Gly Lys
    1475                1480                1485

Ala Glu Leu Glu Asp Gly Ala Tyr Arg Ile Lys Gln Lys Gly Ile
    1490                1495                1500

Leu Gly Tyr Ser Gln Ile Gly Ala Gly Val Tyr Lys Glu Gly Thr
    1505                1510                1515

Phe His Thr Met Trp His Val Thr Arg Gly Ala Val Leu Met His
    1520                1525                1530

Lys Gly Lys Arg Ile Glu Pro Ser Trp Ala Asp Val Lys Lys Asp
    1535                1540                1545

Leu Ile Ser Tyr Gly Gly Gly Trp Lys Leu Glu Gly Glu Trp Lys
    1550                1555                1560

Glu Gly Glu Glu Val Gln Val Leu Ala Leu Glu Pro Gly Lys Asn
    1565                1570                1575

Pro Arg Ala Val Gln Thr Lys Pro Gly Leu Phe Lys Thr Asn Ala
    1580                1585                1590
```

-continued

Gly Thr Ile Gly Ala Val Ser Leu Asp Phe Ser Pro Gly Thr Ser
1595 1600 1605

Gly Ser Pro Ile Ile Asp Lys Lys Gly Lys Val Val Gly Leu Tyr
1610 1615 1620

Gly Asn Gly Val Val Thr Arg Ser Gly Ala Tyr Val Ser Ala Ile
1625 1630 1635

Ala Gln Thr Glu Lys Ser Ile Glu Asp Asn Pro Glu Ile Glu Asp
1640 1645 1650

Asp Ile Phe Arg Lys Arg Arg Leu Thr Ile Met Asp Leu His Pro
1655 1660 1665

Gly Ala Gly Lys Thr Lys Arg Tyr Leu Pro Ala Ile Val Arg Glu
1670 1675 1680

Ala Ile Lys Arg Gly Leu Arg Thr Leu Ile Leu Ala Pro Thr Arg
1685 1690 1695

Val Val Ala Ala Glu Met Glu Glu Ala Leu Arg Gly Leu Pro Ile
1700 1705 1710

Arg Tyr Gln Thr Pro Ala Ile Arg Ala Val His Thr Gly Arg Glu
1715 1720 1725

Ile Val Asp Leu Met Cys His Ala Thr Phe Thr Met Arg Leu Leu
1730 1735 1740

Ser Pro Val Arg Val Pro Asn Tyr Asn Leu Ile Ile Met Asp Glu
1745 1750 1755

Ala His Phe Thr Asp Pro Ala Ser Ile Ala Ala Arg Gly Tyr Ile
1760 1765 1770

Ser Thr Arg Val Glu Met Gly Glu Ala Ala Gly Ile Phe Met Thr
1775 1780 1785

Ala Thr Pro Pro Gly Ser Arg Asp Pro Phe Pro Gln Ser Asn Ala
1790 1795 1800

Pro Ile Ile Asp Glu Glu Arg Glu Ile Pro Glu Arg Ser Trp Asn
1805 1810 1815

Ser Gly His Glu Trp Val Thr Asp Phe Lys Gly Lys Thr Val Trp
1820 1825 1830

Phe Val Pro Ser Ile Lys Ala Gly Asn Asp Ile Ala Ala Cys Leu
1835 1840 1845

Arg Lys Asn Gly Lys Lys Val Ile Gln Leu Ser Arg Lys Thr Phe
1850 1855 1860

Asp Ser Glu Tyr Val Lys Thr Arg Thr Asn Asp Trp Asp Phe Val
1865 1870 1875

Val Thr Thr Asp Ile Ser Glu Met Gly Ala Asn Phe Lys Ala Glu
1880 1885 1890

Arg Val Ile Asp Pro Arg Arg Cys Met Lys Pro Val Ile Leu Thr
1895 1900 1905

Asp Gly Glu Glu Arg Val Ile Leu Ala Gly Pro Met Pro Val Thr
1910 1915 1920

His Ser Ser Ala Ala Gln Arg Arg Gly Arg Ile Gly Arg Asn Pro
1925 1930 1935

Lys Asn Glu Asn Asp Gln Tyr Ile Tyr Met Gly Glu Pro Leu Glu
1940 1945 1950

Asn Asp Glu Asp Cys Ala His Trp Lys Glu Ala Lys Met Leu Leu
1955 1960 1965

Asp Asn Ile Asn Thr Pro Glu Gly Ile Ile Pro Ser Met Phe Glu
1970 1975 1980

Pro Glu Arg Glu Lys Val Asp Ala Ile Asp Gly Glu Tyr Arg Leu

```
    1985                1990                1995

Arg Gly  Glu Ala Arg Lys Thr  Phe Val Asp Leu Met  Arg Arg Gly
    2000                2005                2010

Asp Leu  Pro Val Trp Leu Ala  Tyr Arg Val Ala Ala  Glu Gly Ile
    2015                2020                2025

Asn Tyr  Ala Asp Arg Arg Trp  Cys Phe Asp Gly Val  Lys Asn Asn
    2030                2035                2040

Gln Ile  Leu Glu Glu Asn Val  Glu Val Glu Ile Trp  Thr Lys Glu
    2045                2050                2055

Gly Glu  Arg Lys Lys Leu Lys  Pro Arg Trp Leu Asp  Ala Arg Ile
    2060                2065                2070

Tyr Ser  Asp Pro Leu Ala Leu  Lys Glu Phe Lys Glu  Phe Ala Ala
    2075                2080                2085

Gly Arg  Lys Ser Leu Thr Leu  Asn Leu Ile Thr Glu  Met Gly Arg
    2090                2095                2100

Leu Pro  Thr Phe Met Thr Gln  Lys Ala Arg Asp Ala  Leu Asp Asn
    2105                2110                2115

Leu Ala  Val Leu His Thr Ala  Glu Ala Gly Gly Arg  Ala Tyr Asn
    2120                2125                2130

His Ala  Leu Ser Glu Leu Pro  Glu Thr Leu Glu Thr  Leu Leu Leu
    2135                2140                2145

Leu Thr  Leu Leu Ala Thr Val  Thr Gly Gly Ile Phe  Leu Phe Leu
    2150                2155                2160

Met Ser  Ala Arg Gly Ile Gly  Lys Met Thr Leu Gly  Met Cys Cys
    2165                2170                2175

Ile Ile  Thr Ala Ser Ile Leu  Leu Trp Tyr Ala Gln  Ile Gln Pro
    2180                2185                2190

His Trp  Ile Ala Ala Ser Ile  Ile Leu Glu Phe Phe  Leu Ile Val
    2195                2200                2205

Leu Leu  Ile Pro Glu Pro Glu  Lys Gln Arg Thr Pro  Gln Asp Asn
    2210                2215                2220

Gln Leu  Thr Tyr Val Val Ile  Ala Ile Leu Thr Val  Val Ala Ala
    2225                2230                2235

Thr Met  Ala Asn Glu Met Gly  Phe Leu Glu Lys Thr  Lys Lys Asp
    2240                2245                2250

Leu Gly  Leu Gly Ser Ile Ala  Thr Gln Gln Pro Glu  Ser Asn Ile
    2255                2260                2265

Leu Asp  Ile Asp Leu Arg Pro  Ala Ser Ala Trp Thr  Leu Tyr Ala
    2270                2275                2280

Val Ala  Thr Thr Phe Val Thr  Pro Met Leu Arg His  Ser Ile Glu
    2285                2290                2295

Asn Ser  Ser Val Asn Val Ser  Leu Thr Ala Ile Ala  Asn Gln Ala
    2300                2305                2310

Thr Val  Leu Met Gly Leu Gly  Lys Gly Trp Pro Leu  Ser Lys Met
    2315                2320                2325

Asp Ile  Gly Val Pro Leu Leu  Ala Ile Gly Cys Tyr  Ser Gln Val
    2330                2335                2340

Asn Pro  Ile Thr Leu Thr Ala  Ala Leu Phe Leu Leu  Val Ala His
    2345                2350                2355

Tyr Ala  Ile Ile Gly Pro Gly  Leu Gln Ala Lys Ala  Thr Arg Glu
    2360                2365                2370

Ala Gln  Lys Arg Ala Ala Ala  Gly Ile Met Lys Asn  Pro Thr Val
    2375                2380                2385
```

```
Asp Gly  Ile Thr Val Ile Asp  Leu Asp Pro Ile Pro  Tyr Asp Pro
    2390                 2395                 2400

Lys Phe  Glu Lys Gln Leu Gly  Gln Val Met Leu Leu  Val Leu Cys
    2405                 2410                 2415

Val Thr  Gln Val Leu Met Met  Arg Thr Thr Trp Ala  Leu Cys Glu
    2420                 2425                 2430

Ala Leu  Thr Leu Ala Thr Gly  Pro Ile Ser Thr Leu  Trp Glu Gly
    2435                 2440                 2445

Asn Pro  Gly Arg Phe Trp Asn  Thr Thr Ile Ala Val  Ser Met Ala
    2450                 2455                 2460

Asn Ile  Phe Arg Gly Ser Tyr  Leu Ala Gly Ala Gly  Leu Leu Phe
    2465                 2470                 2475

Ser Ile  Met Lys Asn Thr Thr  Asn Thr Arg Arg Gly  Thr Gly Asn
    2480                 2485                 2490

Ile Gly  Glu Thr Leu Gly Glu  Lys Trp Lys Ser Arg  Leu Asn Ala
    2495                 2500                 2505

Leu Gly  Lys Ser Glu Phe Gln  Ile Tyr Lys Lys Ser  Gly Ile Gln
    2510                 2515                 2520

Glu Val  Asp Arg Thr Leu Ala  Lys Glu Gly Ile Lys  Arg Gly Glu
    2525                 2530                 2535

Thr Asp  His His Ala Val Ser  Arg Gly Ser Ala Lys  Leu Arg Trp
    2540                 2545                 2550

Phe Val  Glu Arg Asn Met Val  Thr Pro Glu Gly Lys  Val Val Asp
    2555                 2560                 2565

Leu Gly  Cys Gly Arg Gly Gly  Trp Ser Tyr Tyr Cys  Gly Gly Leu
    2570                 2575                 2580

Lys Asn  Val Arg Glu Val Lys  Gly Leu Thr Lys Gly  Gly Pro Gly
    2585                 2590                 2595

His Glu  Glu Pro Ile Pro Met  Ser Thr Tyr Gly Trp  Asn Leu Val
    2600                 2605                 2610

Arg Leu  Gln Ser Gly Val Asp  Val Phe Phe Ile Pro  Pro Glu Lys
    2615                 2620                 2625

Cys Asp  Thr Leu Leu Cys Asp  Ile Gly Glu Ser Ser  Pro Asn Pro
    2630                 2635                 2640

Thr Val  Glu Ala Gly Arg Thr  Leu Arg Val Leu Asn  Leu Val Glu
    2645                 2650                 2655

Asn Trp  Leu Asn Asn Asn Thr  Gln Phe Cys Ile Lys  Val Leu Asn
    2660                 2665                 2670

Pro Tyr  Met Pro Ser Val Ile  Glu Lys Met Glu Ala  Leu Gln Arg
    2675                 2680                 2685

Lys Tyr  Gly Gly Ala Leu Val  Arg Asn Pro Leu Ser  Arg Asn Ser
    2690                 2695                 2700

Thr His  Glu Met Tyr Trp Val  Ser Asn Ala Ser Gly  Asn Ile Val
    2705                 2710                 2715

Ser Ser  Val Asn Met Ile Ser  Arg Met Leu Ile Asn  Arg Phe Thr
    2720                 2725                 2730

Met Arg  Tyr Lys Lys Ala Thr  Tyr Glu Pro Asp Val  Asp Leu Gly
    2735                 2740                 2745

Ser Gly  Thr Arg Asn Ile Gly  Ile Glu Ser Glu Ile  Pro Asn Leu
    2750                 2755                 2760

Asp Ile  Ile Gly Lys Arg Ile  Glu Lys Ile Lys Gln  Glu His Glu
    2765                 2770                 2775
```

```
Thr Ser  Trp His Tyr Asp Gln  Asp His Pro Tyr Lys  Thr Trp Ala
    2780                 2785                 2790

Tyr His  Gly Ser Tyr Glu Thr  Lys Gln Thr Gly Ser  Ala Ser Ser
    2795                 2800                 2805

Met Val  Asn Gly Val Val Arg  Leu Leu Thr Lys Pro  Trp Asp Val
    2810                 2815                 2820

Val Pro  Met Val Thr Gln Met  Ala Met Thr Asp Thr  Thr Pro Phe
    2825                 2830                 2835

Gly Gln  Gln Arg Val Phe Lys  Glu Lys Val Asp Thr  Arg Thr Gln
    2840                 2845                 2850

Glu Pro  Lys Glu Gly Thr Lys  Lys Leu Met Lys Ile  Thr Ala Glu
    2855                 2860                 2865

Trp Leu  Trp Lys Glu Leu Gly  Lys Lys Lys Thr Pro  Arg Met Cys
    2870                 2875                 2880

Thr Arg  Glu Glu Phe Thr Arg  Lys Val Arg Ser Asn  Ala Ala Leu
    2885                 2890                 2895

Gly Ala  Ile Phe Thr Asp Glu  Asn Lys Trp Lys Ser  Ala Arg Glu
    2900                 2905                 2910

Ala Val  Glu Asp Ser Arg Phe  Trp Glu Leu Val Asp  Lys Glu Arg
    2915                 2920                 2925

Asn Leu  His Leu Glu Gly Lys  Cys Glu Thr Cys Val  Tyr Asn Met
    2930                 2935                 2940

Met Gly  Lys Arg Glu Lys Lys  Leu Gly Glu Phe Gly  Lys Ala Lys
    2945                 2950                 2955

Gly Ser  Arg Ala Ile Trp Tyr  Met Trp Leu Gly Ala  Arg Phe Leu
    2960                 2965                 2970

Glu Phe  Glu Ala Leu Gly Phe  Leu Asn Glu Asp His  Trp Phe Ser
    2975                 2980                 2985

Arg Glu  Asn Ser Leu Ser Gly  Val Glu Gly Glu Gly  Leu His Lys
    2990                 2995                 3000

Leu Gly  Tyr Ile Leu Arg Asp  Val Ser Lys Lys Glu  Gly Gly Ala
    3005                 3010                 3015

Met Tyr  Ala Asp Asp Thr Ala  Gly Trp Asp Thr Arg  Ile Thr Leu
    3020                 3025                 3030

Glu Asp  Leu Lys Asn Glu Glu  Met Val Thr Asn His  Met Glu Gly
    3035                 3040                 3045

Glu His  Lys Lys Leu Ala Glu  Ala Ile Phe Lys Leu  Thr Tyr Gln
    3050                 3055                 3060

Asn Lys  Val Val Arg Val Gln  Arg Pro Thr Pro Arg  Gly Thr Val
    3065                 3070                 3075

Met Asp  Ile Ile Ser Arg Arg  Asp Gln Arg Gly Ser  Gly Gln Val
    3080                 3085                 3090

Gly Thr  Tyr Gly Leu Asn Thr  Phe Thr Asn Met Glu  Ala Gln Leu
    3095                 3100                 3105

Ile Arg  Gln Met Glu Gly Glu  Gly Val Phe Lys Ser  Ile Gln His
    3110                 3115                 3120

Leu Thr  Ile Thr Glu Glu Ile  Ala Val Gln Asn Trp  Leu Ala Arg
    3125                 3130                 3135

Val Gly  Arg Glu Arg Leu Ser  Arg Met Ala Ile Ser  Gly Asp Asp
    3140                 3145                 3150

Cys Val  Val Lys Pro Leu Asp  Asp Arg Phe Ala Ser  Ala Leu Thr
    3155                 3160                 3165

Ala Leu  Asn Asp Met Gly Lys  Ile Arg Lys Asp Ile  Gln Gln Trp
```

3170 3175 3180

Glu Pro Ser Arg Gly Trp Asn Asp Trp Thr Gln Val Pro Phe Cys
3185 3190 3195

Ser His His Phe His Glu Leu Ile Met Lys Asp Gly Arg Val Leu
3200 3205 3210

Val Val Pro Cys Arg Asn Gln Asp Glu Leu Ile Gly Arg Ala Arg
3215 3220 3225

Ile Ser Gln Gly Ala Gly Trp Ser Leu Arg Glu Thr Ala Cys Leu
3230 3235 3240

Gly Lys Ser Tyr Ala Gln Met Trp Ser Leu Met Tyr Phe His Arg
3245 3250 3255

Arg Asp Leu Arg Leu Ala Ala Asn Ala Ile Cys Ser Ala Val Pro
3260 3265 3270

Ser His Trp Val Pro Thr Ser Arg Thr Thr Trp Ser Ile His Ala
3275 3280 3285

Lys His Glu Trp Met Thr Thr Glu Asp Met Leu Thr Val Trp Asn
3290 3295 3300

Arg Val Trp Ile Gln Glu Asn Pro Trp Met Glu Asp Lys Thr Pro
3305 3310 3315

Val Glu Ser Trp Glu Glu Ile Pro Tyr Leu Gly Lys Arg Glu Asp
3320 3325 3330

Gln Trp Cys Gly Ser Leu Ile Gly Leu Thr Ser Arg Ala Thr Trp
3335 3340 3345

Ala Lys Asn Ile Gln Ala Ala Ile Asn Gln Val Arg Ser Leu Ile
3350 3355 3360

Gly Asn Glu Glu Tyr Thr Asp Tyr Met Pro Ser Met Lys Arg Phe
3365 3370 3375

Arg Arg Glu Glu Glu Glu Ala Gly Val Leu Trp
3380 3385

<210> SEQ ID NO 20
<211> LENGTH: 10723
<212> TYPE: DNA
<213> ORGANISM: Artificial Sequence
<220> FEATURE:
<223> OTHER INFORMATION: Derived from Dengue virus serotype 2/Dengue virus serotype 4, MVS

<400> SEQUENCE: 20
agttgttagt ctacgtggac cgacaaagac agattctttg agggagctaa gctcaatgta 60
gttctaacag tttttttaatt agagagcaga tctctgatga ataaccaacg gaaaaaggcg 120
aaaaacacgc ctttcaatat gctgaaacgc gagagaaacc gcgtgtcgac tgtgcaacag 180
ctgacaaaga gattctcact tggaatgctg cagggacgag gacctttaaa actgttcatg 240
gccctggtgg cgttccttcg tttcctaaca atcccaccaa cagcagggat attgaagaga 300
tggggaacaa ttaaaaaatc aaaagctatt aatgttttga gagggttcag gaaagagatt 360
ggaaggatgc tgaacatctt gaataggaga cgcagctctg caggcatgat cattatgctg 420
attccaacag tgatggcgtt ccatttaacc acgcgtgatg gcgaacccct catgatagtg 480
gcaaaacatg aaagggggag acctctcttg tttaagacaa cagaggggat caacaaatgc 540
actctcattg ccatggactt gggtgaaatg tgtgaggaca ctgtcacgta taaatgcccc 600
ttactggtca ataccgaacc tgaagacatt gattgctggt gcaatctcac gtctacctgg 660
gtcatgtatg ggacatgcac ccagagcgga gaacggagac gagagaagcg ctcagtagct 720

-continued

```
ttaacaccac attcaggaat gggattggaa acaagagctg agacatggat gtcatcggaa    780
ggggcttgga agcatgctca gagagtagag agctggatac tcagaaaccc aggattcgcg    840
ctcttggcag gatttatggc ttatatgatt gggcaaacag gaatccagcg aactgtcttc    900
tttgtcctaa tgatgctggt cgccccatcc tacggaatgc gatgcgtagg agtaggaaac    960
agagactttg tggaaggagt ctcaggtgga gcatgggtcg atctggtgct agaacatgga   1020
ggatgcgtca caaccatggc ccagggaaaa ccaaccttgg attttgaact gactaagaca   1080
acagccaagg aagtggctct gttaagaacc tattgcattg aagcctcaat atcaaacata   1140
accacggcaa caagatgtcc aacgcaagga gagccttatc taaaagagga acaagaccaa   1200
cagtacattt gccggagaga tgtggtagac agagggtggg gcaatggctg tggcttgttt   1260
ggaaaaggag gagttgtgac atgtgcgaag ttttcatgtt cggggaagat aacaggcaat   1320
ttggtccaaa ttgagaacct tgaatacaca gtggttgtaa cagtccacaa tggagacacc   1380
catgcagtag gaaatgacac gtccaatcat ggagttacag ccacgataac tcccaggtca   1440
ccatcggtgg aagtcaaatt gccggactat ggagaactaa cactcgattg tgaacccagg   1500
tctggaattg actttaatga gatgattctg atgaaaatga aaaagaaaac atggcttgtg   1560
cataagcaat ggtttttgga tctacctcta ccatggacag caggagcaga cacatcagag   1620
gttcactgga attacaaaga gagaatggtg acatttaagg ttcctcatgc caagagacag   1680
gatgtgacag tgctgggatc tcaggaagga gccatgcatt ctgccctcgc tggagccaca   1740
gaagtggact ccggtgatgg aaatcacatg tttgcaggac atctcaagtg caaagtccgt   1800
atggagaaat tgagaatcaa gggaatgtca tacacgatgt gttcaggaaa gttctcaatt   1860
gacaaagaga tggcagaaac acagcatggg acaacagtgg tgaaagtcaa gtatgaaggt   1920
gctggagctc cgtgtaaagt ccccatagag ataagagatg tgaacaagga aaaagtggtt   1980
gggcgtatca tctcatccac ccctttggct gagaatacca acagtgtaac caacatagag   2040
ttagaacccc cctttgggga cagctacata gtgataggtg ttggaaacag tgcattaaca   2100
ctccattggt tcaggaaagg gagttccatt ggcaagatgt ttgagtccac atacagaggt   2160
gcaaaacgaa tggccattct aggtgaaaca gcttgggatt ttggttccgt tggtggactg   2220
ttcacatcat tgggaaaggc tgtgcaccag gtttttggaa gtgtgtatac aaccctgttt   2280
ggaggagtct catggatgat tagaatccta attgggttcc tagtgttgtg gattggcacg   2340
aactcaagga acacttcaat ggctatgacg tgcatagctg ccggcattgt gacactgtat   2400
ttgggagtca tggtgcaggc cgatagtggt tgcgttgtga gctggaaaaa caaagaactg   2460
aaatgtggca gtgggatttt catcacagac aacgtgcaca catggacaga acaatacaag   2520
ttccaaccag aatccccttc aaaactagct tcagctatcc agaaagccca tgaagaggac   2580
atttgtggaa tccgctcagt aacaagactg gagaatctga tgtggaaaca aataacacca   2640
gaattgaatc acattctatc agaaaatgag gtgaagttaa ctattatgac aggagacatc   2700
aaaggaatca tgcaggcagg aaaacgatct ctgcggcctc agcccactga gctgaagtat   2760
tcatggaaaa catggggcaa agcaaaaatg ctctctacag agtctcataa ccagaccttt   2820
ctcattgatg gccccgaaac agcagaatgc cccaacacaa atagagcttg gaattcgttg   2880
gaagttgaag actatggctt tggagtattc accaccaata tatggctaaa attgaaagaa   2940
aaacaggatg tattctgcga ctcaaaactc atgtcagcgg ccataaaaga caacagagcc   3000
gtccatgccg atatgggtta ttggatagaa agtgcactca atgacacatg gaagatagag   3060
aaagcctctt tcattgaagt taaaaactgc cactggccaa aatcacacac cctctggagc   3120
```

-continued

```
aatggagtgc tagaaagtga gatgataatt ccaaagaatc tcgctggacc agtgtctcaa   3180
cacaactata gaccaggcta ccatacacaa ataacaggac catggcatct aggtaagctt   3240
gagatggact ttgatttctg tgatggaaca acagtggtag tgactgagga ctgcggaaat   3300
agaggaccct ctttgagaac aaccactgcc tctggaaaac tcataacaga atggtgctgc   3360
cgatcttgca cattaccacc gctaagatac agaggtgagg atgggtgctg gtacgggatg   3420
gaaatcagac cattgaagga gaaagaagag aatttggtca actccttggt cacagctgga   3480
catgggcagg tcgacaactt ttcactagga gtcttgggaa tggcattgtt cctggaggaa   3540
atgcttagga cccgagtagg aacgaaacat gcaatactac tagttgcagt ttcttttgtg   3600
acattgatca cagggaacat gtcctttaga gacctgggaa gagtgatggt tatggtaggc   3660
gccactatga cgggtgacat aggtatgggc gtgacttatc ttgccctact agcagccttc   3720
aaagtcagac caacttttgc agctggacta ctcttgagaa agctgacctc cagggaattg   3780
atgatgacta ctataggaat tgtactcctc tcccagagca ccataccaga gaccattctt   3840
gagttgactg atgcgttagc cttaggcatg atggtcctca aaatggtgag aaatatggaa   3900
aagtatcaat tggcagtgac tatcatggct atcttgtgcg tcccaaacgc agtgatatta   3960
caaaacgcat ggaaagtgag ttgcacaata ttggcagtgg tgtccgtttc cccactgttc   4020
ttaacatcct cacagcaaaa aacagattgg ataccattag cattgacgat caaaggtctc   4080
aatccaacag ctatttttct aacaaccctc tcaagaacca gcaagaaaag gagctggcca   4140
ttaaatgagg ctatcatggc agtcgggatg gtgagcattt tagccagttc tctcctaaaa   4200
aatgatattc ccatgacagg accattagtg gctggagggc tcctcactgt gtgctacgtg   4260
ctcactggac gatcggccga tttggaactg gagagagcag ccgatgtcaa atgggaagac   4320
caggcagaga tatcaggaag cagtccaatc ctgtcaataa caatatcaga agatggtagc   4380
atgtcgataa aaaatgaaga ggaagaacaa acactgacca tactcattag aacaggattg   4440
ctggtgatct caggactttt tcctgtatca ataccaatca cggcagcagc atggtacctg   4500
tgggaagtga agaaacaacg ggccggagta ttgtgggatg ttccttcacc cccacccatg   4560
ggaaaggctg aactggaaga tggagcctat agaattaagc aaaaagggat tcttggatat   4620
tcccagatcg gagccggagt ttacaaagaa ggaacattcc atacaatgtg gcatgtcaca   4680
cgtggcgctg ttctaatgca taaaggaaag aggattgaac catcatgggc ggacgtcaag   4740
aaagacctaa tatcatatgg aggaggctgg aagttagaag gagaatggaa ggaaggagaa   4800
gaagtccagg tattggcact ggagcctgga aaaaatccaa gagccgtcca aacgaaacct   4860
ggtcttttca aaaccaacgc cggaacaata ggtgctgtat ctctggactt ttctcctgga   4920
acgtcaggat ctccaattat cgacaaaaaa ggaaaagttg tgggtcttta tggtaatggt   4980
gttgttacaa ggagtggagc atatgtgagt gctatagccc agactgaaaa aagcattgaa   5040
gacaacccag agatcgaaga tgacattttc cgaaagagaa gactgaccat catggacctc   5100
cacccaggag cgggaaagac gaagagatac cttccggcca tagtcagaga agctataaaa   5160
cggggtttga gaacattaat cttggccccc actagagttg tggcagctga aatggaggaa   5220
gcccttagag gacttccaat aagataccag accccagcca tcagagctgt gcacaccggg   5280
cgggagattg tggacctaat gtgtcatgcc acatttacca tgaggctgct atcaccagtt   5340
agagtgccaa actacaacct gattatcatg gacgaagccc atttcacaga tccagcaagt   5400
atagcagcta gaggatacat ctcaactcga gtggagatgg gtgaggcagc tgggattttt   5460
```

-continued

```
atgacagcca ctcccccggg aagcagagac ccatttcctc agagcaatgc accaatcata   5520
gatgaagaaa gagaaatccc tgaacgctcg tggaattccg gacatgaatg ggtcacggat   5580
tttaaaggga agactgtttg gttcgttcca agtataaaag caggaaatga tatagcagct   5640
tgcctgagga aaaatggaaa gaaagtgata caactcagta ggaagacctt tgattctgag   5700
tatgtcaaga ctagaaccaa tgattgggac ttcgtggtta caactgacat ttcagaaatg   5760
ggtgccaatt tcaaggctga gagggttata gaccccagac gctgcatgaa accagtcata   5820
ctaacagatg gtgaagagcg ggtgattctg gcaggaccta tgccagtgac ccactctagt   5880
gcagcacaaa gaagagggag aataggaaga aatccaaaaa atgagaatga ccagtacata   5940
tacatggggg aacctctgga aaatgatgaa gactgtgcac actggaaaga agctaaaatg   6000
ctcctagata acatcaacac gccagaagga atcattccta gcatgttcga accagagcgt   6060
gaaaaggtgg atgccattga tggcgaatac cgcttgagag gagaagcaag gaaaaccttt   6120
gtagacttaa tgagaagagg agacctacca gtctggttgg cctacagagt ggcagctgaa   6180
ggcatcaact acgcagacag aaggtggtgt tttgatggag tcaagaacaa ccaaatccta   6240
gaagaaaacg tggaagttga aatctggaca aaagaagggg aaaggaagaa attgaaaccc   6300
agatggttgg atgctaggat ctattctgac ccactggcgc taaaagaatt taaggaattt   6360
gcagccggaa gaaagtctct gaccctgaac ctaatcacag aaatgggtag gctcccaacc   6420
ttcatgactc agaaggtaag agacgcactg gacaacttag cagtgctgca cacggctgag   6480
gcaggtggaa gggcgtacaa ccatgctctc agtgaactgc cggagaccct ggagacattg   6540
cttttactga cacttctggc tacagtcacg ggagggatct tttattcttg gatgagcgca   6600
aggggcatag ggaagatgac cctgggaatg tgctgcataa tcacggctag catcctccta   6660
tggtacgcac aaatacagcc acactggata gcagcttcaa taatactgga gtttttctc    6720
atagttttgc ttattccaga acctgaaaaa cagagaacac cccaagacaa ccaactgacc   6780
tacgttgtca tagccatcct cacagtggtg gccgcaacca tggcaaacga gatgggtttc   6840
ctagaaaaaa cgaagaaaga tctcggattg ggaagcattg caacccagca acccgagagc   6900
aacatcctgg acatagatct acgtcctgca tcagcatgga cgctgtatgc cgtggccaca   6960
acatttgtta caccaatgtt gagacatagc attgaaaatt cctcagtgaa tgtgtcccta   7020
acagccatag ccaaccaagc cacagtgtta atgggtctcg ggaaaggatg gccattgtca   7080
aagatggaca tcggagttcc ccttctcgcc attggatgct actcacaagt caaccccata   7140
actctcacag cagctctttt cttattggta gcacattatg ccatcatagg gccaggactc   7200
caagcaaaag caaccagaga agctcagaaa agagcagcgg cgggcatcat gaaaaaccca   7260
actgtcgatg gaataacagt gattgaccta gatccaatac cttatgatcc aaagtttgaa   7320
aagcagttgg gacaagtaat gctcctagtc ctctgcgtga ctcaagtatt gatgatgagg   7380
actacatggg ctctgtgtga ggctttaacc ttagctaccg ggcccatctc cacattgtgg   7440
gaaggaaatc cagggaggtt ttggaacact accattgcgg tgtcaatggc taacattttt   7500
agagggagtt acttggccgg agctggactt ctcttttcta ttatgaagaa cacaaccaac   7560
acaagaaggg gaactggcaa cataggagag acgcttggag agaaatggaa aagccgattg   7620
aacgcattgg gaaaaagtga attccagatc tacaagaaaa gtggaatcca ggaagtggat   7680
agaaccttag caaaagaagg cattaaaaga ggagaaacgg accatcacgc tgtgtcgcga   7740
ggctcagcaa aactgagatg gttcgttgag agaaacatgg tcacaccaga agggaaagta   7800
gtggacctcg gttgtggcag aggaggctgg tcatactatt gtggaggact aaagaatgta   7860
```

```
agagaagtca aaggcctaac aaaaggagga ccaggacacg aagaacccat ccccatgtca   7920
acatatgggt ggaatctagt gcgtcttcaa agtggagttg acgttttctt catcccgcca   7980
gaaaagtgtg acacattatt gtgtgacata ggggagtcat caccaaatcc cacagtggaa   8040
gcaggacgaa cactcagagt ccttaactta gtagaaaatt ggttgaacaa caacactcaa   8100
ttttgcataa aggttctcaa cccatatatg ccctcagtca tagaaaaaat ggaagcacta   8160
caaaggaaat atggaggagc cttagtgagg aatccactct cacgaaactc cacacatgag   8220
atgtactggg tatccaatgc ttccgggaac atagtgtcat cagtgaacat gatttcaagg   8280
atgttgatca acagatttac aatgagatac aagaaagcca cttacgagcc ggatgttgac   8340
ctcggaagcg gaacccgtaa catcgggatt gaaagtgaga taccaaacct agatataatt   8400
gggaaaagaa tagaaaaaat aaagcaagag catgaaacat catggcacta tgaccaagac   8460
cacccataca aaacgtgggc ataccatggt agctatgaaa caaaacagac tggatcagca   8520
tcatccatgg tcaacggagt ggtcaggctg ctgacaaaac cttgggacgt cgtccccatg   8580
gtgacacaga tggcaatgac agacacgact ccatttggac aacagcgcgt tttaaagag    8640
aaagtggaca cgagaaccca agaaccgaaa gaaggcacga agaaactaat gaaaataaca   8700
gcagagtggc tttggaaaga attagggaag aaaaagacac ccaggatgtg caccagagaa   8760
gaattcacaa gaaaggtgag aagcaatgca gccttggggg ccatattcac tgatgagaac   8820
aagtggaagt cggcacgtga ggctgttgaa gatagtaggt tttgggagct ggttgacaag   8880
gaaaggaatc tccatcttga aggaaagtgt gaaacatgtg tgtacaacat gatgggaaaa   8940
agagagaaga agctagggga attcggcaag gcaaaaggca gcagagccat atggtacatg   9000
tggcttggag cacgcttctt agagtttgaa gccctaggat tcttaaatga agatcactgg   9060
ttctccagag agaactccct gagtggagtg gaaggagaag ggctgcacaa gctaggttac   9120
attctaagag acgtgagcaa gaaagaggga ggagcaatgt atgccgatga caccgcagga   9180
tgggatacaa gaatcacact agaagaccta aaaaatgaag aaatggtaac aaaccacatg   9240
gaaggagaac acaagaaact agccgaggcc attttcaaac taacgtacca aaacaaggtg   9300
gtgcgtgtgc aaagaccaac accaagaggc acagtaatgg acatcatatc gagaagagac   9360
caaagaggta gtggacaagt tggcacctat ggactcaata ctttcaccaa tatggaagcc   9420
caactaatca gacagatgga gggagaagga gtctttaaaa gcattcagca cctaacaatc   9480
acagaagaaa tcgctgtgca aaactggtta gcaagagtgg ggcgcgaaag gttatcaaga   9540
atggccatca gtggagatga ttgtgttgtg aaacctttag atgacaggtt cgcaagcgct   9600
ttaacagctc taaatgacat gggaaagatt aggaaagaca tacaacaatg ggaaccttca   9660
agaggatgga atgattggac acaagtgccc ttctgttcac accatttcca tgagttaatc   9720
atgaaagacg gtcgcgtact cgttgttccc tgtagaaacc aagatgaact gattggcaga   9780
gcccgaatct cccaaggagc agggtggtct ttgcgggaga cggcctgttt ggggaagtct   9840
tacgcccaaa tgtggagctt gatgtacttc cacagacgcg acctcaggct ggcggcaaat   9900
gctatttgct cggcagtacc atcacattgg gttccaacaa gtcgaacaac ctggtccata   9960
catgctaaac atgaatggat gacaacggaa gacatgctga cagtctggaa cagggtgtgg  10020
attcaagaaa acccatggat ggaagacaaa actccagtgg aatcatggga ggaaatccca  10080
tacttgggga aaagagaaga ccaatggtgc ggctcattga ttgggttaac aagcagggcc  10140
acctgggcaa agaacatcca agcagcaata aatcaagtta gatcccttat aggcaatgaa  10200
```

```
gaatacacag attacatgcc atccatgaaa agattcagaa gagaagagga agaagcagga  10260

gttctgtggt agaaagcaaa actaacatga aacaaggcta gaagtcaggt cggattaagc  10320

catagtacgg aaaaaactat gctacctgtg agccccgtcc aaggacgtta aaagaagtca  10380

ggccatcata aatgccatag cttgagtaaa ctatgcagcc tgtagctcca cctgagaagg  10440

tgtaaaaaat ccgggaggcc acaaaccatg gaagctgtac gcatggcgta gtggactagc  10500

ggttagagga gacccctccc ttacaaatcg cagcaacaat gggggcccaa ggcgagatga  10560

agctgtagtc tcgctggaag gactagaggt tagaggagac ccccccgaaa caaaaaacag  10620

catattgacg ctgggaaaga ccagagatcc tgctgtctcc tcagcatcat tccaggcaca  10680

gaacgccaga aaatggaatg gtgctgttga atcaacaggt tct                   10723
```

```
<210> SEQ ID NO 21
<211> LENGTH: 3391
<212> TYPE: PRT
<213> ORGANISM: Artificial Sequence
<220> FEATURE:
<223> OTHER INFORMATION: Derived from Dengue virus serotype 2/Dengue
      virus serotype 4, MVS

<400> SEQUENCE: 21

Met Asn Asn Gln Arg Lys Lys Ala Lys Asn Thr Pro Phe Asn Met Leu
1               5                   10                  15

Lys Arg Glu Arg Asn Arg Val Ser Thr Val Gln Gln Leu Thr Lys Arg
            20                  25                  30

Phe Ser Leu Gly Met Leu Gln Gly Arg Gly Pro Leu Lys Leu Phe Met
        35                  40                  45

Ala Leu Val Ala Phe Leu Arg Phe Leu Thr Ile Pro Pro Thr Ala Gly
    50                  55                  60

Ile Leu Lys Arg Trp Gly Thr Ile Lys Lys Ser Lys Ala Ile Asn Val
65                  70                  75                  80

Leu Arg Gly Phe Arg Lys Glu Ile Gly Arg Met Leu Asn Ile Leu Asn
                85                  90                  95

Arg Arg Arg Ser Ser Ala Gly Met Ile Ile Met Leu Ile Pro Thr Val
            100                 105                 110

Met Ala Phe His Leu Thr Thr Arg Asp Gly Glu Pro Leu Met Ile Val
        115                 120                 125

Ala Lys His Glu Arg Gly Arg Pro Leu Leu Phe Lys Thr Thr Glu Gly
    130                 135                 140

Ile Asn Lys Cys Thr Leu Ile Ala Met Asp Leu Gly Glu Met Cys Glu
145                 150                 155                 160

Asp Thr Val Thr Tyr Lys Cys Pro Leu Leu Val Asn Thr Glu Pro Glu
                165                 170                 175

Asp Ile Asp Cys Trp Cys Asn Leu Thr Ser Thr Trp Val Met Tyr Gly
            180                 185                 190

Thr Cys Thr Gln Ser Gly Glu Arg Arg Arg Glu Lys Arg Ser Val Ala
        195                 200                 205

Leu Thr Pro His Ser Gly Met Gly Leu Glu Thr Arg Ala Glu Thr Trp
    210                 215                 220

Met Ser Ser Glu Gly Ala Trp Lys His Ala Gln Arg Val Glu Ser Trp
225                 230                 235                 240

Ile Leu Arg Asn Pro Gly Phe Ala Leu Leu Ala Gly Phe Met Ala Tyr
                245                 250                 255

Met Ile Gly Gln Thr Gly Ile Gln Arg Thr Val Phe Phe Val Leu Met
            260                 265                 270
```

```
Met Leu Val Ala Pro Ser Tyr Gly Met Arg Cys Val Gly Val Gly Asn
        275                 280                 285

Arg Asp Phe Val Glu Gly Val Ser Gly Gly Ala Trp Val Asp Leu Val
    290                 295                 300

Leu Glu His Gly Gly Cys Val Thr Thr Met Ala Gln Gly Lys Pro Thr
305                 310                 315                 320

Leu Asp Phe Glu Leu Thr Lys Thr Thr Ala Lys Glu Val Ala Leu Leu
                325                 330                 335

Arg Thr Tyr Cys Ile Glu Ala Ser Ile Ser Asn Ile Thr Thr Ala Thr
            340                 345                 350

Arg Cys Pro Thr Gln Gly Glu Pro Tyr Leu Lys Glu Glu Gln Asp Gln
        355                 360                 365

Gln Tyr Ile Cys Arg Arg Asp Val Val Asp Arg Gly Trp Gly Asn Gly
    370                 375                 380

Cys Gly Leu Phe Gly Lys Gly Gly Val Val Thr Cys Ala Lys Phe Ser
385                 390                 395                 400

Cys Ser Gly Lys Ile Thr Gly Asn Leu Val Gln Ile Glu Asn Leu Glu
                405                 410                 415

Tyr Thr Val Val Val Thr Val His Asn Gly Asp Thr His Ala Val Gly
            420                 425                 430

Asn Asp Thr Ser Asn His Gly Val Thr Ala Thr Ile Thr Pro Arg Ser
        435                 440                 445

Pro Ser Val Glu Val Lys Leu Pro Asp Tyr Gly Glu Leu Thr Leu Asp
    450                 455                 460

Cys Glu Pro Arg Ser Gly Ile Asp Phe Asn Glu Met Ile Leu Met Lys
465                 470                 475                 480

Met Lys Lys Lys Thr Trp Leu Val His Lys Gln Trp Phe Leu Asp Leu
                485                 490                 495

Pro Leu Pro Trp Thr Ala Gly Ala Asp Thr Ser Glu Val His Trp Asn
            500                 505                 510

Tyr Lys Glu Arg Met Val Thr Phe Lys Val Pro His Ala Lys Arg Gln
        515                 520                 525

Asp Val Thr Val Leu Gly Ser Gln Glu Gly Ala Met His Ser Ala Leu
    530                 535                 540

Ala Gly Ala Thr Glu Val Asp Ser Gly Asp Gly Asn His Met Phe Ala
545                 550                 555                 560

Gly His Leu Lys Cys Lys Val Arg Met Glu Lys Leu Arg Ile Lys Gly
                565                 570                 575

Met Ser Tyr Thr Met Cys Ser Gly Lys Phe Ser Ile Asp Lys Glu Met
            580                 585                 590

Ala Glu Thr Gln His Gly Thr Thr Val Val Lys Val Lys Tyr Glu Gly
        595                 600                 605

Ala Gly Ala Pro Cys Lys Val Pro Ile Glu Ile Arg Asp Val Asn Lys
    610                 615                 620

Glu Lys Val Val Gly Arg Ile Ile Ser Ser Thr Pro Leu Ala Glu Asn
625                 630                 635                 640

Thr Asn Ser Val Thr Asn Ile Glu Leu Glu Pro Pro Phe Gly Asp Ser
                645                 650                 655

Tyr Ile Val Ile Gly Val Gly Asn Ser Ala Leu Thr Leu His Trp Phe
            660                 665                 670

Arg Lys Gly Ser Ser Ile Gly Lys Met Phe Glu Ser Thr Tyr Arg Gly
        675                 680                 685
```

-continued

```
Ala Lys Arg Met Ala Ile Leu Gly Glu Thr Ala Trp Asp Phe Gly Ser
    690                 695                 700

Val Gly Gly Leu Phe Thr Ser Leu Gly Lys Ala Val His Gln Val Phe
705                 710                 715                 720

Gly Ser Val Tyr Thr Thr Leu Phe Gly Gly Val Ser Trp Met Ile Arg
                725                 730                 735

Ile Leu Ile Gly Phe Leu Val Leu Trp Ile Gly Thr Asn Ser Arg Asn
            740                 745                 750

Thr Ser Met Ala Met Thr Cys Ile Ala Ala Gly Ile Val Thr Leu Tyr
        755                 760                 765

Leu Gly Val Met Val Gln Ala Asp Ser Gly Cys Val Val Ser Trp Lys
    770                 775                 780

Asn Lys Glu Leu Lys Cys Gly Ser Gly Ile Phe Ile Thr Asp Asn Val
785                 790                 795                 800

His Thr Trp Thr Glu Gln Tyr Lys Phe Gln Pro Glu Ser Pro Ser Lys
                805                 810                 815

Leu Ala Ser Ala Ile Gln Lys Ala His Glu Glu Asp Ile Cys Gly Ile
            820                 825                 830

Arg Ser Val Thr Arg Leu Glu Asn Leu Met Trp Lys Gln Ile Thr Pro
        835                 840                 845

Glu Leu Asn His Ile Leu Ser Glu Asn Glu Val Lys Leu Thr Ile Met
    850                 855                 860

Thr Gly Asp Ile Lys Gly Ile Met Gln Ala Gly Lys Arg Ser Leu Arg
865                 870                 875                 880

Pro Gln Pro Thr Glu Leu Lys Tyr Ser Trp Lys Thr Trp Gly Lys Ala
                885                 890                 895

Lys Met Leu Ser Thr Glu Ser His Asn Gln Thr Phe Leu Ile Asp Gly
            900                 905                 910

Pro Glu Thr Ala Glu Cys Pro Asn Thr Asn Arg Ala Trp Asn Ser Leu
        915                 920                 925

Glu Val Glu Asp Tyr Gly Phe Gly Val Phe Thr Thr Asn Ile Trp Leu
    930                 935                 940

Lys Leu Lys Glu Lys Gln Asp Val Phe Cys Asp Ser Lys Leu Met Ser
945                 950                 955                 960

Ala Ala Ile Lys Asp Asn Arg Ala Val His Ala Asp Met Gly Tyr Trp
                965                 970                 975

Ile Glu Ser Ala Leu Asn Asp Thr Trp Lys Ile Glu Lys Ala Ser Phe
            980                 985                 990

Ile Glu Val Lys Asn Cys His Trp  Pro Lys Ser His Thr  Leu Trp Ser
        995                 1000                1005

Asn Gly  Val Leu Glu Ser Glu  Met Ile Ile Pro Lys  Asn Leu Ala
    1010                1015                1020

Gly Pro  Val Ser Gln His Asn  Tyr Arg Pro Gly Tyr  His Thr Gln
    1025                1030                1035

Ile Thr  Gly Pro Trp His Leu  Gly Lys Leu Glu Met  Asp Phe Asp
    1040                1045                1050

Phe Cys  Asp Gly Thr Thr Val  Val Val Thr Glu Asp  Cys Gly Asn
    1055                1060                1065

Arg Gly  Pro Ser Leu Arg Thr  Thr Thr Ala Ser Gly  Lys Leu Ile
    1070                1075                1080

Thr Glu  Trp Cys Cys Arg Ser  Cys Thr Leu Pro Pro  Leu Arg Tyr
    1085                1090                1095

Arg Gly  Glu Asp Gly Cys Trp  Tyr Gly Met Glu Ile  Arg Pro Leu
```

```
    1100                1105                1110

Lys Glu  Lys Glu Glu Asn Leu  Val Asn Ser Leu Val  Thr Ala Gly
    1115                1120                1125

His Gly  Gln Val Asp Asn Phe  Ser Leu Gly Val Leu  Gly Met Ala
    1130                1135                1140

Leu Phe  Leu Glu Glu Met Leu  Arg Thr Arg Val Gly  Thr Lys His
    1145                1150                1155

Ala Ile  Leu Leu Val Ala Val  Ser Phe Val Thr Leu  Ile Thr Gly
    1160                1165                1170

Asn Met  Ser Phe Arg Asp Leu  Gly Arg Val Met Val  Met Val Gly
    1175                1180                1185

Ala Thr  Met Thr Gly Asp Ile  Gly Met Gly Val Thr  Tyr Leu Ala
    1190                1195                1200

Leu Leu  Ala Ala Phe Lys Val  Arg Pro Thr Phe Ala  Ala Gly Leu
    1205                1210                1215

Leu Leu  Arg Lys Leu Thr Ser  Arg Glu Leu Met Met  Thr Thr Ile
    1220                1225                1230

Gly Ile  Val Leu Leu Ser Gln  Ser Thr Ile Pro Glu  Thr Ile Leu
    1235                1240                1245

Glu Leu  Thr Asp Ala Leu Ala  Leu Gly Met Met Val  Leu Lys Met
    1250                1255                1260

Val Arg  Asn Met Glu Lys Tyr  Gln Leu Ala Val Thr  Ile Met Ala
    1265                1270                1275

Ile Leu  Cys Val Pro Asn Ala  Val Ile Leu Gln Asn  Ala Trp Lys
    1280                1285                1290

Val Ser  Cys Thr Ile Leu Ala  Val Val Ser Val Ser  Pro Leu Phe
    1295                1300                1305

Leu Thr  Ser Ser Gln Gln Lys  Thr Asp Trp Ile Pro  Leu Ala Leu
    1310                1315                1320

Thr Ile  Lys Gly Leu Asn Pro  Thr Ala Ile Phe Leu  Thr Thr Leu
    1325                1330                1335

Ser Arg  Thr Ser Lys Lys Arg  Ser Trp Pro Leu Asn  Glu Ala Ile
    1340                1345                1350

Met Ala  Val Gly Met Val Ser  Ile Leu Ala Ser Ser  Leu Leu Lys
    1355                1360                1365

Asn Asp  Ile Pro Met Thr Gly  Pro Leu Val Ala Gly  Gly Leu Leu
    1370                1375                1380

Thr Val  Cys Tyr Val Leu Thr  Gly Arg Ser Ala Asp  Leu Glu Leu
    1385                1390                1395

Glu Arg  Ala Ala Asp Val Lys  Trp Glu Asp Gln Ala  Glu Ile Ser
    1400                1405                1410

Gly Ser  Ser Pro Ile Leu Ser  Ile Thr Ile Ser Glu  Asp Gly Ser
    1415                1420                1425

Met Ser  Ile Lys Asn Glu Glu  Glu Glu Gln Thr Leu  Thr Ile Leu
    1430                1435                1440

Ile Arg  Thr Gly Leu Leu Val  Ile Ser Gly Leu Phe  Pro Val Ser
    1445                1450                1455

Ile Pro  Ile Thr Ala Ala Ala  Trp Tyr Leu Trp Glu  Val Lys Lys
    1460                1465                1470

Gln Arg  Ala Gly Val Leu Trp  Asp Val Pro Ser Pro  Pro Pro Met
    1475                1480                1485

Gly Lys  Ala Glu Leu Glu Asp  Gly Ala Tyr Arg Ile  Lys Gln Lys
    1490                1495                1500
```

-continued

```
Gly Ile  Leu Gly Tyr Ser Gln  Ile Gly Ala Gly Val  Tyr Lys Glu
    1505                 1510                 1515

Gly Thr  Phe His Thr Met Trp  His Val Thr Arg Gly  Ala Val Leu
    1520                 1525                 1530

Met His  Lys Gly Lys Arg Ile  Glu Pro Ser Trp Ala  Asp Val Lys
    1535                 1540                 1545

Lys Asp  Leu Ile Ser Tyr Gly  Gly Gly Trp Lys Leu  Glu Gly Glu
    1550                 1555                 1560

Trp Lys  Glu Gly Glu Glu Val  Gln Val Leu Ala Leu  Glu Pro Gly
    1565                 1570                 1575

Lys Asn  Pro Arg Ala Val Gln  Thr Lys Pro Gly Leu  Phe Lys Thr
    1580                 1585                 1590

Asn Ala  Gly Thr Ile Gly Ala  Val Ser Leu Asp Phe  Ser Pro Gly
    1595                 1600                 1605

Thr Ser  Gly Ser Pro Ile Ile  Asp Lys Lys Gly Lys  Val Val Gly
    1610                 1615                 1620

Leu Tyr  Gly Asn Gly Val Val  Thr Arg Ser Gly Ala  Tyr Val Ser
    1625                 1630                 1635

Ala Ile  Ala Gln Thr Glu Lys  Ser Ile Glu Asp Asn  Pro Glu Ile
    1640                 1645                 1650

Glu Asp  Asp Ile Phe Arg Lys  Arg Arg Leu Thr Ile  Met Asp Leu
    1655                 1660                 1665

His Pro  Gly Ala Gly Lys Thr  Lys Arg Tyr Leu Pro  Ala Ile Val
    1670                 1675                 1680

Arg Glu  Ala Ile Lys Arg Gly  Leu Arg Thr Leu Ile  Leu Ala Pro
    1685                 1690                 1695

Thr Arg  Val Val Ala Ala Glu  Met Glu Glu Ala Leu  Arg Gly Leu
    1700                 1705                 1710

Pro Ile  Arg Tyr Gln Thr Pro  Ala Ile Arg Ala Val  His Thr Gly
    1715                 1720                 1725

Arg Glu  Ile Val Asp Leu Met  Cys His Ala Thr Phe  Thr Met Arg
    1730                 1735                 1740

Leu Leu  Ser Pro Val Arg Val  Pro Asn Tyr Asn Leu  Ile Ile Met
    1745                 1750                 1755

Asp Glu  Ala His Phe Thr Asp  Pro Ala Ser Ile Ala  Ala Arg Gly
    1760                 1765                 1770

Tyr Ile  Ser Thr Arg Val Glu  Met Gly Glu Ala Ala  Gly Ile Phe
    1775                 1780                 1785

Met Thr  Ala Thr Pro Pro Gly  Ser Arg Asp Pro Phe  Pro Gln Ser
    1790                 1795                 1800

Asn Ala  Pro Ile Ile Asp Glu  Glu Arg Glu Ile Pro  Glu Arg Ser
    1805                 1810                 1815

Trp Asn  Ser Gly His Glu Trp  Val Thr Asp Phe Lys  Gly Lys Thr
    1820                 1825                 1830

Val Trp  Phe Val Pro Ser Ile  Lys Ala Gly Asn Asp  Ile Ala Ala
    1835                 1840                 1845

Cys Leu  Arg Lys Asn Gly Lys  Lys Val Ile Gln Leu  Ser Arg Lys
    1850                 1855                 1860

Thr Phe  Asp Ser Glu Tyr Val  Lys Thr Arg Thr Asn  Asp Trp Asp
    1865                 1870                 1875

Phe Val  Val Thr Thr Asp Ile  Ser Glu Met Gly Ala  Asn Phe Lys
    1880                 1885                 1890
```

```
Ala Glu  Arg Val Ile Asp Pro  Arg Arg Cys Met Lys  Pro Val Ile
    1895                 1900                 1905

Leu Thr  Asp Gly Glu Glu Arg  Val Ile Leu Ala Gly  Pro Met Pro
    1910                 1915                 1920

Val Thr  His Ser Ser Ala Ala  Gln Arg Arg Gly Arg  Ile Gly Arg
    1925                 1930                 1935

Asn Pro  Lys Asn Glu Asn Asp  Gln Tyr Ile Tyr Met  Gly Glu Pro
    1940                 1945                 1950

Leu Glu  Asn Asp Glu Asp Cys  Ala His Trp Lys Glu  Ala Lys Met
    1955                 1960                 1965

Leu Leu  Asp Asn Ile Asn Thr  Pro Glu Gly Ile Ile  Pro Ser Met
    1970                 1975                 1980

Phe Glu  Pro Glu Arg Glu Lys  Val Asp Ala Ile Asp  Gly Glu Tyr
    1985                 1990                 1995

Arg Leu  Arg Gly Glu Ala Arg  Lys Thr Phe Val Asp  Leu Met Arg
    2000                 2005                 2010

Arg Gly  Asp Leu Pro Val Trp  Leu Ala Tyr Arg Val  Ala Ala Glu
    2015                 2020                 2025

Gly Ile  Asn Tyr Ala Asp Arg  Arg Trp Cys Phe Asp  Gly Val Lys
    2030                 2035                 2040

Asn Asn  Gln Ile Leu Glu Glu  Asn Val Glu Val Glu  Ile Trp Thr
    2045                 2050                 2055

Lys Glu  Gly Glu Arg Lys Lys  Leu Lys Pro Arg Trp  Leu Asp Ala
    2060                 2065                 2070

Arg Ile  Tyr Ser Asp Pro Leu  Ala Leu Lys Glu Phe  Lys Glu Phe
    2075                 2080                 2085

Ala Ala  Gly Arg Lys Ser Leu  Thr Leu Asn Leu Ile  Thr Glu Met
    2090                 2095                 2100

Gly Arg  Leu Pro Thr Phe Met  Thr Gln Lys Val Arg  Asp Ala Leu
    2105                 2110                 2115

Asp Asn  Leu Ala Val Leu His  Thr Ala Glu Ala Gly  Gly Arg Ala
    2120                 2125                 2130

Tyr Asn  His Ala Leu Ser Glu  Leu Pro Glu Thr Leu  Glu Thr Leu
    2135                 2140                 2145

Leu Leu  Leu Thr Leu Leu Ala  Thr Val Thr Gly Gly  Ile Phe Leu
    2150                 2155                 2160

Phe Leu  Met Ser Ala Arg Gly  Ile Gly Lys Met Thr  Leu Gly Met
    2165                 2170                 2175

Cys Cys  Ile Ile Thr Ala Ser  Ile Leu Leu Trp Tyr  Ala Gln Ile
    2180                 2185                 2190

Gln Pro  His Trp Ile Ala Ala  Ser Ile Ile Leu Glu  Phe Phe Leu
    2195                 2200                 2205

Ile Val  Leu Leu Ile Pro Glu  Pro Glu Lys Gln Arg  Thr Pro Gln
    2210                 2215                 2220

Asp Asn  Gln Leu Thr Tyr Val  Val Ile Ala Ile Leu  Thr Val Val
    2225                 2230                 2235

Ala Ala  Thr Met Ala Asn Glu  Met Gly Phe Leu Glu  Lys Thr Lys
    2240                 2245                 2250

Lys Asp  Leu Gly Leu Gly Ser  Ile Ala Thr Gln Gln  Pro Glu Ser
    2255                 2260                 2265

Asn Ile  Leu Asp Ile Asp Leu  Arg Pro Ala Ser Ala  Trp Thr Leu
    2270                 2275                 2280

Tyr Ala  Val Ala Thr Thr Phe  Val Thr Pro Met Leu  Arg His Ser
```

```
    2285                2290                2295

Ile Glu  Asn Ser Ser Val Asn  Val Ser Leu Thr Ala  Ile Ala Asn
    2300                2305                2310

Gln Ala  Thr Val Leu Met Gly  Leu Gly Lys Gly Trp  Pro Leu Ser
    2315                2320                2325

Lys Met  Asp Ile Gly Val Pro  Leu Leu Ala Ile Gly  Cys Tyr Ser
    2330                2335                2340

Gln Val  Asn Pro Ile Thr Leu  Thr Ala Ala Leu Phe  Leu Leu Val
    2345                2350                2355

Ala His  Tyr Ala Ile Ile Gly  Pro Gly Leu Gln Ala  Lys Ala Thr
    2360                2365                2370

Arg Glu  Ala Gln Lys Arg Ala  Ala Ala Gly Ile Met  Lys Asn Pro
    2375                2380                2385

Thr Val  Asp Gly Ile Thr Val  Ile Asp Leu Asp Pro  Ile Pro Tyr
    2390                2395                2400

Asp Pro  Lys Phe Glu Lys Gln  Leu Gly Gln Val Met  Leu Leu Val
    2405                2410                2415

Leu Cys  Val Thr Gln Val Leu  Met Met Arg Thr Thr  Trp Ala Leu
    2420                2425                2430

Cys Glu  Ala Leu Thr Leu Ala  Thr Gly Pro Ile Ser  Thr Leu Trp
    2435                2440                2445

Glu Gly  Asn Pro Gly Arg Phe  Trp Asn Thr Thr Ile  Ala Val Ser
    2450                2455                2460

Met Ala  Asn Ile Phe Arg Gly  Ser Tyr Leu Ala Gly  Ala Gly Leu
    2465                2470                2475

Leu Phe  Ser Ile Met Lys Asn  Thr Thr Asn Thr Arg  Arg Gly Thr
    2480                2485                2490

Gly Asn  Ile Gly Glu Thr Leu  Gly Glu Lys Trp Lys  Ser Arg Leu
    2495                2500                2505

Asn Ala  Leu Gly Lys Ser Glu  Phe Gln Ile Tyr Lys  Lys Ser Gly
    2510                2515                2520

Ile Gln  Glu Val Asp Arg Thr  Leu Ala Lys Glu Gly  Ile Lys Arg
    2525                2530                2535

Gly Glu  Thr Asp His His Ala  Val Ser Arg Gly Ser  Ala Lys Leu
    2540                2545                2550

Arg Trp  Phe Val Glu Arg Asn  Met Val Thr Pro Glu  Gly Lys Val
    2555                2560                2565

Val Asp  Leu Gly Cys Gly Arg  Gly Gly Trp Ser Tyr  Tyr Cys Gly
    2570                2575                2580

Gly Leu  Lys Asn Val Arg Glu  Val Lys Gly Leu Thr  Lys Gly Gly
    2585                2590                2595

Pro Gly  His Glu Glu Pro Ile  Pro Met Ser Thr Tyr  Gly Trp Asn
    2600                2605                2610

Leu Val  Arg Leu Gln Ser Gly  Val Asp Val Phe Phe  Ile Pro Pro
    2615                2620                2625

Glu Lys  Cys Asp Thr Leu Leu  Cys Asp Ile Gly Glu  Ser Ser Pro
    2630                2635                2640

Asn Pro  Thr Val Glu Ala Gly  Arg Thr Leu Arg Val  Leu Asn Leu
    2645                2650                2655

Val Glu  Asn Trp Leu Asn Asn  Asn Thr Gln Phe Cys  Ile Lys Val
    2660                2665                2670

Leu Asn  Pro Tyr Met Pro Ser  Val Ile Glu Lys Met  Glu Ala Leu
    2675                2680                2685
```

-continued

```
Gln Arg Lys Tyr Gly Gly Ala Leu Val Arg Asn Pro Leu Ser Arg
    2690                2695                2700

Asn Ser Thr His Glu Met Tyr Trp Val Ser Asn Ala Ser Gly Asn
    2705                2710                2715

Ile Val Ser Ser Val Asn Met Ile Ser Arg Met Leu Ile Asn Arg
    2720                2725                2730

Phe Thr Met Arg Tyr Lys Lys Ala Thr Tyr Glu Pro Asp Val Asp
    2735                2740                2745

Leu Gly Ser Gly Thr Arg Asn Ile Gly Ile Glu Ser Glu Ile Pro
    2750                2755                2760

Asn Leu Asp Ile Ile Gly Lys Arg Ile Glu Lys Ile Lys Gln Glu
    2765                2770                2775

His Glu Thr Ser Trp His Tyr Asp Gln Asp His Pro Tyr Lys Thr
    2780                2785                2790

Trp Ala Tyr His Gly Ser Tyr Glu Thr Lys Gln Thr Gly Ser Ala
    2795                2800                2805

Ser Ser Met Val Asn Gly Val Val Arg Leu Leu Thr Lys Pro Trp
    2810                2815                2820

Asp Val Val Pro Met Val Thr Gln Met Ala Met Thr Asp Thr Thr
    2825                2830                2835

Pro Phe Gly Gln Gln Arg Val Phe Lys Glu Lys Val Asp Thr Arg
    2840                2845                2850

Thr Gln Glu Pro Lys Glu Gly Thr Lys Lys Leu Met Lys Ile Thr
    2855                2860                2865

Ala Glu Trp Leu Trp Lys Glu Leu Gly Lys Lys Lys Thr Pro Arg
    2870                2875                2880

Met Cys Thr Arg Glu Glu Phe Thr Arg Lys Val Arg Ser Asn Ala
    2885                2890                2895

Ala Leu Gly Ala Ile Phe Thr Asp Glu Asn Lys Trp Lys Ser Ala
    2900                2905                2910

Arg Glu Ala Val Glu Asp Ser Arg Phe Trp Glu Leu Val Asp Lys
    2915                2920                2925

Glu Arg Asn Leu His Leu Glu Gly Lys Cys Glu Thr Cys Val Tyr
    2930                2935                2940

Asn Met Met Gly Lys Arg Glu Lys Lys Leu Gly Glu Phe Gly Lys
    2945                2950                2955

Ala Lys Gly Ser Arg Ala Ile Trp Tyr Met Trp Leu Gly Ala Arg
    2960                2965                2970

Phe Leu Glu Phe Glu Ala Leu Gly Phe Leu Asn Glu Asp His Trp
    2975                2980                2985

Phe Ser Arg Glu Asn Ser Leu Ser Gly Val Glu Gly Glu Gly Leu
    2990                2995                3000

His Lys Leu Gly Tyr Ile Leu Arg Asp Val Ser Lys Lys Glu Gly
    3005                3010                3015

Gly Ala Met Tyr Ala Asp Asp Thr Ala Gly Trp Asp Thr Arg Ile
    3020                3025                3030

Thr Leu Glu Asp Leu Lys Asn Glu Glu Met Val Thr Asn His Met
    3035                3040                3045

Glu Gly Glu His Lys Lys Leu Ala Glu Ala Ile Phe Lys Leu Thr
    3050                3055                3060

Tyr Gln Asn Lys Val Val Arg Val Gln Arg Pro Thr Pro Arg Gly
    3065                3070                3075
```

```
Thr Val  Met Asp Ile Ile Ser  Arg Arg Asp Gln Arg  Gly Ser Gly
    3080                 3085                 3090

Gln Val  Gly Thr Tyr Gly Leu  Asn Thr Phe Thr Asn  Met Glu Ala
    3095                 3100                 3105

Gln Leu  Ile Arg Gln Met Glu  Gly Glu Gly Val Phe  Lys Ser Ile
    3110                 3115                 3120

Gln His  Leu Thr Ile Thr Glu  Glu Ile Ala Val Gln  Asn Trp Leu
    3125                 3130                 3135

Ala Arg  Val Gly Arg Glu Arg  Leu Ser Arg Met Ala  Ile Ser Gly
    3140                 3145                 3150

Asp Asp  Cys Val Val Lys Pro  Leu Asp Asp Arg Phe  Ala Ser Ala
    3155                 3160                 3165

Leu Thr  Ala Leu Asn Asp Met  Gly Lys Ile Arg Lys  Asp Ile Gln
    3170                 3175                 3180

Gln Trp  Glu Pro Ser Arg Gly  Trp Asn Asp Trp Thr  Gln Val Pro
    3185                 3190                 3195

Phe Cys  Ser His His Phe His  Glu Leu Ile Met Lys  Asp Gly Arg
    3200                 3205                 3210

Val Leu  Val Val Pro Cys Arg  Asn Gln Asp Glu Leu  Ile Gly Arg
    3215                 3220                 3225

Ala Arg  Ile Ser Gln Gly Ala  Gly Trp Ser Leu Arg  Glu Thr Ala
    3230                 3235                 3240

Cys Leu  Gly Lys Ser Tyr Ala  Gln Met Trp Ser Leu  Met Tyr Phe
    3245                 3250                 3255

His Arg  Arg Asp Leu Arg Leu  Ala Ala Asn Ala Ile  Cys Ser Ala
    3260                 3265                 3270

Val Pro  Ser His Trp Val Pro  Thr Ser Arg Thr Thr  Trp Ser Ile
    3275                 3280                 3285

His Ala  Lys His Glu Trp Met  Thr Thr Glu Asp Met  Leu Thr Val
    3290                 3295                 3300

Trp Asn  Arg Val Trp Ile Gln  Glu Asn Pro Trp Met  Glu Asp Lys
    3305                 3310                 3315

Thr Pro  Val Glu Ser Trp Glu  Glu Ile Pro Tyr Leu  Gly Lys Arg
    3320                 3325                 3330

Glu Asp  Gln Trp Cys Gly Ser  Leu Ile Gly Leu Thr  Ser Arg Ala
    3335                 3340                 3345

Thr Trp  Ala Lys Asn Ile Gln  Ala Ala Ile Asn Gln  Val Arg Ser
    3350                 3355                 3360

Leu Ile  Gly Asn Glu Glu Tyr  Thr Asp Tyr Met Pro  Ser Met Lys
    3365                 3370                 3375

Arg Phe  Arg Arg Glu Glu Glu  Glu Ala Gly Val Leu  Trp
    3380                 3385                 3390
```

```
<210> SEQ ID NO 22
<211> LENGTH: 10723
<212> TYPE: DNA
<213> ORGANISM: Artificial Sequence
<220> FEATURE:
<223> OTHER INFORMATION: Derived from Dengue virus serotype 2/Dengue
      virus serotype 4, DENV-4e

<400> SEQUENCE: 22

agttgttagt ctacgtggac cgacaaagac agattctttg agggagctaa gctcaatgta     60

gttctaacag tttttaatt agagagcaga tctctgatga ataaccaacg gaaaaaggcg    120

aaaaacacgc ctttcaatat gctgaaacgc gagagaaacc gcgtgtcgac tgtgcaacag    180
```

-continued

```
ctgacaaaga gattctcact tggaatgctg cagggacgag gaccattaaa actgttcatg    240
gccctggtgg cgttccttcg tttcctaaca atcccaccaa cagcagggat attgaagaga    300
tggggaacaa ttaaaaaatc aaaagctatt aatgttttga gagggttcag gaaagagatt    360
ggaaggatgc tgaacatctt gaataggaga cgcagctcaa cgataacatt gctgtacttg    420
attcccaccg taatggcgtt tcacttgtca acgcgtgatg gcgaacccct catgatagtg    480
gcaaaacatg aaagggggag acctctcttg tttaagacaa cagaggggat caacaaatgc    540
actctcattg ccatggactt gggtgaaatg tgtgaggaca ctgtcacgta taaatgcccc    600
ttactggtca ataccgaacc tgaagacatt gattgctggt gcaatctcac gtctacctgg    660
gtcatgtatg ggacatgcac ccagagcgga gaacggagac gagagaagcg ctcagtagct    720
ttaacaccac attcaggaat gggattggaa acaagagctg agacatggat gtcatcggaa    780
ggggcttgga agcatgctca gagagtagag agctggatac tcagaaaccc aggattcgcg    840
ctcttggcag gatttatggc ttatatgatt gggcaaacag gaatccagcg aactgtcttc    900
tttgtcctaa tgatgctggt cgccccatcc tacggaatgc gatgcgtagg agtaggaaac    960
agagactttg tggaaggagt ctcaggtgga gcatgggtcg atctggtgct agaacatgga   1020
ggatgcgtca caaccatggc ccagggaaaa ccaaccttgg attttgaact gactaagaca   1080
acagccaagg aagtggctct gttaagaacc tattgcattg aagcctcaat atcaaacata   1140
accacggcaa caagatgtcc aacgcaagga gagccttatc taaaagagga acaagaccaa   1200
cagtacattt gccggagaga tgtggtagac agagggtggg gcaatggctg tggcttgttt   1260
ggaaaaggag gagttgtgac atgtgcgaag ttttcatgtt cggggaagat aacaggcaat   1320
ttggtccaaa ttgagaacct tgaatacaca gtggttgtaa cagtccacaa tggagacacc   1380
catgcagtag gaaatgacac gtccaatcat ggagttacag ccacgataac tcccaggtca   1440
ccatcggtgg aagtcaaatt gccggactat ggagaactaa cactcgattg tgaacccagg   1500
tctggaattg actttaatga gatgattctg atgaaaatga aaaagaaaac atggcttgtg   1560
cataagcaat ggtttttgga tctacctcta ccatggacag caggagcaga cacatcagag   1620
gttcactgga attacaaaga gagaatggtg acatttaagg ttcctcatgc caagagacag   1680
gatgtgacag tgctgggatc tcaggaagga gccatgcatt ctgccctcgc tggagccaca   1740
gaagtggact ccggtgatgg aaatcacatg tttgcaggac atctcaagtg caaagtccgt   1800
atggagaaat tgagaatcaa gggaatgtca tacacgatgt gttcaggaaa gttctcaatt   1860
gacaaagaga tggcagaaac acagcatggg acaacagtgg tgaaagtcaa gtatgaaggt   1920
gctggagctc cgtgtaaagt ccccatagag ataagagatg tgaacaagga aaaagtggtt   1980
gggcgtatca tctcatccac ccctttggct gagaatacca acagtgtaac caacatagag   2040
ttagaacccc cctttgggga cagctacata gtgataggtg ttggaaacag tgcattaaca   2100
ctccattggt tcaggaaagg gagttccatt ggcaagatgt ttgagtccac atacagaggt   2160
gcaaaacgaa tggccattct aggtgaaaca gcttgggatt ttggttccgt tggtggactg   2220
ttcacatcat tgggaaaggc tgtgcaccag gtttttggaa gtgtgtatac aaccctgttt   2280
ggaggagtct catggatgat tagaatccta attgggttcc tagtgttgtg gattggcacg   2340
aactcaagga acacttcaat ggctatgacg tgcatagctg ccggcattgt gacactgtat   2400
ttgggagtca tggtgcaggc cgatagtggt tgcgttgtga gctggaaaaa caaagaactg   2460
aaatgtggca gtgggatttt catcacagac aacgtgcaca catggacaga acaatacaag   2520
```

-continued

```
ttccaaccag aatccccttc aaaactagct tcagctatcc agaaagccca tgaagaggac   2580
atttgtggaa tccgctcagt aacaagactg gagaatctga tgtggaaaca aataacacca   2640
gaattgaatc acattctatc agaaaatgag gtgaagttaa ctattatgac aggagacatc   2700
aaaggaatca tgcaggcagg aaaacgatct ctgcggcctc agcccactga gctgaagtat   2760
tcatggaaaa catggggcaa agcaaaaatg ctctctacag agtctcataa ccagaccttt   2820
ctcattgatg gccccgaaac agcagaatgc cccaacacaa atagagcttg gaattcgttg   2880
gaagttgaag actatggctt tggagtattc accaccaata tatggctaaa attgaaagaa   2940
aaacaggatg tattctgcga ctcaaaactc atgtcagcgg ccataaaaga caacagagcc   3000
gtccatgccg atatgggtta ttggatagaa agtgcactca atgacacatg gaagatagag   3060
aaagcctctt tcattgaagt taaaaactgc cactggccaa aatcacacac cctctggagc   3120
aatggagtgc tagaaagtga gatgataatt ccaaagaatc tcgctggacc agtgtctcaa   3180
cacaactata gaccaggcta ccatacacaa ataacaggac catggcatct aggtaagctt   3240
gagatggact ttgatttctg tgatggaaca acagtggtag tgactgagga ctgcggaaat   3300
agaggaccct ctttgagaac aaccactgcc tctggaaaac tcataacaga atggtgctgc   3360
cgatcttgca cattaccacc gctaagatac agaggtgagg atgggtgctg gtacgggatg   3420
gaaatcagac cattgaagga gaaagaagag aatttggtca actccttggt cacagctgga   3480
catgggcagg tcgacaactt ttcactagga gtcttgggaa tggcattgtt cctggaggaa   3540
atgcttagga cccgagtagg aacgaaacat gcaatactac tagttgcagt ttcttttgtg   3600
acattgatca cagggaacat gtcctttaga gacctgggaa gagtgatggt tatggtaggc   3660
gccactatga cggatgacat aggtatgggc gtgacttatc ttgccctact agcagccttc   3720
aaagtcagac caacttttgc agctggacta ctcttgagaa agctgacctc caaggaattg   3780
atgatgacta ctataggaat tgtactcctc tcccagagca ccataccaga gaccattctt   3840
gagttgactg atgcgttagc cttaggcatg atggtcctca aaatggtgag aaatatggaa   3900
aagtatcaat tggcagtgac tatcatggct atcttgtgcg tcccaaacgc agtgatatta   3960
caaaacgcat ggaaagtgag ttgcacaata ttggcagtgg tgtccgtttc cccactgttc   4020
ttaacatcct cacagcaaaa aacagattgg ataccattag cattgacgat caaaggtctc   4080
aatccaacag ctatttttct aacaaccctc tcaagaacca gcaagaaaag gagctggcca   4140
ttaaatgagg ctatcatggc agtcgggatg gtgagcattt tagccagttc tctcctaaaa   4200
aatgatattc ccatgacagg accattagtg gctggagggc tcctcactgt gtgctacgtg   4260
ctcactggac gatcggccga tttggaactg gagagagcag ccgatgtcaa atgggaagac   4320
caggcagaga tatcaggaag cagtccaatc ctgtcaataa caatatcaga agatggtagc   4380
atgtcgataa aaaatgaaga ggaagaacaa acactgacca tactcattag aacaggattg   4440
ctggtgatct caggactttt tcctgtatca ataccaatca cggcagcagc atggtacctg   4500
tgggaagtga agaaacaacg ggccggagta ttgtgggatg ttccttcacc cccacccatg   4560
ggaaaggctg aactggaaga tggagcctat agaattaagc aaaaagggat tcttggatat   4620
tcccagatcg gagccggagt ttacaaagaa ggaacattcc atacaatgtg gcatgtcaca   4680
cgtggcgctg ttctaatgca taaaggaaag aggattgaac catcatgggc ggacgtcaag   4740
aaagacctaa tatcatatgg aggaggctgg aagttagaag gagaatggaa ggaaggagaa   4800
gaagtccagg tattggcact ggagcctgga aaaaatccaa gagccgtcca aacgaaacct   4860
ggtcttttca aaaccaacgc cggaacaata ggtgctgtat ctctggactt ttctcctgga   4920
```

-continued

```
acgtcaggat ctccaattat cgacaaaaaa ggaaaagttg tgggtcttta tggtaatggt   4980
gttgttacaa ggagtggagc atatgtgagt gctatagccc agactgaaaa aagcattgaa   5040
gacaacccag agatcgaaga tgacattttc cgaaagagaa gactgaccat catggacctc   5100
cacccaggag cgggaaagac gaagagatac cttccggcca tagtcagaga agctataaaa   5160
cggggtttga gaacattaat cttggccccc actagagttg tggcagctga aatggaggaa   5220
gcccttagag gacttccaat aagataccag accccagcca tcagagctgt gcacaccggg   5280
cgggagattg tggacctaat gtgtcatgcc acatttacca tgaggctgct atcaccagtt   5340
agagtgccaa actacaacct gattatcatg gacgaagccc atttcacaga cccagcaagt   5400
atagcagcta gaggatacat ctcaactcga gtggagatgg gtgaggcagc tgggattttt   5460
atgacagcca ctcccccggg aagcagagac ccatttcctc agagcaatgc accaatcata   5520
gatgaagaaa gagaaatccc tgaacgctcg tggaattccg gacatgaatg ggtcacggat   5580
tttaaaggga agactgtttg gttcgttcca agtataaaag caggaaatga tatagcagct   5640
tgcctgagga aaaatggaaa gaaagtgata caactcagta ggaagacctt tgattctgag   5700
tatgtcaaga ctagaaccaa tgattgggac ttcgtggtta caactgacat ttcagaaatg   5760
ggtgccaatt tcaaggctga gagggttata gaccccagac gctgcatgaa accagtcata   5820
ctaacagatg gtgaagagcg ggtgattctg gcaggaccta tgccagtgac ccactctagt   5880
gcagcacaaa gaagagggag aataggaaga aatccaaaaa atgagaatga ccagtacata   5940
tacatggggg aacctctgga aaatgatgaa gactgtgcac actggaaaga agctaaaatg   6000
ctcctagata acatcaacac gccagaagga atcattccta gcatgttcga accagagcgt   6060
gaaaaggtgg atgccattga tggcgaatac cgcttgagag gagaagcaag gaaaaccttt   6120
gtagacttaa tgagaagagg agacctacca gtctggttgg cctacagagt ggcagctgaa   6180
ggcatcaact acgcagacag aaggtggtgt tttgatggag tcaagaacaa ccaaatccta   6240
gaagaaaacg tggaagttga aatctggaca aaagaagggg aaaggaagaa attgaaaccc   6300
agatggttgg atgctaggat ctattctgac ccactggcgc taaaagaatt taaggaattt   6360
gcagccggaa gaaagtctct gaccctgaac ctaatcacag aaatgggtag gctcccaacc   6420
ttcatgactc agaaggcaag agacgcactg gacaacttag cagtgctgca cacggctgag   6480
gcaggtggaa gggcgtacaa ccatgctctc agtgaactgc cggagaccct ggagacattg   6540
cttttactga cacttctggc tacagtcacg ggagggatct tttattcttt gatgagcgca   6600
aggggcatag ggaagatgac cctgggaatg tgctgcataa tcacggctag catcctccta   6660
tggtacgcac aaatacagcc acactggata gcagcttcaa taatactgga gtttttctc    6720
atagttttgc ttattccaga acctgaaaaa cagagaacac cccaagacaa ccaactgacc   6780
tacgttgtca tagccatcct cacagtggtg gccgcaacca tggcaaacga gatgggtttc   6840
ctagaaaaaa cgaagaaaga tctcggattg ggaagcattg caacccagca acccgagagc   6900
aacatcctgg acatagatct acgtcctgca tcagcatgga cgctgtatgc cgtggccaca   6960
acatttgtta caccaatgtt gagacatagc attgaaaatt cctcagtgaa tgtgtcccta   7020
acagctatag ccaaccaagc cacagtgtta atgggtctcg ggaaaggatg gccattgtca   7080
aagatggaca tcggagttcc ccttctcgcc attggatgct actcacaagt caaccccata   7140
actctcacag cagctctttt cttattggta gcacattatg ccatcatagg gccaggactc   7200
caagcaaaag caaccagaga agctcagaaa agagcagcgg cgggcatcat gaaaaaccca   7260
```

-continued

```
actgtcgatg gaataacagt gattgaccta gatccaatac cttatgatcc aaagtttgaa   7320
aagcagttgg gacaagtaat gctcctagtc ctctgcgtga ctcaagtatt gatgatgagg   7380
actacatggg ctctgtgtga ggctttaacc ttagctaccg ggcccatctc cacattgtgg   7440
gaaggaaatc cagggaggtt ttggaacact accattgcgg tgtcaatggc taacattttt   7500
agagggagtt acttggccgg agctggactt ctcttttcta ttatgaagaa cacaaccaac   7560
acaagaaggg gaactggcaa cataggagag acgcttggag agaaatggaa aagccgattg   7620
aacgcattgg gaaaaagtga attccagatc tacaagaaaa gtggaatcca ggaagtggat   7680
agaaccttag caaaagaagg cattaaaaga ggagaaacgg accatcacgc tgtgtcgcga   7740
ggctcagcaa aactgagatg gttcgttgag agaaacatgg tcacaccaga agggaaagta   7800
gtggacctcg gttgtggcag aggaggctgg tcatactatt gtggaggact aaagaatgta   7860
agagaagtca aaggcctaac aaaaggagga ccaggacacg aagaacccat ccccatgtca   7920
acatatgggt ggaatctagt gcgtcttcaa agtggagttg acgttttctt catcccgcca   7980
gaaaagtgtg acacattatt gtgtgacata ggggagtcat caccaaatcc cacagtggaa   8040
gcaggacgaa cactcagagt ccttaactta gtagaaaatt ggttgaacaa caacactcaa   8100
ttttgcataa aggttctcaa cccatatatg ccctcagtca tagaaaaaat ggaagcacta   8160
caaaggaaat atggaggagc cttagtgagg aatccactct cacgaaactc cacacatgag   8220
atgtactggg tatccaatgc ttccgggaac atagtgtcat cagtgaacat gatttcaagg   8280
atgttgatca acagatttac aatgagatac aagaaagcca cttacgagcc ggatgttgac   8340
ctcggaagcg gaacccgtaa catcgggatt gaaagtgaga taccaaacct agatataatt   8400
gggaaaagaa tagaaaaaat aaagcaagag catgaaacat catggcacta tgaccaagac   8460
cacccataca aaacgtgggc ataccatggt agctatgaaa caaaacagac tggatcagca   8520
tcatccatgg tcaacggagt ggtcaggctg ctgacaaaac cttgggacgt cgtccccatg   8580
gtgacacaga tggcaatgac agacacgact ccatttggac aacagcgcgt tttaaaagag   8640
aaagtggaca cgagaaccca agaaccgaaa gaaggcacga agaaactaat gaaaataaca   8700
gcagagtggc tttggaaaga attagggaag aaaaagacac ccaggatgtg caccagagaa   8760
gaattcacaa gaaaggtgag aagcaatgca gccttggggg ccatattcac tgatgagaac   8820
aagtggaagt cggcacgtga ggctgttgaa gatagtaggt tttgggagct ggttgacaag   8880
gaaaggaatc tccatcttga aggaaagtgt gaaacatgtg tgtacaacat gatgggaaaa   8940
agagagaaga agctagggga attcggcaag gcaaaaggca gcagagccat atggtacatg   9000
tggcttggag cacgcttctt agagtttgaa gccctaggat tcttaaatga agatcactgg   9060
ttctccagag agaactccct gagtggagtg gaaggagaag ggctgcacaa gctaggttac   9120
attctaagag acgtgagcaa gaaagaggga ggagcaatgt atgccgatga caccgcagga   9180
tgggatacaa gaatcacact agaagaccta aaaaatgaag aaatggtaac aaaccacatg   9240
gaaggagaac acaagaaact agccgaggcc attttcaaac taacgtacca aaacaaggtg   9300
gtgcgtgtgc aaagaccaac accaagaggc acagtaatgg acatcatatc gagaagagac   9360
caaagaggta gtggacaagt tggcacctat ggactcaata ctttcaccaa tatggaagcc   9420
caactaatca gacagatgga gggagaagga gtctttaaaa gcattcagca cctaacaatc   9480
acagaagaaa tcgctgtgca aaactggtta gcaagagtgg ggcgcgaaag gttatcaaga   9540
atggccatca gtggagatga ttgtgttgtg aaacctttag atgacaggtt cgcaagcgct   9600
ttaacagctc taaatgacat gggaaagatt aggaaagaca tacaacaatg ggaaccttca   9660
```

```
agaggatgga atgattggac acaagtgccc ttctgttcac accatttcca tgagttaatc   9720

atgaaagacg gtcgcgtact cgttgttcca tgtagaaacc aagatgaact gattggcaga   9780

gcccgaatct cccaaggagc agggtggtct ttgcgggaga cggcctgttt ggggaagtct   9840

tacgcccaaa tgtggagctt gatgtacttc cacagacgcg acctcaggct ggcggcaaat   9900

gctatttgct cggcagtacc atcacattgg gttccaacaa gtcgaacaac ctggtccata   9960

catgctaaac atgaatggat gacaacggaa gacatgctga cagtctggaa cagggtgtgg  10020

attcaagaaa acccatggat ggaagacaaa actccagtgg aatcatggga ggaaatccca  10080

tacttgggga aaagagaaga ccaatggtgc ggctcattga ttgggttaac aagcagggcc  10140

acctgggcaa agaacatcca agcagcaata aatcaagtta gatcccttat aggcaatgaa  10200

gaatacacag attacatgcc atccatgaaa agattcagaa gagaagagga agaagcagga  10260

gttctgtggt agaaagcaaa actaacatga aacaaggcta gaagtcaggt cggattaagc  10320

catagtacgg aaaaaactat gctacctgtg agccccgtcc aaggacgtta aaagaagtca  10380

ggccatcata aatgccatag cttgagtaaa ctatgcagcc tgtagctcca cctgagaagg  10440

tgtaaaaaat ccgggaggcc acaaaccatg gaagctgtac gcatggcgta gtggactagc  10500

ggttagagga gacccctccc ttacaaatcg cagcaacaat gggggcccaa ggcgagatga  10560

agctgtagtc tcgctggaag gactagaggt tagaggagac ccccccgaaa caaaaaacag  10620

catattgacg ctgggaaaga ccagagatcc tgctgtctcc tcagcatcat tccaggcaca  10680

gaacgccaga aaatggaatg gtgctgttga atcaacaggt tct                   10723
```

<210> SEQ ID NO 23
<211> LENGTH: 3391
<212> TYPE: PRT
<213> ORGANISM: Artificial Sequence
<220> FEATURE:
<223> OTHER INFORMATION: Derived from Dengue virus serotype 2/Dengue
      virus serotype 4, DEN-4e

<400> SEQUENCE: 23

```
Met Asn Asn Gln Arg Lys Lys Ala Lys Asn Thr Pro Phe Asn Met Leu
1               5                   10                  15

Lys Arg Glu Arg Asn Arg Val Ser Thr Val Gln Gln Leu Thr Lys Arg
            20                  25                  30

Phe Ser Leu Gly Met Leu Gln Gly Arg Gly Pro Leu Lys Leu Phe Met
        35                  40                  45

Ala Leu Val Ala Phe Leu Arg Phe Leu Thr Ile Pro Pro Thr Ala Gly
    50                  55                  60

Ile Leu Lys Arg Trp Gly Thr Ile Lys Lys Ser Lys Ala Ile Asn Val
65                  70                  75                  80

Leu Arg Gly Phe Arg Lys Glu Ile Gly Arg Met Leu Asn Ile Leu Asn
                85                  90                  95

Arg Arg Arg Ser Ser Thr Ile Thr Leu Leu Tyr Leu Ile Pro Thr Val
            100                 105                 110

Met Ala Phe His Leu Ser Thr Arg Asp Gly Glu Pro Leu Met Ile Val
        115                 120                 125

Ala Lys His Glu Arg Gly Arg Pro Leu Leu Phe Lys Thr Thr Glu Gly
    130                 135                 140

Ile Asn Lys Cys Thr Leu Ile Ala Met Asp Leu Gly Glu Met Cys Glu
145                 150                 155                 160

Asp Thr Val Thr Tyr Lys Cys Pro Leu Leu Val Asn Thr Glu Pro Glu
```

-continued

```
                165                 170                 175

Asp Ile Asp Cys Trp Cys Asn Leu Thr Ser Thr Trp Val Met Tyr Gly
            180                 185                 190

Thr Cys Thr Gln Ser Gly Glu Arg Arg Arg Glu Lys Arg Ser Val Ala
        195                 200                 205

Leu Thr Pro His Ser Gly Met Gly Leu Glu Thr Arg Ala Glu Thr Trp
    210                 215                 220

Met Ser Ser Glu Gly Ala Trp Lys His Ala Gln Arg Val Glu Ser Trp
225                 230                 235                 240

Ile Leu Arg Asn Pro Gly Phe Ala Leu Leu Ala Gly Phe Met Ala Tyr
                245                 250                 255

Met Ile Gly Gln Thr Gly Ile Gln Arg Thr Val Phe Phe Val Leu Met
            260                 265                 270

Met Leu Val Ala Pro Ser Tyr Gly Met Arg Cys Val Gly Val Gly Asn
        275                 280                 285

Arg Asp Phe Val Glu Gly Val Ser Gly Gly Ala Trp Val Asp Leu Val
    290                 295                 300

Leu Glu His Gly Gly Cys Val Thr Thr Met Ala Gln Gly Lys Pro Thr
305                 310                 315                 320

Leu Asp Phe Glu Leu Thr Lys Thr Thr Ala Lys Glu Val Ala Leu Leu
                325                 330                 335

Arg Thr Tyr Cys Ile Glu Ala Ser Ile Ser Asn Ile Thr Thr Ala Thr
            340                 345                 350

Arg Cys Pro Thr Gln Gly Glu Pro Tyr Leu Lys Glu Glu Gln Asp Gln
        355                 360                 365

Gln Tyr Ile Cys Arg Arg Asp Val Val Asp Arg Gly Trp Gly Asn Gly
    370                 375                 380

Cys Gly Leu Phe Gly Lys Gly Gly Val Val Thr Cys Ala Lys Phe Ser
385                 390                 395                 400

Cys Ser Gly Lys Ile Thr Gly Asn Leu Val Gln Ile Glu Asn Leu Glu
                405                 410                 415

Tyr Thr Val Val Val Thr Val His Asn Gly Asp Thr His Ala Val Gly
            420                 425                 430

Asn Asp Thr Ser Asn His Gly Val Thr Ala Thr Ile Thr Pro Arg Ser
        435                 440                 445

Pro Ser Val Glu Val Lys Leu Pro Asp Tyr Gly Glu Leu Thr Leu Asp
    450                 455                 460

Cys Glu Pro Arg Ser Gly Ile Asp Phe Asn Glu Met Ile Leu Met Lys
465                 470                 475                 480

Met Lys Lys Lys Thr Trp Leu Val His Lys Gln Trp Phe Leu Asp Leu
                485                 490                 495

Pro Leu Pro Trp Thr Ala Gly Ala Asp Thr Ser Glu Val His Trp Asn
            500                 505                 510

Tyr Lys Glu Arg Met Val Thr Phe Lys Val Pro His Ala Lys Arg Gln
        515                 520                 525

Asp Val Thr Val Leu Gly Ser Gln Glu Gly Ala Met His Ser Ala Leu
    530                 535                 540

Ala Gly Ala Thr Glu Val Asp Ser Gly Asp Gly Asn His Met Phe Ala
545                 550                 555                 560

Gly His Leu Lys Cys Lys Val Arg Met Glu Lys Leu Arg Ile Lys Gly
                565                 570                 575

Met Ser Tyr Thr Met Cys Ser Gly Lys Phe Ser Ile Asp Lys Glu Met
            580                 585                 590
```

```
Ala Glu Thr Gln His Gly Thr Thr Val Val Lys Val Lys Tyr Glu Gly
        595                 600                 605

Ala Gly Ala Pro Cys Lys Val Pro Ile Glu Ile Arg Asp Val Asn Lys
    610                 615                 620

Glu Lys Val Val Gly Arg Ile Ile Ser Ser Thr Pro Leu Ala Glu Asn
625                 630                 635                 640

Thr Asn Ser Val Thr Asn Ile Glu Leu Glu Pro Pro Phe Gly Asp Ser
                645                 650                 655

Tyr Ile Val Ile Gly Val Gly Asn Ser Ala Leu Thr Leu His Trp Phe
            660                 665                 670

Arg Lys Gly Ser Ser Ile Gly Lys Met Phe Glu Ser Thr Tyr Arg Gly
        675                 680                 685

Ala Lys Arg Met Ala Ile Leu Gly Glu Thr Ala Trp Asp Phe Gly Ser
    690                 695                 700

Val Gly Gly Leu Phe Thr Ser Leu Gly Lys Ala Val His Gln Val Phe
705                 710                 715                 720

Gly Ser Val Tyr Thr Thr Leu Phe Gly Gly Val Ser Trp Met Ile Arg
                725                 730                 735

Ile Leu Ile Gly Phe Leu Val Leu Trp Ile Gly Thr Asn Ser Arg Asn
            740                 745                 750

Thr Ser Met Ala Met Thr Cys Ile Ala Ala Gly Ile Val Thr Leu Tyr
        755                 760                 765

Leu Gly Val Met Val Gln Ala Asp Ser Gly Cys Val Val Ser Trp Lys
    770                 775                 780

Asn Lys Glu Leu Lys Cys Gly Ser Gly Ile Phe Ile Thr Asp Asn Val
785                 790                 795                 800

His Thr Trp Thr Glu Gln Tyr Lys Phe Gln Pro Glu Ser Pro Ser Lys
                805                 810                 815

Leu Ala Ser Ala Ile Gln Lys Ala His Glu Glu Asp Ile Cys Gly Ile
            820                 825                 830

Arg Ser Val Thr Arg Leu Glu Asn Leu Met Trp Lys Gln Ile Thr Pro
        835                 840                 845

Glu Leu Asn His Ile Leu Ser Glu Asn Glu Val Lys Leu Thr Ile Met
    850                 855                 860

Thr Gly Asp Ile Lys Gly Ile Met Gln Ala Gly Lys Arg Ser Leu Arg
865                 870                 875                 880

Pro Gln Pro Thr Glu Leu Lys Tyr Ser Trp Lys Thr Trp Gly Lys Ala
                885                 890                 895

Lys Met Leu Ser Thr Glu Ser His Asn Gln Thr Phe Leu Ile Asp Gly
            900                 905                 910

Pro Glu Thr Ala Glu Cys Pro Asn Thr Asn Arg Ala Trp Asn Ser Leu
        915                 920                 925

Glu Val Glu Asp Tyr Gly Phe Gly Val Phe Thr Thr Asn Ile Trp Leu
    930                 935                 940

Lys Leu Lys Glu Lys Gln Asp Val Phe Cys Asp Ser Lys Leu Met Ser
945                 950                 955                 960

Ala Ala Ile Lys Asp Asn Arg Ala Val His Ala Asp Met Gly Tyr Trp
                965                 970                 975

Ile Glu Ser Ala Leu Asn Asp Thr Trp Lys Ile Glu Lys Ala Ser Phe
            980                 985                 990

Ile Glu Val Lys Asn Cys His Trp  Pro Lys Ser His Thr  Leu Trp Ser
        995                 1000                1005
```

```
Asn Gly  Val Leu Glu Ser Glu  Met Ile Ile Pro Lys  Asn Leu Ala
    1010                 1015                 1020

Gly Pro  Val Ser Gln His Asn  Tyr Arg Pro Gly Tyr  His Thr Gln
    1025                 1030                 1035

Ile Thr  Gly Pro Trp His Leu  Gly Lys Leu Glu Met  Asp Phe Asp
    1040                 1045                 1050

Phe Cys  Asp Gly Thr Thr Val  Val Val Thr Glu Asp  Cys Gly Asn
    1055                 1060                 1065

Arg Gly  Pro Ser Leu Arg Thr  Thr Thr Ala Ser Gly  Lys Leu Ile
    1070                 1075                 1080

Thr Glu  Trp Cys Cys Arg Ser  Cys Thr Leu Pro Pro  Leu Arg Tyr
    1085                 1090                 1095

Arg Gly  Glu Asp Gly Cys Trp  Tyr Gly Met Glu Ile  Arg Pro Leu
    1100                 1105                 1110

Lys Glu  Lys Glu Glu Asn Leu  Val Asn Ser Leu Val  Thr Ala Gly
    1115                 1120                 1125

His Gly  Gln Val Asp Asn Phe  Ser Leu Gly Val Leu  Gly Met Ala
    1130                 1135                 1140

Leu Phe  Leu Glu Glu Met Leu  Arg Thr Arg Val Gly  Thr Lys His
    1145                 1150                 1155

Ala Ile  Leu Leu Val Ala Val  Ser Phe Val Thr Leu  Ile Thr Gly
    1160                 1165                 1170

Asn Met  Ser Phe Arg Asp Leu  Gly Arg Val Met Val  Met Val Gly
    1175                 1180                 1185

Ala Thr  Met Thr Asp Asp Ile  Gly Met Gly Val Thr  Tyr Leu Ala
    1190                 1195                 1200

Leu Leu  Ala Ala Phe Lys Val  Arg Pro Thr Phe Ala  Ala Gly Leu
    1205                 1210                 1215

Leu Leu  Arg Lys Leu Thr Ser  Lys Glu Leu Met Met  Thr Thr Ile
    1220                 1225                 1230

Gly Ile  Val Leu Leu Ser Gln  Ser Thr Ile Pro Glu  Thr Ile Leu
    1235                 1240                 1245

Glu Leu  Thr Asp Ala Leu Ala  Leu Gly Met Met Val  Leu Lys Met
    1250                 1255                 1260

Val Arg  Asn Met Glu Lys Tyr  Gln Leu Ala Val Thr  Ile Met Ala
    1265                 1270                 1275

Ile Leu  Cys Val Pro Asn Ala  Val Ile Leu Gln Asn  Ala Trp Lys
    1280                 1285                 1290

Val Ser  Cys Thr Ile Leu Ala  Val Val Ser Val Ser  Pro Leu Phe
    1295                 1300                 1305

Leu Thr  Ser Ser Gln Gln Lys  Thr Asp Trp Ile Pro  Leu Ala Leu
    1310                 1315                 1320

Thr Ile  Lys Gly Leu Asn Pro  Thr Ala Ile Phe Leu  Thr Thr Leu
    1325                 1330                 1335

Ser Arg  Thr Ser Lys Lys Arg  Ser Trp Pro Leu Asn  Glu Ala Ile
    1340                 1345                 1350

Met Ala  Val Gly Met Val Ser  Ile Leu Ala Ser Ser  Leu Leu Lys
    1355                 1360                 1365

Asn Asp  Ile Pro Met Thr Gly  Pro Leu Val Ala Gly  Gly Leu Leu
    1370                 1375                 1380

Thr Val  Cys Tyr Val Leu Thr  Gly Arg Ser Ala Asp  Leu Glu Leu
    1385                 1390                 1395

Glu Arg  Ala Ala Asp Val Lys  Trp Glu Asp Gln Ala  Glu Ile Ser
```

```
    1400                1405                1410

Gly Ser  Ser Pro Ile Leu Ser  Ile Thr Ile Ser Glu  Asp Gly Ser
    1415                1420                1425

Met Ser  Ile Lys Asn Glu Glu  Glu Glu Gln Thr Leu  Thr Ile Leu
    1430                1435                1440

Ile Arg  Thr Gly Leu Leu Val  Ile Ser Gly Leu Phe  Pro Val Ser
    1445                1450                1455

Ile Pro  Ile Thr Ala Ala Ala  Trp Tyr Leu Trp Glu  Val Lys Lys
    1460                1465                1470

Gln Arg  Ala Gly Val Leu Trp  Asp Val Pro Ser Pro  Pro Pro Met
    1475                1480                1485

Gly Lys  Ala Glu Leu Glu Asp  Gly Ala Tyr Arg Ile  Lys Gln Lys
    1490                1495                1500

Gly Ile  Leu Gly Tyr Ser Gln  Ile Gly Ala Gly Val  Tyr Lys Glu
    1505                1510                1515

Gly Thr  Phe His Thr Met Trp  His Val Thr Arg Gly  Ala Val Leu
    1520                1525                1530

Met His  Lys Gly Lys Arg Ile  Glu Pro Ser Trp Ala  Asp Val Lys
    1535                1540                1545

Lys Asp  Leu Ile Ser Tyr Gly  Gly Gly Trp Lys Leu  Glu Gly Glu
    1550                1555                1560

Trp Lys  Glu Gly Glu Glu Val  Gln Val Leu Ala Leu  Glu Pro Gly
    1565                1570                1575

Lys Asn  Pro Arg Ala Val Gln  Thr Lys Pro Gly Leu  Phe Lys Thr
    1580                1585                1590

Asn Ala  Gly Thr Ile Gly Ala  Val Ser Leu Asp Phe  Ser Pro Gly
    1595                1600                1605

Thr Ser  Gly Ser Pro Ile Ile  Asp Lys Lys Gly Lys  Val Val Gly
    1610                1615                1620

Leu Tyr  Gly Asn Gly Val Val  Thr Arg Ser Gly Ala  Tyr Val Ser
    1625                1630                1635

Ala Ile  Ala Gln Thr Glu Lys  Ser Ile Glu Asp Asn  Pro Glu Ile
    1640                1645                1650

Glu Asp  Asp Ile Phe Arg Lys  Arg Arg Leu Thr Ile  Met Asp Leu
    1655                1660                1665

His Pro  Gly Ala Gly Lys Thr  Lys Arg Tyr Leu Pro  Ala Ile Val
    1670                1675                1680

Arg Glu  Ala Ile Lys Arg Gly  Leu Arg Thr Leu Ile  Leu Ala Pro
    1685                1690                1695

Thr Arg  Val Val Ala Ala Glu  Met Glu Glu Ala Leu  Arg Gly Leu
    1700                1705                1710

Pro Ile  Arg Tyr Gln Thr Pro  Ala Ile Arg Ala Val  His Thr Gly
    1715                1720                1725

Arg Glu  Ile Val Asp Leu Met  Cys His Ala Thr Phe  Thr Met Arg
    1730                1735                1740

Leu Leu  Ser Pro Val Arg Val  Pro Asn Tyr Asn Leu  Ile Ile Met
    1745                1750                1755

Asp Glu  Ala His Phe Thr Asp  Pro Ala Ser Ile Ala  Ala Arg Gly
    1760                1765                1770

Tyr Ile  Ser Thr Arg Val Glu  Met Gly Glu Ala Ala  Gly Ile Phe
    1775                1780                1785

Met Thr  Ala Thr Pro Pro Gly  Ser Arg Asp Pro Phe  Pro Gln Ser
    1790                1795                1800
```

```
Asn Ala  Pro Ile Ile Asp Glu  Glu Arg Glu Ile Pro  Glu Arg Ser
    1805                 1810                 1815

Trp Asn  Ser Gly His Glu Trp  Val Thr Asp Phe Lys  Gly Lys Thr
    1820                 1825                 1830

Val Trp  Phe Val Pro Ser Ile  Lys Ala Gly Asn Asp  Ile Ala Ala
    1835                 1840                 1845

Cys Leu  Arg Lys Asn Gly Lys  Lys Val Ile Gln Leu  Ser Arg Lys
    1850                 1855                 1860

Thr Phe  Asp Ser Glu Tyr Val  Lys Thr Arg Thr Asn  Asp Trp Asp
    1865                 1870                 1875

Phe Val  Val Thr Thr Asp Ile  Ser Glu Met Gly Ala  Asn Phe Lys
    1880                 1885                 1890

Ala Glu  Arg Val Ile Asp Pro  Arg Arg Cys Met Lys  Pro Val Ile
    1895                 1900                 1905

Leu Thr  Asp Gly Glu Glu Arg  Val Ile Leu Ala Gly  Pro Met Pro
    1910                 1915                 1920

Val Thr  His Ser Ser Ala Ala  Gln Arg Arg Gly Arg  Ile Gly Arg
    1925                 1930                 1935

Asn Pro  Lys Asn Glu Asn Asp  Gln Tyr Ile Tyr Met  Gly Glu Pro
    1940                 1945                 1950

Leu Glu  Asn Asp Glu Asp Cys  Ala His Trp Lys Glu  Ala Lys Met
    1955                 1960                 1965

Leu Leu  Asp Asn Ile Asn Thr  Pro Glu Gly Ile Ile  Pro Ser Met
    1970                 1975                 1980

Phe Glu  Pro Glu Arg Glu Lys  Val Asp Ala Ile Asp  Gly Glu Tyr
    1985                 1990                 1995

Arg Leu  Arg Gly Glu Ala Arg  Lys Thr Phe Val Asp  Leu Met Arg
    2000                 2005                 2010

Arg Gly  Asp Leu Pro Val Trp  Leu Ala Tyr Arg Val  Ala Ala Glu
    2015                 2020                 2025

Gly Ile  Asn Tyr Ala Asp Arg  Arg Trp Cys Phe Asp  Gly Val Lys
    2030                 2035                 2040

Asn Asn  Gln Ile Leu Glu Glu  Asn Val Glu Val Glu  Ile Trp Thr
    2045                 2050                 2055

Lys Glu  Gly Glu Arg Lys Lys  Leu Lys Pro Arg Trp  Leu Asp Ala
    2060                 2065                 2070

Arg Ile  Tyr Ser Asp Pro Leu  Ala Leu Lys Glu Phe  Lys Glu Phe
    2075                 2080                 2085

Ala Ala  Gly Arg Lys Ser Leu  Thr Leu Asn Leu Ile  Thr Glu Met
    2090                 2095                 2100

Gly Arg  Leu Pro Thr Phe Met  Thr Gln Lys Ala Arg  Asp Ala Leu
    2105                 2110                 2115

Asp Asn  Leu Ala Val Leu His  Thr Ala Glu Ala Gly  Gly Arg Ala
    2120                 2125                 2130

Tyr Asn  His Ala Leu Ser Glu  Leu Pro Glu Thr Leu  Glu Thr Leu
    2135                 2140                 2145

Leu Leu  Leu Thr Leu Leu Ala  Thr Val Thr Gly Gly  Ile Phe Leu
    2150                 2155                 2160

Phe Leu  Met Ser Ala Arg Gly  Ile Gly Lys Met Thr  Leu Gly Met
    2165                 2170                 2175

Cys Cys  Ile Ile Thr Ala Ser  Ile Leu Leu Trp Tyr  Ala Gln Ile
    2180                 2185                 2190
```

```
Gln Pro  His Trp Ile Ala Ala  Ser Ile Ile Leu Glu  Phe Phe Leu
    2195                 2200                 2205

Ile Val  Leu Leu Ile Pro Glu  Pro Glu Lys Gln Arg  Thr Pro Gln
    2210                 2215                 2220

Asp Asn  Gln Leu Thr Tyr Val  Val Ile Ala Ile Leu  Thr Val Val
    2225                 2230                 2235

Ala Ala  Thr Met Ala Asn Glu  Met Gly Phe Leu Glu  Lys Thr Lys
    2240                 2245                 2250

Lys Asp  Leu Gly Leu Gly Ser  Ile Ala Thr Gln Gln  Pro Glu Ser
    2255                 2260                 2265

Asn Ile  Leu Asp Ile Asp Leu  Arg Pro Ala Ser Ala  Trp Thr Leu
    2270                 2275                 2280

Tyr Ala  Val Ala Thr Thr Phe  Val Thr Pro Met Leu  Arg His Ser
    2285                 2290                 2295

Ile Glu  Asn Ser Ser Val Asn  Val Ser Leu Thr Ala  Ile Ala Asn
    2300                 2305                 2310

Gln Ala  Thr Val Leu Met Gly  Leu Gly Lys Gly Trp  Pro Leu Ser
    2315                 2320                 2325

Lys Met  Asp Ile Gly Val Pro  Leu Leu Ala Ile Gly  Cys Tyr Ser
    2330                 2335                 2340

Gln Val  Asn Pro Ile Thr Leu  Thr Ala Ala Leu Phe  Leu Leu Val
    2345                 2350                 2355

Ala His  Tyr Ala Ile Ile Gly  Pro Gly Leu Gln Ala  Lys Ala Thr
    2360                 2365                 2370

Arg Glu  Ala Gln Lys Arg Ala  Ala Ala Gly Ile Met  Lys Asn Pro
    2375                 2380                 2385

Thr Val  Asp Gly Ile Thr Val  Ile Asp Leu Asp Pro  Ile Pro Tyr
    2390                 2395                 2400

Asp Pro  Lys Phe Glu Lys Gln  Leu Gly Gln Val Met  Leu Leu Val
    2405                 2410                 2415

Leu Cys  Val Thr Gln Val Leu  Met Met Arg Thr Thr  Trp Ala Leu
    2420                 2425                 2430

Cys Glu  Ala Leu Thr Leu Ala  Thr Gly Pro Ile Ser  Thr Leu Trp
    2435                 2440                 2445

Glu Gly  Asn Pro Gly Arg Phe  Trp Asn Thr Thr Ile  Ala Val Ser
    2450                 2455                 2460

Met Ala  Asn Ile Phe Arg Gly  Ser Tyr Leu Ala Gly  Ala Gly Leu
    2465                 2470                 2475

Leu Phe  Ser Ile Met Lys Asn  Thr Thr Asn Thr Arg  Arg Gly Thr
    2480                 2485                 2490

Gly Asn  Ile Gly Glu Thr Leu  Gly Glu Lys Trp Lys  Ser Arg Leu
    2495                 2500                 2505

Asn Ala  Leu Gly Lys Ser Glu  Phe Gln Ile Tyr Lys  Lys Ser Gly
    2510                 2515                 2520

Ile Gln  Glu Val Asp Arg Thr  Leu Ala Lys Glu Gly  Ile Lys Arg
    2525                 2530                 2535

Gly Glu  Thr Asp His His Ala  Val Ser Arg Gly Ser  Ala Lys Leu
    2540                 2545                 2550

Arg Trp  Phe Val Glu Arg Asn  Met Val Thr Pro Glu  Gly Lys Val
    2555                 2560                 2565

Val Asp  Leu Gly Cys Gly Arg  Gly Gly Trp Ser Tyr  Tyr Cys Gly
    2570                 2575                 2580

Gly Leu  Lys Asn Val Arg Glu  Val Lys Gly Leu Thr  Lys Gly Gly
```

-continued

```
    2585                2590                2595

Pro Gly  His Glu Glu Pro Ile  Pro Met Ser Thr Tyr  Gly Trp Asn
    2600                2605                2610

Leu Val  Arg Leu Gln Ser Gly  Val Asp Val Phe Phe  Ile Pro Pro
    2615                2620                2625

Glu Lys  Cys Asp Thr Leu Leu  Cys Asp Ile Gly Glu  Ser Ser Pro
    2630                2635                2640

Asn Pro  Thr Val Glu Ala Gly  Arg Thr Leu Arg Val  Leu Asn Leu
    2645                2650                2655

Val Glu  Asn Trp Leu Asn Asn  Asn Thr Gln Phe Cys  Ile Lys Val
    2660                2665                2670

Leu Asn  Pro Tyr Met Pro Ser  Val Ile Glu Lys Met  Glu Ala Leu
    2675                2680                2685

Gln Arg  Lys Tyr Gly Gly Ala  Leu Val Arg Asn Pro  Leu Ser Arg
    2690                2695                2700

Asn Ser  Thr His Glu Met Tyr  Trp Val Ser Asn Ala  Ser Gly Asn
    2705                2710                2715

Ile Val  Ser Ser Val Asn Met  Ile Ser Arg Met Leu  Ile Asn Arg
    2720                2725                2730

Phe Thr  Met Arg Tyr Lys Lys  Ala Thr Tyr Glu Pro  Asp Val Asp
    2735                2740                2745

Leu Gly  Ser Gly Thr Arg Asn  Ile Gly Ile Glu Ser  Glu Ile Pro
    2750                2755                2760

Asn Leu  Asp Ile Ile Gly Lys  Arg Ile Glu Lys Ile  Lys Gln Glu
    2765                2770                2775

His Glu  Thr Ser Trp His Tyr  Asp Gln Asp His Pro  Tyr Lys Thr
    2780                2785                2790

Trp Ala  Tyr His Gly Ser Tyr  Glu Thr Lys Gln Thr  Gly Ser Ala
    2795                2800                2805

Ser Ser  Met Val Asn Gly Val  Val Arg Leu Leu Thr  Lys Pro Trp
    2810                2815                2820

Asp Val  Val Pro Met Val Thr  Gln Met Ala Met Thr  Asp Thr Thr
    2825                2830                2835

Pro Phe  Gly Gln Gln Arg Val  Phe Lys Glu Lys Val  Asp Thr Arg
    2840                2845                2850

Thr Gln  Glu Pro Lys Glu Gly  Thr Lys Lys Leu Met  Lys Ile Thr
    2855                2860                2865

Ala Glu  Trp Leu Trp Lys Glu  Leu Gly Lys Lys Lys  Thr Pro Arg
    2870                2875                2880

Met Cys  Thr Arg Glu Glu Phe  Thr Arg Lys Val Arg  Ser Asn Ala
    2885                2890                2895

Ala Leu  Gly Ala Ile Phe Thr  Asp Glu Asn Lys Trp  Lys Ser Ala
    2900                2905                2910

Arg Glu  Ala Val Glu Asp Ser  Arg Phe Trp Glu Leu  Val Asp Lys
    2915                2920                2925

Glu Arg  Asn Leu His Leu Glu  Gly Lys Cys Glu Thr  Cys Val Tyr
    2930                2935                2940

Asn Met  Met Gly Lys Arg Glu  Lys Lys Leu Gly Glu  Phe Gly Lys
    2945                2950                2955

Ala Lys  Gly Ser Arg Ala Ile  Trp Tyr Met Trp Leu  Gly Ala Arg
    2960                2965                2970

Phe Leu  Glu Phe Glu Ala Leu  Gly Phe Leu Asn Glu  Asp His Trp
    2975                2980                2985
```

```
Phe Ser Arg Glu Asn Ser Leu Ser Gly Val Glu Gly Glu Gly Leu
    2990                3995                3000

His Lys Leu Gly Tyr Ile Leu Arg Asp Val Ser Lys Lys Glu Gly
    3005                3010                3015

Gly Ala Met Tyr Ala Asp Asp Thr Ala Gly Trp Asp Thr Arg Ile
    3020                3025                3030

Thr Leu Glu Asp Leu Lys Asn Glu Glu Met Val Thr Asn His Met
    3035                3040                3045

Glu Gly Glu His Lys Lys Leu Ala Glu Ala Ile Phe Lys Leu Thr
    3050                3055                3060

Tyr Gln Asn Lys Val Val Arg Val Gln Arg Pro Thr Pro Arg Gly
    3065                3070                3075

Thr Val Met Asp Ile Ile Ser Arg Arg Asp Gln Arg Gly Ser Gly
    3080                3085                3090

Gln Val Gly Thr Tyr Gly Leu Asn Thr Phe Thr Asn Met Glu Ala
    3095                3100                3105

Gln Leu Ile Arg Gln Met Glu Gly Glu Gly Val Phe Lys Ser Ile
    3110                3115                3120

Gln His Leu Thr Ile Thr Glu Glu Ile Ala Val Gln Asn Trp Leu
    3125                3130                3135

Ala Arg Val Gly Arg Glu Arg Leu Ser Arg Met Ala Ile Ser Gly
    3140                3145                3150

Asp Asp Cys Val Val Lys Pro Leu Asp Asp Arg Phe Ala Ser Ala
    3155                3160                3165

Leu Thr Ala Leu Asn Asp Met Gly Lys Ile Arg Lys Asp Ile Gln
    3170                3175                3180

Gln Trp Glu Pro Ser Arg Gly Trp Asn Asp Trp Thr Gln Val Pro
    3185                3190                3195

Phe Cys Ser His His Phe His Glu Leu Ile Met Lys Asp Gly Arg
    3200                3205                3210

Val Leu Val Val Pro Cys Arg Asn Gln Asp Glu Leu Ile Gly Arg
    3215                3220                3225

Ala Arg Ile Ser Gln Gly Ala Gly Trp Ser Leu Arg Glu Thr Ala
    3230                3235                3240

Cys Leu Gly Lys Ser Tyr Ala Gln Met Trp Ser Leu Met Tyr Phe
    3245                3250                3255

His Arg Arg Asp Leu Arg Leu Ala Ala Asn Ala Ile Cys Ser Ala
    3260                3265                3270

Val Pro Ser His Trp Val Pro Thr Ser Arg Thr Thr Trp Ser Ile
    3275                3280                3285

His Ala Lys His Glu Trp Met Thr Thr Glu Asp Met Leu Thr Val
    3290                3295                3300

Trp Asn Arg Val Trp Ile Gln Glu Asn Pro Trp Met Glu Asp Lys
    3305                3310                3315

Thr Pro Val Glu Ser Trp Glu Glu Ile Pro Tyr Leu Gly Lys Arg
    3320                3325                3330

Glu Asp Gln Trp Cys Gly Ser Leu Ile Gly Leu Thr Ser Arg Ala
    3335                3340                3345

Thr Trp Ala Lys Asn Ile Gln Ala Ala Ile Asn Gln Val Arg Ser
    3350                3355                3360

Leu Ile Gly Asn Glu Glu Tyr Thr Asp Tyr Met Pro Ser Met Lys
    3365                3370                3375
```

```
Arg Phe  Arg Arg Glu Glu Glu  Glu Ala Gly Val Leu  Trp
    3380                 3385                 3390


<210> SEQ ID NO 24
<211> LENGTH: 10723
<212> TYPE: DNA
<213> ORGANISM: Artificial Sequence
<220> FEATURE:
<223> OTHER INFORMATION: Derived from Dengue virus serotype 2/Dengue
      virus serotype 4, DEN, 4h

<400> SEQUENCE: 24

agttgttagt ctacgtggac cgacaaagac agattctttg agggagctaa gctcaatgta     60

gttctaacag tttttaatt agagagcaga tctctgatga ataaccaacg gaaaaaggcg    120

aaaaacacgc ctttcaatat gctgaaacgc gagagaaacc gcgtgtcgac tgtgcaacag    180

ctgacaaaga gattctcact tggaatgctg cagggacgag gaccattaaa actgttcatg    240

gccctggtgg cgttccttcg tttcctaaca atcccaccaa cagcagggat attgaagaga    300

tggggaacaa ttaaaaaatc aaaagctatt aatgttttga gagggttcag gaaagagatt    360

ggaaggatgc tgaacatctt gaataggaga cgcagctctg caggcatgat cattatgctg    420

attccaacag tgatggcgtt ccatttaacc acgcgtgatg gcgaacccct catgatagtg    480

gcaaaacatg aaagggggag acctctcttg tttaagacaa cagaggggat caacaaatgc    540

actctcattg ccatggactt gggtgaaatg tgtgaggaca ctgtcacgta taaatgcccc    600

ttactggtca ataccgaacc tgaagacatt gattgctggt gcaatctcac gtctacctgg    660

gtcatgtatg ggacatgcac ccagagcgga gaacggagac gagagaagcg ctcagtagct    720

ttaacaccac attcaggaat gggattggaa acaagagctg agacatggat gtcatcggaa    780

ggggcttgga agcatgctca gagagtagag agctggatac tcagaaaccc aggattcgcg    840

ctcttggcag gatttatggc ttatatgatt gggcaaacag gaatccagcg aactgtcttc    900

tttgtcctaa tgatgctggt cgccccatcc tacggaatgc gatgcgtagg agtaggaaac    960

agagactttg tggaaggagt ctcaggtgga gcatgggtcg atctggtgct agaacatgga   1020

ggatgcgtca caaccatggc ccagggaaaa ccaaccttgg attttgaact gactaagaca   1080

acagccaagg aagtggctct gttaagaacc tattgcattg aagcctcaat atcaaacata   1140

accacggcaa caagatgtcc aacgcaagga gagccttatc taaaagagga acaagaccaa   1200

cagtacattt gccggagaga tgtggtagac agagggtggg gcaatggctg tggcttgttt   1260

ggaaaaggag gagttgtgac atgtgcgaag ttttcatgtt cggggaagat aacaggcaat   1320

ttggtccaaa ttgagaacct tgaatacaca gtggttgtaa cagtccacaa tggagacacc   1380

catgcagtag gaaatgacac gtccaatcat ggagttacag ccacgataac tcccaggtca   1440

ccatcggtgg aagtcaaatt gccggactat ggagaactaa cactcgattg tgaacccagg   1500

tctggaattg actttaatga gatgattctg atgaaaatga aaaagaaaac atggcttgtg   1560

cataagcaat ggtttttgga tctacctcta ccatggacag caggagcaga cacatcagag   1620

gttcactgga attacaaaga gagaatggtg acatttaagg ttcctcatgc caagagacag   1680

gatgtgacag tgctgggatc tcaggaagga gccatgcatt ctgccctcgc tggagccaca   1740

gaagtggact ccggtgatgg aaatcacatg tttgcaggac atctcaagtg caaagtccgt   1800

atggagaaat tgagaatcaa gggaatgtca tacacgatgt gttcaggaaa gttctcaatt   1860

gacaaagaga tggcagaaac acagcatggg acaacagtgg tgaaagtcaa gtatgaaggt   1920

gctggagctc cgtgtaaagt ccccatagag ataagagatg tgaacaagga aaaagtggtt   1980
```

gggcgtatca tctcatccac ccctttggct gagaatacca acagtgtaac caacatagag 2040
ttagaacccc cctttgggga cagctacata gtgataggtg ttggaaacag tgcattaaca 2100
ctccattggt tcaggaaagg gagttccatt ggcaagatgt ttgagtccac atacagaggt 2160
gcaaaacgaa tggccattct aggtaaaaca gcttgggatt ttggttccgt tggtggactg 2220
ttcacatcat tgggaaaggc tgtgcaccag gtttttggaa gtgtgtatac aaccctgttt 2280
ggaggagtct catggatgat tagaatccta attgggttcc tagtgttgtg gattggcacg 2340
aactcaagga acacttcaat ggctatgacg tgcatagctg ccggcattgt gacactgtat 2400
ttgggagtca tggtgcaggc cgatagtggt tgcgttgtga gctggaaaaa caaagaactg 2460
aaatgtggca gtgggatttt catcacagac aacgtgcaca catggacaga acaatacaag 2520
ttccaaccag aatccccttc aaaactagct tcagctatcc agaaagccca tgaagaggac 2580
atttgtggaa tccgctcagt aacaagactg gagaatctga tgtggaaaca aataacacca 2640
gaattgaatc acattctatc agaaaatgag gtgaagttaa ctattatgac aggagacatc 2700
aaaggaatca tgcaggcagg aaaacgatct ctgcggcctc agcccactga gctgaagtat 2760
tcatggaaaa catggggcaa agcaaaaatg ctctctacag agtctcataa ccagaccttt 2820
ctcattgatg gccccgaaac agcagaatgc cccaacacaa atagagcttg gaattcgttg 2880
gaagttgaag actatggctt tggagtattc accaccaata tatggctaaa attgaaagaa 2940
aaacaggatg tattctgcga ctcaaaactc atgtcagcgg ccataaaaga caacagagcc 3000
gtccatgccg atatgggtta ttggatagaa agtgcactca atgacacatg gaagatagag 3060
aaagcctctt tcattgaagt taaaaactgc cactggccaa aatcacacac cctctggagc 3120
aatggagtgc tagaaagtga gatgataatt ccaaagaatc tcgctggacc agtgtctcaa 3180
cacaactata gaccaggcta ccatacacaa ataacaggac catggcatct aggtaagctt 3240
gagatggact ttgatttctg tgatggaaca acagtggtag tgactgagga ctgcggaaat 3300
agaggaccct ctttgagaac aaccactgcc tctggaaaac tcataacaga atggtgctgc 3360
cgatcttgca cattaccacc gctaagatac agaggtgagg atgggtgctg gtacgggatg 3420
gaaatcagac cattgaagga gaaagaagag aatttggtca actccttggt cacagctgga 3480
catgggcagg tcgacaactt ttcactagga gtcttgggaa tggcattgtt cctggaggaa 3540
atgcttagga cccgagtagg aacgaaacat gcaatactac tagttgcagt ttcttttgtg 3600
acattgatca cagggaacat gtcctttaga gacctgggaa gagtgatggt tatggtaggc 3660
gccactatga cggatgacat aggtatgggc gtgacttatc ttgccctact agcagccttc 3720
aaagtcagac caacttttgc agctggacta ctcttgagaa agctgacctc caaggaattg 3780
atgatgacta ctataggaat tgtactcctc tcccagagca ccataccaga gaccattctt 3840
gagttgactg atgcgttagc cttaggcatg atggtcctca aaatggtgag aaatatggaa 3900
aagtatcaat tggcagtgac tatcatggct atcttgtgcg tcccaaacgc agtgatatta 3960
caaaacgcat ggaaagtgag ttgcacaata ttggcagtgg tgtccgtttc cccactgttc 4020
ttaacatcct cacagcaaaa aacagattgg ataccattag cattgacgat caaaggtctc 4080
aatccaacag ctatttttct aacaaccctc tcaagaacca gcaagaaaag gagctggcca 4140
ttaaatgagg ctatcatggc agtcgggatg gtgagcattt tagccagttc tctcctaaaa 4200
aatgatattc ccatgacagg accattagtg gctggagggc tcctcactgt gtgctacgtg 4260
ctcactggac gatcggccga tttggaactg gagagagcag ccgatgtcaa atgggaagac 4320

-continued caggcagaga tatcaggaag cagtccaatc ctgtcaataa caatatcaga agatggtagc 4380
atgtcgataa aaaatgaaga ggaagaacaa acactgacca tactcattag aacaggattg 4440
ctggtgatct caggactttt tcctgtatca ataccaatca cggcagcagc atggtacctg 4500
tgggaagtga agaaacaacg ggccggagta ttgtgggatg ttccttcacc cccacccatg 4560
ggaaaggctg aactggaaga tggagcctat agaattaagc aaaaagggat tcttggatat 4620
tcccagatcg gagccggagt ttacaaagaa ggaacattcc atacaatgtg gcatgtcaca 4680
cgtggcgctg ttctaatgca taaaggaaag aggattgaac catcatgggc ggacgtcaag 4740
aaagacctaa tatcatatgg aggaggctgg aagttagaag gagaatggaa ggaaggagaa 4800
gaagtccagg tattggcact ggagcctgga aaaaatccaa gagccgtcca aacgaaacct 4860
ggtcttttca aaaccaacgc cggaacaata ggtgctgtat ctctggactt ttctcctgga 4920
acgtcaggat ctccaattat cgacaaaaaa ggaaaagttg tgggtcttta tggtaatggt 4980
gttgttacaa ggagtggagc atatgtgagt gctatagccc agactgaaaa aagcattgaa 5040
gacaacccag agatcgaaga tgacattttc cgaaagagaa gactgaccat catggacctc 5100
cacccaggag cgggaaagac gaagagatac cttccggcca tagtcagaga agctataaaa 5160
cggggtttga gaacattaat cttggccccc actagagttg tggcagctga aatggaggaa 5220
gcccttagag gacttccaat aagataccag accccagcca tcagagctgt gcacaccggg 5280
cgggagattg tggacctaat gtgtcatgcc acatttacca tgaggctgct atcaccagtt 5340
agagtgccaa actacaacct gattatcatg gacgaagccc atttcacaga cccagcaagt 5400
atagcagcta gaggatacat ctcaactcga gtggagatgg gtgaggcagc tgggattttt 5460
atgacagcca ctcccccggg aagcagagac ccatttcctc agagcaatgc accaatcata 5520
gatgaagaaa gagaaatccc tgaacgctcg tggaattccg gacatgaatg ggtcacggat 5580
tttaaaggga agactgtttg gttcgttcca agtataaaag caggaaatga tatagcagct 5640
tgcctgagga aaaatggaaa gaaagtgata caactcagta ggaagacctt tgattctgag 5700
tatgtcaaga ctagaaccaa tgattgggac ttcgtggtta caactgacat ttcagaaatg 5760
ggtgccaatt tcaaggctga gagggttata gaccccagac gctgcatgaa accagtcata 5820
ctaacagatg gtgaagagcg ggtgattctg gcaggaccta tgccagtgac ccactctagt 5880
gcagcacaaa gaagagggag aataggaaga aatccaaaaa atgagaatga ccagtacata 5940
tacatggggg aacctctgga aaatgatgaa gactgtgcac actggaaaga agctaaaatg 6000
ctcctagata acatcaacac gccagaagga atcattccta gcatgttcga accagagcgt 6060
gaaaaggtgg atgccattga tggcgaatac cgcttgagag gagaagcaag gaaaaccttt 6120
gtagacttaa tgagaagagg agacctacca gtctggttgg cctacagagt ggcagctgaa 6180
ggcatcaact acgcagacag aaggtggtgt tttgatggag tcaagaacaa ccaaatccta 6240
gaagaaaacg tggaagttga aatctggaca aaagaagggg aaaggaagaa attgaaaccc 6300
agatggttgg atgctaggat ctattctgac ccactggcgc taaaagaatt taaggaattt 6360
gcagccggaa gaaagtctct gaccctgaac ctaatcacag aaatgggtag gctcccaacc 6420
ttcatgactc agaaggcaag agacgcactg gacaacttag cagtgctgca cacggctgag 6480
gcaggtggaa gggcgtacaa ccatgctctc agtgaactgc cggagaccct ggagacattg 6540
cttttactga cacttctggc tacagtcacg ggagggatct tttattcttt gatgagcgca 6600
aggggcatag ggaagatgac cctgggaatg tgctgcataa tcacggctag catcctccta 6660
tggtacgcac aaatacagcc acactggata gcagcttcaa taatactgga gtttttctc 6720

```
atagttttgc ttattccaga acctgaaaaa cagagaacac cccaagacaa ccaactgacc   6780
tacgttgtca tagccatcct cacagtggtg gccgcaacca tggcaaacga gatgggtttc   6840
ctagaaaaaa cgaagaaaga tctcggattg ggaagcattg caacccagca acccgagagc   6900
aacatcctgg acatagatct acgtcctgca tcagcatgga cgctgtatgc cgtggccaca   6960
acatttgtta caccaatgtt gagacatagc attgaaaatt cctcagtgaa tgtgtcccta   7020
acagctatag ccaaccaagc cacagtgtta atgggtctcg ggaaaggatg gccattgtca   7080
aagatggaca tcggagttcc ccttctcgcc attggatgct actcacaagt caaccccata   7140
actctcacag cagctctttt cttattggta gcacattatg ccatcatagg gccaggactc   7200
caagcaaaag caaccagaga agctcagaaa agagcagcgg cgggcatcat gaaaaaccca   7260
actgtcgatg gaataacagt gattgaccta gatccaatac cttatgatcc aaagtttgaa   7320
aagcagttgg gacaagtaat gctcctagtc ctctgcgtga ctcaagtatt gatgatgagg   7380
actacatggg ctctgtgtga ggctttaacc ttagctaccg ggcccatctc cacattgtgg   7440
gaaggaaatc cagggaggtt ttggaacact accattgcgg tgtcaatggc taacattttt   7500
agagggagtt acttggccgg agctggactt ctcttttcta ttatgaagaa cacaaccaac   7560
acaagaaggg gaactggcaa cataggagag acgcttggag agaaatggaa aagccgattg   7620
aacgcattgg gaaaaagtga attccagatc tacaagaaaa gtggaatcca ggaagtggat   7680
agaaccttag caaaagaagg cattaaaaga ggagaaacgg accatcacgc tgtgtcgcga   7740
ggctcagcaa aactgagatg gttcgttgag agaaacatgg tcacaccaga agggaaagta   7800
gtggacctcg gttgtggcag aggaggctgg tcatactatt gtggaggact aaagaatgta   7860
agagaagtca aaggcctaac aaaaggagga ccaggacacg aagaacccat ccccatgtca   7920
acatatgggt ggaatctagt gcgtcttcaa agtggagttg acgttttctt catcccgcca   7980
gaaaagtgtg acacattatt gtgtgacata ggggagtcat caccaaatcc cacagtggaa   8040
gcaggacgaa cactcagagt ccttaactta gtagaaaatt ggttgaacaa caacactcaa   8100
ttttgcataa aggttctcaa cccatatatg ccctcagtca tagaaaaaat ggaagcacta   8160
caaaggaaat atggaggagc cttagtgagg aatccactct cacgaaactc cacacatgag   8220
atgtactggg tatccaatgc ttccgggaac atagtgtcat cagtgaacat gatttcaagg   8280
atgttgatca acagatttac aatgagatac aagaaagcca cttacgagcc ggatgttgac   8340
ctcggaagcg gaacccgtaa catcgggatt gaaagtgaga taccaaacct agatataatt   8400
gggaaaagaa tagaaaaaat aaagcaagag catgaaacat catggcacta tgaccaagac   8460
cacccataca aaacgtgggc ataccatggt agctatgaaa caaaacagac tggatcagca   8520
tcatccatgg tcaacggagt ggtcaggctg ctgacaaaac cttgggacgt cgtccccatg   8580
gtgacacaga tggcaatgac agacacgact ccatttggac aacagcgcgt tttaaagag    8640
aaagtggaca cgagaaccca agaaccgaaa gaaggcacga agaaactaat gaaaataaca   8700
gcagagtggc tttggaaaga attagggaag aaaaagacac ccaggatgtg caccagagaa   8760
gaattcacaa gaaaggtgag aagcaatgca gccttggggg ccatattcac tgatgagaac   8820
aagtggaagt cggcacgtga ggctgttgaa gatagtaggt tttgggagct ggttgacaag   8880
gaaaggaatc tccatcttga aggaaagtgt gaaacatgtg tgtacaacat gatgggaaaa   8940
agagagaaga agctagggga attcggcaag gcaaaaggca gcagagccat atggtacatg   9000
tggcttggag cacgcttctt agagtttgaa gccctaggat tcttaaatga agatcactgg   9060
```

```
ttctccagag agaactccct gagtggagtg gaaggagaag ggctgcacaa gctaggttac   9120

attctaagag acgtgagcaa gaaagaggga ggagcaatgt atgccgatga caccgcagga   9180

tgggatacaa gaatcacact agaagaccta aaaaatgaag aaatggtaac aaaccacatg   9240

gaaggagaac acaagaaact agccgaggcc attttcaaac taacgtacca aaacaaggtg   9300

gtgcgtgtgc aaagaccaac accaagaggc acagtaatgg acatcatatc gagaagagac   9360

caaagaggta gtggacaagt tggcacctat ggactcaata ctttcaccaa tatggaagcc   9420

caactaatca gacagatgga gggagaagga gtctttaaaa gcattcagca cctaacaatc   9480

acagaagaaa tcgctgtgca aaactggtta gcaagagtgg ggcgcgaaag gttatcaaga   9540

atggccatca gtggagatga ttgtgttgtg aaacctttag atgacaggtt cgcaagcgct   9600

ttaacagctc taaatgacat gggaaagatt aggaaagaca tacaacaatg ggaaccttca   9660

agaggatgga atgattggac acaagtgccc ttctgttcac accatttcca tgagttaatc   9720

atgaaagacg gtcgcgtact cgttgttcca tgtagaaacc aagatgaact gattggcaga   9780

gcccgaatct cccaaggagc agggtggtct ttgcgggaga cggcctgttt ggggaagtct   9840

tacgcccaaa tgtggagctt gatgtacttc cacagacgcg acctcaggct ggcggcaaat   9900

gctatttgct cggcagtacc atcacattgg gttccaacaa gtcgaacaac ctggtccata   9960

catgctaaac atgaatggat gacaacggaa gacatgctga cagtctggaa cagggtgtgg  10020

attcaagaaa acccatggat ggaagacaaa actccagtgg aatcatggga ggaaatccca  10080

tacttgggga aaagagaaga ccaatggtgc ggctcattga ttgggttaac aagcagggcc  10140

acctgggcaa agaacatcca agcagcaata aatcaagtta gatcccttat aggcaatgaa  10200

gaatacacag attacatgcc atccatgaaa agattcagaa gagaagagga agaagcagga  10260

gttctgtggt agaaagcaaa actaacatga aacaaggcta gaagtcaggt cggattaagc  10320

catagtacgg aaaaaactat gctacctgtg agccccgtcc aaggacgtta aaagaagtca  10380

ggccatcata aatgccatag cttgagtaaa ctatgcagcc tgtagctcca cctgagaagg  10440

tgtaaaaaat ccgggaggcc acaaaccatg gaagctgtac gcatggcgta gtggactagc  10500

ggttagagga gacccctccc ttacaaatcg cagcaacaat gggggcccaa ggcgagatga  10560

agctgtagtc tcgctggaag gactagaggt tagaggagac ccccccgaaa caaaaaacag  10620

catattgacg ctgggaaaga ccagagatcc tgctgtctcc tcagcatcat tccaggcaca  10680

gaacgccaga aaatggaatg gtgctgttga atcaacaggt tct                    10723
```

<210> SEQ ID NO 25
<211> LENGTH: 3391
<212> TYPE: PRT
<213> ORGANISM: Artificial Sequence
<220> FEATURE:
<223> OTHER INFORMATION: Derived from Dengue virus serotype 2/Dengue virus serotype 4, DEN4h

<400> SEQUENCE: 25

```
Met Asn Asn Gln Arg Lys Lys Ala Lys Asn Thr Pro Phe Asn Met Leu
1               5                   10                  15

Lys Arg Glu Arg Asn Arg Val Ser Thr Val Gln Gln Leu Thr Lys Arg
            20                  25                  30

Phe Ser Leu Gly Met Leu Gln Gly Arg Gly Pro Leu Lys Leu Phe Met
        35                  40                  45

Ala Leu Val Ala Phe Leu Arg Phe Leu Thr Ile Pro Pro Thr Ala Gly
    50                  55                  60
```

-continued

```
Ile Leu Lys Arg Trp Gly Thr Ile Lys Lys Ser Lys Ala Ile Asn Val
65                  70                  75                  80

Leu Arg Gly Phe Arg Lys Glu Ile Gly Arg Met Leu Asn Ile Leu Asn
                85                  90                  95

Arg Arg Arg Ser Ser Ala Gly Met Ile Ile Met Leu Ile Pro Thr Val
            100                 105                 110

Met Ala Phe His Leu Thr Thr Arg Asp Gly Glu Pro Leu Met Ile Val
        115                 120                 125

Ala Lys His Glu Arg Gly Arg Pro Leu Leu Phe Lys Thr Thr Glu Gly
    130                 135                 140

Ile Asn Lys Cys Thr Leu Ile Ala Met Asp Leu Gly Glu Met Cys Glu
145                 150                 155                 160

Asp Thr Val Thr Tyr Lys Cys Pro Leu Leu Val Asn Thr Glu Pro Glu
                165                 170                 175

Asp Ile Asp Cys Trp Cys Asn Leu Thr Ser Thr Trp Val Met Tyr Gly
            180                 185                 190

Thr Cys Thr Gln Ser Gly Glu Arg Arg Arg Glu Lys Arg Ser Val Ala
        195                 200                 205

Leu Thr Pro His Ser Gly Met Gly Leu Glu Thr Arg Ala Glu Thr Trp
    210                 215                 220

Met Ser Ser Glu Gly Ala Trp Lys His Ala Gln Arg Val Glu Ser Trp
225                 230                 235                 240

Ile Leu Arg Asn Pro Gly Phe Ala Leu Leu Ala Gly Phe Met Ala Tyr
                245                 250                 255

Met Ile Gly Gln Thr Gly Ile Gln Arg Thr Val Phe Phe Val Leu Met
            260                 265                 270

Met Leu Val Ala Pro Ser Tyr Gly Met Arg Cys Val Gly Val Gly Asn
        275                 280                 285

Arg Asp Phe Val Glu Gly Val Ser Gly Gly Ala Trp Val Asp Leu Val
    290                 295                 300

Leu Glu His Gly Gly Cys Val Thr Thr Met Ala Gln Gly Lys Pro Thr
305                 310                 315                 320

Leu Asp Phe Glu Leu Thr Lys Thr Thr Ala Lys Glu Val Ala Leu Leu
                325                 330                 335

Arg Thr Tyr Cys Ile Glu Ala Ser Ile Ser Asn Ile Thr Thr Ala Thr
            340                 345                 350

Arg Cys Pro Thr Gln Gly Glu Pro Tyr Leu Lys Glu Glu Gln Asp Gln
        355                 360                 365

Gln Tyr Ile Cys Arg Arg Asp Val Val Asp Arg Gly Trp Gly Asn Gly
    370                 375                 380

Cys Gly Leu Phe Gly Lys Gly Gly Val Val Thr Cys Ala Lys Phe Ser
385                 390                 395                 400

Cys Ser Gly Lys Ile Thr Gly Asn Leu Val Gln Ile Glu Asn Leu Glu
                405                 410                 415

Tyr Thr Val Val Val Thr Val His Asn Gly Asp Thr His Ala Val Gly
            420                 425                 430

Asn Asp Thr Ser Asn His Gly Val Thr Ala Thr Ile Thr Pro Arg Ser
        435                 440                 445

Pro Ser Val Glu Val Lys Leu Pro Asp Tyr Gly Glu Leu Thr Leu Asp
    450                 455                 460

Cys Glu Pro Arg Ser Gly Ile Asp Phe Asn Glu Met Ile Leu Met Lys
465                 470                 475                 480

Met Lys Lys Lys Thr Trp Leu Val His Lys Gln Trp Phe Leu Asp Leu
```

-continued

```
                485                 490                 495

Pro Leu Pro Trp Thr Ala Gly Ala Asp Thr Ser Glu Val His Trp Asn
            500                 505                 510

Tyr Lys Glu Arg Met Val Thr Phe Lys Val Pro His Ala Lys Arg Gln
        515                 520                 525

Asp Val Thr Val Leu Gly Ser Gln Glu Gly Ala Met His Ser Ala Leu
    530                 535                 540

Ala Gly Ala Thr Glu Val Asp Ser Gly Asp Gly Asn His Met Phe Ala
545                 550                 555                 560

Gly His Leu Lys Cys Lys Val Arg Met Glu Lys Leu Arg Ile Lys Gly
                565                 570                 575

Met Ser Tyr Thr Met Cys Ser Gly Lys Phe Ser Ile Asp Lys Glu Met
            580                 585                 590

Ala Glu Thr Gln His Gly Thr Thr Val Val Lys Val Lys Tyr Glu Gly
        595                 600                 605

Ala Gly Ala Pro Cys Lys Val Pro Ile Glu Ile Arg Asp Val Asn Lys
    610                 615                 620

Glu Lys Val Val Gly Arg Ile Ile Ser Ser Thr Pro Leu Ala Glu Asn
625                 630                 635                 640

Thr Asn Ser Val Thr Asn Ile Glu Leu Glu Pro Pro Phe Gly Asp Ser
                645                 650                 655

Tyr Ile Val Ile Gly Val Gly Asn Ser Ala Leu Thr Leu His Trp Phe
            660                 665                 670

Arg Lys Gly Ser Ser Ile Gly Lys Met Phe Glu Ser Thr Tyr Arg Gly
        675                 680                 685

Ala Lys Arg Met Ala Ile Leu Gly Lys Thr Ala Trp Asp Phe Gly Ser
    690                 695                 700

Val Gly Gly Leu Phe Thr Ser Leu Gly Lys Ala Val His Gln Val Phe
705                 710                 715                 720

Gly Ser Val Tyr Thr Thr Leu Phe Gly Gly Val Ser Trp Met Ile Arg
                725                 730                 735

Ile Leu Ile Gly Phe Leu Val Leu Trp Ile Gly Thr Asn Ser Arg Asn
            740                 745                 750

Thr Ser Met Ala Met Thr Cys Ile Ala Ala Gly Ile Val Thr Leu Tyr
        755                 760                 765

Leu Gly Val Met Val Gln Ala Asp Ser Gly Cys Val Val Ser Trp Lys
    770                 775                 780

Asn Lys Glu Leu Lys Cys Gly Ser Gly Ile Phe Ile Thr Asp Asn Val
785                 790                 795                 800

His Thr Trp Thr Glu Gln Tyr Lys Phe Gln Pro Glu Ser Pro Ser Lys
                805                 810                 815

Leu Ala Ser Ala Ile Gln Lys Ala His Glu Glu Asp Ile Cys Gly Ile
            820                 825                 830

Arg Ser Val Thr Arg Leu Glu Asn Leu Met Trp Lys Gln Ile Thr Pro
        835                 840                 845

Glu Leu Asn His Ile Leu Ser Glu Asn Glu Val Lys Leu Thr Ile Met
    850                 855                 860

Thr Gly Asp Ile Lys Gly Ile Met Gln Ala Gly Lys Arg Ser Leu Arg
865                 870                 875                 880

Pro Gln Pro Thr Glu Leu Lys Tyr Ser Trp Lys Thr Trp Gly Lys Ala
                885                 890                 895

Lys Met Leu Ser Thr Glu Ser His Asn Gln Thr Phe Leu Ile Asp Gly
            900                 905                 910
```

```
Pro Glu Thr Ala Glu Cys Pro Asn Thr Asn Arg Ala Trp Asn Ser Leu
        915                 920                 925

Glu Val Glu Asp Tyr Gly Phe Gly Val Phe Thr Thr Asn Ile Trp Leu
    930                 935                 940

Lys Leu Lys Glu Lys Gln Asp Val Phe Cys Asp Ser Lys Leu Met Ser
945                 950                 955                 960

Ala Ala Ile Lys Asp Asn Arg Ala Val His Ala Asp Met Gly Tyr Trp
                965                 970                 975

Ile Glu Ser Ala Leu Asn Asp Thr Trp Lys Ile Glu Lys Ala Ser Phe
            980                 985                 990

Ile Glu Val Lys Asn Cys His Trp  Pro Lys Ser His Thr  Leu Trp Ser
        995                 1000                1005

Asn Gly  Val Leu Glu Ser Glu  Met Ile Ile Pro Lys  Asn Leu Ala
    1010                 1015                 1020

Gly Pro  Val Ser Gln His Asn  Tyr Arg Pro Gly Tyr  His Thr Gln
    1025                 1030                 1035

Ile Thr  Gly Pro Trp His Leu  Gly Lys Leu Glu Met  Asp Phe Asp
    1040                 1045                 1050

Phe Cys  Asp Gly Thr Thr Val  Val Val Thr Glu Asp  Cys Gly Asn
    1055                 1060                 1065

Arg Gly  Pro Ser Leu Arg Thr  Thr Thr Ala Ser Gly  Lys Leu Ile
    1070                 1075                 1080

Thr Glu  Trp Cys Cys Arg Ser  Cys Thr Leu Pro Pro  Leu Arg Tyr
    1085                 1090                 1095

Arg Gly  Glu Asp Gly Cys Trp  Tyr Gly Met Glu Ile  Arg Pro Leu
    1100                 1105                 1110

Lys Glu  Lys Glu Glu Asn Leu  Val Asn Ser Leu Val  Thr Ala Gly
    1115                 1120                 1125

His Gly  Gln Val Asp Asn Phe  Ser Leu Gly Val Leu  Gly Met Ala
    1130                 1135                 1140

Leu Phe  Leu Glu Glu Met Leu  Arg Thr Arg Val Gly  Thr Lys His
    1145                 1150                 1155

Ala Ile  Leu Leu Val Ala Val  Ser Phe Val Thr Leu  Ile Thr Gly
    1160                 1165                 1170

Asn Met  Ser Phe Arg Asp Leu  Gly Arg Val Met Val  Met Val Gly
    1175                 1180                 1185

Ala Thr  Met Thr Asp Asp Ile  Gly Met Gly Val Thr  Tyr Leu Ala
    1190                 1195                 1200

Leu Leu  Ala Ala Phe Lys Val  Arg Pro Thr Phe Ala  Ala Gly Leu
    1205                 1210                 1215

Leu Leu  Arg Lys Leu Thr Ser  Lys Glu Leu Met Met  Thr Thr Ile
    1220                 1225                 1230

Gly Ile  Val Leu Leu Ser Gln  Ser Thr Ile Pro Glu  Thr Ile Leu
    1235                 1240                 1245

Glu Leu  Thr Asp Ala Leu Ala  Leu Gly Met Met Val  Leu Lys Met
    1250                 1255                 1260

Val Arg  Asn Met Glu Lys Tyr  Gln Leu Ala Val Thr  Ile Met Ala
    1265                 1270                 1275

Ile Leu  Cys Val Pro Asn Ala  Val Ile Leu Gln Asn  Ala Trp Lys
    1280                 1285                 1290

Val Ser  Cys Thr Ile Leu Ala  Val Val Ser Val Ser  Pro Leu Phe
    1295                 1300                 1305
```

```
Leu Thr  Ser Ser Gln Gln Lys  Thr Asp Trp Ile Pro  Leu Ala Leu
    1310                 1315                 1320

Thr Ile  Lys Gly Leu Asn Pro  Thr Ala Ile Phe Leu  Thr Thr Leu
    1325                 1330                 1335

Ser Arg  Thr Ser Lys Lys Arg  Ser Trp Pro Leu Asn  Glu Ala Ile
    1340                 1345                 1350

Met Ala  Val Gly Met Val Ser  Ile Leu Ala Ser Ser  Leu Leu Lys
    1355                 1360                 1365

Asn Asp  Ile Pro Met Thr Gly  Pro Leu Val Ala Gly  Gly Leu Leu
    1370                 1375                 1380

Thr Val  Cys Tyr Val Leu Thr  Gly Arg Ser Ala Asp  Leu Glu Leu
    1385                 1390                 1395

Glu Arg  Ala Ala Asp Val Lys  Trp Glu Asp Gln Ala  Glu Ile Ser
    1400                 1405                 1410

Gly Ser  Ser Pro Ile Leu Ser  Ile Thr Ile Ser Glu  Asp Gly Ser
    1415                 1420                 1425

Met Ser  Ile Lys Asn Glu Glu  Glu Glu Gln Thr Leu  Thr Ile Leu
    1430                 1435                 1440

Ile Arg  Thr Gly Leu Leu Val  Ile Ser Gly Leu Phe  Pro Val Ser
    1445                 1450                 1455

Ile Pro  Ile Thr Ala Ala Ala  Trp Tyr Leu Trp Glu  Val Lys Lys
    1460                 1465                 1470

Gln Arg  Ala Gly Val Leu Trp  Asp Val Pro Ser Pro  Pro Pro Met
    1475                 1480                 1485

Gly Lys  Ala Glu Leu Glu Asp  Gly Ala Tyr Arg Ile  Lys Gln Lys
    1490                 1495                 1500

Gly Ile  Leu Gly Tyr Ser Gln  Ile Gly Ala Gly Val  Tyr Lys Glu
    1505                 1510                 1515

Gly Thr  Phe His Thr Met Trp  His Val Thr Arg Gly  Ala Val Leu
    1520                 1525                 1530

Met His  Lys Gly Lys Arg Ile  Glu Pro Ser Trp Ala  Asp Val Lys
    1535                 1540                 1545

Lys Asp  Leu Ile Ser Tyr Gly  Gly Gly Trp Lys Leu  Glu Gly Glu
    1550                 1555                 1560

Trp Lys  Glu Gly Glu Glu Val  Gln Val Leu Ala Leu  Glu Pro Gly
    1565                 1570                 1575

Lys Asn  Pro Arg Ala Val Gln  Thr Lys Pro Gly Leu  Phe Lys Thr
    1580                 1585                 1590

Asn Ala  Gly Thr Ile Gly Ala  Val Ser Leu Asp Phe  Ser Pro Gly
    1595                 1600                 1605

Thr Ser  Gly Ser Pro Ile Ile  Asp Lys Lys Gly Lys  Val Val Gly
    1610                 1615                 1620

Leu Tyr  Gly Asn Gly Val Val  Thr Arg Ser Gly Ala  Tyr Val Ser
    1625                 1630                 1635

Ala Ile  Ala Gln Thr Glu Lys  Ser Ile Glu Asp Asn  Pro Glu Ile
    1640                 1645                 1650

Glu Asp  Asp Ile Phe Arg Lys  Arg Arg Leu Thr Ile  Met Asp Leu
    1655                 1660                 1665

His Pro  Gly Ala Gly Lys Thr  Lys Arg Tyr Leu Pro  Ala Ile Val
    1670                 1675                 1680

Arg Glu  Ala Ile Lys Arg Gly  Leu Arg Thr Leu Ile  Leu Ala Pro
    1685                 1690                 1695

Thr Arg  Val Val Ala Ala Glu  Met Glu Glu Ala Leu  Arg Gly Leu
```

```
    1700                1705                1710

Pro Ile  Arg Tyr Gln Thr Pro  Ala Ile Arg Ala Val  His Thr Gly
    1715                1720                1725

Arg Glu  Ile Val Asp Leu Met  Cys His Ala Thr Phe  Thr Met Arg
    1730                1735                1740

Leu Leu  Ser Pro Val Arg Val  Pro Asn Tyr Asn Leu  Ile Ile Met
    1745                1750                1755

Asp Glu  Ala His Phe Thr Asp  Pro Ala Ser Ile Ala  Ala Arg Gly
    1760                1765                1770

Tyr Ile  Ser Thr Arg Val Glu  Met Gly Glu Ala Ala  Gly Ile Phe
    1775                1780                1785

Met Thr  Ala Thr Pro Pro Gly  Ser Arg Asp Pro Phe  Pro Gln Ser
    1790                1795                1800

Asn Ala  Pro Ile Ile Asp Glu  Glu Arg Glu Ile Pro  Glu Arg Ser
    1805                1810                1815

Trp Asn  Ser Gly His Glu Trp  Val Thr Asp Phe Lys  Gly Lys Thr
    1820                1825                1830

Val Trp  Phe Val Pro Ser Ile  Lys Ala Gly Asn Asp  Ile Ala Ala
    1835                1840                1845

Cys Leu  Arg Lys Asn Gly Lys  Lys Val Ile Gln Leu  Ser Arg Lys
    1850                1855                1860

Thr Phe  Asp Ser Glu Tyr Val  Lys Thr Arg Thr Asn  Asp Trp Asp
    1865                1870                1875

Phe Val  Val Thr Thr Asp Ile  Ser Glu Met Gly Ala  Asn Phe Lys
    1880                1885                1890

Ala Glu  Arg Val Ile Asp Pro  Arg Arg Cys Met Lys  Pro Val Ile
    1895                1900                1905

Leu Thr  Asp Gly Glu Glu Arg  Val Ile Leu Ala Gly  Pro Met Pro
    1910                1915                1920

Val Thr  His Ser Ser Ala Ala  Gln Arg Arg Gly Arg  Ile Gly Arg
    1925                1930                1935

Asn Pro  Lys Asn Glu Asn Asp  Gln Tyr Ile Tyr Met  Gly Glu Pro
    1940                1945                1950

Leu Glu  Asn Asp Glu Asp Cys  Ala His Trp Lys Glu  Ala Lys Met
    1955                1960                1965

Leu Leu  Asp Asn Ile Asn Thr  Pro Glu Gly Ile Ile  Pro Ser Met
    1970                1975                1980

Phe Glu  Pro Glu Arg Glu Lys  Val Asp Ala Ile Asp  Gly Glu Tyr
    1985                1990                1995

Arg Leu  Arg Gly Glu Ala Arg  Lys Thr Phe Val Asp  Leu Met Arg
    2000                2005                2010

Arg Gly  Asp Leu Pro Val Trp  Leu Ala Tyr Arg Val  Ala Ala Glu
    2015                2020                2025

Gly Ile  Asn Tyr Ala Asp Arg  Arg Trp Cys Phe Asp  Gly Val Lys
    2030                2035                2040

Asn Asn  Gln Ile Leu Glu Glu  Asn Val Glu Val Glu  Ile Trp Thr
    2045                2050                2055

Lys Glu  Gly Glu Arg Lys Lys  Leu Lys Pro Arg Trp  Leu Asp Ala
    2060                2065                2070

Arg Ile  Tyr Ser Asp Pro Leu  Ala Leu Lys Glu Phe  Lys Glu Phe
    2075                2080                2085

Ala Ala  Gly Arg Lys Ser Leu  Thr Leu Asn Leu Ile  Thr Glu Met
    2090                2095                2100
```

```
Gly Arg  Leu Pro Thr Phe Met  Thr Gln Lys Ala Arg  Asp Ala Leu
    2105                 2110                 2115

Asp Asn  Leu Ala Val Leu His  Thr Ala Glu Ala Gly  Gly Arg Ala
    2120                 2125                 2130

Tyr Asn  His Ala Leu Ser Glu  Leu Pro Glu Thr Leu  Glu Thr Leu
    2135                 2140                 2145

Leu Leu  Leu Thr Leu Leu Ala  Thr Val Thr Gly Gly  Ile Phe Leu
    2150                 2155                 2160

Phe Leu  Met Ser Ala Arg Gly  Ile Gly Lys Met Thr  Leu Gly Met
    2165                 2170                 2175

Cys Cys  Ile Ile Thr Ala Ser  Ile Leu Leu Trp Tyr  Ala Gln Ile
    2180                 2185                 2190

Gln Pro  His Trp Ile Ala Ala  Ser Ile Ile Leu Glu  Phe Phe Leu
    2195                 2200                 2205

Ile Val  Leu Leu Ile Pro Glu  Pro Glu Lys Gln Arg  Thr Pro Gln
    2210                 2215                 2220

Asp Asn  Gln Leu Thr Tyr Val  Val Ile Ala Ile Leu  Thr Val Val
    2225                 2230                 2235

Ala Ala  Thr Met Ala Asn Glu  Met Gly Phe Leu Glu  Lys Thr Lys
    2240                 2245                 2250

Lys Asp  Leu Gly Leu Gly Ser  Ile Ala Thr Gln Gln  Pro Glu Ser
    2255                 2260                 2265

Asn Ile  Leu Asp Ile Asp Leu  Arg Pro Ala Ser Ala  Trp Thr Leu
    2270                 2275                 2280

Tyr Ala  Val Ala Thr Thr Phe  Val Thr Pro Met Leu  Arg His Ser
    2285                 2290                 2295

Ile Glu  Asn Ser Ser Val Asn  Val Ser Leu Thr Ala  Ile Ala Asn
    2300                 2305                 2310

Gln Ala  Thr Val Leu Met Gly  Leu Gly Lys Gly Trp  Pro Leu Ser
    2315                 2320                 2325

Lys Met  Asp Ile Gly Val Pro  Leu Leu Ala Ile Gly  Cys Tyr Ser
    2330                 2335                 2340

Gln Val  Asn Pro Ile Thr Leu  Thr Ala Ala Leu Phe  Leu Leu Val
    2345                 2350                 2355

Ala His  Tyr Ala Ile Ile Gly  Pro Gly Leu Gln Ala  Lys Ala Thr
    2360                 2365                 2370

Arg Glu  Ala Gln Lys Arg Ala  Ala Ala Gly Ile Met  Lys Asn Pro
    2375                 2380                 2385

Thr Val  Asp Gly Ile Thr Val  Ile Asp Leu Asp Pro  Ile Pro Tyr
    2390                 2395                 2400

Asp Pro  Lys Phe Glu Lys Gln  Leu Gly Gln Val Met  Leu Leu Val
    2405                 2410                 2415

Leu Cys  Val Thr Gln Val Leu  Met Met Arg Thr Thr  Trp Ala Leu
    2420                 2425                 2430

Cys Glu  Ala Leu Thr Leu Ala  Thr Gly Pro Ile Ser  Thr Leu Trp
    2435                 2440                 2445

Glu Gly  Asn Pro Gly Arg Phe  Trp Asn Thr Thr Ile  Ala Val Ser
    2450                 2455                 2460

Met Ala  Asn Ile Phe Arg Gly  Ser Tyr Leu Ala Gly  Ala Gly Leu
    2465                 2470                 2475

Leu Phe  Ser Ile Met Lys Asn  Thr Thr Asn Thr Arg  Arg Gly Thr
    2480                 2485                 2490
```

```
Gly Asn  Ile Gly Glu Thr Leu  Gly Glu Lys Trp Lys  Ser Arg Leu
    2495                 2500                 2505

Asn Ala  Leu Gly Lys Ser Glu  Phe Gln Ile Tyr Lys  Lys Ser Gly
    2510                 2515                 2520

Ile Gln  Glu Val Asp Arg Thr  Leu Ala Lys Glu Gly  Ile Lys Arg
    2525                 2530                 2535

Gly Glu  Thr Asp His His Ala  Val Ser Arg Gly Ser  Ala Lys Leu
    2540                 2545                 2550

Arg Trp  Phe Val Glu Arg Asn  Met Val Thr Pro Glu  Gly Lys Val
    2555                 2560                 2565

Val Asp  Leu Gly Cys Gly Arg  Gly Gly Trp Ser Tyr  Tyr Cys Gly
    2570                 2575                 2580

Gly Leu  Lys Asn Val Arg Glu  Val Lys Gly Leu Thr  Lys Gly Gly
    2585                 2590                 2595

Pro Gly  His Glu Glu Pro Ile  Pro Met Ser Thr Tyr  Gly Trp Asn
    2600                 2605                 2610

Leu Val  Arg Leu Gln Ser Gly  Val Asp Val Phe Phe  Ile Pro Pro
    2615                 2620                 2625

Glu Lys  Cys Asp Thr Leu Leu  Cys Asp Ile Gly Glu  Ser Ser Pro
    2630                 2635                 2640

Asn Pro  Thr Val Glu Ala Gly  Arg Thr Leu Arg Val  Leu Asn Leu
    2645                 2650                 2655

Val Glu  Asn Trp Leu Asn Asn  Asn Thr Gln Phe Cys  Ile Lys Val
    2660                 2665                 2670

Leu Asn  Pro Tyr Met Pro Ser  Val Ile Glu Lys Met  Glu Ala Leu
    2675                 2680                 2685

Gln Arg  Lys Tyr Gly Gly Ala  Leu Val Arg Asn Pro  Leu Ser Arg
    2690                 2695                 2700

Asn Ser  Thr His Glu Met Tyr  Trp Val Ser Asn Ala  Ser Gly Asn
    2705                 2710                 2715

Ile Val  Ser Ser Val Asn Met  Ile Ser Arg Met Leu  Ile Asn Arg
    2720                 2725                 2730

Phe Thr  Met Arg Tyr Lys Lys  Ala Thr Tyr Glu Pro  Asp Val Asp
    2735                 2740                 2745

Leu Gly  Ser Gly Thr Arg Asn  Ile Gly Ile Glu Ser  Glu Ile Pro
    2750                 2755                 2760

Asn Leu  Asp Ile Ile Gly Lys  Arg Ile Glu Lys Ile  Lys Gln Glu
    2765                 2770                 2775

His Glu  Thr Ser Trp His Tyr  Asp Gln Asp His Pro  Tyr Lys Thr
    2780                 2785                 2790

Trp Ala  Tyr His Gly Ser Tyr  Glu Thr Lys Gln Thr  Gly Ser Ala
    2795                 2800                 2805

Ser Ser  Met Val Asn Gly Val  Val Arg Leu Leu Thr  Lys Pro Trp
    2810                 2815                 2820

Asp Val  Val Pro Met Val Thr  Gln Met Ala Met Thr  Asp Thr Thr
    2825                 2830                 2835

Pro Phe  Gly Gln Gln Arg Val  Phe Lys Glu Lys Val  Asp Thr Arg
    2840                 2845                 2850

Thr Gln  Glu Pro Lys Glu Gly  Thr Lys Lys Leu Met  Lys Ile Thr
    2855                 2860                 2865

Ala Glu  Trp Leu Trp Lys Glu  Leu Gly Lys Lys Lys  Thr Pro Arg
    2870                 2875                 2880

Met Cys  Thr Arg Glu Glu Phe  Thr Arg Lys Val Arg  Ser Asn Ala
```

```
    2885                2890                2895

Ala Leu Gly Ala Ile Phe Thr Asp Glu Asn Lys Trp Lys Ser Ala
    2900                2905                2910

Arg Glu Ala Val Glu Asp Ser Arg Phe Trp Glu Leu Val Asp Lys
    2915                2920                2925

Glu Arg Asn Leu His Leu Glu Gly Lys Cys Glu Thr Cys Val Tyr
    2930                2935                2940

Asn Met Met Gly Lys Arg Glu Lys Lys Leu Gly Glu Phe Gly Lys
    2945                2950                2955

Ala Lys Gly Ser Arg Ala Ile Trp Tyr Met Trp Leu Gly Ala Arg
    2960                2965                2970

Phe Leu Glu Phe Glu Ala Leu Gly Phe Leu Asn Glu Asp His Trp
    2975                2980                2985

Phe Ser Arg Glu Asn Ser Leu Ser Gly Val Glu Gly Glu Gly Leu
    2990                2995                3000

His Lys Leu Gly Tyr Ile Leu Arg Asp Val Ser Lys Lys Glu Gly
    3005                3010                3015

Gly Ala Met Tyr Ala Asp Asp Thr Ala Gly Trp Asp Thr Arg Ile
    3020                3025                3030

Thr Leu Glu Asp Leu Lys Asn Glu Glu Met Val Thr Asn His Met
    3035                3040                3045

Glu Gly Glu His Lys Lys Leu Ala Glu Ala Ile Phe Lys Leu Thr
    3050                3055                3060

Tyr Gln Asn Lys Val Val Arg Val Gln Arg Pro Thr Pro Arg Gly
    3065                3070                3075

Thr Val Met Asp Ile Ile Ser Arg Arg Asp Gln Arg Gly Ser Gly
    3080                3085                3090

Gln Val Gly Thr Tyr Gly Leu Asn Thr Phe Thr Asn Met Glu Ala
    3095                3100                3105

Gln Leu Ile Arg Gln Met Glu Gly Glu Gly Val Phe Lys Ser Ile
    3110                3115                3120

Gln His Leu Thr Ile Thr Glu Glu Ile Ala Val Gln Asn Trp Leu
    3125                3130                3135

Ala Arg Val Gly Arg Glu Arg Leu Ser Arg Met Ala Ile Ser Gly
    3140                3145                3150

Asp Asp Cys Val Val Lys Pro Leu Asp Asp Arg Phe Ala Ser Ala
    3155                3160                3165

Leu Thr Ala Leu Asn Asp Met Gly Lys Ile Arg Lys Asp Ile Gln
    3170                3175                3180

Gln Trp Glu Pro Ser Arg Gly Trp Asn Asp Trp Thr Gln Val Pro
    3185                3190                3195

Phe Cys Ser His His Phe His Glu Leu Ile Met Lys Asp Gly Arg
    3200                3205                3210

Val Leu Val Val Pro Cys Arg Asn Gln Asp Glu Leu Ile Gly Arg
    3215                3220                3225

Ala Arg Ile Ser Gln Gly Ala Gly Trp Ser Leu Arg Glu Thr Ala
    3230                3235                3240

Cys Leu Gly Lys Ser Tyr Ala Gln Met Trp Ser Leu Met Tyr Phe
    3245                3250                3255

His Arg Arg Asp Leu Arg Leu Ala Ala Asn Ala Ile Cys Ser Ala
    3260                3265                3270

Val Pro Ser His Trp Val Pro Thr Ser Arg Thr Thr Trp Ser Ile
    3275                3280                3285
```

```
His Ala Lys His Glu Trp Met Thr Thr Glu Asp Met Leu Thr Val
    3290                3295                3300

Trp Asn Arg Val Trp Ile Gln Glu Asn Pro Trp Met Glu Asp Lys
    3305                3310                3315

Thr Pro Val Glu Ser Trp Glu Glu Ile Pro Tyr Leu Gly Lys Arg
    3320                3325                3330

Glu Asp Gln Trp Cys Gly Ser Leu Ile Gly Leu Thr Ser Arg Ala
    3335                3340                3345

Thr Trp Ala Lys Asn Ile Gln Ala Ala Ile Asn Gln Val Arg Ser
    3350                3355                3360

Leu Ile Gly Asn Glu Glu Tyr Thr Asp Tyr Met Pro Ser Met Lys
    3365                3370                3375

Arg Phe Arg Arg Glu Glu Glu Glu Ala Gly Val Leu Trp
    3380                3385                3390


<210> SEQ ID NO 26
<211> LENGTH: 5
<212> TYPE: PRT
<213> ORGANISM: Artificial Sequence
<220> FEATURE:
<223> OTHER INFORMATION: Derived from Dengue-2 virus

<400> SEQUENCE: 26

Gly Arg Ile Gly Arg
1               5


<210> SEQ ID NO 27
<211> LENGTH: 5
<212> TYPE: PRT
<213> ORGANISM: Artificial Sequence
<220> FEATURE:
<223> OTHER INFORMATION: Derived from Dengue-2 virus

<400> SEQUENCE: 27

Gly Ala Gly Lys Thr
1               5


<210> SEQ ID NO 28
<211> LENGTH: 10723
<212> TYPE: DNA
<213> ORGANISM: Artificial Sequence
<220> FEATURE:
<223> OTHER INFORMATION: Derived from Dengue virus serotype 2/Dengue
      virus serotype 4, DenVax-4g

<400> SEQUENCE: 28

agttgttagt ctacgtggac cgacaaagac agattctttg agggagctaa gctcaacgta     60

gttctaacag ttttttaatt agagagcaga tctctgatga ataaccaacg gaaaaaggcg    120

aaaaacacgc ctttcaatat gctgaaacgc gagagaaacc gcgtgtcgac tgtgcaacag    180

ctgacaaaga gattctcact tggaatgctg cagggacgag gaccattaaa actgttcatg    240

gccctggtgg cgttccttcg tttcctaaca atcccaccaa cagcagggat attgaagaga    300

tggggaacaa ttaaaaaatc aaaagctatt aatgttttga gagggttcag gaaagagatt    360

ggaaggatgc tgaacatctt gaataggaga cgcagctctg caggcatgat cattatgctg    420

attccaacag tgatggcgtt ccatttaacc acgcgtgatg gcgaacccct catgatagtg    480

gcaaaacatg aaagggggag acctctcttg tttaagacaa cagaggggat caacaaatgc    540

actctcattg ccatggactt gggtgaaatg tgtgaggaca ctgtcacgta taaatgcccc    600
```

-continued

```
ttactggtca ataccgaacc tgaagacatt gattgctggt gcaatctcac gtctacctgg    660
gtcatgtatg ggacatgcac ccagagcgga gaacggagac gagagaagcg ctcagtagct    720
ttaacaccac attcaggaat gggattggaa acaagagctg agacatggat gtcatcggaa    780
ggggcttgga agcatgctca gagagtagag agctggatac tcagaaaccc aggattcgcg    840
ctcttggcag gatttatggc ttatatgatt gggcaaacag gaatccagcg aactgtcttc    900
tttgtcctaa tgatgctggt cgccccatcc tacggaatgc gatgcgtagg agtaggaaac    960
agagactttg tggaaggagt ctcaggtgga gcatgggtcg atctggtgct agaacatgga   1020
ggatgcgtca caaccatggc ccagggaaaa ccaaccttgg attttgaact gactaagaca   1080
acagccaagg aagtggctct gttaagaacc tattgcattg aagcctcaat atcaaacata   1140
accacggcaa caagatgtcc aacgcaagga gagccttatc taaaagagga acaagaccaa   1200
cagtacattt gccggagaga tgtggtagac agagggtggg gcaatggctg tggcttgttt   1260
ggaaaaggag gagttgtgac atgtgcgaag ttttcatgtt cggggaagat aacaggcaat   1320
ttggtccaaa ttgagaacct tgaatacaca gtggttgtaa cagtccacaa tggagacacc   1380
catgcagtag gaaatgacac gtccaatcat ggagttacag ccacgataac tcccaggtca   1440
ccatcggtgg aagtcaaatt gccggactat ggagaactaa cactcgattg tgaacccagg   1500
tctggaattg actttaatga gatgattctg atgaaaatga aaaagaaaac atggcttgtg   1560
cataagcaat ggtttttgga tctacctcta ccatggacag caggagcaga cacatcagag   1620
gttcactgga attacaaaga gagaatggtg acatttaagg ttcctcatgc caagagacag   1680
gatgtgacag tgctgggatc tcaggaagga gccatgcatt ctgccctcgc tggagccaca   1740
gaagtggact ccggtgatgg aaatcacatg tttgcaggac atctcaagtg caaagtccgt   1800
atggagaaat tgagaatcaa gggaatgtca tacacgatgt gttcaggaaa gttctcaatt   1860
gacaaagaga tggcagaaac acagcatggg acaacagtgg tgaaagtcaa gtatgaaggt   1920
gctggagctc cgtgtaaagt ccccatagag ataagagatg tgaacaagga aaaagtggtt   1980
gggcgtatca tctcatccac cccttttggct gagaatacca acagtgtaac caacatagag  2040
ttagaacccc cctttgggga cagctacata gtgataggtg ttggaaacag tgcattaaca   2100
ctccattggt tcaggaaagg gagttccatt ggcaagatgt ttgagtccac atacagaggt   2160
gcaaaacgaa tggccattct aggtgaaaca gcttgggatt ttggttccgt tggtggactg   2220
ttcacatcat tgggaaaggc tgtgcaccag gtttttggaa gtgtgtatac aaccctgttt   2280
ggaggagtct catggatgat tagaatccta attgggttcc tagtgttgtg gattggcacg   2340
aactcaagga acacttcaat ggctatgacg tgcatagctg ccggcattgt gacactgtat   2400
ttgggagtca tggtgcaggc cgatagtggt tgcgttgtga gctggaaaaa caaagaactg   2460
aaatgtggca gtgggatttt catcacagac aacgtgcaca catggacaga acaatacaag   2520
ttccaaccag aatccccttc aaaactagct tcagctatcc agaaagccca tgaagaggac   2580
atttgtggaa tccgctcagt aacaagactg gagaatctga tgtggaaaca aataacacca   2640
gaattgaatc acattctatc agaaaatgag gtgaagttaa ctattatgac aggagacatc   2700
aaaggaatca tgcaggcagg aaaacgatct ctgcggcctc agcccactga gctgaagtat   2760
tcatggaaaa catggggcaa agcaaaaatg ctctctacag agtctcataa ccagaccttt   2820
ctcattgatg gccccgaaac agcagaatgc cccaacacaa atagagcttg gaattcgttg   2880
gaagttgaag actatggctt tggagtattc accaccaata tatggctaaa attgaaagaa   2940
aaacaggatg tattctgcga ctcaaaactc atgtcagcgg ccataaaaga caacagagcc   3000
```

-continued

```
gtccatgccg atatgggtta ttggatagaa agtgcactca atgacacatg gaagatagag   3060
aaagcctctt tcattgaagt taaaaactgc cactggccaa aatcacacac cctctggagc   3120
aatggagtgc tagaaagtga gatgataatt ccaaagaatc tcgctggacc agtgtctcaa   3180
cacaactata gaccaggcta ccatacacaa ataacaggac catggcatct aggtaagctt   3240
gagatggact ttgatttctg tgatggaaca acagtggtag tgactgagga ctgcggaaat   3300
agaggaccct ctttgagaac aaccactgcc tctggaaaac tcataacaga atggtgctgc   3360
cgatcttgca cattaccacc gctaagatac agaggtgagg atgggtgctg gtacgggatg   3420
gaaatcagac cattgaagga gaaagaagag aatttggtca actccttggt cacagctgga   3480
catgggcagg tcgacaactt ttcactagga gtcttgggaa tggcattgtt cctggaggaa   3540
atgcttagga cccgagtagg aacgaaacat gcaatactac tagttgcagt ttcttttgtg   3600
acattgatca cagggaacat gtcctttaga gacctgggaa gagtgatggt tatggtaggc   3660
gccactatga cggatgacat aggtatgggc gtgacttatc ttgccctact agcagccttc   3720
aaagtcagac caacttttgc agctggacta ctcttgagaa agctgacctc caaggaattg   3780
atgatgacta ctataggaat tgtactcctc tcccagagca ccataccaga gaccattctt   3840
gagttgactg atgcgttagc cttaggcatg atggtcctca aaatggtgag aaatatggaa   3900
aagtatcaat tggcagtgac tatcatggct atcttgtgcg tcccaaacgc agtgatatta   3960
caaaacgcat ggaaagtgag ttgcacaata ttggcagtgg tgtccgtttc cccactgctc   4020
ttaacatcct cacagcaaaa aacagattgg ataccattag cattgacgat caaaggtctc   4080
aatccaacag ctatttttct aacaaccctc tcaagaacca gcaagaaaag gagctggcca   4140
ttaaatgagg ctatcatggc agtcgggatg gtgagcattt tagccagttc tctcctaaaa   4200
aatgatattc ccatgacagg accattagtg gctggagggc tcctcactgt gtgctacgtg   4260
ctcactggac gatcggccga tttggaactg gagagagcag ccgatgtcaa atgggaagac   4320
caggcagaga tatcaggaag cagtccaatc ctgtcaataa caatatcaga agatggtagc   4380
atgtcgataa aaaatgaaga ggaagaacaa acactgacca tactcattag aacaggattg   4440
ctggtgatct caggactttt tcctgtatca ataccaatca cggcagcagc atggtacctg   4500
tgggaagtga agaaacaacg ggccggagta ttgtgggatg ttccttcacc cccacccatg   4560
ggaaaggctg aactggaaga tggagcctat agaattaagc aaaaagggat tcttggatat   4620
tcccagatcg gagccggagt ttacaaagaa ggaacattcc atacaatgtg gcatgtcaca   4680
cgtggcgctg ttctaatgca taaaggaaag aggattgaac catcatgggc ggacgtcaag   4740
aaagacctaa tatcatatgg aggaggctgg aagttagaag gagaatggaa ggaaggagaa   4800
gaagtccagg tattggcact ggagcctgga aaaaatccaa gagccgtcca aacgaaacct   4860
ggtcttttca aaaccaacgc cggaacaata ggtgctgtat ctctggactt ttctcctgga   4920
acgtcaggat ctccaattat cgacaaaaaa ggaaaagttg tgggtcttta tggtaatggt   4980
gttgttacaa ggagtggagc atatgtgagt gctatagccc agactgaaaa aagcattgaa   5040
gacaacccag agatcgaaga tgacattttc cgaaagagaa gactgaccat catggacctc   5100
cacccaggag cgggaaagac gaagagatac cttccggcca tagtcagaga agctataaaa   5160
cggggtttga gaacattaat cttggccccc actagagttg tggcagctga aatggaggaa   5220
gcccttagag gacttccaat aagataccag accccagcca tcagagctgt gcacaccggg   5280
cgggagattg tggacctaat gtgtcatgcc acatttacca tgaggctgct atcaccagtt   5340
```

-continued agagtgccaa actacaacct gattatcatg gacgaagccc atttcacaga cccagcaagt 5400
atagcagcta gaggatacat ctcaactcga gtggagatgg gtgaggcagc tgggattttt 5460
atgacagcca ctcccccggg aagcagagac ccatttcctc agagcaatgc accaatcata 5520
gatgaagaaa gagaaatccc tgaacgctcg tggaattccg gacatgaatg ggtcacggat 5580
tttaaaggga agactgtttg gttcgttcca agtataaaag caggaaatga tatagcagct 5640
tgcctgagga aaaatggaaa gaaagtgata caactcagta ggaagacctt tgattctgag 5700
tatgtcaaga ctagaaccaa tgattgggac ttcgtggtta caactgacat ttcagaaatg 5760
ggtgccaatt tcaaggctga gagggttata gaccccagac gctgcatgaa accagtcata 5820
ctaacagatg gtgaagagcg ggtgattctg gcaggaccta tgccagtgac ccactctagt 5880
gcagcacaaa gaagagggag aataggaaga aatccaaaaa atgagaatga ccagtacata 5940
tacatggggg aacctctgga aaatgatgaa gactgtgcac actggaaaga agctaaaatg 6000
ctcctagata acatcaacac gccagaagga atcattccta gcatgttcga accagagcgt 6060
gaaaaggtgg atgccattga tggcgaatac cgcttgagag gagaagcaag gaaaaccttt 6120
gtagacttaa tgagaagagg agacctacca gtctggttgg cctacagagt ggcagctgaa 6180
ggcatcaact acgcagacag aaggtggtgt tttgatggag tcaagaacaa ccaaatccta 6240
gaagaaaacg tggaagttga aatctggaca aaagaagggg aaaggaagaa attgaaaccc 6300
agatggttgg atgctaggat ctattctgac ccactggcgc taaaagaatt taaggaattt 6360
gcagccggaa gaaagtctct gaccctgaac ctaatcacag aaatgggtag gctcccaacc 6420
ttcatgactc agaaggcaag agacgcactg gacaacttag cagtgctgca cacggctgag 6480
gcaggtggaa gggcgtacaa ccatgctctc agtgaactgc cggagaccct ggagacattg 6540
cttttactga cacttctggc tacagtcacg ggagggatct tttattcttt gatgagcgga 6600
aggggcatag ggaagatgac cctgggaatg tgctgcataa tcacggctag catcctccta 6660
tggtacgcac aaatacagcc acactggata gcagcttcaa taatactgga gtttttctc 6720
atagttttgc ttattccaga acctgaaaaa cagagaacac cccaagacaa ccaactgacc 6780
tacgttgtca tagccatcct cacagtggtg gccgcaacca tggcaaacga gatgggtttc 6840
ctagaaaaaa cgaagaaaga tctcggattg ggaagcattg caacccagca acccgagagc 6900
aacatcctgg acatagatct acgtcctgca tcagcatgga cgctgtatgc cgtggccaca 6960
acatttgtta caccaatgtt gagacatagc attgaaaatt cctcagtgaa tgtgtcccta 7020
acagctatag ccaaccaagc cacagtgtta atgggtctcg ggaaaggatg gccattgtca 7080
aagatggaca tcggagttcc ccttctcgcc attggatgct actcacaagt caaccccata 7140
actctcacag cagctctttt cttattggta gcacattatg ccatcatagg gccaggactc 7200
caagcaaaag caaccagaga agctcagaaa agagcagcgg cgggcatcat gaaaaaccca 7260
actgtcgatg gaataacagt gattgaccta gatccaatac cttatgatcc aaagtttgaa 7320
aagcagttgg gacaagtaat gctcctagtc ctctgcgtga ctcaagtatt gatgatgagg 7380
actacatggg ctctgtgtga ggctttaacc ttagctaccg ggcccatctc cacattgtgg 7440
gaaggaaatc cagggaggtt ttggaacact accattgcgg tgtcaatggc taacattttt 7500
agagggagtt acttggccgg agctggactt ctcttttcta ttatgaagaa cacaaccaac 7560
acaagaaggg gaactggcaa cataggagag acgcttggag agaaatggaa aagccgattg 7620
aacgcattgg gaaaaagtga attccagatc tacaagaaaa gtggaatcca ggaagtggat 7680
agaaccttag caaaagaagg cattaaaaga ggagaaacgg accatcacgc tgtgtcgcga 7740

-continued

```
ggctcagcaa aactgagatg gttcgttgag agaaacatgg tcacaccaga agggaaagta   7800
gtggacctcg gttgtggcag aggaggctgg tcatactatt gtggaggact aaagaatgta   7860
agagaagtca aaggcctaac aaaaggagga ccaggacacg aagaacccat ccccatgtca   7920
acatatgggt ggaatctagt gcgtcttcaa agtggagttg acgttttctt catcccgcca   7980
gaaaagtgtg acacattatt gtgtgacata ggggagtcat caccaaatcc cacagtggaa   8040
gcaggacgaa cactcagagt ccttaactta gtagaaaatt ggttgaacaa caacactcaa   8100
ttttgcataa aggttctcaa cccatatatg ccctcagtca tagaaaaaat ggaagcacta   8160
caaaggaaat atggaggagc cttagtgagg aatccactct cacgaaactc cacacatgag   8220
atgtactggg tatccaatgc ttccgggaac atagtgtcat cagtgaacat gatttcaagg   8280
atgttgatca acagatttac aatgagatac aagaaagcca cttacgagcc ggatgttgac   8340
ctcggaagcg gaacccgtaa catcgggatt gaaagtgaga taccaaacct agatataatt   8400
gggaaaagaa tagaaaaaat aaagcaagag catgaaacat catggcacta tgaccaagac   8460
cacccataca aaacgtgggc ataccatggt agctatgaaa caaaacagac tggatcagca   8520
tcatccatgg tcaacggagt ggtcaggctg ctgacaaaac cttgggacgt cgtccccatg   8580
gtgacacaga tggcaatgac agacacgact ccatttggac aacagcgcgt tttaaagag    8640
aaagtggaca cgagaaccca agaaccgaaa gaaggcacga agaaactaat gaaaataaca   8700
gcagagtggc tttggaaaga attagggaag aaaaagacac ccaggatgtg caccagagaa   8760
gaattcacaa gaaaggtgag aagcaatgca gccttggggg ccatattcac tgatgagaac   8820
aagtggaagt cggcacgtga ggctgttgaa gatagtaggt tttgggagct ggttgacaag   8880
gaaaggaatc tccatcttga aggaaagtgt gaaacatgtg tgtacaacat gatgggaaaa   8940
agagagaaga agctagggga attcggcaag gcaaaaggca gcagagccat atggtacatg   9000
tggcttggag cacgcttctt agagtttgaa gccctaggat tcttaaatga agatcactgg   9060
ttctccagag agaactccct gagtggagtg gaaggagaag ggctgcacaa gctaggttac   9120
attctaagag acgtgagcaa gaaagaggga ggagcaatgt atgccgatga caccgcagga   9180
tgggatacaa gaatcacact agaagaccta aaaaatgaag aaatggtaac aaaccacatg   9240
gaaggagaac acaagaaact agccgaggcc attttcaaac taacgtacca aaacaaggtg   9300
gtgcgtgtgc aaagaccaac accaagaggc acagtaatgg acatcatatc gagaagagac   9360
caaagaggta gtggacaagt tggcacctat ggactcaata ctttcaccaa tatggaagcc   9420
caactaatca gacagatgga gggagaagga gtctttaaaa gcattcagca cctaacaatc   9480
acagaagaaa tcgctgtgca aaactggtta gcaagagtgg ggcgcgaaag gttatcaaga   9540
atggccatca gtggagatga ttgtgttgtg aaacctttag atgacaggtt cgcaagcgct   9600
ttaacagctc taaatgacat gggaaagatt aggaaagaca tacaacaatg ggaaccttca   9660
agaggatgga atgattggac acaagtgccc ttctgttcac accatttcca tgagttaatc   9720
atgaaagacg gtcgcgtact cgttgttcca tgtagaaacc aagatgaact gattggcaga   9780
gcccgaatct cccaaggagc agggtggtct ttgcgggaga cggcctgttt ggggaagtct   9840
tacgcccaaa tgtggagctt gatgtacttc cacagacgcg acctcaggct ggcggcaaat   9900
gctatttgct cggcagtacc atcacattgg gttccaacaa gtcgaacaac ctggtccata   9960
catgctaaac atgaatggat gacaacggaa gacatgctga cagtctggaa cagggtgtgg  10020
attcaagaaa acccatggat ggaagacaaa actccagtgg aatcatggga ggaaatccca  10080
```

-continued

```
tacttgggga aaagagaaga ccaatggtgc ggctcattga ttgggttaac aagcagggcc  10140

acctgggcaa agaacatcca agcagcaata aatcaagtta gatcccttat aggcaatgaa  10200

gaatacacag attacatgcc atccatgaaa agattcagaa gagaagagga agaagcagga  10260

gttctgtggt agaaagcaaa actaacatga aacaaggcta gaagtcaggt cggattaagc  10320

catagtacgg aaaaaactat gctacctgtg agccccgtcc aaggacgtta aaagaagtca  10380

ggccatcata aatgccatag cttgagtaaa ctatgcagcc tgtagctcca cctgagaagg  10440

tgtaaaaaat ccgggaggcc acaaaccatg gaagctgtac gcatggcgta gtggactagc  10500

ggttagagga gacccctccc ttacaaatcg cagcaacaat gggggcccaa ggcgagatga  10560

agctgtagtc tcgctggaag gactagaggt tagaggagac ccccccgaaa caaaaaacag  10620

catattgacg ctgggaaaga ccagagatcc tgctgtctcc tcagcatcat tccaggcaca  10680

gaacgccaga aaatggaatg gtgctgttga atcaacaggt tct                   10723
```

```
<210> SEQ ID NO 29
<211> LENGTH: 3391
<212> TYPE: PRT
<213> ORGANISM: Artificial Sequence
<220> FEATURE:
<223> OTHER INFORMATION: Derived from Dengue virus serotype 2/Dengue
      virus serotype 4, DenVax-4g

<400> SEQUENCE: 29

Met Asn Asn Gln Arg Lys Lys Ala Lys Asn Thr Pro Phe Asn Met Leu
1               5                   10                  15

Lys Arg Glu Arg Asn Arg Val Ser Thr Val Gln Gln Leu Thr Lys Arg
            20                  25                  30

Phe Ser Leu Gly Met Leu Gln Gly Arg Gly Pro Leu Lys Leu Phe Met
        35                  40                  45

Ala Leu Val Ala Phe Leu Arg Phe Leu Thr Ile Pro Pro Thr Ala Gly
    50                  55                  60

Ile Leu Lys Arg Trp Gly Thr Ile Lys Lys Ser Lys Ala Ile Asn Val
65                  70                  75                  80

Leu Arg Gly Phe Arg Lys Glu Ile Gly Arg Met Leu Asn Ile Leu Asn
                85                  90                  95

Arg Arg Arg Ser Ser Ala Gly Met Ile Ile Met Leu Ile Pro Thr Val
            100                 105                 110

Met Ala Phe His Leu Thr Thr Arg Asp Gly Glu Pro Leu Met Ile Val
        115                 120                 125

Ala Lys His Glu Arg Gly Arg Pro Leu Leu Phe Lys Thr Thr Glu Gly
    130                 135                 140

Ile Asn Lys Cys Thr Leu Ile Ala Met Asp Leu Gly Glu Met Cys Glu
145                 150                 155                 160

Asp Thr Val Thr Tyr Lys Cys Pro Leu Leu Val Asn Thr Glu Pro Glu
                165                 170                 175

Asp Ile Asp Cys Trp Cys Asn Leu Thr Ser Thr Trp Val Met Tyr Gly
            180                 185                 190

Thr Cys Thr Gln Ser Gly Glu Arg Arg Arg Glu Lys Arg Ser Val Ala
        195                 200                 205

Leu Thr Pro His Ser Gly Met Gly Leu Glu Thr Arg Ala Glu Thr Trp
    210                 215                 220

Met Ser Ser Glu Gly Ala Trp Lys His Ala Gln Arg Val Glu Ser Trp
225                 230                 235                 240

Ile Leu Arg Asn Pro Gly Phe Ala Leu Leu Ala Gly Phe Met Ala Tyr
```

-continued

```
                245                 250                 255

Met Ile Gly Gln Thr Gly Ile Gln Arg Thr Val Phe Phe Val Leu Met
            260                 265                 270

Met Leu Val Ala Pro Ser Tyr Gly Met Arg Cys Val Gly Val Gly Asn
        275                 280                 285

Arg Asp Phe Val Glu Gly Val Ser Gly Gly Ala Trp Val Asp Leu Val
    290                 295                 300

Leu Glu His Gly Gly Cys Val Thr Thr Met Ala Gln Gly Lys Pro Thr
305                 310                 315                 320

Leu Asp Phe Glu Leu Thr Lys Thr Thr Ala Lys Glu Val Ala Leu Leu
                325                 330                 335

Arg Thr Tyr Cys Ile Glu Ala Ser Ile Ser Asn Ile Thr Thr Ala Thr
            340                 345                 350

Arg Cys Pro Thr Gln Gly Glu Pro Tyr Leu Lys Glu Glu Gln Asp Gln
        355                 360                 365

Gln Tyr Ile Cys Arg Arg Asp Val Val Asp Arg Gly Trp Gly Asn Gly
    370                 375                 380

Cys Gly Leu Phe Gly Lys Gly Gly Val Val Thr Cys Ala Lys Phe Ser
385                 390                 395                 400

Cys Ser Gly Lys Ile Thr Gly Asn Leu Val Gln Ile Glu Asn Leu Glu
                405                 410                 415

Tyr Thr Val Val Val Thr Val His Asn Gly Asp Thr His Ala Val Gly
            420                 425                 430

Asn Asp Thr Ser Asn His Gly Val Thr Ala Thr Ile Thr Pro Arg Ser
        435                 440                 445

Pro Ser Val Glu Val Lys Leu Pro Asp Tyr Gly Glu Leu Thr Leu Asp
    450                 455                 460

Cys Glu Pro Arg Ser Gly Ile Asp Phe Asn Glu Met Ile Leu Met Lys
465                 470                 475                 480

Met Lys Lys Lys Thr Trp Leu Val His Lys Gln Trp Phe Leu Asp Leu
                485                 490                 495

Pro Leu Pro Trp Thr Ala Gly Ala Asp Thr Ser Glu Val His Trp Asn
            500                 505                 510

Tyr Lys Glu Arg Met Val Thr Phe Lys Val Pro His Ala Lys Arg Gln
        515                 520                 525

Asp Val Thr Val Leu Gly Ser Gln Glu Gly Ala Met His Ser Ala Leu
    530                 535                 540

Ala Gly Ala Thr Glu Val Asp Ser Gly Asp Gly Asn His Met Phe Ala
545                 550                 555                 560

Gly His Leu Lys Cys Lys Val Arg Met Glu Lys Leu Arg Ile Lys Gly
                565                 570                 575

Met Ser Tyr Thr Met Cys Ser Gly Lys Phe Ser Ile Asp Lys Glu Met
            580                 585                 590

Ala Glu Thr Gln His Gly Thr Thr Val Val Lys Val Lys Tyr Glu Gly
        595                 600                 605

Ala Gly Ala Pro Cys Lys Val Pro Ile Glu Ile Arg Asp Val Asn Lys
    610                 615                 620

Glu Lys Val Val Gly Arg Ile Ile Ser Ser Thr Pro Leu Ala Glu Asn
625                 630                 635                 640

Thr Asn Ser Val Thr Asn Ile Glu Leu Glu Pro Pro Phe Gly Asp Ser
                645                 650                 655

Tyr Ile Val Ile Gly Val Gly Asn Ser Ala Leu Thr Leu His Trp Phe
            660                 665                 670
```

```
Arg Lys Gly Ser Ser Ile Gly Lys Met Phe Glu Ser Thr Tyr Arg Gly
        675                 680                 685

Ala Lys Arg Met Ala Ile Leu Gly Glu Thr Ala Trp Asp Phe Gly Ser
    690                 695                 700

Val Gly Gly Leu Phe Thr Ser Leu Gly Lys Ala Val His Gln Val Phe
705                 710                 715                 720

Gly Ser Val Tyr Thr Thr Leu Phe Gly Gly Val Ser Trp Met Ile Arg
                725                 730                 735

Ile Leu Ile Gly Phe Leu Val Leu Trp Ile Gly Thr Asn Ser Arg Asn
            740                 745                 750

Thr Ser Met Ala Met Thr Cys Ile Ala Ala Gly Ile Val Thr Leu Tyr
        755                 760                 765

Leu Gly Val Met Val Gln Ala Asp Ser Gly Cys Val Val Ser Trp Lys
    770                 775                 780

Asn Lys Glu Leu Lys Cys Gly Ser Gly Ile Phe Ile Thr Asp Asn Val
785                 790                 795                 800

His Thr Trp Thr Glu Gln Tyr Lys Phe Gln Pro Glu Ser Pro Ser Lys
                805                 810                 815

Leu Ala Ser Ala Ile Gln Lys Ala His Glu Glu Asp Ile Cys Gly Ile
            820                 825                 830

Arg Ser Val Thr Arg Leu Glu Asn Leu Met Trp Lys Gln Ile Thr Pro
        835                 840                 845

Glu Leu Asn His Ile Leu Ser Glu Asn Glu Val Lys Leu Thr Ile Met
    850                 855                 860

Thr Gly Asp Ile Lys Gly Ile Met Gln Ala Gly Lys Arg Ser Leu Arg
865                 870                 875                 880

Pro Gln Pro Thr Glu Leu Lys Tyr Ser Trp Lys Thr Trp Gly Lys Ala
                885                 890                 895

Lys Met Leu Ser Thr Glu Ser His Asn Gln Thr Phe Leu Ile Asp Gly
            900                 905                 910

Pro Glu Thr Ala Glu Cys Pro Asn Thr Asn Arg Ala Trp Asn Ser Leu
        915                 920                 925

Glu Val Glu Asp Tyr Gly Phe Gly Val Phe Thr Thr Asn Ile Trp Leu
    930                 935                 940

Lys Leu Lys Glu Lys Gln Asp Val Phe Cys Asp Ser Lys Leu Met Ser
945                 950                 955                 960

Ala Ala Ile Lys Asp Asn Arg Ala Val His Ala Asp Met Gly Tyr Trp
                965                 970                 975

Ile Glu Ser Ala Leu Asn Asp Thr Trp Lys Ile Glu Lys Ala Ser Phe
            980                 985                 990

Ile Glu Val Lys Asn Cys His Trp  Pro Lys Ser His Thr  Leu Trp Ser
        995                 1000                1005

Asn Gly  Val Leu Glu Ser Glu  Met Ile Ile Pro Lys  Asn Leu Ala
    1010                1015                1020

Gly Pro  Val Ser Gln His Asn  Tyr Arg Pro Gly Tyr  His Thr Gln
    1025                1030                1035

Ile Thr  Gly Pro Trp His Leu  Gly Lys Leu Glu Met  Asp Phe Asp
    1040                1045                1050

Phe Cys  Asp Gly Thr Thr Val  Val Val Thr Glu Asp  Cys Gly Asn
    1055                1060                1065

Arg Gly  Pro Ser Leu Arg Thr  Thr Thr Ala Ser Gly  Lys Leu Ile
    1070                1075                1080
```

```
Thr Glu  Trp Cys Cys Arg Ser  Cys Thr Leu Pro Pro  Leu Arg Tyr
    1085                 1090                 1095

Arg Gly  Glu Asp Gly Cys Trp  Tyr Gly Met Glu Ile  Arg Pro Leu
    1100                 1105                 1110

Lys Glu  Lys Glu Glu Asn Leu  Val Asn Ser Leu Val  Thr Ala Gly
    1115                 1120                 1125

His Gly  Gln Val Asp Asn Phe  Ser Leu Gly Val Leu  Gly Met Ala
    1130                 1135                 1140

Leu Phe  Leu Glu Glu Met Leu  Arg Thr Arg Val Gly  Thr Lys His
    1145                 1150                 1155

Ala Ile  Leu Leu Val Ala Val  Ser Phe Val Thr Leu  Ile Thr Gly
    1160                 1165                 1170

Asn Met  Ser Phe Arg Asp Leu  Gly Arg Val Met Val  Met Val Gly
    1175                 1180                 1185

Ala Thr  Met Thr Asp Asp Ile  Gly Met Gly Val Thr  Tyr Leu Ala
    1190                 1195                 1200

Leu Leu  Ala Ala Phe Lys Val  Arg Pro Thr Phe Ala  Ala Gly Leu
    1205                 1210                 1215

Leu Leu  Arg Lys Leu Thr Ser  Lys Glu Leu Met Met  Thr Thr Ile
    1220                 1225                 1230

Gly Ile  Val Leu Leu Ser Gln  Ser Thr Ile Pro Glu  Thr Ile Leu
    1235                 1240                 1245

Glu Leu  Thr Asp Ala Leu Ala  Leu Gly Met Met Val  Leu Lys Met
    1250                 1255                 1260

Val Arg  Asn Met Glu Lys Tyr  Gln Leu Ala Val Thr  Ile Met Ala
    1265                 1270                 1275

Ile Leu  Cys Val Pro Asn Ala  Val Ile Leu Gln Asn  Ala Trp Lys
    1280                 1285                 1290

Val Ser  Cys Thr Ile Leu Ala  Val Val Ser Val Ser  Pro Leu Leu
    1295                 1300                 1305

Leu Thr  Ser Ser Gln Gln Lys  Thr Asp Trp Ile Pro  Leu Ala Leu
    1310                 1315                 1320

Thr Ile  Lys Gly Leu Asn Pro  Thr Ala Ile Phe Leu  Thr Thr Leu
    1325                 1330                 1335

Ser Arg  Thr Ser Lys Lys Arg  Ser Trp Pro Leu Asn  Glu Ala Ile
    1340                 1345                 1350

Met Ala  Val Gly Met Val Ser  Ile Leu Ala Ser Ser  Leu Leu Lys
    1355                 1360                 1365

Asn Asp  Ile Pro Met Thr Gly  Pro Leu Val Ala Gly  Gly Leu Leu
    1370                 1375                 1380

Thr Val  Cys Tyr Val Leu Thr  Gly Arg Ser Ala Asp  Leu Glu Leu
    1385                 1390                 1395

Glu Arg  Ala Ala Asp Val Lys  Trp Glu Asp Gln Ala  Glu Ile Ser
    1400                 1405                 1410

Gly Ser  Ser Pro Ile Leu Ser  Ile Thr Ile Ser Glu  Asp Gly Ser
    1415                 1420                 1425

Met Ser  Ile Lys Asn Glu Glu  Glu Glu Gln Thr Leu  Thr Ile Leu
    1430                 1435                 1440

Ile Arg  Thr Gly Leu Leu Val  Ile Ser Gly Leu Phe  Pro Val Ser
    1445                 1450                 1455

Ile Pro  Ile Thr Ala Ala Ala  Trp Tyr Leu Trp Glu  Val Lys Lys
    1460                 1465                 1470

Gln Arg  Ala Gly Val Leu Trp  Asp Val Pro Ser Pro  Pro Pro Met
```

```
    1475                1480                1485

Gly Lys  Ala Glu Leu Glu Asp  Gly Ala Tyr Arg Ile  Lys Gln Lys
    1490                1495                1500

Gly Ile  Leu Gly Tyr Ser Gln  Ile Gly Ala Gly Val  Tyr Lys Glu
    1505                1510                1515

Gly Thr  Phe His Thr Met Trp  His Val Thr Arg Gly  Ala Val Leu
    1520                1525                1530

Met His  Lys Gly Lys Arg Ile  Glu Pro Ser Trp Ala  Asp Val Lys
    1535                1540                1545

Lys Asp  Leu Ile Ser Tyr Gly  Gly Gly Trp Lys Leu  Glu Gly Glu
    1550                1555                1560

Trp Lys  Glu Gly Glu Glu Val  Gln Val Leu Ala Leu  Glu Pro Gly
    1565                1570                1575

Lys Asn  Pro Arg Ala Val Gln  Thr Lys Pro Gly Leu  Phe Lys Thr
    1580                1585                1590

Asn Ala  Gly Thr Ile Gly Ala  Val Ser Leu Asp Phe  Ser Pro Gly
    1595                1600                1605

Thr Ser  Gly Ser Pro Ile Ile  Asp Lys Lys Gly Lys  Val Val Gly
    1610                1615                1620

Leu Tyr  Gly Asn Gly Val Val  Thr Arg Ser Gly Ala  Tyr Val Ser
    1625                1630                1635

Ala Ile  Ala Gln Thr Glu Lys  Ser Ile Glu Asp Asn  Pro Glu Ile
    1640                1645                1650

Glu Asp  Asp Ile Phe Arg Lys  Arg Arg Leu Thr Ile  Met Asp Leu
    1655                1660                1665

His Pro  Gly Ala Gly Lys Thr  Lys Arg Tyr Leu Pro  Ala Ile Val
    1670                1675                1680

Arg Glu  Ala Ile Lys Arg Gly  Leu Arg Thr Leu Ile  Leu Ala Pro
    1685                1690                1695

Thr Arg  Val Val Ala Ala Glu  Met Glu Glu Ala Leu  Arg Gly Leu
    1700                1705                1710

Pro Ile  Arg Tyr Gln Thr Pro  Ala Ile Arg Ala Val  His Thr Gly
    1715                1720                1725

Arg Glu  Ile Val Asp Leu Met  Cys His Ala Thr Phe  Thr Met Arg
    1730                1735                1740

Leu Leu  Ser Pro Val Arg Val  Pro Asn Tyr Asn Leu  Ile Ile Met
    1745                1750                1755

Asp Glu  Ala His Phe Thr Asp  Pro Ala Ser Ile Ala  Ala Arg Gly
    1760                1765                1770

Tyr Ile  Ser Thr Arg Val Glu  Met Gly Glu Ala Ala  Gly Ile Phe
    1775                1780                1785

Met Thr  Ala Thr Pro Pro Gly  Ser Arg Asp Pro Phe  Pro Gln Ser
    1790                1795                1800

Asn Ala  Pro Ile Ile Asp Glu  Glu Arg Glu Ile Pro  Glu Arg Ser
    1805                1810                1815

Trp Asn  Ser Gly His Glu Trp  Val Thr Asp Phe Lys  Gly Lys Thr
    1820                1825                1830

Val Trp  Phe Val Pro Ser Ile  Lys Ala Gly Asn Asp  Ile Ala Ala
    1835                1840                1845

Cys Leu  Arg Lys Asn Gly Lys  Lys Val Ile Gln Leu  Ser Arg Lys
    1850                1855                1860

Thr Phe  Asp Ser Glu Tyr Val  Lys Thr Arg Thr Asn  Asp Trp Asp
    1865                1870                1875
```

Phe Val Val Thr Thr Asp Ile Ser Glu Met Gly Ala Asn Phe Lys
1880 1885 1890

Ala Glu Arg Val Ile Asp Pro Arg Arg Cys Met Lys Pro Val Ile
1895 1900 1905

Leu Thr Asp Gly Glu Glu Arg Val Ile Leu Ala Gly Pro Met Pro
1910 1915 1920

Val Thr His Ser Ser Ala Ala Gln Arg Arg Gly Arg Ile Gly Arg
1925 1930 1935

Asn Pro Lys Asn Glu Asn Asp Gln Tyr Ile Tyr Met Gly Glu Pro
1940 1945 1950

Leu Glu Asn Asp Glu Asp Cys Ala His Trp Lys Glu Ala Lys Met
1955 1960 1965

Leu Leu Asp Asn Ile Asn Thr Pro Glu Gly Ile Ile Pro Ser Met
1970 1975 1980

Phe Glu Pro Glu Arg Glu Lys Val Asp Ala Ile Asp Gly Glu Tyr
1985 1990 1995

Arg Leu Arg Gly Glu Ala Arg Lys Thr Phe Val Asp Leu Met Arg
2000 2005 2010

Arg Gly Asp Leu Pro Val Trp Leu Ala Tyr Arg Val Ala Ala Glu
2015 2020 2025

Gly Ile Asn Tyr Ala Asp Arg Arg Trp Cys Phe Asp Gly Val Lys
2030 2035 2040

Asn Asn Gln Ile Leu Glu Glu Asn Val Glu Val Glu Ile Trp Thr
2045 2050 2055

Lys Glu Gly Glu Arg Lys Lys Leu Lys Pro Arg Trp Leu Asp Ala
2060 2065 2070

Arg Ile Tyr Ser Asp Pro Leu Ala Leu Lys Glu Phe Lys Glu Phe
2075 2080 2085

Ala Ala Gly Arg Lys Ser Leu Thr Leu Asn Leu Ile Thr Glu Met
2090 2095 2100

Gly Arg Leu Pro Thr Phe Met Thr Gln Lys Ala Arg Asp Ala Leu
2105 2110 2115

Asp Asn Leu Ala Val Leu His Thr Ala Glu Ala Gly Gly Arg Ala
2120 2125 2130

Tyr Asn His Ala Leu Ser Glu Leu Pro Glu Thr Leu Glu Thr Leu
2135 2140 2145

Leu Leu Leu Thr Leu Leu Ala Thr Val Thr Gly Gly Ile Phe Leu
2150 2155 2160

Phe Leu Met Ser Gly Arg Gly Ile Gly Lys Met Thr Leu Gly Met
2165 2170 2175

Cys Cys Ile Ile Thr Ala Ser Ile Leu Leu Trp Tyr Ala Gln Ile
2180 2185 2190

Gln Pro His Trp Ile Ala Ala Ser Ile Ile Leu Glu Phe Phe Leu
2195 2200 2205

Ile Val Leu Leu Ile Pro Glu Pro Glu Lys Gln Arg Thr Pro Gln
2210 2215 2220

Asp Asn Gln Leu Thr Tyr Val Val Ile Ala Ile Leu Thr Val Val
2225 2230 2235

Ala Ala Thr Met Ala Asn Glu Met Gly Phe Leu Glu Lys Thr Lys
2240 2245 2250

Lys Asp Leu Gly Leu Gly Ser Ile Ala Thr Gln Gln Pro Glu Ser
2255 2260 2265

-continued

```
Asn Ile  Leu Asp Ile Asp Leu  Arg Pro Ala Ser Ala  Trp Thr Leu
    2270                 2275                 2280

Tyr Ala  Val Ala Thr Thr Phe  Val Thr Pro Met Leu  Arg His Ser
    2285                 2290                 2295

Ile Glu  Asn Ser Ser Val Asn  Val Ser Leu Thr Ala  Ile Ala Asn
    2300                 2305                 2310

Gln Ala  Thr Val Leu Met Gly  Leu Gly Lys Gly Trp  Pro Leu Ser
    2315                 2320                 2325

Lys Met  Asp Ile Gly Val Pro  Leu Leu Ala Ile Gly  Cys Tyr Ser
    2330                 2335                 2340

Gln Val  Asn Pro Ile Thr Leu  Thr Ala Ala Leu Phe  Leu Leu Val
    2345                 2350                 2355

Ala His  Tyr Ala Ile Ile Gly  Pro Gly Leu Gln Ala  Lys Ala Thr
    2360                 2365                 2370

Arg Glu  Ala Gln Lys Arg Ala  Ala Ala Gly Ile Met  Lys Asn Pro
    2375                 2380                 2385

Thr Val  Asp Gly Ile Thr Val  Ile Asp Leu Asp Pro  Ile Pro Tyr
    2390                 2395                 2400

Asp Pro  Lys Phe Glu Lys Gln  Leu Gly Gln Val Met  Leu Leu Val
    2405                 2410                 2415

Leu Cys  Val Thr Gln Val Leu  Met Met Arg Thr Thr  Trp Ala Leu
    2420                 2425                 2430

Cys Glu  Ala Leu Thr Leu Ala  Thr Gly Pro Ile Ser  Thr Leu Trp
    2435                 2440                 2445

Glu Gly  Asn Pro Gly Arg Phe  Trp Asn Thr Thr Ile  Ala Val Ser
    2450                 2455                 2460

Met Ala  Asn Ile Phe Arg Gly  Ser Tyr Leu Ala Gly  Ala Gly Leu
    2465                 2470                 2475

Leu Phe  Ser Ile Met Lys Asn  Thr Thr Asn Thr Arg  Arg Gly Thr
    2480                 2485                 2490

Gly Asn  Ile Gly Glu Thr Leu  Gly Glu Lys Trp Lys  Ser Arg Leu
    2495                 2500                 2505

Asn Ala  Leu Gly Lys Ser Glu  Phe Gln Ile Tyr Lys  Lys Ser Gly
    2510                 2515                 2520

Ile Gln  Glu Val Asp Arg Thr  Leu Ala Lys Glu Gly  Ile Lys Arg
    2525                 2530                 2535

Gly Glu  Thr Asp His His Ala  Val Ser Arg Gly Ser  Ala Lys Leu
    2540                 2545                 2550

Arg Trp  Phe Val Glu Arg Asn  Met Val Thr Pro Glu  Gly Lys Val
    2555                 2560                 2565

Val Asp  Leu Gly Cys Gly Arg  Gly Gly Trp Ser Tyr  Tyr Cys Gly
    2570                 2575                 2580

Gly Leu  Lys Asn Val Arg Glu  Val Lys Gly Leu Thr  Lys Gly Gly
    2585                 2590                 2595

Pro Gly  His Glu Glu Pro Ile  Pro Met Ser Thr Tyr  Gly Trp Asn
    2600                 2605                 2610

Leu Val  Arg Leu Gln Ser Gly  Val Asp Val Phe Phe  Ile Pro Pro
    2615                 2620                 2625

Glu Lys  Cys Asp Thr Leu Leu  Cys Asp Ile Gly Glu  Ser Ser Pro
    2630                 2635                 2640

Asn Pro  Thr Val Glu Ala Gly  Arg Thr Leu Arg Val  Leu Asn Leu
    2645                 2650                 2655

Val Glu  Asn Trp Leu Asn Asn  Asn Thr Gln Phe Cys  Ile Lys Val
```

2660 2665 2670

Leu Asn Pro Tyr Met Pro Ser Val Ile Glu Lys Met Glu Ala Leu
2675 2680 2685

Gln Arg Lys Tyr Gly Gly Ala Leu Val Arg Asn Pro Leu Ser Arg
2690 2695 2700

Asn Ser Thr His Glu Met Tyr Trp Val Ser Asn Ala Ser Gly Asn
2705 2710 2715

Ile Val Ser Ser Val Asn Met Ile Ser Arg Met Leu Ile Asn Arg
2720 2725 2730

Phe Thr Met Arg Tyr Lys Lys Ala Thr Tyr Glu Pro Asp Val Asp
2735 2740 2745

Leu Gly Ser Gly Thr Arg Asn Ile Gly Ile Glu Ser Glu Ile Pro
2750 2755 2760

Asn Leu Asp Ile Ile Gly Lys Arg Ile Glu Lys Ile Lys Gln Glu
2765 2770 2775

His Glu Thr Ser Trp His Tyr Asp Gln Asp His Pro Tyr Lys Thr
2780 2785 2790

Trp Ala Tyr His Gly Ser Tyr Glu Thr Lys Gln Thr Gly Ser Ala
2795 2800 2805

Ser Ser Met Val Asn Gly Val Val Arg Leu Leu Thr Lys Pro Trp
2810 2815 2820

Asp Val Val Pro Met Val Thr Gln Met Ala Met Thr Asp Thr Thr
2825 2830 2835

Pro Phe Gly Gln Gln Arg Val Phe Lys Glu Lys Val Asp Thr Arg
2840 2845 2850

Thr Gln Glu Pro Lys Glu Gly Thr Lys Lys Leu Met Lys Ile Thr
2855 2860 2865

Ala Glu Trp Leu Trp Lys Glu Leu Gly Lys Lys Lys Thr Pro Arg
2870 2875 2880

Met Cys Thr Arg Glu Glu Phe Thr Arg Lys Val Arg Ser Asn Ala
2885 2890 2895

Ala Leu Gly Ala Ile Phe Thr Asp Glu Asn Lys Trp Lys Ser Ala
2900 2905 2910

Arg Glu Ala Val Glu Asp Ser Arg Phe Trp Glu Leu Val Asp Lys
2915 2920 2925

Glu Arg Asn Leu His Leu Glu Gly Lys Cys Glu Thr Cys Val Tyr
2930 2935 2940

Asn Met Met Gly Lys Arg Glu Lys Lys Leu Gly Glu Phe Gly Lys
2945 2950 2955

Ala Lys Gly Ser Arg Ala Ile Trp Tyr Met Trp Leu Gly Ala Arg
2960 2965 2970

Phe Leu Glu Phe Glu Ala Leu Gly Phe Leu Asn Glu Asp His Trp
2975 2980 2985

Phe Ser Arg Glu Asn Ser Leu Ser Gly Val Glu Gly Glu Gly Leu
2990 2995 3000

His Lys Leu Gly Tyr Ile Leu Arg Asp Val Ser Lys Lys Glu Gly
3005 3010 3015

Gly Ala Met Tyr Ala Asp Asp Thr Ala Gly Trp Asp Thr Arg Ile
3020 3025 3030

Thr Leu Glu Asp Leu Lys Asn Glu Glu Met Val Thr Asn His Met
3035 3040 3045

Glu Gly Glu His Lys Lys Leu Ala Glu Ala Ile Phe Lys Leu Thr
3050 3055 3060

```
Tyr Gln Asn Lys Val Val Arg Val Gln Arg Pro Thr Pro Arg Gly
    3065                3070                3075

Thr Val Met Asp Ile Ile Ser Arg Arg Asp Gln Arg Gly Ser Gly
    3080                3085                3090

Gln Val Gly Thr Tyr Gly Leu Asn Thr Phe Thr Asn Met Glu Ala
    3095                3100                3105

Gln Leu Ile Arg Gln Met Glu Gly Glu Gly Val Phe Lys Ser Ile
    3110                3115                3120

Gln His Leu Thr Ile Thr Glu Glu Ile Ala Val Gln Asn Trp Leu
    3125                3130                3135

Ala Arg Val Gly Arg Glu Arg Leu Ser Arg Met Ala Ile Ser Gly
    3140                3145                3150

Asp Asp Cys Val Val Lys Pro Leu Asp Asp Arg Phe Ala Ser Ala
    3155                3160                3165

Leu Thr Ala Leu Asn Asp Met Gly Lys Ile Arg Lys Asp Ile Gln
    3170                3175                3180

Gln Trp Glu Pro Ser Arg Gly Trp Asn Asp Trp Thr Gln Val Pro
    3185                3190                3195

Phe Cys Ser His His Phe His Glu Leu Ile Met Lys Asp Gly Arg
    3200                3205                3210

Val Leu Val Val Pro Cys Arg Asn Gln Asp Glu Leu Ile Gly Arg
    3215                3220                3225

Ala Arg Ile Ser Gln Gly Ala Gly Trp Ser Leu Arg Glu Thr Ala
    3230                3235                3240

Cys Leu Gly Lys Ser Tyr Ala Gln Met Trp Ser Leu Met Tyr Phe
    3245                3250                3255

His Arg Arg Asp Leu Arg Leu Ala Ala Asn Ala Ile Cys Ser Ala
    3260                3265                3270

Val Pro Ser His Trp Val Pro Thr Ser Arg Thr Thr Trp Ser Ile
    3275                3280                3285

His Ala Lys His Glu Trp Met Thr Thr Glu Asp Met Leu Thr Val
    3290                3295                3300

Trp Asn Arg Val Trp Ile Gln Glu Asn Pro Trp Met Glu Asp Lys
    3305                3310                3315

Thr Pro Val Glu Ser Trp Glu Glu Ile Pro Tyr Leu Gly Lys Arg
    3320                3325                3330

Glu Asp Gln Trp Cys Gly Ser Leu Ile Gly Leu Thr Ser Arg Ala
    3335                3340                3345

Thr Trp Ala Lys Asn Ile Gln Ala Ala Ile Asn Gln Val Arg Ser
    3350                3355                3360

Leu Ile Gly Asn Glu Glu Tyr Thr Asp Tyr Met Pro Ser Met Lys
    3365                3370                3375

Arg Phe Arg Arg Glu Glu Glu Glu Ala Gly Val Leu Trp
    3380                3385                3390
```

<210> SEQ ID NO 30
<211> LENGTH: 10723
<212> TYPE: DNA
<213> ORGANISM: Artificial Sequence
<220> FEATURE:
<223> OTHER INFORMATION: Derived from Dengue virus serotype 2/Dengue virus serotype 4, Denvax-4f

<400> SEQUENCE: 30
agttgttagt ctacgtggac cgacaaagac agattctttg agggagctaa gctcaatgta 60

-continued

```
gttctaacag tttttaatt agagagcaga tctctgatga ataaccaacg gaaaaaggcg    120
aaaaacacgc ctttcaatat gctgaaacgc gagagaaacc gcgtgtcgac tgtgcaacag    180
ctgacaaaga gattctcact tggaatgctg cagggacgag gaccattaaa actgttcatg    240
gccctggtgg cgttccttcg tttcctaaca atcccaccaa cagcagggat attgaagaga    300
tggggaacaa ttaaaaaatc aaaagctatt aatgttttga gagggttcag gaaagagatt    360
ggaaggatgc tgaacatctt gaataggaga cgcagctctg caggcatgat cattatgctg    420
attccaacag tgatggcgtt ccatttaacc acgcgtgatg gcgaacccct catgatagtg    480
gcaaaacatg aaagggggag acctctcttg tttaagacaa cagaggggat caacaaatgc    540
actctcattg ccatggactt gggtgaaatg tgtgaggaca ctgtcacgta taaatgcccc    600
ttactggtca ataccgaacc tgaagacatt gattgctggt gcaatctcac gtctacctgg    660
gtcatgtatg ggacatgcac ccagagcgga gaacggagac gagagaagcg ctcagtagct    720
ttaacaccac attcaggaat gggattggaa acaagagctg agacatggat gtcatcggaa    780
ggggcttgga agcatgctca gagagtagag agctggatac tcagaaaccc aggattcgcg    840
ctcttggcag gatttatggc ttatatgatt gggcaaacag gaatccagcg aactgtcttc    900
tttgtcctaa tgatgctggt cgccccatcc tacggaatgc gatgcgtagg agtaggaaac    960
agagactttg tggaaggagt ctcaggtgga gcatgggtcg atctggtgct agaacatgga   1020
ggatgcgtca caaccatggc ccagggaaaa ccaaccttgg attttgaact gactaagaca   1080
acagccaagg aagtggctct gttaagaacc tattgcattg aagcctcaat atcaaacata   1140
accacggcaa caagatgtcc aacgcaagga gagccttatc taaaagagga acaagaccaa   1200
cagtacattt gccggagaga tgtggtagac agagggtggg gcaatggctg tggcttgttt   1260
ggaaaaggag gagttgtgac atgtgcgaag ttttcatgtt cggggaagat aacaggcaat   1320
ttggtccaaa ttgagaacct tgaatacaca gtggttgtaa cagtccacaa tggagacacc   1380
catgcagtag gaaatgacac gtccaatcat ggagttacag ccacgataac tcccaggtca   1440
ccatcggtgg aagtcaaatt gccggactat ggagaactaa cactcgattg tgaacccagg   1500
tctggaattg actttaatga gatgattctg atgaaaatga aaaagaaaac atggcttgtg   1560
cataagcaat ggtttttgga tctacctcta ccatggacag caggagcaga cacatcagag   1620
gttcactgga attacaaaga gagaatggtg acatttaagg ttcctcatgc caagagacag   1680
gatgtgacag tgctgggatc tcaggaagga gccatgcatt ctgccctcgc tggagccaca   1740
gaagtggact ccggtgatgg aaatcacatg tttgcaggac atctcaagtg caaagtccgt   1800
atggagaaat tgagaatcaa gggaatgtca tacacgatgt gttcaggaaa gttctcaatt   1860
gacaaagaga tggcagaaac acagcatggg acaacagtgg tgaaagtcaa gtatgaaggt   1920
gctggagctc cgtgtaaagt ccccatagag ataagagatg tgaacaagga aaaagtggtt   1980
gggcgtatca tctcatccac ccctttggct gagaatacca acagtgtaac caacatagag   2040
ttagaacccc cctttgggga cagctacata gtgataggtg ttggaaacag tgcattaaca   2100
ctccattggt tcaggaaagg gagttccatt ggcaagatgt ttgagtccac atacagaggt   2160
gcaaaacgaa tggccattct aggtgaaaca gcttgggatt ttggttccgt tggtggactg   2220
ttcacatcat tgggaaaggc tgtgcaccag gtttttggaa gtgtgtatac aaccctgttt   2280
ggaggagtct catggatgat tagaatccta attgggttcc tagtgttgtg gattggcacg   2340
aactcaagga acacttcaat ggctatgacg tgcatagctg ccggcattgt gacactgtat   2400
```

-continued

```
ttgggagtca tggtgcaggc cgatagtggt tgcgttgtga gctggaaaaa caaagaactg   2460
aaatgtggca gtgggatttt catcacagac aacgtgcaca catggacaga acaatacaag   2520
ttccaaccag aatccccttc aaaactagct tcagctatcc agaaagccca tgaagaggac   2580
atttgtggaa tccgctcagt aacaagactg gagaatctga tgtggaaaca aataacacca   2640
gaattgaatc acattctatc agaaaatgag gtgaagttaa ctattatgac aggagacatc   2700
aaaggaatca tgcaggcagg aaaacgatct ctgcggcctc agcccactga gctgaagtat   2760
tcatggaaaa catggggcaa agcaaaaatg ctctctacag agtctcataa ccagaccttt   2820
ctcattgatg gccccgaaac agcagaatgc cccaacacaa atagagcttg gaattcgttg   2880
gaagttgaag actatggctt tggagtattc accaccaata tatggctaaa attgaaagaa   2940
aaacaggatg tattctgcga ctcaaaactc atgtcagcgg ccataaaaga caacagagcc   3000
gtccatgccg atatgggtta ttggatagaa agtgcactca atgacacatg gaagatagag   3060
aaagcctctt tcattgaagt taaaaactgc cactggccaa aatcacacac cctctggagc   3120
aatggagtgc tagaaagtga gatgataatt ccaaagaatc tcgctggacc agtgtctcaa   3180
cacaactata gaccaggcta ccatacacaa ataacaggac catggcatct aggtaagctt   3240
gagatggact ttgatttctg tgatggaaca acagtggtag tgactgagga ctgcggaaat   3300
agaggaccct ctttgagaac aaccactgcc tctggaaaac tcataacaga atggtgctgc   3360
cgatcttgca cattaccacc gctaagatac agaggtgagg atgggtgctg gtacgggatg   3420
gaaatcagac cattgaagga gaaagaagag aatttggtca actccttggt cacagctgga   3480
catgggcagg tcgacaactt ttcactagga gtcttgggaa tggcattgtt cctggaggaa   3540
atgcttagga cccgagtagg aacgaaacat gcaatactac tagttgcagt ttcttttgtg   3600
acattgatca cagggaacat gtcctttaga gacctgggaa gagtgatggt tatggtaggc   3660
gccactatga cggatgacat aggtatgggc gtgacttatc ttgccctact agcagccttc   3720
aaagtcagac caacttttgc agctggacta ctcttgagaa agctgacctc caaggaattg   3780
atgatgacta ctataggaat tgtactcctc tcccagagca ccataccaga gaccattctt   3840
gagttgactg atgcgttagc cttaggcatg atggtcctca aaatggtgag aaatatggaa   3900
aagtatcaat tggcagtgac tatcatggct atcttgtgcg tcccaaacgc agtgatatta   3960
caaaacgcat ggaaagtgag ttgcacaata ttggcagtgg tgtccgtttc cccactgctc   4020
ttaacatcct cacagcaaaa aacagattgg ataccattag cattgacgat caaaggtctc   4080
aatccaacag ctatttttct aacaaccctc tcaagaacca gcaagaaaag gagctggcca   4140
ttaaatgagg ctatcatggc agtcgggatg gtgagcattt tagccagttc tctcctaaaa   4200
aatgatattc ccatgacagg accattagtg gctggagggc tcctcactgt gtgctacgtg   4260
ctcactggac gatcggccga tttggaactg gagagagcag ccgatgtcaa atgggaagac   4320
caggcagaga tatcaggaag cagtccaatc ctgtcaataa caatatcaga agatggtagc   4380
atgtcgataa aaaatgaaga ggaagaacaa acactgacca tactcattag aacaggattg   4440
ctggtgatct caggactttt tcctgtatca ataccaatca cggcagcagc atggtacctg   4500
tgggaagtga agaaacaacg ggccggagta ttgtgggatg ttccttcacc cccacccatg   4560
ggaaaggctg aactggaaga tggagcctat agaattaagc aaaaagggat tcttggatat   4620
tcccagatcg gagccggagt ttacaaagaa ggaacattcc atacaatgtg gcatgtcaca   4680
cgtggcgctg ttctaatgca taaaggaaag aggattgaac catcatgggc ggacgtcaag   4740
aaagacctaa tatcatatgg aggaggctgg aagttagaag gagaatggaa ggaaggagaa   4800
```

-continued

```
gaagtccagg tattggcact ggagcctgga aaaaatccaa gagccgtcca aacgaaacct   4860
ggtcttttca aaaccaacgc cggaacaata ggtgctgtat ctctggactt ttctcctgga   4920
acgtcaggat ctccaattat cgacaaaaaa ggaaaagttg tgggtcttta tggtaatggt   4980
gttgttacaa ggagtggagc atatgtgagt gctatagccc agactgaaaa aagcattgaa   5040
gacaacccag agatcgaaga tgacattttc cgaaagagaa gactgaccat catggacctc   5100
cacccaggag cgggaaagac gaagagatac cttccggcca tagtcagaga agctataaaa   5160
cggggtttga gaacattaat cttggccccc actagagttg tggcagctga aatggaggaa   5220
gcccttagag gacttccaat aagataccag accccagcca tcagagctgt gcacaccggg   5280
cgggagattg tggacctaat gtgtcatgcc acatttacca tgaggctgct atcaccagtt   5340
agagtgccaa actacaacct gattatcatg gacgaagccc atttcacaga cccagcaagt   5400
atagcagcta gaggatacat ctcaactcga gtggagatgg gtgaggcagc tgggattttt   5460
atgacagcca ctcccccggg aagcagagac ccatttcctc agagcaatgc accaatcata   5520
gatgaagaaa gagaaatccc tgaacgctcg tggaattccg gacatgaatg ggtcacggat   5580
tttaaaggga agactgtttg gttcgttcca agtataaaag caggaaatga tatagcagct   5640
tgcctgagga aaaatggaaa gaaagtgata caactcagta ggaagacctt tgattctgag   5700
tatgtcaaga ctagaaccaa tgattgggac ttcgtggtta caactgacat ttcagaaatg   5760
ggtgccaatt tcaaggctga gagggttata gaccccagac gctgcatgaa accagtcata   5820
ctaacagatg gtgaagagcg ggtgattctg gcaggaccta tgccagtgac ccactctagt   5880
gcagcacaaa gaagagggag aataggaaga aatccaaaaa atgagaatga ccagtacata   5940
tacatggggg aacctctgga aaatgatgaa gactgtgcac actggaaaga agctaaaatg   6000
ctcctagata acatcaacac gccagaagga atcattccta gcatgttcga accagagcgt   6060
gaaaaggtgg atgccattga tggcgaatac cgcttgagag gagaagcaag gaaaaccttt   6120
gtagacttaa tgagaagagg agacctacca gtctggttgg cctacagagt ggcagctgaa   6180
ggcatcaact acgcagacag aaggtggtgt tttgatggag tcaagaacaa ccaaatccta   6240
gaagaaaacg tggaagttga aatctggaca aaagaagggg aaaggaagaa attgaaaccc   6300
agatggttgg atgctaggat ctattctgac ccactggcgc taaaagaatt taaggaattt   6360
gcagccggaa gaaagtctct gaccctgaac ctaatcacag aaatgggtag gctcccaacc   6420
ttcatgactc agaaggcaag agacgcactg gacaacttag cagtgctgca cacggctgag   6480
gcaggtggaa gggcgtacaa ccatgctctc agtgaactgc cggagaccct ggagacattg   6540
cttttactga cacttctggc tacagtcacg ggagggatct tttattcttt gatgagcgga   6600
aggggcatag ggaagatgac cctgggaatg tgctgcataa tcacggctag catcctccta   6660
tggtacgcac aaatacagcc acactggata gcagcttcaa taatactgga gtttttttctc   6720
atagttttgc ttattccaga acctgaaaaa cagagaacac cccaagacaa ccaactgacc   6780
tacgttgtca tagccatcct cacagtggtg gccgcaacca tggcaaacga gatgggtttc   6840
ctagaaaaaa cgaagaaaga tctcggattg ggaagcattg caacccagca acccgagagc   6900
aacatcctgg acatagatct acgtcctgca tcagcatgga cgctgtatgc cgtggccaca   6960
acatttgtta caccaatgtt gagacatagc attgaaaatt cctcagtgaa tgtgtcccta   7020
acagctatag ccaaccaagc cacagtgtta atgggtctcg ggaaaggatg gccattgtca   7080
aagatggaca tcggagttcc ccttctcgcc attggatgct actcacaagt caaccccata   7140
```

actctcacag cagctctttt cttattggta gcacattatg ccatcatagg gccaggactc 7200
caagcaaaag caaccagaga agctcagaaa agagcagcgg cgggcatcat gaaaaaccca 7260
actgtcgatg gaataacagt gattgaccta gatccaatac cttatgatcc aaagtttgaa 7320
aagcagttgg gacaagtaat gctcctagtc ctctgcgtga ctcaagtatt gatgatgagg 7380
actacatggg ctctgtgtga ggctttaacc ttagctaccg ggcccatctc cacattgtgg 7440
gaaggaaatc cagggaggtt ttggaacact accattgcgg tgtcaatggc taacattttt 7500
agagggagtt acttggccgg agctggactt ctcttttcta ttatgaagaa cacaaccaac 7560
acaagaaggg gaactggcaa cataggagag acgcttggag agaaatggaa aagccgattg 7620
aacgcattgg gaaaaagtga attccagatc tacaagaaaa gtggaatcca ggaagtggat 7680
agaaccttag caaaagaagg cattaaaaga ggagaaacgg accatcacgc tgtgtcgcga 7740
ggctcagcaa aactgagatg gttcgttgag agaaacatgg tcacaccaga agggaaagta 7800
gtggacctcg gttgtggcag aggaggctgg tcatactatt gtggaggact aaagaatgta 7860
agagaagtca aaggcctaac aaaaggagga ccaggacacg aagaacccat ccccatgtca 7920
acatatgggt ggaatctagt gcgtcttcaa agtggagttg acgttttctt catcccgcca 7980
gaaaagtgtg acacattatt gtgtgacata ggggagtcat caccaaatcc cacagtggaa 8040
gcaggacgaa cactcagagt ccttaactta gtagaaaatt ggttgaacaa caacactcaa 8100
ttttgcataa aggttctcaa cccatatatg ccctcagtca tagaaaaaat ggaagcacta 8160
caaaggaaat atggaggagc cttagtgagg aatccactct cacgaaactc cacacatgag 8220
atgtactggg tatccaatgc ttccgggaac atagtgtcat cagtgaacat gatttcaagg 8280
atgttgatca acagatttac aatgagatac aagaaagcca cttacgagcc ggatgttgac 8340
ctcggaagcg gaacccgtaa catcgggatt gaaagtgaga taccaaacct agatataatt 8400
gggaaaagaa tagaaaaaat aaagcaagag catgaaacat catggcacta tgaccaagac 8460
cacccataca aaacgtgggc ataccatggt agctatgaaa caaaacagac tggatcagca 8520
tcatccatgg tcaacggagt ggtcaggctg ctgacaaaac cttgggacgt cgtccccatg 8580
gtgacacaga tggcaatgac agacacgact ccatttggac aacagcgcgt tttaaagag 8640 aaagtggaca cgagaaccca agaaccgaaa gaaggcacga agaaactaat gaaaataaca 8700
gcagagtggc tttggaaaga attagggaag aaaaagacac ccaggatgtg caccagagaa 8760
gaattcacaa gaaaggtgag aagcaatgca gccttggggg ccatattcac tgatgagaac 8820
aagtggaagt cggcacgtga ggctgttgaa gatagtaggt tttgggagct ggttgacaag 8880
gaaaggaatc tccatcttga aggaaagtgt gaaacatgtg tgtacaacat gatgggaaaa 8940
agagagaaga agctagggga attcggcaag gcaaaaggca gcagagccat atggtacatg 9000
tggcttggag cacgcttctt agagtttgaa gccctaggat tcttaaatga agatcactgg 9060
ttctccagag agaactccct gagtggagtg gaaggagaag ggctgcacaa gctaggttac 9120
attctaagag acgtgagcaa gaaagaggga ggagcaatgt atgccgatga caccgcagga 9180
tgggatacaa gaatcacact agaagaccta aaaaatgaag aaatggtaac aaaccacatg 9240
gaaggagaac acaagaaact agccgaggcc attttcaaac taacgtacca aaacaaggtg 9300
gtgcgtgtgc aaagaccaac accaagaggc acagtaatgg acatcatatc gagaagagac 9360
caaagaggta gtggacaagt tggcacctat ggactcaata ctttcaccaa tatggaagcc 9420
caactaatca gacagatgga gggagaagga gtctttaaaa gcattcagca cctaacaatc 9480
acagaagaaa tcgctgtgca aaactggtta gcaagagtgg ggcgcgaaag gttatcaaga 9540
atggccatca gtggagatga ttgtgttgtg aaacctttag atgacaggtt cgcaagcgct 9600
ttaacagctc taaatgacat gggaaagatt aggaaagaca tacaacaatg ggaaccttca 9660
agaggatgga atgattggac acaagtgccc ttctgttcac accatttcca tgagttaatc 9720
atgaaagacg gtcgcgtact cgttgttcca tgtagaaacc aagatgaact gattggcaga 9780
gcccgaatct cccaaggagc agggtggtct ttgcgggaga cggcctgttt ggggaagtct 9840
tacgcccaaa tgtggagctt gatgtacttc cacagacgcg acctcaggct ggcggcaaat 9900
gctatttgct cggcagtacc atcacattgg gttccaacaa gtcgaacaac ctggtccata 9960
catgctaaac atgaatggat gacaacggaa gacatgctga cagtctggaa cagggtgtgg 10020
attcaagaaa acccatggat ggaagacaaa actccagtgg aatcatggga ggaaatccca 10080
tacttgggga aaagagaaga ccaatggtgc ggctcattga ttgggttaac aagcagggcc 10140
acctgggcaa agaacatcca agcagcaata aatcaagtta gatcccttat aggcaatgaa 10200
gaatacacag attacatgcc atccatgaaa agattcagaa gagaagagga agaagcagga 10260
gttctgtggt agaaagcaaa actaacatga aacaaggcta gaagtcaggt cggattaagc 10320
catagtacgg aaaaaactat gctacctgtg agccccgtcc aaggacgtta aaagaagtca 10380
ggccatcata aatgccatag cttgagtaaa ctatgcagcc tgtagctcca cctgagaagg 10440
tgtaaaaaat ccgggaggcc acaaaccatg gaagctgtac gcatggcgta gtggactagc 10500
ggttagagga gacccctccc ttacaaatcg cagcaacaat gggggcccaa ggcgagatga 10560
agctgtagtc tcgctggaag gactagaggt tagaggagac ccccccgaaa caaaaaacag 10620
catattgacg ctgggaaaga ccagagatcc tgctgtctcc tcagcatcat tccaggcaca 10680
gaacgccaga aaatggaatg gtgctgttga atcaacaggt tct 10723

<210> SEQ ID NO 31
<211> LENGTH: 3391
<212> TYPE: PRT
<213> ORGANISM: Artificial Sequence
<220> FEATURE:
<223> OTHER INFORMATION: Derived from Dengue virus serotype 2/Dengue
virus serotype 4, DenVax-4f

<400> SEQUENCE: 31

Met Asn Asn Gln Arg Lys Lys Ala Lys Asn Thr Pro Phe Asn Met Leu
1 5 10 15

Lys Arg Glu Arg Asn Arg Val Ser Thr Val Gln Gln Leu Thr Lys Arg
20 25 30

Phe Ser Leu Gly Met Leu Gln Gly Arg Gly Pro Leu Lys Leu Phe Met
35 40 45

Ala Leu Val Ala Phe Leu Arg Phe Leu Thr Ile Pro Pro Thr Ala Gly
50 55 60

Ile Leu Lys Arg Trp Gly Thr Ile Lys Lys Ser Lys Ala Ile Asn Val
65 70 75 80

Leu Arg Gly Phe Arg Lys Glu Ile Gly Arg Met Leu Asn Ile Leu Asn
85 90 95

Arg Arg Arg Ser Ser Ala Gly Met Ile Ile Met Leu Ile Pro Thr Val
100 105 110

Met Ala Phe His Leu Thr Thr Arg Asp Gly Glu Pro Leu Met Ile Val
115 120 125

Ala Lys His Glu Arg Gly Arg Pro Leu Leu Phe Lys Thr Thr Glu Gly
130 135 140

-continued

Ile Asn Lys Cys Thr Leu Ile Ala Met Asp Leu Gly Glu Met Cys Glu
145 150 155 160

Asp Thr Val Thr Tyr Lys Cys Pro Leu Leu Val Asn Thr Glu Pro Glu
165 170 175

Asp Ile Asp Cys Trp Cys Asn Leu Thr Ser Thr Trp Val Met Tyr Gly
180 185 190

Thr Cys Thr Gln Ser Gly Glu Arg Arg Arg Glu Lys Arg Ser Val Ala
195 200 205

Leu Thr Pro His Ser Gly Met Gly Leu Glu Thr Arg Ala Glu Thr Trp
210 215 220

Met Ser Ser Glu Gly Ala Trp Lys His Ala Gln Arg Val Glu Ser Trp
225 230 235 240

Ile Leu Arg Asn Pro Gly Phe Ala Leu Leu Ala Gly Phe Met Ala Tyr
245 250 255

Met Ile Gly Gln Thr Gly Ile Gln Arg Thr Val Phe Phe Val Leu Met
260 265 270

Met Leu Val Ala Pro Ser Tyr Gly Met Arg Cys Val Gly Val Gly Asn
275 280 285

Arg Asp Phe Val Glu Gly Val Ser Gly Gly Ala Trp Val Asp Leu Val
290 295 300

Leu Glu His Gly Gly Cys Val Thr Thr Met Ala Gln Gly Lys Pro Thr
305 310 315 320

Leu Asp Phe Glu Leu Thr Lys Thr Thr Ala Lys Glu Val Ala Leu Leu
325 330 335

Arg Thr Tyr Cys Ile Glu Ala Ser Ile Ser Asn Ile Thr Thr Ala Thr
340 345 350

Arg Cys Pro Thr Gln Gly Glu Pro Tyr Leu Lys Glu Glu Gln Asp Gln
355 360 365

Gln Tyr Ile Cys Arg Arg Asp Val Val Asp Arg Gly Trp Gly Asn Gly
370 375 380

Cys Gly Leu Phe Gly Lys Gly Gly Val Val Thr Cys Ala Lys Phe Ser
385 390 395 400

Cys Ser Gly Lys Ile Thr Gly Asn Leu Val Gln Ile Glu Asn Leu Glu
405 410 415

Tyr Thr Val Val Val Thr Val His Asn Gly Asp Thr His Ala Val Gly
420 425 430

Asn Asp Thr Ser Asn His Gly Val Thr Ala Thr Ile Thr Pro Arg Ser
435 440 445

Pro Ser Val Glu Val Lys Leu Pro Asp Tyr Gly Glu Leu Thr Leu Asp
450 455 460

Cys Glu Pro Arg Ser Gly Ile Asp Phe Asn Glu Met Ile Leu Met Lys
465 470 475 480

Met Lys Lys Lys Thr Trp Leu Val His Lys Gln Trp Phe Leu Asp Leu
485 490 495

Pro Leu Pro Trp Thr Ala Gly Ala Asp Thr Ser Glu Val His Trp Asn
500 505 510

Tyr Lys Glu Arg Met Val Thr Phe Lys Val Pro His Ala Lys Arg Gln
515 520 525

Asp Val Thr Val Leu Gly Ser Gln Glu Gly Ala Met His Ser Ala Leu
530 535 540

Ala Gly Ala Thr Glu Val Asp Ser Gly Asp Gly Asn His Met Phe Ala
545 550 555 560

Gly His Leu Lys Cys Lys Val Arg Met Glu Lys Leu Arg Ile Lys Gly

```
                565                 570                 575

Met Ser Tyr Thr Met Cys Ser Gly Lys Phe Ser Ile Asp Lys Glu Met
            580                 585                 590

Ala Glu Thr Gln His Gly Thr Thr Val Val Lys Val Lys Tyr Glu Gly
        595                 600                 605

Ala Gly Ala Pro Cys Lys Val Pro Ile Glu Ile Arg Asp Val Asn Lys
    610                 615                 620

Glu Lys Val Val Gly Arg Ile Ile Ser Ser Thr Pro Leu Ala Glu Asn
625                 630                 635                 640

Thr Asn Ser Val Thr Asn Ile Glu Leu Glu Pro Pro Phe Gly Asp Ser
                645                 650                 655

Tyr Ile Val Ile Gly Val Gly Asn Ser Ala Leu Thr Leu His Trp Phe
            660                 665                 670

Arg Lys Gly Ser Ser Ile Gly Lys Met Phe Glu Ser Thr Tyr Arg Gly
        675                 680                 685

Ala Lys Arg Met Ala Ile Leu Gly Glu Thr Ala Trp Asp Phe Gly Ser
    690                 695                 700

Val Gly Gly Leu Phe Thr Ser Leu Gly Lys Ala Val His Gln Val Phe
705                 710                 715                 720

Gly Ser Val Tyr Thr Thr Leu Phe Gly Gly Val Ser Trp Met Ile Arg
                725                 730                 735

Ile Leu Ile Gly Phe Leu Val Leu Trp Ile Gly Thr Asn Ser Arg Asn
            740                 745                 750

Thr Ser Met Ala Met Thr Cys Ile Ala Ala Gly Ile Val Thr Leu Tyr
        755                 760                 765

Leu Gly Val Met Val Gln Ala Asp Ser Gly Cys Val Val Ser Trp Lys
    770                 775                 780

Asn Lys Glu Leu Lys Cys Gly Ser Gly Ile Phe Ile Thr Asp Asn Val
785                 790                 795                 800

His Thr Trp Thr Glu Gln Tyr Lys Phe Gln Pro Glu Ser Pro Ser Lys
                805                 810                 815

Leu Ala Ser Ala Ile Gln Lys Ala His Glu Glu Asp Ile Cys Gly Ile
            820                 825                 830

Arg Ser Val Thr Arg Leu Glu Asn Leu Met Trp Lys Gln Ile Thr Pro
        835                 840                 845

Glu Leu Asn His Ile Leu Ser Glu Asn Glu Val Lys Leu Thr Ile Met
    850                 855                 860

Thr Gly Asp Ile Lys Gly Ile Met Gln Ala Gly Lys Arg Ser Leu Arg
865                 870                 875                 880

Pro Gln Pro Thr Glu Leu Lys Tyr Ser Trp Lys Thr Trp Gly Lys Ala
                885                 890                 895

Lys Met Leu Ser Thr Glu Ser His Asn Gln Thr Phe Leu Ile Asp Gly
            900                 905                 910

Pro Glu Thr Ala Glu Cys Pro Asn Thr Asn Arg Ala Trp Asn Ser Leu
        915                 920                 925

Glu Val Glu Asp Tyr Gly Phe Gly Val Phe Thr Thr Asn Ile Trp Leu
    930                 935                 940

Lys Leu Lys Glu Lys Gln Asp Val Phe Cys Asp Ser Lys Leu Met Ser
945                 950                 955                 960

Ala Ala Ile Lys Asp Asn Arg Ala Val His Ala Asp Met Gly Tyr Trp
                965                 970                 975

Ile Glu Ser Ala Leu Asn Asp Thr Trp Lys Ile Glu Lys Ala Ser Phe
            980                 985                 990
```

```
Ile Glu Val Lys Asn Cys His Trp  Pro Lys Ser His Thr  Leu Trp Ser
        995                 1000                 1005

Asn Gly  Val Leu Glu Ser Glu  Met Ile Ile Pro Lys  Asn Leu Ala
    1010                 1015                 1020

Gly Pro  Val Ser Gln His Asn  Tyr Arg Pro Gly Tyr  His Thr Gln
    1025                 1030                 1035

Ile Thr  Gly Pro Trp His Leu  Gly Lys Leu Glu Met  Asp Phe Asp
    1040                 1045                 1050

Phe Cys  Asp Gly Thr Thr Val  Val Val Thr Glu Asp  Cys Gly Asn
    1055                 1060                 1065

Arg Gly  Pro Ser Leu Arg Thr  Thr Thr Ala Ser Gly  Lys Leu Ile
    1070                 1075                 1080

Thr Glu  Trp Cys Cys Arg Ser  Cys Thr Leu Pro Pro  Leu Arg Tyr
    1085                 1090                 1095

Arg Gly  Glu Asp Gly Cys Trp  Tyr Gly Met Glu Ile  Arg Pro Leu
    1100                 1105                 1110

Lys Glu  Lys Glu Glu Asn Leu  Val Asn Ser Leu Val  Thr Ala Gly
    1115                 1120                 1125

His Gly  Gln Val Asp Asn Phe  Ser Leu Gly Val Leu  Gly Met Ala
    1130                 1135                 1140

Leu Phe  Leu Glu Glu Met Leu  Arg Thr Arg Val Gly  Thr Lys His
    1145                 1150                 1155

Ala Ile  Leu Leu Val Ala Val  Ser Phe Val Thr Leu  Ile Thr Gly
    1160                 1165                 1170

Asn Met  Ser Phe Arg Asp Leu  Gly Arg Val Met Val  Met Val Gly
    1175                 1180                 1185

Ala Thr  Met Thr Asp Asp Ile  Gly Met Gly Val Thr  Tyr Leu Ala
    1190                 1195                 1200

Leu Leu  Ala Ala Phe Lys Val  Arg Pro Thr Phe Ala  Ala Gly Leu
    1205                 1210                 1215

Leu Leu  Arg Lys Leu Thr Ser  Lys Glu Leu Met Met  Thr Thr Ile
    1220                 1225                 1230

Gly Ile  Val Leu Leu Ser Gln  Ser Thr Ile Pro Glu  Thr Ile Leu
    1235                 1240                 1245

Glu Leu  Thr Asp Ala Leu Ala  Leu Gly Met Met Val  Leu Lys Met
    1250                 1255                 1260

Val Arg  Asn Met Glu Lys Tyr  Gln Leu Ala Val Thr  Ile Met Ala
    1265                 1270                 1275

Ile Leu  Cys Val Pro Asn Ala  Val Ile Leu Gln Asn  Ala Trp Lys
    1280                 1285                 1290

Val Ser  Cys Thr Ile Leu Ala  Val Val Ser Val Ser  Pro Leu Leu
    1295                 1300                 1305

Leu Thr  Ser Ser Gln Gln Lys  Thr Asp Trp Ile Pro  Leu Ala Leu
    1310                 1315                 1320

Thr Ile  Lys Gly Leu Asn Pro  Thr Ala Ile Phe Leu  Thr Thr Leu
    1325                 1330                 1335

Ser Arg  Thr Ser Lys Lys Arg  Ser Trp Pro Leu Asn  Glu Ala Ile
    1340                 1345                 1350

Met Ala  Val Gly Met Val Ser  Ile Leu Ala Ser Ser  Leu Leu Lys
    1355                 1360                 1365

Asn Asp  Ile Pro Met Thr Gly  Pro Leu Val Ala Gly  Gly Leu Leu
    1370                 1375                 1380
```

```
Thr Val  Cys Tyr Val Leu Thr  Gly Arg Ser Ala Asp  Leu Glu Leu
    1385                 1390                 1395

Glu Arg  Ala Ala Asp Val Lys  Trp Glu Asp Gln Ala  Glu Ile Ser
    1400                 1405                 1410

Gly Ser  Ser Pro Ile Leu Ser  Ile Thr Ile Ser Glu  Asp Gly Ser
    1415                 1420                 1425

Met Ser  Ile Lys Asn Glu Glu  Glu Glu Gln Thr Leu  Thr Ile Leu
    1430                 1435                 1440

Ile Arg  Thr Gly Leu Leu Val  Ile Ser Gly Leu Phe  Pro Val Ser
    1445                 1450                 1455

Ile Pro  Ile Thr Ala Ala Ala  Trp Tyr Leu Trp Glu  Val Lys Lys
    1460                 1465                 1470

Gln Arg  Ala Gly Val Leu Trp  Asp Val Pro Ser Pro  Pro Pro Met
    1475                 1480                 1485

Gly Lys  Ala Glu Leu Glu Asp  Gly Ala Tyr Arg Ile  Lys Gln Lys
    1490                 1495                 1500

Gly Ile  Leu Gly Tyr Ser Gln  Ile Gly Ala Gly Val  Tyr Lys Glu
    1505                 1510                 1515

Gly Thr  Phe His Thr Met Trp  His Val Thr Arg Gly  Ala Val Leu
    1520                 1525                 1530

Met His  Lys Gly Lys Arg Ile  Glu Pro Ser Trp Ala  Asp Val Lys
    1535                 1540                 1545

Lys Asp  Leu Ile Ser Tyr Gly  Gly Gly Trp Lys Leu  Glu Gly Glu
    1550                 1555                 1560

Trp Lys  Glu Gly Glu Glu Val  Gln Val Leu Ala Leu  Glu Pro Gly
    1565                 1570                 1575

Lys Asn  Pro Arg Ala Val Gln  Thr Lys Pro Gly Leu  Phe Lys Thr
    1580                 1585                 1590

Asn Ala  Gly Thr Ile Gly Ala  Val Ser Leu Asp Phe  Ser Pro Gly
    1595                 1600                 1605

Thr Ser  Gly Ser Pro Ile Ile  Asp Lys Lys Gly Lys  Val Val Gly
    1610                 1615                 1620

Leu Tyr  Gly Asn Gly Val Val  Thr Arg Ser Gly Ala  Tyr Val Ser
    1625                 1630                 1635

Ala Ile  Ala Gln Thr Glu Lys  Ser Ile Glu Asp Asn  Pro Glu Ile
    1640                 1645                 1650

Glu Asp  Asp Ile Phe Arg Lys  Arg Arg Leu Thr Ile  Met Asp Leu
    1655                 1660                 1665

His Pro  Gly Ala Gly Lys Thr  Lys Arg Tyr Leu Pro  Ala Ile Val
    1670                 1675                 1680

Arg Glu  Ala Ile Lys Arg Gly  Leu Arg Thr Leu Ile  Leu Ala Pro
    1685                 1690                 1695

Thr Arg  Val Val Ala Ala Glu  Met Glu Glu Ala Leu  Arg Gly Leu
    1700                 1705                 1710

Pro Ile  Arg Tyr Gln Thr Pro  Ala Ile Arg Ala Val  His Thr Gly
    1715                 1720                 1725

Arg Glu  Ile Val Asp Leu Met  Cys His Ala Thr Phe  Thr Met Arg
    1730                 1735                 1740

Leu Leu  Ser Pro Val Arg Val  Pro Asn Tyr Asn Leu  Ile Ile Met
    1745                 1750                 1755

Asp Glu  Ala His Phe Thr Asp  Pro Ala Ser Ile Ala  Ala Arg Gly
    1760                 1765                 1770

Tyr Ile  Ser Thr Arg Val Glu  Met Gly Glu Ala Ala  Gly Ile Phe
```

```
    1775                1780                1785

Met Thr  Ala Thr Pro Pro Gly  Ser Arg Asp Pro Phe  Pro Gln Ser
    1790                1795                1800

Asn Ala  Pro Ile Ile Asp Glu  Glu Arg Glu Ile Pro  Glu Arg Ser
    1805                1810                1815

Trp Asn  Ser Gly His Glu Trp  Val Thr Asp Phe Lys  Gly Lys Thr
    1820                1825                1830

Val Trp  Phe Val Pro Ser Ile  Lys Ala Gly Asn Asp  Ile Ala Ala
    1835                1840                1845

Cys Leu  Arg Lys Asn Gly Lys  Lys Val Ile Gln Leu  Ser Arg Lys
    1850                1855                1860

Thr Phe  Asp Ser Glu Tyr Val  Lys Thr Arg Thr Asn  Asp Trp Asp
    1865                1870                1875

Phe Val  Val Thr Thr Asp Ile  Ser Glu Met Gly Ala  Asn Phe Lys
    1880                1885                1890

Ala Glu  Arg Val Ile Asp Pro  Arg Arg Cys Met Lys  Pro Val Ile
    1895                1900                1905

Leu Thr  Asp Gly Glu Glu Arg  Val Ile Leu Ala Gly  Pro Met Pro
    1910                1915                1920

Val Thr  His Ser Ser Ala Ala  Gln Arg Arg Gly Arg  Ile Gly Arg
    1925                1930                1935

Asn Pro  Lys Asn Glu Asn Asp  Gln Tyr Ile Tyr Met  Gly Glu Pro
    1940                1945                1950

Leu Glu  Asn Asp Glu Asp Cys  Ala His Trp Lys Glu  Ala Lys Met
    1955                1960                1965

Leu Leu  Asp Asn Ile Asn Thr  Pro Glu Gly Ile Ile  Pro Ser Met
    1970                1975                1980

Phe Glu  Pro Glu Arg Glu Lys  Val Asp Ala Ile Asp  Gly Glu Tyr
    1985                1990                1995

Arg Leu  Arg Gly Glu Ala Arg  Lys Thr Phe Val Asp  Leu Met Arg
    2000                2005                2010

Arg Gly  Asp Leu Pro Val Trp  Leu Ala Tyr Arg Val  Ala Ala Glu
    2015                2020                2025

Gly Ile  Asn Tyr Ala Asp Arg  Arg Trp Cys Phe Asp  Gly Val Lys
    2030                2035                2040

Asn Asn  Gln Ile Leu Glu Glu  Asn Val Glu Val Glu  Ile Trp Thr
    2045                2050                2055

Lys Glu  Gly Glu Arg Lys Lys  Leu Lys Pro Arg Trp  Leu Asp Ala
    2060                2065                2070

Arg Ile  Tyr Ser Asp Pro Leu  Ala Leu Lys Glu Phe  Lys Glu Phe
    2075                2080                2085

Ala Ala  Gly Arg Lys Ser Leu  Thr Leu Asn Leu Ile  Thr Glu Met
    2090                2095                2100

Gly Arg  Leu Pro Thr Phe Met  Thr Gln Lys Ala Arg  Asp Ala Leu
    2105                2110                2115

Asp Asn  Leu Ala Val Leu His  Thr Ala Glu Ala Gly  Gly Arg Ala
    2120                2125                2130

Tyr Asn  His Ala Leu Ser Glu  Leu Pro Glu Thr Leu  Glu Thr Leu
    2135                2140                2145

Leu Leu  Leu Thr Leu Leu Ala  Thr Val Thr Gly Gly  Ile Phe Leu
    2150                2155                2160

Phe Leu  Met Ser Gly Arg Gly  Ile Gly Lys Met Thr  Leu Gly Met
    2165                2170                2175
```

```
Cys Cys  Ile Ile Thr Ala Ser  Ile Leu Leu Trp Tyr  Ala Gln Ile
    2180                 2185                 2190

Gln Pro  His Trp Ile Ala Ala  Ser Ile Ile Leu Glu  Phe Phe Leu
    2195                 2200                 2205

Ile Val  Leu Leu Ile Pro Glu  Pro Glu Lys Gln Arg  Thr Pro Gln
    2210                 2215                 2220

Asp Asn  Gln Leu Thr Tyr Val  Val Ile Ala Ile Leu  Thr Val Val
    2225                 2230                 2235

Ala Ala  Thr Met Ala Asn Glu  Met Gly Phe Leu Glu  Lys Thr Lys
    2240                 2245                 2250

Lys Asp  Leu Gly Leu Gly Ser  Ile Ala Thr Gln Gln  Pro Glu Ser
    2255                 2260                 2265

Asn Ile  Leu Asp Ile Asp Leu  Arg Pro Ala Ser Ala  Trp Thr Leu
    2270                 2275                 2280

Tyr Ala  Val Ala Thr Thr Phe  Val Thr Pro Met Leu  Arg His Ser
    2285                 2290                 2295

Ile Glu  Asn Ser Ser Val Asn  Val Ser Leu Thr Ala  Ile Ala Asn
    2300                 2305                 2310

Gln Ala  Thr Val Leu Met Gly  Leu Gly Lys Gly Trp  Pro Leu Ser
    2315                 2320                 2325

Lys Met  Asp Ile Gly Val Pro  Leu Leu Ala Ile Gly  Cys Tyr Ser
    2330                 2335                 2340

Gln Val  Asn Pro Ile Thr Leu  Thr Ala Ala Leu Phe  Leu Leu Val
    2345                 2350                 2355

Ala His  Tyr Ala Ile Ile Gly  Pro Gly Leu Gln Ala  Lys Ala Thr
    2360                 2365                 2370

Arg Glu  Ala Gln Lys Arg Ala  Ala Ala Gly Ile Met  Lys Asn Pro
    2375                 2380                 2385

Thr Val  Asp Gly Ile Thr Val  Ile Asp Leu Asp Pro  Ile Pro Tyr
    2390                 2395                 2400

Asp Pro  Lys Phe Glu Lys Gln  Leu Gly Gln Val Met  Leu Leu Val
    2405                 2410                 2415

Leu Cys  Val Thr Gln Val Leu  Met Met Arg Thr Thr  Trp Ala Leu
    2420                 2425                 2430

Cys Glu  Ala Leu Thr Leu Ala  Thr Gly Pro Ile Ser  Thr Leu Trp
    2435                 2440                 2445

Glu Gly  Asn Pro Gly Arg Phe  Trp Asn Thr Thr Ile  Ala Val Ser
    2450                 2455                 2460

Met Ala  Asn Ile Phe Arg Gly  Ser Tyr Leu Ala Gly  Ala Gly Leu
    2465                 2470                 2475

Leu Phe  Ser Ile Met Lys Asn  Thr Thr Asn Thr Arg  Arg Gly Thr
    2480                 2485                 2490

Gly Asn  Ile Gly Glu Thr Leu  Gly Glu Lys Trp Lys  Ser Arg Leu
    2495                 2500                 2505

Asn Ala  Leu Gly Lys Ser Glu  Phe Gln Ile Tyr Lys  Lys Ser Gly
    2510                 2515                 2520

Ile Gln  Glu Val Asp Arg Thr  Leu Ala Lys Glu Gly  Ile Lys Arg
    2525                 2530                 2535

Gly Glu  Thr Asp His His Ala  Val Ser Arg Gly Ser  Ala Lys Leu
    2540                 2545                 2550

Arg Trp  Phe Val Glu Arg Asn  Met Val Thr Pro Glu  Gly Lys Val
    2555                 2560                 2565
```

-continued

```
Val Asp Leu Gly Cys Gly Arg Gly Gly Trp Ser Tyr Tyr Cys Gly
    2570                2575                2580

Gly Leu Lys Asn Val Arg Glu Val Lys Gly Leu Thr Lys Gly Gly
    2585                2590                2595

Pro Gly His Glu Glu Pro Ile Pro Met Ser Thr Tyr Gly Trp Asn
    2600                2605                2610

Leu Val Arg Leu Gln Ser Gly Val Asp Val Phe Phe Ile Pro Pro
    2615                2620                2625

Glu Lys Cys Asp Thr Leu Leu Cys Asp Ile Gly Glu Ser Ser Pro
    2630                2635                2640

Asn Pro Thr Val Glu Ala Gly Arg Thr Leu Arg Val Leu Asn Leu
    2645                2650                2655

Val Glu Asn Trp Leu Asn Asn Asn Thr Gln Phe Cys Ile Lys Val
    2660                2665                2670

Leu Asn Pro Tyr Met Pro Ser Val Ile Glu Lys Met Glu Ala Leu
    2675                2680                2685

Gln Arg Lys Tyr Gly Gly Ala Leu Val Arg Asn Pro Leu Ser Arg
    2690                2695                2700

Asn Ser Thr His Glu Met Tyr Trp Val Ser Asn Ala Ser Gly Asn
    2705                2710                2715

Ile Val Ser Ser Val Asn Met Ile Ser Arg Met Leu Ile Asn Arg
    2720                2725                2730

Phe Thr Met Arg Tyr Lys Lys Ala Thr Tyr Glu Pro Asp Val Asp
    2735                2740                2745

Leu Gly Ser Gly Thr Arg Asn Ile Gly Ile Glu Ser Glu Ile Pro
    2750                2755                2760

Asn Leu Asp Ile Ile Gly Lys Arg Ile Glu Lys Ile Lys Gln Glu
    2765                2770                2775

His Glu Thr Ser Trp His Tyr Asp Gln Asp His Pro Tyr Lys Thr
    2780                2785                2790

Trp Ala Tyr His Gly Ser Tyr Glu Thr Lys Gln Thr Gly Ser Ala
    2795                2800                2805

Ser Ser Met Val Asn Gly Val Val Arg Leu Leu Thr Lys Pro Trp
    2810                2815                2820

Asp Val Val Pro Met Val Thr Gln Met Ala Met Thr Asp Thr Thr
    2825                2830                2835

Pro Phe Gly Gln Gln Arg Val Phe Lys Glu Lys Val Asp Thr Arg
    2840                2845                2850

Thr Gln Glu Pro Lys Glu Gly Thr Lys Lys Leu Met Lys Ile Thr
    2855                2860                2865

Ala Glu Trp Leu Trp Lys Glu Leu Gly Lys Lys Lys Thr Pro Arg
    2870                2875                2880

Met Cys Thr Arg Glu Glu Phe Thr Arg Lys Val Arg Ser Asn Ala
    2885                2890                2895

Ala Leu Gly Ala Ile Phe Thr Asp Glu Asn Lys Trp Lys Ser Ala
    2900                2905                2910

Arg Glu Ala Val Glu Asp Ser Arg Phe Trp Glu Leu Val Asp Lys
    2915                2920                2925

Glu Arg Asn Leu His Leu Glu Gly Lys Cys Glu Thr Cys Val Tyr
    2930                2935                2940

Asn Met Met Gly Lys Arg Glu Lys Lys Leu Gly Glu Phe Gly Lys
    2945                2950                2955

Ala Lys Gly Ser Arg Ala Ile Trp Tyr Met Trp Leu Gly Ala Arg
```

```
    2960                2965                2970

Phe Leu  Glu Phe Glu Ala Leu  Gly Phe Leu Asn Glu  Asp His Trp
    2975                2980                2985

Phe Ser  Arg Glu Asn Ser Leu  Ser Gly Val Glu Gly  Glu Gly Leu
    2990                2995                3000

His Lys  Leu Gly Tyr Ile Leu  Arg Asp Val Ser Lys  Lys Glu Gly
    3005                3010                3015

Gly Ala  Met Tyr Ala Asp Asp  Thr Ala Gly Trp Asp  Thr Arg Ile
    3020                3025                3030

Thr Leu  Glu Asp Leu Lys Asn  Glu Glu Met Val Thr  Asn His Met
    3035                3040                3045

Glu Gly  Glu His Lys Lys Leu  Ala Glu Ala Ile Phe  Lys Leu Thr
    3050                3055                3060

Tyr Gln  Asn Lys Val Val Arg  Val Gln Arg Pro Thr  Pro Arg Gly
    3065                3070                3075

Thr Val  Met Asp Ile Ile Ser  Arg Arg Asp Gln Arg  Gly Ser Gly
    3080                3085                3090

Gln Val  Gly Thr Tyr Gly Leu  Asn Thr Phe Thr Asn  Met Glu Ala
    3095                3100                3105

Gln Leu  Ile Arg Gln Met Glu  Gly Glu Gly Val Phe  Lys Ser Ile
    3110                3115                3120

Gln His  Leu Thr Ile Thr Glu  Glu Ile Ala Val Gln  Asn Trp Leu
    3125                3130                3135

Ala Arg  Val Gly Arg Glu Arg  Leu Ser Arg Met Ala  Ile Ser Gly
    3140                3145                3150

Asp Asp  Cys Val Val Lys Pro  Leu Asp Asp Arg Phe  Ala Ser Ala
    3155                3160                3165

Leu Thr  Ala Leu Asn Asp Met  Gly Lys Ile Arg Lys  Asp Ile Gln
    3170                3175                3180

Gln Trp  Glu Pro Ser Arg Gly  Trp Asn Asp Trp Thr  Gln Val Pro
    3185                3190                3195

Phe Cys  Ser His His Phe His  Glu Leu Ile Met Lys  Asp Gly Arg
    3200                3205                3210

Val Leu  Val Val Pro Cys Arg  Asn Gln Asp Glu Leu  Ile Gly Arg
    3215                3220                3225

Ala Arg  Ile Ser Gln Gly Ala  Gly Trp Ser Leu Arg  Glu Thr Ala
    3230                3235                3240

Cys Leu  Gly Lys Ser Tyr Ala  Gln Met Trp Ser Leu  Met Tyr Phe
    3245                3250                3255

His Arg  Arg Asp Leu Arg Leu  Ala Ala Asn Ala Ile  Cys Ser Ala
    3260                3265                3270

Val Pro  Ser His Trp Val Pro  Thr Ser Arg Thr Thr  Trp Ser Ile
    3275                3280                3285

His Ala  Lys His Glu Trp Met  Thr Thr Glu Asp Met  Leu Thr Val
    3290                3295                3300

Trp Asn  Arg Val Trp Ile Gln  Glu Asn Pro Trp Met  Glu Asp Lys
    3305                3310                3315

Thr Pro  Val Glu Ser Trp Glu  Glu Ile Pro Tyr Leu  Gly Lys Arg
    3320                3325                3330

Glu Asp  Gln Trp Cys Gly Ser  Leu Ile Gly Leu Thr  Ser Arg Ala
    3335                3340                3345

Thr Trp  Ala Lys Asn Ile Gln  Ala Ala Ile Asn Gln  Val Arg Ser
    3350                3355                3360
```

```
Leu Ile  Gly Asn Glu Glu Tyr  Thr Asp Tyr Met Pro  Ser Met Lys
    3365                 3370                 3375

Arg Phe  Arg Arg Glu Glu Glu  Glu Ala Gly Val Leu  Trp
    3380                 3385                 3390


<210> SEQ ID NO 32
<211> LENGTH: 10723
<212> TYPE: DNA
<213> ORGANISM: Artificial Sequence
<220> FEATURE:
<223> OTHER INFORMATION: Derived from Dengue virus serotype 2/Dengue
      virus serotype 4, DenVax-4j

<400> SEQUENCE: 32

agttgttagt ctacgtggac cgacaaagac agattctttg agggagctaa gctcaacgta     60

gttctaacag tttttaatt agagagcaga tctctgatga ataaccaacg gaaaaaggcg    120

aaaaacacgc ctttcaatat gctgaaacgc gagagaaacc gcgtgtcgac tgtgcaacag    180

ctgacaaaga gattctcact tggaatgctg cagggacgag gaccattaaa actgttcatg    240

gccctggtgg cgttccttcg tttcctaaca atcccaccaa cagcagggat attgaagaga    300

tggggaacaa ttaaaaaatc aaaagctatt aatgttttga gagggttcag gaaagagatt    360

ggaaggatgc tgaacatctt gaataggaga cgcagctctg caggcatgat cattatgctg    420

attccaacag tgatggcgtt ccatttaacc acgcgtgatg gcgaacccct catgatagtg    480

gcaaaacatg aaagggggag acctctcttg tttaagacaa cagaggggat caacaaatgc    540

actctcattg ccatggactt gggtgaaatg tgtgaggaca ctgtcacgta taaatgcccc    600

ttactggtca ataccgaacc tgaagacatt gattgctggt gcaatctcac gtctacctgg    660

gtcatgtatg ggacatgcac ccagagcgga gaacggagac gagagaagcg ctcagtagct    720

ttaacaccac attcaggaat gggattggaa acaagagctg agacatggat gtcatcggaa    780

ggggcttgga agcatgctca gagagtagag agctggatac tcagaaaccc aggattcgcg    840

ctcttggcag gatttatggc ttatatgatt gggcaaacag gaatccagcg aactgtcttc    900

tttgtcctaa tgatgctggt cgccccatcc tacggaatgc gatgcgtagg agtaggaaac    960

agagactttg tggaaggagt ctcaggtgga gcatgggtcg atctggtgct agaacatgga   1020

ggatgcgtca caaccatggc ccagggaaaa ccaaccttgg attttgaact gactaagaca   1080

acagccaagg aagtggctct gttaagaacc tattgcattg aagcctcaat atcaaacata   1140

accacggcaa caagatgtcc aacgcaagga gagccttatc taaaagagga acaagaccaa   1200

cagtacattt gccggagaga tgtggtagac agagggtggg gcaatggctg tggcttgttt   1260

ggaaaaggag gagttgtgac atgtgcgaag ttttcatgtt cggggaagat aacaggcaat   1320

ttggtccaaa ttgagaacct tgaatacaca gtggttgtaa cagtccacaa tggagacacc   1380

catgcagtag gaaatgacac gtccaatcat ggagttacag ccacgataac tcccaggtca   1440

ccatcggtgg aagtcaaatt gccggactat ggagaactaa cactcgattg tgaacccagg   1500

tctggaattg actttaatga gatgattctg atgaaaatga aaaagaaaac atggcttgtg   1560

cataagcaat ggtttttgga tctacctcta ccatggacag caggagcaga cacatcagag   1620

gttcactgga attacaaaga gagaatggtg acatttaagg ttcctcatgc caagagacag   1680

gatgtgacag tgctgggatc tcaggaagga gccatgcatt ctgccctcgc tggagccaca   1740

gaagtggact ccggtgatgg aaatcacatg tttgcaggac atctcaagtg caaagtccgt   1800

atggagaaat tgagaatcaa gggaatgtca tacacgatgt gttcaggaaa gttctcaatt   1860
```

gacaaagaga tggcagaaac acagcatggg acaacagtgg tgaaagtcaa gtatgaaggt 1920
gctggagctc cgtgtaaagt ccccatagag ataagagatg tgaacaagga aaaagtggtt 1980
gggcgtatca tctcatccac ccctttggct gagaatacca acagtgtaac caacatagag 2040
ttagaacccc cctttgggga cagctacata gtgataggtg ttggaaacag tgcattaaca 2100
ctccattggt tcaggaaagg gagttccatt ggcaagatgt ttgagtccac atacagaggt 2160
gcaaaacgaa tggccattct aggtgaaaca gcttgggatt ttggttccgt tggtggactg 2220
ttcacatcat tgggaaaggc tgtgcaccag gtttttggaa gtgtgtatac aaccctgttt 2280
ggaggagtct catggatgat tagaatccta attgggttcc tagtgttgtg gattggcacg 2340
aactcaagga acacttcaat ggctatgacg tgcatagctg ccggcattgt gacactgtat 2400
ttgggagtca tggtgcaggc cgatagtggt tgcgttgtga gctggaaaaa caaagaactg 2460
aaatgtggca gtgggatttt catcacagac aacgtgcaca catggacaga acaatacaag 2520
ttccaaccag aatccccttc aaaactagct tcagctatcc agaaagccca tgaagaggac 2580
atttgtggaa tccgctcagt aacaagactg gagaatctga tgtggaaaca aataacacca 2640
gaattgaatc acattctatc agaaaatgag gtgaagttaa ctattatgac aggagacatc 2700
aaaggaatca tgcaggcagg aaaacgatct ctgcggcctc agcccactga gctgaagtat 2760
tcatggaaaa catggggcaa agcaaaaatg ctctctacag agtctcataa ccagaccttt 2820
ctcattgatg gccccgaaac agcagaatgc cccaacacaa atagagcttg gaattcgttg 2880
gaagttgaag actatggctt tggagtattc accaccaata tatggctaaa attgaaagaa 2940
aaacaggatg tattctgcga ctcaaaactc atgtcagcgg ccataaaaga caacagagcc 3000
gtccatgccg atatgggtta ttggatagaa agtgcactca atgacacatg gaagatagag 3060
aaagcctctt tcattgaagt taaaaactgc cactggccaa aatcacacac cctctggagc 3120
aatggagtgc tagaaagtga gatgataatt ccaaagaatc tcgctggacc agtgtctcaa 3180
cacaactata gaccaggcta ccatacacaa ataacaggac catggcatct aggtaagctt 3240
gagatggact ttgatttctg tgatggaaca acagtggtag tgactgagga ctgcggaaat 3300
agaggaccct ctttgagaac aaccactgcc tctggaaaac tcataacaga atggtgctgc 3360
cgatcttgca cattaccacc gctaagatac agaggtgagg atgggtgctg gtacgggatg 3420
gaaatcagac cattgaagga gaaagaagag aatttggtca actccttggt cacagctgga 3480
catgggcagg tcgacaactt ttcactagga gtcttgggaa tggcattgtt cctggaggaa 3540
atgcttagga cccgagtagg aacgaaacat gcaatactac tagttgcagt ttcttttgtg 3600
acattgatca cagggaacat gtcctttaga gacctgggaa gagtgatggt tatggtaggc 3660
gccactatga cggatgacat aggtatgggc gtgacttatc ttgccctact agcagccttc 3720
aaagtcagac caacttttgc agctggacta ctcttgagaa agctgacctc caaggaattg 3780
atgatgacta ctataggaat tgtactcctc tcccagagca ccataccaga gaccattctt 3840
gagttgactg atgcgttagc cttaggcatg atggtcctca aaatggtgag aaatatggaa 3900
aagtatcaat tggcagtgac tatcatggct atcttgtgcg tcccaaacgc agtgatatta 3960
caaaacgcat ggaaagtgag ttgcacaata ttggcagtgg tgtccgtttc cccactgttc 4020
ttaacatcct cacagcaaaa aacagattgg ataccattag cattgacgat caaaggtctc 4080
aatccaacag ctatttttct aacaaccctc tcaagaacca gcaagaaaag gagctggcca 4140
ttaaatgagg ctatcatggc agtcgggatg gtgagcattt tagccagttc tctcctaaaa 4200

```
aatgatattc ccatgacagg accattagtg gctggagggc tcctcactgt gtgctacgtg   4260
ctcactggac gatcggccga tttggaactg gagagagcag ccgatgtcaa atgggaagac   4320
caggcagaga tatcaggaag cagtccaatc ctgtcaataa caatatcaga agatggtagc   4380
atgtcgataa aaaatgaaga ggaagaacaa acactgacca tactcattag aacaggattg   4440
ctggtgatct caggactttt tcctgtatca ataccaatca cggcagcagc atggtacctg   4500
tgggaagtga agaaacaacg ggccggagta ttgtgggatg ttccttcacc cccacccatg   4560
ggaaaggctg aactggaaga tggagcctat agaattaagc aaaaagggat tcttggatat   4620
tcccagatcg gagccggagt ttacaaagaa ggaacattcc atacaatgtg gcatgtcaca   4680
cgtggcgctg ttctaatgca taaaggaaag aggattgaac catcatgggc ggacgtcaag   4740
aaagacctaa tatcatatgg aggaggctgg aagttagaag gagaatggaa ggaaggagaa   4800
gaagtccagg tattggcact ggagcctgga aaaaatccaa gagccgtcca aacgaaacct   4860
ggtcttttca aaaccaacgc cggaacaata ggtgctgtat ctctggactt ttctcctgga   4920
acgtcaggat ctccaattat cgacaaaaaa ggaaaagttg tgggtcttta tggtaatggt   4980
gttgttacaa ggagtggagc atatgtgagt gctatagccc agactgaaaa aagcattgaa   5040
gacaacccag agatcgaaga tgacattttc cgaaagagaa gactgaccat catggacctc   5100
cacccaggag cgggaaagac gaagagatac cttccggcca tagtcagaga agctataaaa   5160
cggggtttga gaacattaat cttggccccc actagagttg tggcagctga aatggaggaa   5220
gcccttagag gacttccaat aagataccag accccagcca tcagagctgt gcacaccggg   5280
cgggagattg tggacctaat gtgtcatgcc acatttacca tgaggctgct atcaccagtt   5340
agagtgccaa actacaacct gattatcatg gacgaagccc atttcacaga cccagcaagt   5400
atagcagcta gaggatacat ctcaactcga gtggagatgg gtgaggcagc tgggattttt   5460
atgacagcca ctcccccggg aagcagagac ccatttcctc agagcaatgc accaatcata   5520
gatgaagaaa gagaaatccc tgaacgctcg tggaattccg gacatgaatg ggtcacggat   5580
tttaaaggga agactgtttg gttcgttcca agtataaaag caggaaatga tatagcagct   5640
tgcctgagga aaaatggaaa gaaagtgata caactcagta ggaagacctt tgattctgag   5700
tatgtcaaga ctagaaccaa tgattgggac ttcgtggtta caactgacat ttcagaaatg   5760
ggtgccaatt tcaaggctga gagggttata gaccccagac gctgcatgaa accagtcata   5820
ctaacagatg gtgaagagcg ggtgattctg gcaggaccta tgccagtgac ccactctagt   5880
gcagcacaaa gaagagggag aataggaaga aatccaaaaa atgagaatga ccagtacata   5940
tacatggggg aacctctgga aaatgatgaa gactgtgcac actggaaaga agctaaaatg   6000
ctcctagata acatcaacac gccagaagga atcattccta gcatgttcga accagagcgt   6060
gaaaaggtgg atgccattga tggcgaatac cgcttgagag gagaagcaag gaaaaccttt   6120
gtagacttaa tgagaagagg agacctacca gtctggttgg cctacagagt ggcagctgaa   6180
ggcatcaact acgcagacag aaggtggtgt tttgatggag tcaagaacaa ccaaatccta   6240
gaagaaaacg tggaagttga aatctggaca aaagaagggg aaaggaagaa attgaaaccc   6300
agatggttgg atgctaggat ctattctgac ccactggcgc taaaagaatt taaggaattt   6360
gcagccggaa gaaagtctct gaccctgaac ctaatcacag aaatgggtag gctcccaacc   6420
ttcatgactc agaaggcaag agacgcactg gacaacttag cagtgctgca cacggctgag   6480
gcaggtggaa gggcgtacaa ccatgctctc agtgaactgc cggagaccct ggagacattg   6540
cttttactga cacttctggc tacagtcacg ggagggatct ttttattctt gatgagcgca   6600
```

```
aggggcatag ggaagatgac cctgggaatg tgctgcataa tcacggctag catcctccta   6660
tggtacgcac aaatacagcc acactggata gcagcttcaa taatactgga gtttttctc    6720
atagttttgc ttattccaga acctgaaaaa cagagaacac cccaagacaa ccaactgacc   6780
tacgttgtca tagccatcct cacagtggtg gccgcaacca tggcaaacga gatgggtttc   6840
ctagaaaaaa cgaagaaaga tctcggattg ggaagcattg caacccagca acccgagagc   6900
aacatcctgg acatagatct acgtcctgca tcagcatgga cgctgtatgc cgtggccaca   6960
acatttgtta caccaatgtt gagacatagc attgaaaatt cctcagtgaa tgtgtcccta   7020
acagctatag ccaaccaagc cacagtgtta atgggtctcg ggaaaggatg gccattgtca   7080
aagatggaca tcggagttcc ccttctcgcc attggatgct actcacaagt caaccccata   7140
actctcacag cagctctttt cttattggta gcacattatg ccatcatagg gccaggactc   7200
caagcaaaag caaccagaga agctcagaaa agagcagcgg cgggcatcat gaaaaaccca   7260
actgtcgatg gaataacagt gattgaccta gatccaatac cttatgatcc aaagtttgaa   7320
aagcagttgg gacaagtaat gctcctagtc ctctgcgtga ctcaagtatt gatgatgagg   7380
actacatggg ctctgtgtga ggctttaacc ttagctaccg ggcccatctc cacattgtgg   7440
gaaggaaatc cagggaggtt ttggaacact accattgcgg tgtcaatggc taacattttt   7500
agagggagtt acttggccgg agctggactt ctcttttcta ttatgaagaa cacaaccaac   7560
acaagaaggg gaactggcaa catagagag acgcttggag agaaatggaa aagccgattg    7620
aacgcattgg gaaaaagtga attccagatc tacaagaaaa gtggaatcca ggaagtggat   7680
agaaccttag caaaagaagg cattaaaaga ggagaaacgg accatcacgc tgtgtcgcga   7740
ggctcagcaa aactgagatg gttcgttgag agaaacatgg tcacaccaga agggaaagta   7800
gtggacctcg gttgtggcag aggaggctgg tcatactatt gtggaggact aaagaatgta   7860
agagaagtca aaggcctaac aaaaggagga ccaggacacg aagaacccat ccccatgtca   7920
acatatgggt ggaatctagt gcgtcttcaa agtggagttg acgttttctt catcccgcca   7980
gaaaagtgtg acacattatt gtgtgacata ggggagtcat caccaaatcc cacagtggaa   8040
gcaggacgaa cactcagagt ccttaactta gtagaaaatt ggttgaacaa caacactcaa   8100
ttttgcataa aggttctcaa cccatatatg ccctcagtca tagaaaaaat ggaagcacta   8160
caaaggaaat atggaggagc cttagtgagg aatccactct cacgaaactc cacacatgag   8220
atgtactggg tatccaatgc ttccgggaac atagtgtcat cagtgaacat gatttcaagg   8280
atgttgatca acagatttac aatgagatac aagaaagcca cttacgagcc ggatgttgac   8340
ctcggaagcg gaacccgtaa catcgggatt gaaagtgaga taccaaacct agatataatt   8400
gggaaaagaa tagaaaaaat aaagcaagag catgaaacat catggcacta tgaccaagac   8460
cacccataca aaacgtgggc ataccatggt agctatgaaa caaaacagac tggatcagca   8520
tcatccatgg tcaacggagt ggtcaggctg ctgacaaaac cttgggacgt cgtccccatg   8580
gtgacacaga tggcaatgac agacacgact ccatttggac aacagcgcgt tttaaagag    8640
aaagtggaca cgagaaccca agaaccgaaa gaaggcacga agaaactaat gaaaataaca   8700
gcagagtggc tttggaaaga attagggaag aaaaagacac ccaggatgtg caccagagaa   8760
gaattcacaa gaaaggtgag aagcaatgca gccttggggg ccatattcac tgatgagaac   8820
aagtggaagt cggcacgtga ggctgttgaa gatagtaggt tttgggagct ggttgacaag   8880
gaaaggaatc tccatcttga aggaaagtgt gaaacatgtg tgtacaacat gatgggaaaa   8940
```

-continued

```
agagagaaga agctagggga attcggcaag gcaaaaggca gcagagccat atggtacatg   9000
tggcttggag cacgcttctt agagtttgaa gccctaggat tcttaaatga agatcactgg   9060
ttctccagag agaactccct gagtggagtg gaaggagaag ggctgcacaa gctaggttac   9120
attctaagag acgtgagcaa gaaagaggga ggagcaatgt atgccgatga caccgcagga   9180
tgggatacaa gaatcacact agaagaccta aaaaatgaag aaatggtaac aaaccacatg   9240
gaaggagaac acaagaaact agccgaggcc attttcaaac taacgtacca aaacaaggtg   9300
gtgcgtgtgc aaagaccaac accaagaggc acagtaatgg acatcatatc gagaagagac   9360
caaagaggta gtggacaagt tggcacctat ggactcaata ctttcaccaa tatggaagcc   9420
caactaatca gacagatgga gggagaagga gtctttaaaa gcattcagca cctaacaatc   9480
acagaagaaa tcgctgtgca aaactggtta gcaagagtgg ggcgcgaaag gttatcaaga   9540
atggccatca gtggagatga ttgtgttgtg aaacctttag atgacaggtt cgcaagcgct   9600
ttaacagctc taaatgacat gggaaagatt aggaaagaca tacaacaatg ggaaccttca   9660
agaggatgga atgattggac acaagtgccc ttctgttcac accatttcca tgagttaatc   9720
atgaaagacg gtcgcgtact cgttgttcca tgtagaaacc aagatgaact gattggcaga   9780
gcccgaatct cccaaggagc agggtggtct ttgcgggaga cggcctgttt ggggaagtct   9840
tacgcccaaa tgtggagctt gatgtacttc cacagacgcg acctcaggct ggcggcaaat   9900
gctatttgct cggcagtacc atcacattgg gttccaacaa gtcgaacaac ctggtccata   9960
catgctaaac atgaatggat gacaacggaa gacatgctga cagtctggaa cagggtgtgg  10020
attcaagaaa acccatggat ggaagacaaa actccagtgg aatcatggga ggaaatccca  10080
tacttgggga aaagagaaga ccaatggtgc ggctcattga ttgggttaac aagcagggcc  10140
acctgggcaa agaacatcca agcagcaata aatcaagtta gatcccttat aggcaatgaa  10200
gaatacacag attacatgcc atccatgaaa agattcagaa gagaagagga agaagcagga  10260
gttctgtggt agaaagcaaa actaacatga aacaaggcta gaagtcaggt cggattaagc  10320
catagtacgg aaaaaactat gctacctgtg agccccgtcc aaggacgtta aaagaagtca  10380
ggccatcata aatgccatag cttgagtaaa ctatgcagcc tgtagctcca cctgagaagg  10440
tgtaaaaaat ccgggaggcc acaaaccatg gaagctgtac gcatggcgta gtggactagc  10500
ggttagagga gacccctccc ttacaaatcg cagcaacaat gggggcccaa ggcgagatga  10560
agctgtagtc tcgctggaag gactagaggt tagaggagac ccccccgaaa caaaaaacag  10620
catattgacg ctgggaaaga ccagagatcc tgctgtctcc tcagcatcat tccaggcaca  10680
gaacgccaga aaatggaatg gtgctgttga atcaacaggt tct                    10723
```

<210> SEQ ID NO 33
<211> LENGTH: 3391
<212> TYPE: PRT
<213> ORGANISM: Artificial Sequence
<220> FEATURE:
<223> OTHER INFORMATION: Derived from Dengue virus serotype 2/Dengue virus serotype 4, DenVax-4j

<400> SEQUENCE: 33

```
Met Asn Asn Gln Arg Lys Lys Ala Lys Asn Thr Pro Phe Asn Met Leu
1               5                   10                  15

Lys Arg Glu Arg Asn Arg Val Ser Thr Val Gln Gln Leu Thr Lys Arg
            20                  25                  30

Phe Ser Leu Gly Met Leu Gln Gly Arg Gly Pro Leu Lys Leu Phe Met
        35                  40                  45
```

-continued

```
Ala Leu Val Ala Phe Leu Arg Phe Leu Thr Ile Pro Pro Thr Ala Gly
    50                  55                  60

Ile Leu Lys Arg Trp Gly Thr Ile Lys Lys Ser Lys Ala Ile Asn Val
65                  70                  75                  80

Leu Arg Gly Phe Arg Lys Glu Ile Gly Arg Met Leu Asn Ile Leu Asn
                85                  90                  95

Arg Arg Arg Ser Ser Ala Gly Met Ile Ile Met Leu Ile Pro Thr Val
            100                 105                 110

Met Ala Phe His Leu Thr Thr Arg Asp Gly Glu Pro Leu Met Ile Val
        115                 120                 125

Ala Lys His Glu Arg Gly Arg Pro Leu Leu Phe Lys Thr Thr Glu Gly
    130                 135                 140

Ile Asn Lys Cys Thr Leu Ile Ala Met Asp Leu Gly Glu Met Cys Glu
145                 150                 155                 160

Asp Thr Val Thr Tyr Lys Cys Pro Leu Leu Val Asn Thr Glu Pro Glu
                165                 170                 175

Asp Ile Asp Cys Trp Cys Asn Leu Thr Ser Thr Trp Val Met Tyr Gly
            180                 185                 190

Thr Cys Thr Gln Ser Gly Glu Arg Arg Arg Glu Lys Arg Ser Val Ala
        195                 200                 205

Leu Thr Pro His Ser Gly Met Gly Leu Glu Thr Arg Ala Glu Thr Trp
    210                 215                 220

Met Ser Ser Glu Gly Ala Trp Lys His Ala Gln Arg Val Glu Ser Trp
225                 230                 235                 240

Ile Leu Arg Asn Pro Gly Phe Ala Leu Leu Ala Gly Phe Met Ala Tyr
                245                 250                 255

Met Ile Gly Gln Thr Gly Ile Gln Arg Thr Val Phe Phe Val Leu Met
            260                 265                 270

Met Leu Val Ala Pro Ser Tyr Gly Met Arg Cys Val Gly Val Gly Asn
        275                 280                 285

Arg Asp Phe Val Glu Gly Val Ser Gly Gly Ala Trp Val Asp Leu Val
    290                 295                 300

Leu Glu His Gly Gly Cys Val Thr Thr Met Ala Gln Gly Lys Pro Thr
305                 310                 315                 320

Leu Asp Phe Glu Leu Thr Lys Thr Thr Ala Lys Glu Val Ala Leu Leu
                325                 330                 335

Arg Thr Tyr Cys Ile Glu Ala Ser Ile Ser Asn Ile Thr Thr Ala Thr
            340                 345                 350

Arg Cys Pro Thr Gln Gly Glu Pro Tyr Leu Lys Glu Glu Gln Asp Gln
        355                 360                 365

Gln Tyr Ile Cys Arg Arg Asp Val Val Asp Arg Gly Trp Gly Asn Gly
    370                 375                 380

Cys Gly Leu Phe Gly Lys Gly Gly Val Val Thr Cys Ala Lys Phe Ser
385                 390                 395                 400

Cys Ser Gly Lys Ile Thr Gly Asn Leu Val Gln Ile Glu Asn Leu Glu
                405                 410                 415

Tyr Thr Val Val Val Thr Val His Asn Gly Asp Thr His Ala Val Gly
            420                 425                 430

Asn Asp Thr Ser Asn His Gly Val Thr Ala Thr Ile Thr Pro Arg Ser
        435                 440                 445

Pro Ser Val Glu Val Lys Leu Pro Asp Tyr Gly Glu Leu Thr Leu Asp
    450                 455                 460
```

-continued

```
Cys Glu Pro Arg Ser Gly Ile Asp Phe Asn Glu Met Ile Leu Met Lys
465                 470                 475                 480

Met Lys Lys Lys Thr Trp Leu Val His Lys Gln Trp Phe Leu Asp Leu
                485                 490                 495

Pro Leu Pro Trp Thr Ala Gly Ala Asp Thr Ser Glu Val His Trp Asn
            500                 505                 510

Tyr Lys Glu Arg Met Val Thr Phe Lys Val Pro His Ala Lys Arg Gln
        515                 520                 525

Asp Val Thr Val Leu Gly Ser Gln Glu Gly Ala Met His Ser Ala Leu
    530                 535                 540

Ala Gly Ala Thr Glu Val Asp Ser Gly Asp Gly Asn His Met Phe Ala
545                 550                 555                 560

Gly His Leu Lys Cys Lys Val Arg Met Glu Lys Leu Arg Ile Lys Gly
                565                 570                 575

Met Ser Tyr Thr Met Cys Ser Gly Lys Phe Ser Ile Asp Lys Glu Met
            580                 585                 590

Ala Glu Thr Gln His Gly Thr Thr Val Val Lys Val Lys Tyr Glu Gly
        595                 600                 605

Ala Gly Ala Pro Cys Lys Val Pro Ile Glu Ile Arg Asp Val Asn Lys
    610                 615                 620

Glu Lys Val Val Gly Arg Ile Ile Ser Ser Thr Pro Leu Ala Glu Asn
625                 630                 635                 640

Thr Asn Ser Val Thr Asn Ile Glu Leu Glu Pro Pro Phe Gly Asp Ser
                645                 650                 655

Tyr Ile Val Ile Gly Val Gly Asn Ser Ala Leu Thr Leu His Trp Phe
            660                 665                 670

Arg Lys Gly Ser Ser Ile Gly Lys Met Phe Glu Ser Thr Tyr Arg Gly
        675                 680                 685

Ala Lys Arg Met Ala Ile Leu Gly Glu Thr Ala Trp Asp Phe Gly Ser
    690                 695                 700

Val Gly Gly Leu Phe Thr Ser Leu Gly Lys Ala Val His Gln Val Phe
705                 710                 715                 720

Gly Ser Val Tyr Thr Thr Leu Phe Gly Gly Val Ser Trp Met Ile Arg
                725                 730                 735

Ile Leu Ile Gly Phe Leu Val Leu Trp Ile Gly Thr Asn Ser Arg Asn
            740                 745                 750

Thr Ser Met Ala Met Thr Cys Ile Ala Ala Gly Ile Val Thr Leu Tyr
        755                 760                 765

Leu Gly Val Met Val Gln Ala Asp Ser Gly Cys Val Val Ser Trp Lys
    770                 775                 780

Asn Lys Glu Leu Lys Cys Gly Ser Gly Ile Phe Ile Thr Asp Asn Val
785                 790                 795                 800

His Thr Trp Thr Glu Gln Tyr Lys Phe Gln Pro Glu Ser Pro Ser Lys
                805                 810                 815

Leu Ala Ser Ala Ile Gln Lys Ala His Glu Glu Asp Ile Cys Gly Ile
            820                 825                 830

Arg Ser Val Thr Arg Leu Glu Asn Leu Met Trp Lys Gln Ile Thr Pro
        835                 840                 845

Glu Leu Asn His Ile Leu Ser Glu Asn Glu Val Lys Leu Thr Ile Met
    850                 855                 860

Thr Gly Asp Ile Lys Gly Ile Met Gln Ala Gly Lys Arg Ser Leu Arg
865                 870                 875                 880

Pro Gln Pro Thr Glu Leu Lys Tyr Ser Trp Lys Thr Trp Gly Lys Ala
```

-continued

```
                885                 890                 895

Lys Met Leu Ser Thr Glu Ser His Asn Gln Thr Phe Leu Ile Asp Gly
            900                 905                 910

Pro Glu Thr Ala Glu Cys Pro Asn Thr Asn Arg Ala Trp Asn Ser Leu
        915                 920                 925

Glu Val Glu Asp Tyr Gly Phe Gly Val Phe Thr Thr Asn Ile Trp Leu
    930                 935                 940

Lys Leu Lys Glu Lys Gln Asp Val Phe Cys Asp Ser Lys Leu Met Ser
945                 950                 955                 960

Ala Ala Ile Lys Asp Asn Arg Ala Val His Ala Asp Met Gly Tyr Trp
                965                 970                 975

Ile Glu Ser Ala Leu Asn Asp Thr Trp Lys Ile Glu Lys Ala Ser Phe
            980                 985                 990

Ile Glu Val Lys Asn Cys His Trp  Pro Lys Ser His Thr  Leu Trp Ser
        995                 1000                1005

Asn Gly  Val Leu Glu Ser Glu  Met Ile Ile Pro Lys  Asn Leu Ala
    1010                 1015                 1020

Gly Pro  Val Ser Gln His Asn  Tyr Arg Pro Gly Tyr  His Thr Gln
    1025                 1030                 1035

Ile Thr  Gly Pro Trp His Leu  Gly Lys Leu Glu Met  Asp Phe Asp
    1040                 1045                 1050

Phe Cys  Asp Gly Thr Thr Val  Val Val Thr Glu Asp  Cys Gly Asn
    1055                 1060                 1065

Arg Gly  Pro Ser Leu Arg Thr  Thr Thr Ala Ser Gly  Lys Leu Ile
    1070                 1075                 1080

Thr Glu  Trp Cys Cys Arg Ser  Cys Thr Leu Pro Pro  Leu Arg Tyr
    1085                 1090                 1095

Arg Gly  Glu Asp Gly Cys Trp  Tyr Gly Met Glu Ile  Arg Pro Leu
    1100                 1105                 1110

Lys Glu  Lys Glu Glu Asn Leu  Val Asn Ser Leu Val  Thr Ala Gly
    1115                 1120                 1125

His Gly  Gln Val Asp Asn Phe  Ser Leu Gly Val Leu  Gly Met Ala
    1130                 1135                 1140

Leu Phe  Leu Glu Glu Met Leu  Arg Thr Arg Val Gly  Thr Lys His
    1145                 1150                 1155

Ala Ile  Leu Leu Val Ala Val  Ser Phe Val Thr Leu  Ile Thr Gly
    1160                 1165                 1170

Asn Met  Ser Phe Arg Asp Leu  Gly Arg Val Met Val  Met Val Gly
    1175                 1180                 1185

Ala Thr  Met Thr Asp Asp Ile  Gly Met Gly Val Thr  Tyr Leu Ala
    1190                 1195                 1200

Leu Leu  Ala Ala Phe Lys Val  Arg Pro Thr Phe Ala  Ala Gly Leu
    1205                 1210                 1215

Leu Leu  Arg Lys Leu Thr Ser  Lys Glu Leu Met Met  Thr Thr Ile
    1220                 1225                 1230

Gly Ile  Val Leu Leu Ser Gln  Ser Thr Ile Pro Glu  Thr Ile Leu
    1235                 1240                 1245

Glu Leu  Thr Asp Ala Leu Ala  Leu Gly Met Met Val  Leu Lys Met
    1250                 1255                 1260

Val Arg  Asn Met Glu Lys Tyr  Gln Leu Ala Val Thr  Ile Met Ala
    1265                 1270                 1275

Ile Leu  Cys Val Pro Asn Ala  Val Ile Leu Gln Asn  Ala Trp Lys
    1280                 1285                 1290
```

```
Val Ser Cys Thr Ile Leu Ala Val Val Ser Val Ser Pro Leu Phe
    1295                1300                1305

Leu Thr Ser Ser Gln Gln Lys Thr Asp Trp Ile Pro Leu Ala Leu
    1310                1315                1320

Thr Ile Lys Gly Leu Asn Pro Thr Ala Ile Phe Leu Thr Thr Leu
    1325                1330                1335

Ser Arg Thr Ser Lys Lys Arg Ser Trp Pro Leu Asn Glu Ala Ile
    1340                1345                1350

Met Ala Val Gly Met Val Ser Ile Leu Ala Ser Ser Leu Leu Lys
    1355                1360                1365

Asn Asp Ile Pro Met Thr Gly Pro Leu Val Ala Gly Gly Leu Leu
    1370                1375                1380

Thr Val Cys Tyr Val Leu Thr Gly Arg Ser Ala Asp Leu Glu Leu
    1385                1390                1395

Glu Arg Ala Ala Asp Val Lys Trp Glu Asp Gln Ala Glu Ile Ser
    1400                1405                1410

Gly Ser Ser Pro Ile Leu Ser Ile Thr Ile Ser Glu Asp Gly Ser
    1415                1420                1425

Met Ser Ile Lys Asn Glu Glu Glu Glu Gln Thr Leu Thr Ile Leu
    1430                1435                1440

Ile Arg Thr Gly Leu Leu Val Ile Ser Gly Leu Phe Pro Val Ser
    1445                1450                1455

Ile Pro Ile Thr Ala Ala Ala Trp Tyr Leu Trp Glu Val Lys Lys
    1460                1465                1470

Gln Arg Ala Gly Val Leu Trp Asp Val Pro Ser Pro Pro Pro Met
    1475                1480                1485

Gly Lys Ala Glu Leu Glu Asp Gly Ala Tyr Arg Ile Lys Gln Lys
    1490                1495                1500

Gly Ile Leu Gly Tyr Ser Gln Ile Gly Ala Gly Val Tyr Lys Glu
    1505                1510                1515

Gly Thr Phe His Thr Met Trp His Val Thr Arg Gly Ala Val Leu
    1520                1525                1530

Met His Lys Gly Lys Arg Ile Glu Pro Ser Trp Ala Asp Val Lys
    1535                1540                1545

Lys Asp Leu Ile Ser Tyr Gly Gly Gly Trp Lys Leu Glu Gly Glu
    1550                1555                1560

Trp Lys Glu Gly Glu Glu Val Gln Val Leu Ala Leu Glu Pro Gly
    1565                1570                1575

Lys Asn Pro Arg Ala Val Gln Thr Lys Pro Gly Leu Phe Lys Thr
    1580                1585                1590

Asn Ala Gly Thr Ile Gly Ala Val Ser Leu Asp Phe Ser Pro Gly
    1595                1600                1605

Thr Ser Gly Ser Pro Ile Ile Asp Lys Lys Gly Lys Val Val Gly
    1610                1615                1620

Leu Tyr Gly Asn Gly Val Val Thr Arg Ser Gly Ala Tyr Val Ser
    1625                1630                1635

Ala Ile Ala Gln Thr Glu Lys Ser Ile Glu Asp Asn Pro Glu Ile
    1640                1645                1650

Glu Asp Asp Ile Phe Arg Lys Arg Arg Leu Thr Ile Met Asp Leu
    1655                1660                1665

His Pro Gly Ala Gly Lys Thr Lys Arg Tyr Leu Pro Ala Ile Val
    1670                1675                1680
```

```
Arg Glu  Ala Ile Lys Arg Gly  Leu Arg Thr Leu Ile  Leu Ala Pro
    1685                 1690                 1695

Thr Arg  Val Val Ala Ala Glu  Met Glu Glu Ala Leu  Arg Gly Leu
    1700                 1705                 1710

Pro Ile  Arg Tyr Gln Thr Pro  Ala Ile Arg Ala Val  His Thr Gly
    1715                 1720                 1725

Arg Glu  Ile Val Asp Leu Met  Cys His Ala Thr Phe  Thr Met Arg
    1730                 1735                 1740

Leu Leu  Ser Pro Val Arg Val  Pro Asn Tyr Asn Leu  Ile Ile Met
    1745                 1750                 1755

Asp Glu  Ala His Phe Thr Asp  Pro Ala Ser Ile Ala  Ala Arg Gly
    1760                 1765                 1770

Tyr Ile  Ser Thr Arg Val Glu  Met Gly Glu Ala Ala  Gly Ile Phe
    1775                 1780                 1785

Met Thr  Ala Thr Pro Pro Gly  Ser Arg Asp Pro Phe  Pro Gln Ser
    1790                 1795                 1800

Asn Ala  Pro Ile Ile Asp Glu  Glu Arg Glu Ile Pro  Glu Arg Ser
    1805                 1810                 1815

Trp Asn  Ser Gly His Glu Trp  Val Thr Asp Phe Lys  Gly Lys Thr
    1820                 1825                 1830

Val Trp  Phe Val Pro Ser Ile  Lys Ala Gly Asn Asp  Ile Ala Ala
    1835                 1840                 1845

Cys Leu  Arg Lys Asn Gly Lys  Lys Val Ile Gln Leu  Ser Arg Lys
    1850                 1855                 1860

Thr Phe  Asp Ser Glu Tyr Val  Lys Thr Arg Thr Asn  Asp Trp Asp
    1865                 1870                 1875

Phe Val  Val Thr Thr Asp Ile  Ser Glu Met Gly Ala  Asn Phe Lys
    1880                 1885                 1890

Ala Glu  Arg Val Ile Asp Pro  Arg Arg Cys Met Lys  Pro Val Ile
    1895                 1900                 1905

Leu Thr  Asp Gly Glu Glu Arg  Val Ile Leu Ala Gly  Pro Met Pro
    1910                 1915                 1920

Val Thr  His Ser Ser Ala Ala  Gln Arg Arg Gly Arg  Ile Gly Arg
    1925                 1930                 1935

Asn Pro  Lys Asn Glu Asn Asp  Gln Tyr Ile Tyr Met  Gly Glu Pro
    1940                 1945                 1950

Leu Glu  Asn Asp Glu Asp Cys  Ala His Trp Lys Glu  Ala Lys Met
    1955                 1960                 1965

Leu Leu  Asp Asn Ile Asn Thr  Pro Glu Gly Ile Ile  Pro Ser Met
    1970                 1975                 1980

Phe Glu  Pro Glu Arg Glu Lys  Val Asp Ala Ile Asp  Gly Glu Tyr
    1985                 1990                 1995

Arg Leu  Arg Gly Glu Ala Arg  Lys Thr Phe Val Asp  Leu Met Arg
    2000                 2005                 2010

Arg Gly  Asp Leu Pro Val Trp  Leu Ala Tyr Arg Val  Ala Ala Glu
    2015                 2020                 2025

Gly Ile  Asn Tyr Ala Asp Arg  Arg Trp Cys Phe Asp  Gly Val Lys
    2030                 2035                 2040

Asn Asn  Gln Ile Leu Glu Glu  Asn Val Glu Val Glu  Ile Trp Thr
    2045                 2050                 2055

Lys Glu  Gly Glu Arg Lys Lys  Leu Lys Pro Arg Trp  Leu Asp Ala
    2060                 2065                 2070

Arg Ile  Tyr Ser Asp Pro Leu  Ala Leu Lys Glu Phe  Lys Glu Phe
```

```
    2075                2080                2085

Ala Ala  Gly Arg Lys Ser Leu  Thr Leu Asn Leu Ile  Thr Glu Met
    2090                2095                2100

Gly Arg  Leu Pro Thr Phe Met  Thr Gln Lys Ala Arg  Asp Ala Leu
    2105                2110                2115

Asp Asn  Leu Ala Val Leu His  Thr Ala Glu Ala Gly  Gly Arg Ala
    2120                2125                2130

Tyr Asn  His Ala Leu Ser Glu  Leu Pro Glu Thr Leu  Glu Thr Leu
    2135                2140                2145

Leu Leu  Leu Thr Leu Leu Ala  Thr Val Thr Gly Gly  Ile Phe Leu
    2150                2155                2160

Phe Leu  Met Ser Ala Arg Gly  Ile Gly Lys Met Thr  Leu Gly Met
    2165                2170                2175

Cys Cys  Ile Ile Thr Ala Ser  Ile Leu Leu Trp Tyr  Ala Gln Ile
    2180                2185                2190

Gln Pro  His Trp Ile Ala Ala  Ser Ile Ile Leu Glu  Phe Phe Leu
    2195                2200                2205

Ile Val  Leu Leu Ile Pro Glu  Pro Glu Lys Gln Arg  Thr Pro Gln
    2210                2215                2220

Asp Asn  Gln Leu Thr Tyr Val  Val Ile Ala Ile Leu  Thr Val Val
    2225                2230                2235

Ala Ala  Thr Met Ala Asn Glu  Met Gly Phe Leu Glu  Lys Thr Lys
    2240                2245                2250

Lys Asp  Leu Gly Leu Gly Ser  Ile Ala Thr Gln Gln  Pro Glu Ser
    2255                2260                2265

Asn Ile  Leu Asp Ile Asp Leu  Arg Pro Ala Ser Ala  Trp Thr Leu
    2270                2275                2280

Tyr Ala  Val Ala Thr Thr Phe  Val Thr Pro Met Leu  Arg His Ser
    2285                2290                2295

Ile Glu  Asn Ser Ser Val Asn  Val Ser Leu Thr Ala  Ile Ala Asn
    2300                2305                2310

Gln Ala  Thr Val Leu Met Gly  Leu Gly Lys Gly Trp  Pro Leu Ser
    2315                2320                2325

Lys Met  Asp Ile Gly Val Pro  Leu Leu Ala Ile Gly  Cys Tyr Ser
    2330                2335                2340

Gln Val  Asn Pro Ile Thr Leu  Thr Ala Ala Leu Phe  Leu Leu Val
    2345                2350                2355

Ala His  Tyr Ala Ile Ile Gly  Pro Gly Leu Gln Ala  Lys Ala Thr
    2360                2365                2370

Arg Glu  Ala Gln Lys Arg Ala  Ala Ala Gly Ile Met  Lys Asn Pro
    2375                2380                2385

Thr Val  Asp Gly Ile Thr Val  Ile Asp Leu Asp Pro  Ile Pro Tyr
    2390                2395                2400

Asp Pro  Lys Phe Glu Lys Gln  Leu Gly Gln Val Met  Leu Leu Val
    2405                2410                2415

Leu Cys  Val Thr Gln Val Leu  Met Met Arg Thr Thr  Trp Ala Leu
    2420                2425                2430

Cys Glu  Ala Leu Thr Leu Ala  Thr Gly Pro Ile Ser  Thr Leu Trp
    2435                2440                2445

Glu Gly  Asn Pro Gly Arg Phe  Trp Asn Thr Thr Ile  Ala Val Ser
    2450                2455                2460

Met Ala  Asn Ile Phe Arg Gly  Ser Tyr Leu Ala Gly  Ala Gly Leu
    2465                2470                2475
```

```
Leu Phe  Ser Ile Met Lys Asn  Thr Thr Asn Thr Arg  Arg Gly Thr
    2480                 2485                 2490

Gly Asn  Ile Gly Glu Thr Leu  Gly Glu Lys Trp Lys  Ser Arg Leu
    2495                 2500                 2505

Asn Ala  Leu Gly Lys Ser Glu  Phe Gln Ile Tyr Lys  Lys Ser Gly
    2510                 2515                 2520

Ile Gln  Glu Val Asp Arg Thr  Leu Ala Lys Glu Gly  Ile Lys Arg
    2525                 2530                 2535

Gly Glu  Thr Asp His His Ala  Val Ser Arg Gly Ser  Ala Lys Leu
    2540                 2545                 2550

Arg Trp  Phe Val Glu Arg Asn  Met Val Thr Pro Glu  Gly Lys Val
    2555                 2560                 2565

Val Asp  Leu Gly Cys Gly Arg  Gly Gly Trp Ser Tyr  Tyr Cys Gly
    2570                 2575                 2580

Gly Leu  Lys Asn Val Arg Glu  Val Lys Gly Leu Thr  Lys Gly Gly
    2585                 2590                 2595

Pro Gly  His Glu Glu Pro Ile  Pro Met Ser Thr Tyr  Gly Trp Asn
    2600                 2605                 2610

Leu Val  Arg Leu Gln Ser Gly  Val Asp Val Phe Phe  Ile Pro Pro
    2615                 2620                 2625

Glu Lys  Cys Asp Thr Leu Leu  Cys Asp Ile Gly Glu  Ser Ser Pro
    2630                 2635                 2640

Asn Pro  Thr Val Glu Ala Gly  Arg Thr Leu Arg Val  Leu Asn Leu
    2645                 2650                 2655

Val Glu  Asn Trp Leu Asn Asn  Asn Thr Gln Phe Cys  Ile Lys Val
    2660                 2665                 2670

Leu Asn  Pro Tyr Met Pro Ser  Val Ile Glu Lys Met  Glu Ala Leu
    2675                 2680                 2685

Gln Arg  Lys Tyr Gly Gly Ala  Leu Val Arg Asn Pro  Leu Ser Arg
    2690                 2695                 2700

Asn Ser  Thr His Glu Met Tyr  Trp Val Ser Asn Ala  Ser Gly Asn
    2705                 2710                 2715

Ile Val  Ser Ser Val Asn Met  Ile Ser Arg Met Leu  Ile Asn Arg
    2720                 2725                 2730

Phe Thr  Met Arg Tyr Lys Lys  Ala Thr Tyr Glu Pro  Asp Val Asp
    2735                 2740                 2745

Leu Gly  Ser Gly Thr Arg Asn  Ile Gly Ile Glu Ser  Glu Ile Pro
    2750                 2755                 2760

Asn Leu  Asp Ile Ile Gly Lys  Arg Ile Glu Lys Ile  Lys Gln Glu
    2765                 2770                 2775

His Glu  Thr Ser Trp His Tyr  Asp Gln Asp His Pro  Tyr Lys Thr
    2780                 2785                 2790

Trp Ala  Tyr His Gly Ser Tyr  Glu Thr Lys Gln Thr  Gly Ser Ala
    2795                 2800                 2805

Ser Ser  Met Val Asn Gly Val  Val Arg Leu Leu Thr  Lys Pro Trp
    2810                 2815                 2820

Asp Val  Val Pro Met Val Thr  Gln Met Ala Met Thr  Asp Thr Thr
    2825                 2830                 2835

Pro Phe  Gly Gln Gln Arg Val  Phe Lys Glu Lys Val  Asp Thr Arg
    2840                 2845                 2850

Thr Gln  Glu Pro Lys Glu Gly  Thr Lys Lys Leu Met  Lys Ile Thr
    2855                 2860                 2865
```

-continued

```
Ala Glu Trp Leu Trp Lys Glu Leu Gly Lys Lys Lys Thr Pro Arg
    2870                2875                2880

Met Cys Thr Arg Glu Glu Phe Thr Arg Lys Val Arg Ser Asn Ala
    2885                2890                2895

Ala Leu Gly Ala Ile Phe Thr Asp Glu Asn Lys Trp Lys Ser Ala
    2900                2905                2910

Arg Glu Ala Val Glu Asp Ser Arg Phe Trp Glu Leu Val Asp Lys
    2915                2920                2925

Glu Arg Asn Leu His Leu Glu Gly Lys Cys Glu Thr Cys Val Tyr
    2930                2935                2940

Asn Met Met Gly Lys Arg Glu Lys Lys Leu Gly Glu Phe Gly Lys
    2945                2950                2955

Ala Lys Gly Ser Arg Ala Ile Trp Tyr Met Trp Leu Gly Ala Arg
    2960                2965                2970

Phe Leu Glu Phe Glu Ala Leu Gly Phe Leu Asn Glu Asp His Trp
    2975                2980                2985

Phe Ser Arg Glu Asn Ser Leu Ser Gly Val Glu Gly Glu Gly Leu
    2990                2995                3000

His Lys Leu Gly Tyr Ile Leu Arg Asp Val Ser Lys Lys Glu Gly
    3005                3010                3015

Gly Ala Met Tyr Ala Asp Asp Thr Ala Gly Trp Asp Thr Arg Ile
    3020                3025                3030

Thr Leu Glu Asp Leu Lys Asn Glu Glu Met Val Thr Asn His Met
    3035                3040                3045

Glu Gly Glu His Lys Lys Leu Ala Glu Ala Ile Phe Lys Leu Thr
    3050                3055                3060

Tyr Gln Asn Lys Val Val Arg Val Gln Arg Pro Thr Pro Arg Gly
    3065                3070                3075

Thr Val Met Asp Ile Ile Ser Arg Arg Asp Gln Arg Gly Ser Gly
    3080                3085                3090

Gln Val Gly Thr Tyr Gly Leu Asn Thr Phe Thr Asn Met Glu Ala
    3095                3100                3105

Gln Leu Ile Arg Gln Met Glu Gly Glu Gly Val Phe Lys Ser Ile
    3110                3115                3120

Gln His Leu Thr Ile Thr Glu Glu Ile Ala Val Gln Asn Trp Leu
    3125                3130                3135

Ala Arg Val Gly Arg Glu Arg Leu Ser Arg Met Ala Ile Ser Gly
    3140                3145                3150

Asp Asp Cys Val Val Lys Pro Leu Asp Asp Arg Phe Ala Ser Ala
    3155                3160                3165

Leu Thr Ala Leu Asn Asp Met Gly Lys Ile Arg Lys Asp Ile Gln
    3170                3175                3180

Gln Trp Glu Pro Ser Arg Gly Trp Asn Asp Trp Thr Gln Val Pro
    3185                3190                3195

Phe Cys Ser His His Phe His Glu Leu Ile Met Lys Asp Gly Arg
    3200                3205                3210

Val Leu Val Val Pro Cys Arg Asn Gln Asp Glu Leu Ile Gly Arg
    3215                3220                3225

Ala Arg Ile Ser Gln Gly Ala Gly Trp Ser Leu Arg Glu Thr Ala
    3230                3235                3240

Cys Leu Gly Lys Ser Tyr Ala Gln Met Trp Ser Leu Met Tyr Phe
    3245                3250                3255
```

-continued

```
His Arg  Arg Asp Leu Arg Leu  Ala Ala Asn Ala Ile  Cys Ser Ala
    3260                 3265                 3270

Val Pro  Ser His Trp Val Pro  Thr Ser Arg Thr Thr  Trp Ser Ile
    3275                 3280                 3285

His Ala  Lys His Glu Trp Met  Thr Thr Glu Asp Met  Leu Thr Val
    3290                 3295                 3300

Trp Asn  Arg Val Trp Ile Gln  Glu Asn Pro Trp Met  Glu Asp Lys
    3305                 3310                 3315

Thr Pro  Val Glu Ser Trp Glu  Glu Ile Pro Tyr Leu  Gly Lys Arg
    3320                 3325                 3330

Glu Asp  Gln Trp Cys Gly Ser  Leu Ile Gly Leu Thr  Ser Arg Ala
    3335                 3340                 3345

Thr Trp  Ala Lys Asn Ile Gln  Ala Ala Ile Asn Gln  Val Arg Ser
    3350                 3355                 3360

Leu Ile  Gly Asn Glu Glu Tyr  Thr Asp Tyr Met Pro  Ser Met Lys
    3365                 3370                 3375

Arg Phe  Arg Arg Glu Glu Glu  Glu Ala Gly Val Leu  Trp
    3380                 3385                 3390
```